United States Patent
Gaudilliere et al.

(10) Patent No.: US 6,828,315 B1
(45) Date of Patent: Dec. 7, 2004

(54) 1-AMINO TRIAZOLOC4,3-A! QUINAZOLINE-5-ONES AND/OR -5-THIONES INHIBITING PHOSPHODIESTERASE IV

(75) Inventors: Bernard Gaudilliere, Nanterre (FR); Remi Lavalette, Longjumeau (FR); Charles Andrianjara, Fresnes (FR); Francine Breuzard, Quincy sous Senart (FR)

(73) Assignee: Warner-Lambert LLC, Morris Plains, NJ (US)

( * ) Notice: Subject to any disclaimer, the term of this patent is extended or adjusted under 35 U.S.C. 154(b) by 0 days.

(21) Appl. No.: 09/980,540
(22) PCT Filed: Apr. 28, 2000
(86) PCT No.: PCT/FR00/01174

§ 371 (c)(1),
(2), (4) Date: Oct. 25, 2001

(87) PCT Pub. No.: WO00/66584

PCT Pub. Date: Nov. 9, 2000

(30) Foreign Application Priority Data

Apr. 28, 1999 (FR) ............................................. 99 05398

(51) Int. Cl.$^7$ ..................... C07D 487/04; A61K 31/505
(52) U.S. Cl. .............................. 514/217.09; 514/228.5; 514/232.2; 514/254.06; 514/267; 540/603; 544/61; 544/132; 544/251
(58) Field of Search ........................... 540/603; 544/61, 544/132, 251; 514/217.09, 228.5, 232.2, 254.06, 267, 233.2

(56) References Cited

U.S. PATENT DOCUMENTS

| | | | |
|---|---|---|---|
| 3,850,932 A | 11/1974 | Kathawala | ................ 260/256.4 |
| 3,865,824 A | 2/1975 | Kobe et al. | .................. 260/248 |

FOREIGN PATENT DOCUMENTS

| | | |
|---|---|---|
| DE | 158549 | 1/1983 |
| EP | 0076199 | 4/1983 |
| EP | 0133234 | 2/1985 |
| WO | 9639408 | 12/1996 |
| WO | 9906404 | 2/1999 |

OTHER PUBLICATIONS

Kappe et al. (Monatshefte fuer Chemie (1967), 98(1), 214–18).*
Misra et al. (Pesticide Science (1982), 13(2), 177–82).*
Omar et al. (Pharmazie (1979), 34(11), 747–8.*
Palfreyman and Souness, "Phosphodiesterase Type IV Inhibitors", *Progress in Medicinal Chemistry*, vol. 33, 1996, pp. 1–52.

Beavo and Reifsnyder, "Primary sequence of cyclic nucleotide phosphodiesterase isozymes and the design of selective inhibitors", *Trends Pharmacol. Sci. ("TIPS")*, vol. 11, 1990, pp. 150–155.

Beavo et al., "Multiple Cyclic Nucleotide Phosphodiesterases", *Molecular Pharmacol.*, vol. 46, 1994, pp. 399–405.

Doherty, "Phosphodiesterase 4 inhibitors as novel anti–inflammatory agents", *Current Opinion Chemical Biology*, vol. 3, 1999, pp. 466–473.

(List continued on next page.)

Primary Examiner—Bruck Kifle
(74) Attorney, Agent, or Firm—Peter C. Richardson; Gregg C. Benson; Robert T. Ronau

(57) ABSTRACT

The present invention relates to triazolo[4,3-a]quinazoline-5-ones and 5-thiones of Formula I and Formula II, whereby I and II are position isomers of group R on nitrogen 3 or 4. Optionally, the invention also relates to the racemic forms, isomers and pharmaceutically acceptable salts thereof. The invention further relates to a method for the production thereof and to compositions containing said derivatives. The compounds act as inhibitors of phosphodiesterase IV (PDE-4) and, as such, have utility in treating asthma, chronic bronchitis, acutte pulmonary attack, atopic dermatitis, pulmonary hypertension, pulmonary insufficiency, cardiac insufficiency, psoriasis, inflammatory conditions of the digestive system such as haemorrhagic rectocolitis and Crohn's disease, acute respiratory distress syndrome, acute pancreatitis, benign hypertrophy of the prostate, rheumatoid arthritis, multiple sclerosis, depression, ischaemia-induced neuronal damage, partial cerebral ischaemia, and cancer such as malignant tumor and chronic lymphoid leukemia.

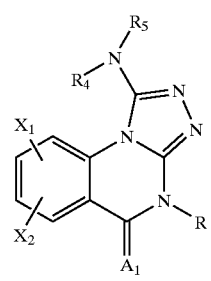

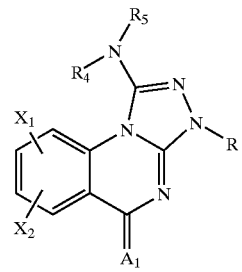

30 Claims, No Drawings-

OTHER PUBLICATIONS

Mohammed and Young, "Clinical aspects and treatment of chronic obstructive pulmonary disease", *Current Opinion in Anti–inflammatory & Immunomodulatory Investigational Drugs*, vol. 1, No. 1, 1999, pp. 21–28.

Schmidt et al., "Selective phosphodiesterase inhibitors for the treatment of bronchial asthma and chronic obstructive pulmonary disease", *Clin. Exp. Allergy*, vol. 29, Suppl. 2, 1999, pp. 99–109.

Nieman et al., "SB 207499 (Ariflo™), a second–generation, selective oral phosphodiesterase type 4 (PDE4) inhibitor, attenuates exercise induced bronchoconstriction in patients with asthma", *American Journal of Respiratory and Critical Care Medicine*, vol. 157, No. 3, 1998, p. A413.

Underwood et al., "The second generation phosphodiesterase (PDE)4 inhibitor, SB 207499, inhibits antigen–induced bronchoconstriction and eosinophilia and LPS–induced airway neutrophilia and edema in the guinea pig", *Eur. Respir. J.*, vol. 12, 1998, abstract No. P663, p. 86s.

Compton et al., "Ariflo™ (SB 207499), a second generation, oral PDE4 inhibitor, improves quality of life in patients with COPD", *American Journal of Respiratory and Critical Care Medicine*, vol. 159, No. 3, 1999, p. A522.

Murdoch et al., "The safety and tolerability of Ariflo™ (SB 207499), a novel & selective phosphodiesterase 4 inhibitor, in healthy male volunteers", *American Journal of Respiratory and Critical Care Medicine*, vol. 157, No. 3, 1998, p. A409.

Yoshihiro Waki et al., "Effects of XT–44, a Phosphodiesterase 4 Inhibitor, in Osteoblastgenesis and Osteoclastgenesis in Culture and Its Therapeutic Effects in Rat Osteopenia Models", *Jpn. J. Pharmacol.*, vol. 79, 1999, pp. 477–483.

Ram and Srimal, "Synthesis of [1,2,4]–Triazoloquinazolinones and Related Compounds as Antihypertensive Agents", *J. Prakt. Chem.*, vol. 332, No. 5, 1990, pp. 629–639.

Burnouf et al., "Synthesis, Structure–Activity Relationships, and Pharmacological Profile of 9–Amino–4–oxo–1–phenyl–3,4,6,7–tetrahydro[1,4]–diazepino[6,7,1–hi]indoles: Discovery of Potent, Selective Phosphodiesterase Type 4 Inhibitors", *J. Med. Chem.*, vol. 43, No. 25, 2000, pp. 4850–4867.

Barnes, "Chronic obstructive pulmonary disease: new opportunities for drug development", *Trends Pharmacol, Sci. ("TIPS")*, vol. 19, 1998, pp. 415–423.

Leckie et al., "Novel therapy for COPD", *Exp. Opin. Invest. Drugs*, vol. 9, No. 1, 2000, pp. 3–23.

* cited by examiner

US 6,828,315 B1

1-AMINO TRIAZOLO[4,3-A] QUINAZOLINE-5-ONES AND/OR -5-THIONES INHIBITING PHOSPHODIESTERASE IV

FIELD OF THE INVENTION

The present invention relates to novel triazolo[4,3-a] quinazoline-5-ones and/or –5-thiones useful for drug preparation for treatment by therapy with a phosphodiesterases 4 inhibitor. These drugs are useful in particular as anti-inflammatories, anti-allergics, bronchodilatators, anti-asthmatics, or TNF α. inhibitors.

BACKGROUND OF THE INVENTION

The cyclic adenosine 3', 5'-monophosphate (AMPc) is an second ubiquitous intracellular messenger, acting as an intermediate between a first messenger (hormone, neurotrasmitter, or autacoid) and the cellular functional responses: the first messenger stimulates enzyme responsible of the AMPc synthesis; AMPc intervenes then, relying of the cells implicated, in very numerous functions: metabolic, contractile, or secretory.

The effects of AMPc terminate when it is broken down by cyclic nucleotide phosphodiesterases, intracellular enzymes that catalyze its hydrolysis into inactive adenosine 5'-monophosphate. In mammals we distinguish at least seven large families of cyclic nucleotide phosphodiesterases (PDE) numbered from 1 to 7 according to their structure, their kinetic behavior, their substrate specificity, or their sensitivity towards effectors (Beavo J. A. et al (1990) Trends Pharmacol. Sci. 11, 150–155. Beavo J. A. et al (1994) Molecular Pharmacol. 46, 399–405). PDE4s are specific to AMPc.

Some phosphodiesterase non-specific inhibitors are known as inhibiting several families of enzymes. This is the case for some methylxanthins like theophyllin. These compounds have a weak therapeutic index, in particular because of their action on some classes of PDE present in cells other than target cells. Additionally, some families of PDE may be selectively inhibited by various pharmacological agents : hydrolysis of cyclic nucleotides slowed down and therefore their concentration increase in only cells the type of PDE sensitive to the inhibitor is found. Of interest are the phosphodiesterases 4 (PDE4), which have been identified in numerous tissues including the central nervous system, heart, vascular endothelium, vascular smooth muscle and the one of air passage muscle, myeloid and lymphoid lines. AMPc increase in cells implicated in inflammation inhibits their activation:inhibition of synthesis and mediator release in mastocytes, monocytes, eosinophil and basophil polynuclears, inhibition of chimiotactism and degranulation of eosinophil and neutrophil polynuclears, inhibition of division and differentiation of lymphocytes.

The cytokins, in particular TNF and interleukins, produced by different leukocyte classes such as T lymphocytes and eosinophil polynuclears, play an important role in the triggering of inflammatory manifestations in particular in response to stimulation by an allergen in respiratory tracts.

Further, AMPc decreases air passage smooth muscular fiber tonicity; PDE4 inhibitors bring about bronchorelaxation.

Chronic obstructive pneumopathy (chronic obstructive pulmonary disease or COPD) is a chronic pathology, of slow evolution, characterized by obstruction of respiratory tracts (associated with inflammation of respiratory tracts and elevated neutrophil count). Pulmonary function alteration is largely irreversible (although improvement is possible after treatment by bronchodilatators).

Clinical presentation of chronic obstructive pneumopathy may fluctuate according to attack severity, going from simple non-invalidating chronic bronchitis to very invalidating conditions like chronic respiratory insufficiencies. The main clinical characteristics of patients suffering from chronic obstructive pneumopathy are chronic bronchitis and/or emphysema (associated with respiratory tract inflammation and/or elevated neutrophil count). Over the last years, some selective inhibitors of second-generation phosphodiesterase 4 have been suggested as potentially efficient agents in treatment of chronic obstructive pneumopathy. See, among others, Doherty, *Chemical Biology* 1999, 3:466–473; Mohammed and al, *Anti-inflammatory & Immunodilatory Investigational Drugs* 1999 1(1):1–28 ; Schmidt and al, *Clinical and Experimental Allergy*, 29, supplement 2, 99–109.

Ariflo that is a PDE 4 inhibitor active by oral route, has been suggested for chronic obstructive pneumopathy treatment. See, among others : Nieman and al, Am J Respir Crit Care Med 1998, 157:A413; Underwood and al, Eur Respir J 1998, 12:86s; Compton and al, Am J Respir Crit Care Med 1999, 159:A522. See also the oral presentation by Compton during the meeting of the "European Respiratory Society" which was held in Madrid, on $12^{th}$ October 1999, as well as the one by Torphy and Underwood during the $4^{th}$ worldwide congress on inflammation which was held in Paris, from $27^{th}$ to $30^{th}$ June 1999. Ariflo is currently under study, in some phase III clinical trials, for chronic obstructive pneumopathy treatment.

However, we should point out that Ariflo has some drawbacks. Indeed some significant adverse events, of the nausea and vomiting type, have been reported after administering of a dose of 20 mg as a single intake. See Murdoch and al, Am J Respir Crit Care Med 1998, 157:A409. Appearance of adverse effects at such low doses will limit the call for Ariflo and prevent use of daily single dosage pharmaceutical, leading therefore to patient discomfort. Osteoporosis is a disease characterized by bone mass decrease and skeleton architecture loss, leading to bone fracture. A large number of women, at the post-menopausal stage, suffer this disease and patient numbers keeps increasing.

Two types of distinct cells exist in bone : osteoblasts, which participate in bone formation; and osteoclasts, which play a role in bone resorption. More particularly, bone mass results from the sum of bone formation by osteoblasts and bone resorption by osteoclasts. Consequently, molecules inhibiting bone resorption induced by osteoclasts are efficient in osteoporosis treatment. Calcitonin, biphosphonates and possibly estrogens are agents fighting against resorption and they are used in the clinical area Molecules stimulating bone formation by osteoblasts also constitute some promising agents in osteoporosis treatment. See also, Yoshihiro et al Jpn. J. Pharmacolog. 1999, 79, 477–483. For several years, extensive research has been performed to obtain and develop powerful PDE4 inhibitors. This has proved to be difficult due to the fact that lots of potential PDE4 inhibitors have some activity on phosphodiesterases in other families.

To date, the lack of selectivity of PDE4 inhibitors represents then an important problem, given the extent of functions regulated by AMPc. There is now a need for powerful and selective PDE4 inhibitors, thus without effect on PDE belonging to other families.

European patent EP 0076199 disclosed compounds with the following general formula:

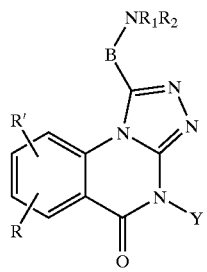

in which R and R', identical or different, represent H, halogen, alkyl $C_{1-3}$, alkoxy or nitro; Y represents alkyl cycloalkyl $C_{3-8}$, alkenyl $C_{2-4}$, aryl ou aralkyl group, and B represents $(CH_2)_n$ with n=1, 2, 3 or $CH(CH_3)$. The use of these compounds is suggested for treatment of asthma, bronchitis and allergic disorders.

Patent DDR158549 disclosed compounds with the following general formula:

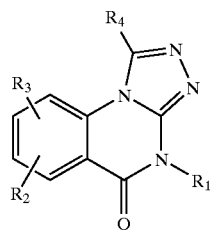

in which $R_1$ represents H, alkyl or aryl; $R_2$ and $R_3$ represent H, alkyl, halogen, OH, SH, O-alkyl, S-alkyl; $R_4$ represents H, alkyl, halogenoalkyl, OH, SH, O-alkyl, S-alkyl, $SO_2$-alkyl, $NH_2$, SCN, aryl, $(CH_2)_n COOalkyl$ and n=0 to 2. The use of these compounds is suggested as am diuretics and antianaphylactics.

Ram and al., in J.Prakt.Chem, 1990, 332(5), 629-39 describe compounds with the following general formula:

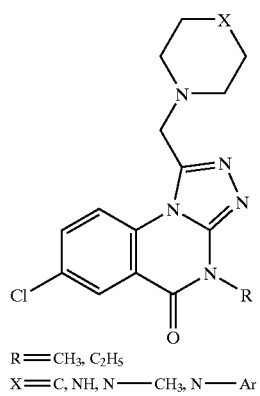

(X)

R = $CH_3$, $C_2H_5$
X = C, NH, N—$CH_3$, N—Ar

The use of these compounds is suggested for treatment of high blood pressure.

SUMMARY OF THE INVENTION

The invention related to triazolo[4,3-a]quinazoline-5-ones and/or –5-thiones of formula I or II:

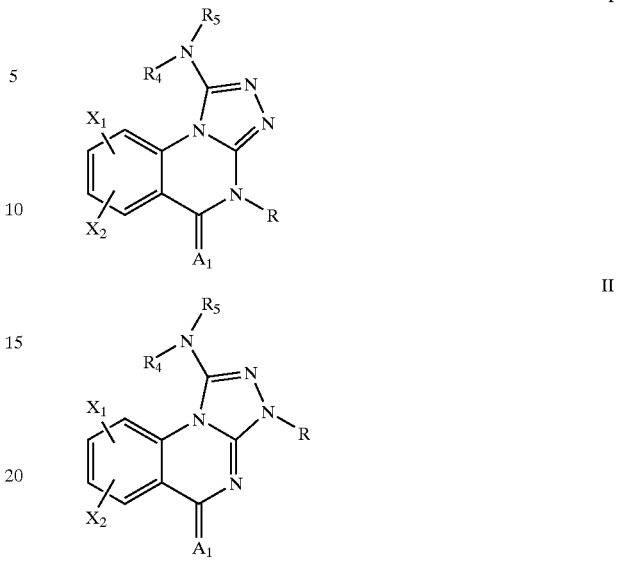

I and II are position isomers of group R on nitrogens 3 or 4, in which:
$A_1$ is O or S;
$X_1$ and $X_2$, similar or different, represent:
hydrogen, hydroxy, halogen, amino, nitro, mercapto, cyano, carboxy, lower alkyl, lower alkoxy or $-S(O)_m R_8$ in which m is 0, 1 or 2 and $R_8$ is a lower alkyl, possibly substituted by one or several halogen atoms,
—CO—$Q_1$—$Q_2$—$Q_3$ in which:
—$Q_1$— is: a simple valence bond, —O—,

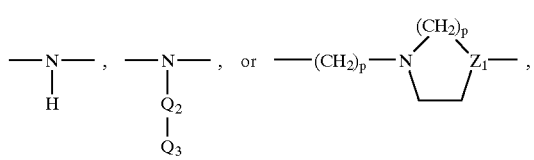

where p is an integer between 0 to 3,
and $Z_1$ is CH, N, O or S,
—$Q_2$— is:
a) —$(CH_2)_q$—, q being equal to 0, 1, 2, 3, or 4, or
b) —$(CH_2$—$CH_2$—$O)_r$—, r being equal to 2, 3, or 4, and
—$Q_3$ is: —H, —OH, lower alkoxy, —O—CO—$X_3$—$NHX_3$ or

in which $X_3$ and $X_4$, similar or different, represent one group lower alkyl, $X_3$ and $X_4$ could be bound to form a cycle, including one or several heteroatoms chosen amongst O, S or N,
—NH—$R_1$ in which $R_1$ represents a lower alkyl group, possibly substituted by one or several groups chosen amongst halogen, hydroxy, cyano, lower alkoxy or —CO—$Q_1$—$Q_2$—$Q_3$, or
—$NR_2R_3$ in which $R_2$ and $R_3$, similar or different, represent a lower alkyl, possibly substituted by one or several hydroxy, halogen, cyano, lower alkoxy or —CO—$Q_1$—$Q_2$—$Q_3$ groups, $R_2$ and $R_3$ being able to be linked to form a cycle, including one or several heteroatoms chosen amongst O, S or N and possibly bridged by a lower alkyl, gem dialkylated or substituted by one or several groups chosen amongst hydroxy, keto, lower alkyl, alkoxy or —CO—$Q_1$—$Q_2$—$Q_3$;

R represents:

lower alkyl, lower alcenyl, lower alkynyl, aryl alkynyl, 2, 3 or 4 pyridylalkyl possibly substituted by a lower alkyl, a lower alkoxy, a

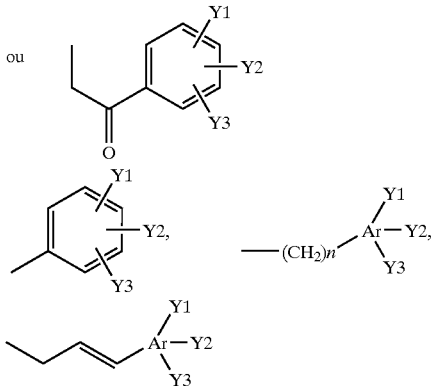

hydroxy, halogen or amino group, in which:

n is an integer between 1 and 5,

Ar is an aromatic cycle including 5 or 6 atoms with 0 to 3 heteroatoms chosen among O, S or N.

Y1, Y2 and Y3, similar or different represent:
hydrogen, hydroxy, mercapto, amino, nitro, halogen, —$NHR_1$, —$NHR_2R_3$, —$(CH_2)_s$—CN, —$(CH_2)_sO$—$Q_1$—$Q_2$—$Q_3$ in which s is an integer between 0 to 6;

lower alkyl, lower alkoxy or —$S(O)_mR_8$ in which m is 0, 1 or 2 and $R_8$ is a lower alkyl, each one may be possibly substituted by one or several halogen atoms; and $R_4$ and $R_5$, represent:

lower alkyl when R4 and R5 are similar, aralkyl, cycloalkyl or cycloalkyl alkyl, when $R_4$ and $R_5$ are different, lower alkyl, $R_4$ and $R_5$ being able to be linked to form a saturated cycle or including one or several double-bonds including one or several heteroatoms chosen among O, S or N and possibly substituted by lower alkyl, hydroxy or lower alkoxy or bridged by a lower alkyl, gem dialkylated or substituted by one or several groups chosen from hydroxy, keto, lower alkyl, lower alkoxy, phenyl alkyl or CO—$Q_1$—$Q_2$—$Q_3$, two atoms of a cycle then formed may also be part of another cycle chosen among phenyl or heteroaryl comprising from 4 to 8 atoms with 1 to 4 heteroatoms;

possibly their racemic forms and their isomers, as well as their pharmaceutically acceptable salts.

Compounds of the present invention are useful as inhibitors, particularly as selective inhibitors of phosphodiesterase enzyme, and more particularly the PDE4 enzyme.

The invention relates also to compounds mainly used as synthesis intermediaries of a formula I or II compounds.

A first series of intermediaries includes compounds having the following general formula III: in which:

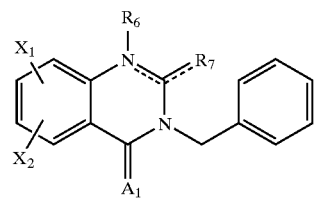

III $X_1$, $X_2$ and $A_1$ are such as defined previously;

the dotted lines represent optional double-bonds;

$R_6$ is hydrogen; and $R_7$ is S or hydrazino;

$R_7$ being able to be linked to nitrogen on $R_6$ to form a cycle, particularly a triazole, possibly substituted by a lower thioalkyl, mercapto or halogen group.

A second series of intermediaries includes compounds having the following general formula IV:

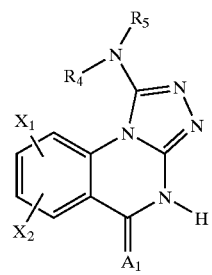

IV in which $X_1$, $X_2$, $A_1$, $R_4$ and $R_5$ are such as previously defined.

A third series of intermediaries includes compounds having the following general formula V:

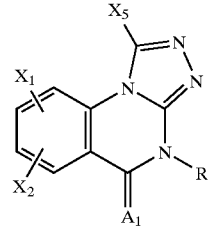

(V)

in which $X_1$, $X_2$, $A_1$ and R are such as previously defined and $X_5$ is a halogen group, particularly F, Br or Cl, —$OCOX_7$, —$OSO_2X_7$ or —$SO_2X_7$ in which $X_7$ is a lower alkyl or an aryl group.

A fourth series of intermediaries include compounds having the following general formula VI

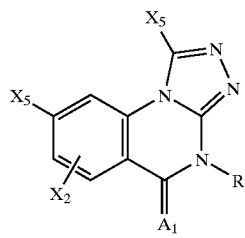
(VI)

in which $X_2$, $X_5$, $A_1$ and R are such as previously defined.

A fifth series of intermediaries include compounds having the following general formula VII:

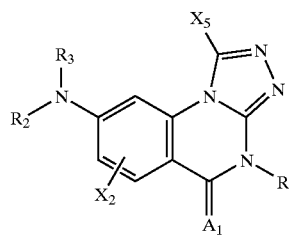
(VII)

in which $X_2$, $A_1$, $R_2$ and $R_3$ are such as previously defined, $X_5$ is a halogen group, particularly F, Br or Cl, —OCOX$_7$, —OSO$_2$X$_7$ or —SO$_2$X$_7$ in which $X_7$ is a lower alkyl or an aryl group.

The invention relates also to a process for producing formula I and II compounds. The process is characterized as including the reaction of general formula IV compounds:

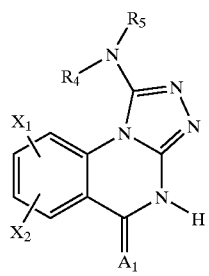
IV in which $X_1$, $X_2$, $A_1$, $R_4$ and $R_5$ are such as previously defined, with a general formula compound

R—X' in which R is such as previously defined and X' is a halogen group, particularly F, Br or Cl, —OCOX$_7$ or —OSO$_2$X$_7$ in which $X_7$ is a lower alkyl or aryl group;

to obtain a mixture of general formula I and II compounds which are then possibly separated.

General formula I compounds can be also prepared by a process characterized in that it includes reacting general formula V compounds:

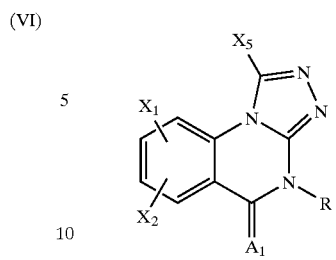
V in which $X_1$, $X_2$, $A_1$ and R are such as previously defined and $X_5$ is a halogen group, particularly F, Br or Cl, —OCOX$_7$, —OSO$_2$X$_7$ or —SO$_2$X$_7$ in which $X_7$ is a lower alkyl or an aryl group; with a general formula compound:

HNR$_4$R$_5$ in which $R_4$ and $R_5$ are such as previously defined, to obtain a general formula I compound.

In particular manner, when $X_1$ is —NR$_2$R$_3$ and —NR$_2$R$_3$ and —NR$_4$R$_5$ are identical, general formula I compounds adhering to this definition can be obtained by reacting with a general formula VI compound:

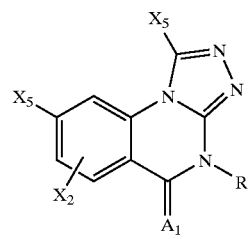
VI in which $X_2$, $X_5$, $A_1$ and R are such as previously defined, with a general formula compound:

HNR$_2$R$_3$ in which $R_2$ and $R_3$ are such as previously defined, to obtain a general formula I compound:

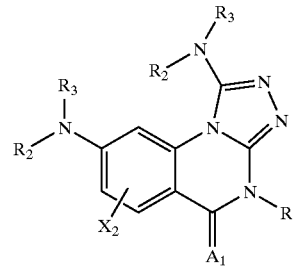
I

Also in particular manner, when $X_1$ is —NR$_2$R$_3$ and —NR$_2$R$_3$ and —NR$_4$R$_5$ are different, general formula I compounds adhering to this definition can be obtained by reacting with a general formula VII compound:

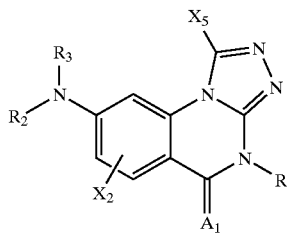

VII in which $X_2$, $X_5$, $A_1$, R, $R_2$ and $R_3$ are such as previously defined, with a general formula compound:

HNR$_4$R$_5$ in which $R_4$ and $R_5$ are such as previously defined, to obtain a general formula I compound:

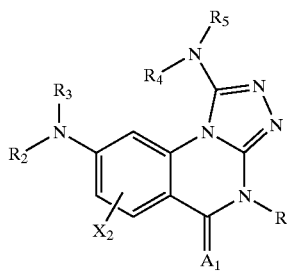

I

Also in particular manner, when $X_1$ is H and $X_2$ is OH, general formula I compounds adhering to this definition can be obtained by subjecting a general formula Ia$_1$ compound: in which $A_1$, R, $R_4$ and $R_5$ are such as previously defined and P is a protector group,

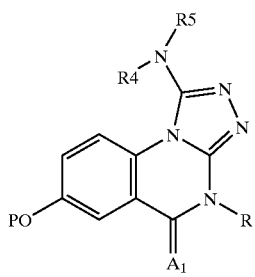

(Ia$_1$)

to conditions allowing protector group P elimination to obtain a general formula I compound.

Also in particular manner, when $X_1$ is H and $X_2$ is NH$_2$, formula I compounds adhering to this definition can be obtained by subjecting a general formula Ia$_2$ compound in which $A_1$, R, $R_4$ and $R_5$ are such as previously defined and $P_1$ is protector group,

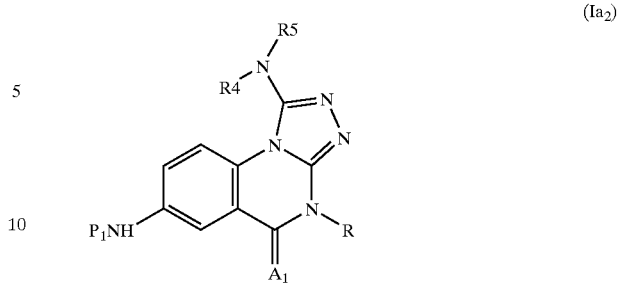

(Ia$_2$)

to conditions allowing elimination of the protector group $P_1$ to obtain a general formula I compound.

Also in particular manner, when $X_1$ is H and $X_2$ is NHR$_2$ in which R2 is such as previously defined formula I compounds adhering to this definition can be obtained by reacting with a general formula Ib compound

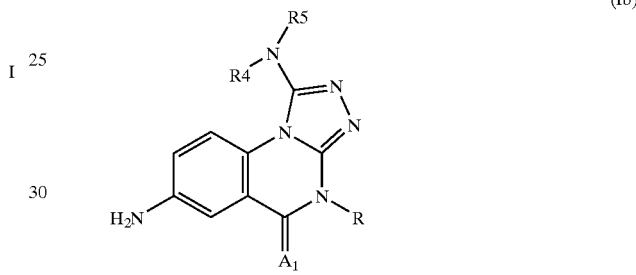

(Ib)

in which $A_1$, R, $R_4$ and $R_5$ are such as previously defined, with a formula $R_2X_5$ compound in which $R_2$ and $X_5$ are such as previously defined, to obtain a general formula I compound.

Moreover, when $X_1$ is H and $X_2$ is NHR$_2$ in which $R_2$ is such as previously defined, formula I compounds adhering to this definition can be also obtained by subjecting a general formula Ib$_2$ compound:

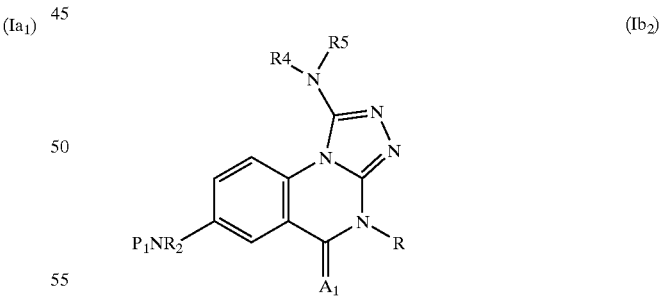

(Ib$_2$)

in which $A_1$, R, $R_4$ and $R_5$ are such as previously defined and $P_1$ is a protector group, to conditions allowing protector group elimination, to obtain a general formula I compound.

Also in particular manner, when $X_1$ is H and $X_2$ is NR$_2$R$_x$ in which $R_2$ is such as previously defined and $R_x$, represents $R_2$ or $R_3$ as previously defined, formula I compounds adhering to this definition can be obtained by reacting with a general formula Ic compound: in which $A_1$, R, $R_2$, $R_4$ and $R_5$ are such as previously described, (Ic)

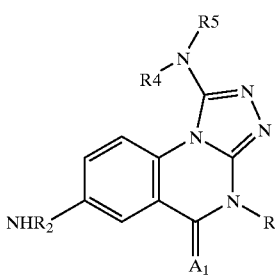

with a formula $R_xX_5$ compound in which $R_x$ and $X_5$ are such as previously defined, to obtain a general formula I compound.

Also in particular manner, when R is

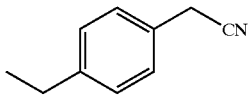

formula I compounds adhering to this definition can be obtained by dehydration of a general formula Ig compound:

(Ig)

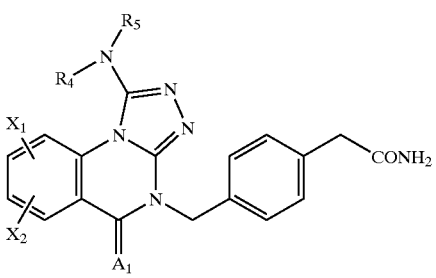

in which $X_1$, $X_2$, $A_1$, $R_4$ and $R_5$ are such as previously defined, to obtain a general formula I compound.

Also in particular manner, when R is

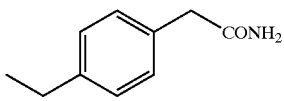

formula I compounds adhering to this definition can be obtained by reacting with a general formula If compound:

(If)

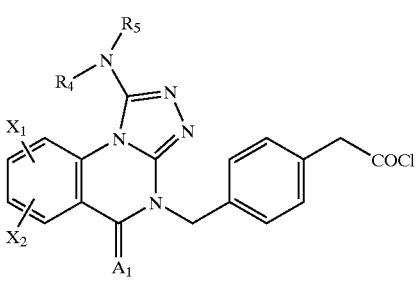

in which $X_1$, $X_2$, $A_1$, $R_4$ and $R_5$ are such as previously defined, with ammonia to obtain a general formula I compound.

Also in particular manner, when R is

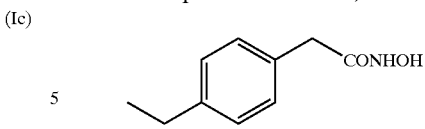

formula I compounds adhering to this definition can be obtained by reacting with a general formula If compound with hydroxylamin to obtain a general formula I compound.

Also in particular manner, when R is

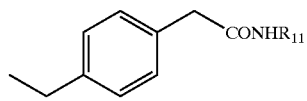

formula I compounds adhering to this definition can be obtained by reacting with a general formula If compound with a formula $R_{11}NH_2$ compound in which $R_{11}$ has the same significance than $R_2$, to obtain a general formula I compound.

Also in particular manner, when R is

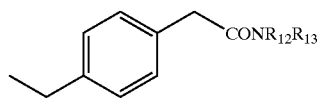

formula I compounds adhering to this definition can be obtained by reacting with a general formula If compound with a formula $HNR_{12}R_{13}$ compound in which $R_{12}$ and $R_{13}$ have the same significance than $R_4$ and $R_5$ respectively, to obtain general formula I compound.

The invention relates also to a pharmaceutical composition including a formula I or II compound and a pharmacologically acceptable carrier.

The invention relates also to the use of a formula I or II compound for drug preparation in treatment disease or illness relying on therapy by phosphodiesterase inhibition, and more particularly of PDE4.

The invention relates also to a treatment method relying on therapy by phosphodiesterase inhibition, and more particularly of PDE4, said method including administering an effective concentration of a formula I or II compound to a patient.

DETAILED DESCRIPTION OF THE INVENTION

The current invention relates also to general formula I or II compounds:

I

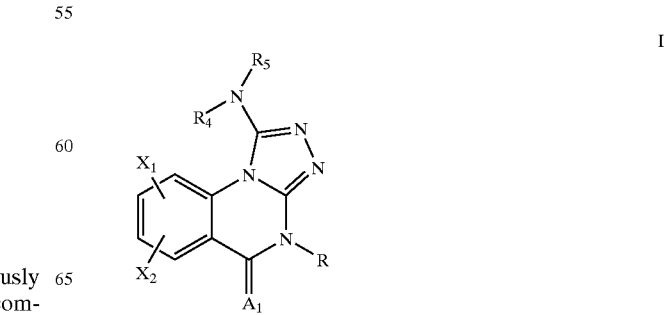

-continued

II

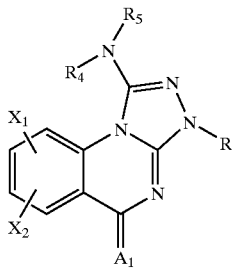

in which $X_1$, $X_2$, $A_1$, R, $R_4$ and $R_5$ are such as previously defined.

The invention relates particularly to general formula I or II compounds in which:
$A_1$ represents an oxygen atom;
$X_1$ represents a hydrogen and $X_2$ is a halogen, amino, lower alkyl, hydroxy or —$NHR_1$ group,
R1 being such as previously defined.
R represents:
a lower alkyl, lower alcenyl, aryl alkynyl, 2-, 3- or 4-pyridylalkyl group possibly substituted on the pyridine ring by a lower alkyl, halogen or hydroxy;

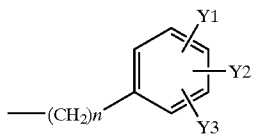

in which:
n is an integer from 1 to 3.
Y1, Y2 and Y3 represent each a hydrogen atom or a lower alkoxy group, more particularly methoxy,
Y1 and Y2 represent each a hydrogen atom and Y3 represents a lower alkoxy group, amino, nitro, hydroxy group, —$(CH_2)_sCO$—$Q_1$—$Q_2$—$Q_3$ group, $(CH_2)_s$—CN group in which, $Q_1$, $Q_2$, $Q_3$ are such as previously defined, or a lower alkyl possibly substituted by one or several halogen atoms, the particularly preferred of the substituent Y3 being the position 4, or,
Y1 represents a hydrogen atom and Y2 and Y3, similar or different, represent a hydroxy, halogen or lower alkoxy group, or

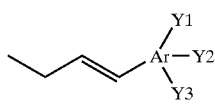

in which:
Ar is such as previously defined;
Y1, Y2 and Y3 represent each a hydrogen atom, or
Y1 and Y2 represent each a hydrogen atom and Y3 is lower alkoxy or halogen;
$R_4$ and $R_5$, represent
lower alkyl when R4 and R5 are similar, aralkyl, cycloalkyl or cycloalkyl alkyl, when $R_4$ and $R_5$ are different,
lower alkyl, $R_4$ and $R_5$ being able to be linked to form a saturated cycle or including one or several double-bonds with one or several heteroatoms chosen among O, S or N and possibly substituted by a lower alkyl, a hydroxy or a lower alkoxy or bridged by a lower alkyl, dialkylated gem or substituted by one or several groups chosen among hydroxy, keto, lower alkyl, lower alkoxy, phenyl alkyl or CO—$Q_1$—$Q_2$—$Q_3$, two atoms of the cycle then formed may also be part of another cycle chosen among phenyl or heteroaryl comprising from 4 to 8 atoms including 1 to 4 heteroatoms;

The invention relates more particularly to general formula I compounds in which:
$X_1$ represents a hydrogen atom,
$X_2$ represents a halogen atom, amino, lower alkyl, hydroxy or —$NHR_1$;
R represents:

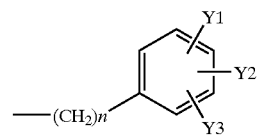

in which:
n is an integer from 1 to 3,
Y1, Y2 and Y3 represent each a hydrogen atom or a lower alkoxy group, more particularly methoxy and in particular 3, 4, 5-trimethoxy,
Y1 and Y2 represent each a hydrogen atom and Y3 represents a lower alkoxy group, amino, nitro, or hydroxy, a lower alkyl group possibly substituted by one or several halogen atoms, a —$(CH_2)_sCO$—$Q_1$—$Q_2$—$Q_3$ group in which s is 0 or 1, $Q_1$ is O, —NH— or a valence bond, $Q_2$ is —$(CH_2)_q$—, q being equal to 0, 1, 2, 3 or 4 and $Q_3$ is H, OH or —$NX_3X_4$ in which $X_3$ and $X_4$ are such as previously defined, a $(CH_2)_s$—CN group in which s is 0 or 1, the position particularly preferred of the substituent Y3 being the position 4, or
Y1 represents a hydrogen atom and Y2 and Y3, similar or different, represent a hydroxy, halogen or lower alkoxy group; or

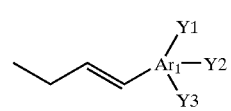

in which:
$Ar_1$ is an aromatic cycle including 6 atoms, one may be a nitrogen atom in position 2, 3 or 4 and preferably in position 3;
Y1, Y2 and Y3 represent each a hydrogen atom, or
Y1 and Y2 represent each a hydrogen atom and Y3 is a lower alkoxy group or a halogen group when $Ar_1$ does not include a nitrogen atom; and
$R_4$ and $R_5$, represent:
lower alkyl when $R_4$ and $R_5$ are similar, aralkyl, cycloalkyl or cycloalkyl alkyl, when $R_4$ and $R_5$ are different,
lower alkyl, $R_4$ and $R_5$ being able to be linked to form a saturated cycle or including one or several double-bonds with one or several heteroatoms chosen among O, S or N and possibly substituted by a lower alkyl, a hydroxy or a lower alkoxy or bridged by a lower alkyl, dialkylated gem or substituted by one or several groups chosen among hydroxy, keto, lower alkyl, lower alkoxy, phenyl alkyl or CO—$Q_1$—$Q_2$—$Q_3$, two atoms from the cycle then formed may also be part of another cycle chosen among phenyl or heteroaryl comprising from 4 to 8 atoms with 1 to 4 heteroatoms;

The invention relates also to general formula I or II compounds in which: $X_1$, $X_2$, $A_1$, $R_4$ and $R_5$ are such as previously defined in the summary of the invention; and R represents:

lower alkynyl, aryl alkynyl, 2-, 3- or 4-pyridylalkyl possibly substituted by a lower alkyl, a lower alkoxy, a hydroxy or a halogen group,

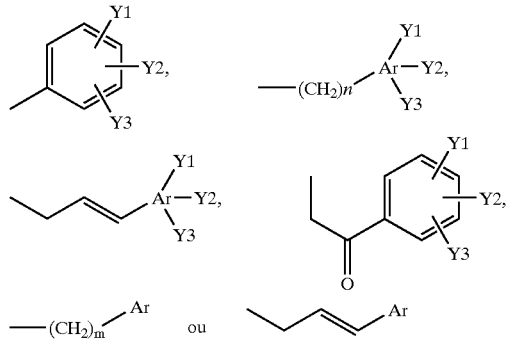

in which:

n is an integer from 1 to 5 and m is an integer from 3 to 5;

Ar is an aromatic cycle including 5 or 6 atoms with 0 to 3 heteroatoms chosen among O, S or N;

Y1, Y2 and Y3, similar or different represent:
hydroxy, mercapto, amino, nitro, halogen, —$(CH_2)_sCO$—$Q_1$—$Q_2$—$Q_3$, $(CH_2)_s$—CN, in which s is an integer from 0 to 6, lower alkyl, lower alkoxy or lower thioalkyl, possibly substituted by one or several halogen atoms.

In another of its embodiments, the current invention relates to general formula I or II compounds in which:

$X_1$, $X_2$, $R_4$ and $R_5$ are such as previously defined in the summary of the invention; and R represents

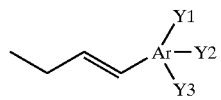

in which:

Ar is an aromatic cycle including 5 or 6 atoms with 0 to 3 heteroatoms chosen among O, S or N (aromatic cycles including 6 atoms, one atom could be a nitrogen in position 2, 3 or 4, preferably in position 3);

Y1, Y2 and Y3, similar or different represent:
hydrogen, hydroxy, mercapto, amino, nitro, halogen, cyano, —$(CH_2)_sCO$—$Q_1$—$Q_2$—$Q_3$ in which s is an integer from 0 to 6, lower alkyl, lower alkoxy or lower thioalkyl, possibly substituted by one or several halogen atoms.

In a preferred manner:

Y1, Y2 and Y3 represent each a hydrogen atom, or

Y1 and Y2 represent each a hydrogen atom and Y3 is a lower alkoxy or halogen.

In another of its embodiments, the current invention relates to general formula I or II compounds in which:

$X_1$, $X_2$, $A_1$, $R_4$ and $R_5$ are such as previously defined above in the summary of the invention; and R represents

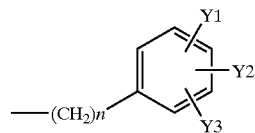

in which:

n is an integer from 1 to 3

Y1, Y2 and Y3, similar or different represent:
hydroxy, mercapto, amino, nitro, halogen, —$(CH_2)_sCO$—$Q_1$—$Q_2$—$Q_3$, $(CH_2)_s$—CN in which s is an integer from 0 to 6, lower alkyl, lower alkoxy or lower thioalkyl, possibly substituted by one or several halogen atoms.

In a preferred manner:

n is an integer from 1 to 3,

Y1, Y2 and Y3 represent each a lower alkoxy group, more particularly methoxy and in particular 3, 4, 5-triméthoxy, Y1 and Y2 represent each a hydrogen atom and Y3 represents a lower alkoxy group, cyano, amino, nitro or hydroxy, a lower alkyl group possibly substituted by one or several halogen atoms or a —$(CH_2)_sCO$—$Q_1$—$Q_2$—$Q_3$ group in which s is 0 or 1, $Q_1$ is O, —NH— or a valence bond, $Q_2$ is —$(CH_2)_q$—, q being equal to 0, 1, 2, 3 or 4 and $Q_3$ is H, OH or —$NX_3X_4$ in which $X_3$ and $X_4$ are such as previously defined, the position particularly preferred of substituent Y3 being position 4, or Y1 represents a hydrogen atom and Y2 and Y3, similar or different, represent a hydroxy, halogen or lower alkoxy group.

In another of its embodiments, the current invention relates to general formula I or II compounds in which $X_1$, $X_2$, $A_1$, $R_4$ and $R_5$ are such as previously defined in the summary of the invention; and R represents:

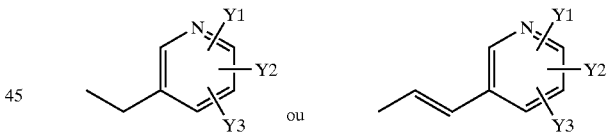

in which:

Y1, Y2 and Y3, similar or different represent:
hydrogen, hydroxy, mercapto, amino, nitro, halogen, —$(CH_2)_sCO$—$Q_1$—$Q_2$—$Q_3$, $(CH_2)_s$—CN, in which s is an integer from 0 to 6, lower alkyl, lower alkoxy or lower thioalkyl, possibly substituted by one or several halogen atoms.

In a preferred manner:

Y1, Y2 and Y3 represent each a hydrogen atom, or

Y1 and Y2 represent each a hydrogen atom and Y3 is lower alkoxy or halogen.

In another of its embodiments, the current invention relates to general formula I or II compounds in which $X_1$, $X_2$, $A_1$, R, $R_4$ and $R_5$ are such as previously defined in the summary of the invention; and when $X_1$ and $X_2$ represent hydrogen, R is not alkyl, phenyl, benzyl or allyl, when $X_1$ represents hydrogen and $X_2$ represents 7-Cl or $CH_3$, R is not alkyl; and when $X_1$ represents hydrogen, $X_2$ is not 8-Cl.

The invention relates also to a group of a formula I or II compounds particularly active as TNFα inhibitors and in which:

$A_1$ is O or S;

$X_1$ and $X_2$, similar or different, represent:
hydrogen, hydroxy, halogen, amino, nitro, mercapto, cyano, carboxy,
lower alkyl, lower alkoxy or —$S(O)_m R_8$ in which m is 0, 1 or 2 and $R_8$ is lower alkyl, possibly substituted by one or several halogen atoms.

In a preferred manner, $X_1$ is H and $X_2$ is halogen, notably 7-Br, or lower alkyl, notably 7-$CH_3$.

R represents:

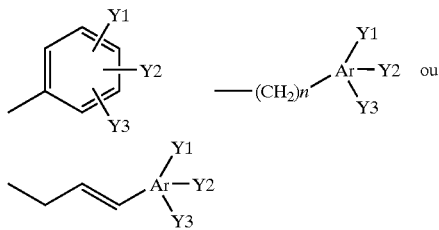

in which:
n is an integer from 1 to 5,
Ar is an aromatic cycle including 5 or 6 atoms with 0 to 3 heteroatoms chosen among O, S or N,
Y1, Y2 and Y3, similar or different represent:
hydrogen, hydroxy, mercapto, amino, nitro, halogen, —$(CH_2)_s CO$—$Q_1$—$Q_2$—$Q_3$, $(CH_2)_s$—CN in which s is an integer from 0 to 6;
lower alkyl, lower alkoxy or —$S(O)_m R_8$ in which m is 0, 1 or 2 and $R_8$ is a lower alkyl, possibly substituted by one or several halogen atoms.

The substituents particularly preferred forming the group R include cinnamyl, 3-pyridyl allyl, paracyano benzyl, dimethoxy benzyl and 3-pyridyl méthyl.

$R_4$ and $R_5$, similar or different, represent:
lower alkyl, $R_4$ and $R_5$ being able to be linked to form a saturated cycle or including one or several double-bonds with one or several heteroatoms chosen among O, S or N and possibly bridged by a lower alkyl, dialkylated gem or substituted by one or several groups chosen among hydroxy, keto, lower alkyl, lower alkoxy, phenyl alkyl or CO—$Q_1$—$Q_2$—$Q_3$. substituants particularly preferred forming the group $NR_4 R_5$ include dimethylamino, pyrrolidine and azepanyl.

Compounds particularly preferred as TNFα inhibitors include the following molecules:

3  7-Bromo-1-dimethylamino-4-(E)-3-pyridin-3-yl-allyl)-4H-[1,2,4]triazolo[4,3-a]quinazolin-5-one
104  1-Dimethylamino-7-methyl-4-(3-pyridin-3-yl-allyl)-4H-[1,2,4]triazolo[4,3-a]quinazolin-5-one
94  4-(3,4-Dimethoxy-benzyl)-7-methyl-1-pyrrolidin-1-yl-4H-[1,2,4]triazolo[4,3-a]quinazolin-5-one
101  4-(1-Dimethylamino-7-methyl-5-oxo-5H-[1,2,4]triazolo[4,3-a]quinazolin-4-ylmethyl)-benzonitrile
85  7-Bromo-1-dimethylamino-4-(3-phenyl-allyl)-4H-[1,2,4]triazolo[4,3-a]quinazolin-5-one
98  7-Methyl-4-(3-phenyl-allyl)-1-pyrrolidin-1-yl-4H-[1,2,4]triazolo[4,3-a]quinazolin-5-one
79  4-(7-Bromo-1-dimethylamino-5-oxo-5H-[1,2,4]triazolo[4,3-a]quinazolin-4-ylmethyl)-benzonitrile
91  1-Azepan-1-yl-7-methyl-4-pyridin-3-ylmethyl-4H-[1,2,4]triazolo[4,3-a]quinazolin-5-one
93  4-(7-Methyl-5-oxo-1-pyrrolidin-1-yl-5H-[1,2,4]triazolo[4,3-a]quinazolin-4-ylmethyl)-benzonitrile
103  1-Dimethylamino-7-methyl-4-((E)-3-phenyl-allyl)-4H-[1,2,4]triazolo[4,3-a]quinazolin-5-one
46  4-(7-Bromo-5-oxo-1-pyrrolidin-1-yl-5H-[1,2,4]triazolo[4,3-a]quinazolin-4-ylmethyl)-benzonitrile
46  1-Azepan-1-yl-7-bromo-4-(3,4-dimethoxy-benzyl)-4H-[1,2,4]triazolo[4,3-a]quinazolin-5one The groups defined above, the following substituents are particularly preferred:

In a general manner for groups $X_1$, $X_2$, $X_3$, $X_4$, R, $R_1$, $R_2$, $R_3$, $R_4$, $R_5$:
halogen : F, Cl, Br, I, preferably Br and Cl,
lower alkyl: linear or branched including 1 to 6, preferably 1 to 3 carbon atoms,
lower alkoxy: linear or branched comprising from 1 to 5, preferably 1 to 3 carbon atoms,
lower alkylthio: linear or branched comprising from 1 to 5, preferably 1 to 3 carbon atoms,
lower alcenyl: comprising from 3 to 6, preferably 3 to 4 carbon atoms, more particularly allyl,
lower alkynyl: comprising from 3 to 9 carbon atoms, more particularly propargyl and phényl-propargyl,
2-, 3- or 4-pyridylalkyl in which alkyl includes from 1 to 5, preferably 1 to 3 carbon atoms,
aryl: comprising from 5 to 8, preferably 5 or 6 atoms,
aralkyl in which alkyl includes from 1 to 6, preferably 1 to 4 carbon atoms,
cycloalkyl including 3 to 8, preferably 3 to 6 carbon atoms,
cycloalkyl alkyl in which alkyl includes from 1 to 6, preferably 1 to 3 atoms de carbone and cycloalkyl include from 3 to 8, de preferably 3 to 6 carbon atoms,
lower alkyl, lower alkoxy or lower alkylthio possibly substituted by one or several halogen atoms: we will prefer trisubstituted groups of type —$(CH_2)_p$—$CF_3$, —O—$(CH_2)_p$—$CF_3$ or —S—$(CH_2)_p$—$CF_3$, in which p is an integer from 0 to 3.

In particular manner for the groups $X_1$ and $X_2$:
—NH—$R_1$, or —$NR_2 R_3$: when lower alkyl is substituted by one or several groups chosen among halogen, hydroxy, cyano, lower alkoxy or CO—$Q_1$—$Q_2$—$Q_3$, the substituents number varies between 1 and 4, preferably between 1 and 2, —$NR_2 R_3$: when $R_2$ and $R_3$ are bound to form a cycle, this cycle is characterized as including preferably:
between 1 and 4, more particularly between 1 and 2 heteroatoms chosen among O, S or N, the cyclic substituents of this type being, in a preferred manner, saturated cycles of type $C_m N$ in which m is an integer from 2 to 7, preferably 4 to 6, particularly preferred cycles being chosen among group including pyrrolidine, piperidine, homopiperidine or cyclooctylamine and
between 0 and 4, in a preferred manner between 0 and 2, more particularly between 1 and 2 substituents chosen among hydroxy, keto, lower alkyl, lower alkoxy or —CO—$Q_1$—$Q_2$—$Q_3$, groups $X_1$ and $X_2$ are particularly localized in position 7 and 8 of aromatic cycle, for formula I and II compounds to which they are bound.

In particular manner for the group R:
the substituents Y1, Y2 and Y3 are particularly localized in position 3 and/or 4 of the aromatic cycle to which they are bound.

In particular manner for the groups $R_4$ and $R_5$:
when $R_4$ and $R_5$ are bound to form a cycle, this cycle is characterized as preferably including:
between 1 and 4 heteroatoms chosen among O, S or N, cyclic substituents of this type being, in a preferred manner, saturated cycles of type $C_mN$, m being an integer between 2 and 7, cycles particularly preferred being chosen among group including pyrrolidine, piperidine, homopiperidine or cyclooctylamine, and
between 0 and 4, in a preferred manner between 0 and 2 substituents chosen among hydroxy, keto, lower alkyl, lower alkoxy or —CO—$Q_1$—$Q_2$—$Q_3$.

Among the preferred compounds of the current invention, we find the following compounds:

1  1-Azepan-1-yl)-7-chloro-4-(3-phenylallyl)-4H-[1,2,4]triazolo[4,3-a]quinazolin-5-one
2  1-(azepan-1-yl)-7-chloro-3-(3-phenylallyl)-3H-[1,2,4]triazolo[4,3-a]quinazolin-5-one
3  7-Bromo-1-dimethylamino-4-((E)-3-pyridin-3-yl-allyl)-4H-[1,2,4]triazolo[4,3-a]quinazolin-5-one
4  7-Bromo-4-pyridin-3-ylmethyl-1-pyrrolidin-1-yl-4H-[1,2,4]triazolo[4,3-a]quinazolin-5-one
5  7-Bromo-3-pyridin-3-ylmethyl-1-pyrrolidin-1-yl-3H-[1,2,4]triazolo[4,3-a]quinazolin-5-one
6  1-Azepan-1-yl-4-(3-phenyl-allyl)-4H-[1,2,4]triazolo[4,3-a]quinazolin-5-one
7  1-(azepan-1-yl)-7-chloro-4-allyl-4H-[1,2,4]triazolo[4,3-a]-quinazolin-5-one
8  1-(azepan-1-yl)-7-chloro-4-4-methylbenzyl)-4H-[1,2,4]triazolo[4,3-a]quinazolin-5-one
9  1-(azepan-1-yl)-7-chloro-4-(2-chlorobenzyl)-4H-[1,2,4]triazolo[4,3-a]quinazolin-5-one
10  1-(azepan-1-yl)-7-chloro-4-(3-chlorobenzyl)-4H-[1,2,4]triazolo[4,3-a]quinazolin-5-one
11  1-(azepan-1-yl)-7-chloro-4-4-chlorobenzyl)-4H-[1,2,4]triazolo[4,3-a]quinazolin-5-one
12  1-(azepan-1-yl)-7-chloro-(4-bromobenzyl)-4H-[1,2,4]triazolo[4,3-a]quinazolin-5-one
13  1-(azepan-1-yl)-7-chloro-4-(4-fluorobenzyl)-4H-[1,2,4]triazolo[4,3-a]quinazolin-5-one
14  1-(azepan-1-yl)-7chloro-4-(4-(trifluoromethyl)benzyl)-4H-[1,2,4]triazolo[4,3-a]quinazolin-5-one
15  1-(azepan-1-yl)-7-chloro-4-4-cyanobenzyl)-4H-[1,2,4]triazolo[4,3-a]quinazolin-5-one
16  1-(azepan-1-yl)-7-chloro-4-(2-methoxybenzyl)-4H-[1,2,4]triazolo[4,3-a]quinazolin-5-one
17  1-(azepan-1-yl)-7-chloro-4-(3-methoxybenzyl)-4H-[1,2,4]triazolo[4,3-a]quinazolin-5-one
18  1-(azepan-1-yl)-7-chloro-4-(4-methoxybenzyl)-4H-[1,2,4]triazolo[4,3-a]quinazolin-5-one
19  1-(azepan-1-yl)-7-chloro-4-(3,4-dichlorobenzyl)-4H-[1,2,4]triazolo[4,3-a]quinazolin-5-one
20  1-(azepan-1-yl)-7-chloro-4(3,4-dimethoxybenzyl)-4H-[1,2,4]triazolo[4,3-a]quinazolin-5-one
21  1-(azepan-1-yl)-7-chloro-4-(2-pyridylmethyl)-4H-[1,2,4]triazolo[4,3-a]quinazolin-5-one
22  1-(azepan-1-yl)-7-chloro-4-(3-pyridylmethyl)-4H-[1,2,4]triazolo(4,3-a]quinazolin-5-one
23  1-(azepan-1-yl)-7-chloro-4-(4-pyridylmethyl)-4H-[1,2,4]triazolo[4,3-a]quinazolin-5-one
24  1-(azepan-1-yl)-7-chloro-4-(2-phenylthyl)-4H-[1,2,4]triazolo[4,3-a]quinazolin-5-one
25  1-(azepan-1-yl)-7-chloro-4-[2-(4-methoxyphenyl)ethyl]-4H-[1,2,4]triazolo[4,3-a]quinazolin-5-one
26  1-(azepan-1-yl)-7-chloro-4-(3-phenylpropyl)-4H-[1,2,4]triazolo[4,3-a]quinazolin-5-one
27  1-Azepan-1-yl-7-chloro-4-(2-oxo-2-phenyl-ethyl)-4H-[1,2,4]triazolo[4,3-a]quinazolin-5-one
28  1-azepan-1-yl)-7-chloro-4-[2-(4-methoxyphenyl)-2-oxoethyl]-4H-[1,2,4]triazolo[4,3-a]quinazolin-5-one
29  1-(azepan-1-yl)-7-chloro-4[2-(4-chlorophenyl)-2-oxoethyl]-4H-[1,2,4]triazolo[4,3-a]quinazolin-5-one
30  5-[(1-(azepan-1-yl)-7-chloro-5-oxo-5H-[1,2,4]triazolo[4,3-a]-quinazolin-4-yl)acetyl]-2-methoxybenzoic acid methyl ester
31  7-Chloro-4-pyridin-3-ylmethyl-1-pyrrolidin-1-yl-4H-[1,2,4]triazolo[4,3-a]quinazolin-5-one
32  1-(azepan-1-yl)-7-bromo-4-(4-chloro-benzyl)-4H-[1,2,4]triazolo[4,3-a]quinazolin-5-one
33  1-Azepan-1-yl)-7-bromo-4-(4-fluoro-benzyl)-4H-[1,2,4]triazolo[4,3-a]quinazolin-5-one
34  4-(1-Azepan-1-yl-7-bromo-5-oxo-5H-[1,2,4]triazolo[4,3-a]quinazolin-4-ylmethyl)-benzonitrile
35  1-Azepan-1-yl-7-bromo-4-(3,4-dimethoxy-benzyl)-4H-[1,2,4]triazolo[4,3-a]quinazolin-5-one
36  1-(azepan-1-yl)-7-bromo-4-(3-pyridinylmethyl)-4H-[1,2,4]triazolo[4,3-a]quinazolin-5-one
37  1-(azepan-1-yl)-7-bromo-4-(3-phenylallyl)-4H-[1,2,4]triazolo[4,3-a]quinazolin-5-one
38  1-Azepan-1-yl-7-bromo-4-[3-(4-chloro-phenyl)-allyl]-4H-[1,2,4]triazolo[4,3-a]quinazolin-5-one
39  1-Azepan-1-yl-7-bromo-4-[3-(4-methoxy-phenyl)-allyl]-4H-[1,2,4]triazolo[4,3-a]quinazolin-5-one
40  1-Azepan-1-yl-7-bromo-4-((E)-3-pyridin-3-yl-allyl)-4H-[1,2,4]triazolo[4,3-a]quinazolin-5-one
41  1-Azepan-1-yl-7-bromo-4-(3-pyridin-4-yl-allyl)-4H-[1,2,4]triazolo[4,3-a]quinazolin-5-one
42  7-Bromo-4-(4-methyl-benzyl)-1-pyrrolidin-1-yl-4H-[1,2,4]triazolo[4,3-a]quinazolin-5-one
43  7-Bromo-4-(4-chloro-benzyl)-1-pyrrolidin-1-yl-4H-[1,2,4]triazolo[4,3-a]quinazolin-5-one
44  7-Bromo-4-(4-fluoro-benzyl)-1-pyrrolidin-1-yl-4H-[1,2,4]triazolo[4,3-a]quinazolin-5-one
45  3-(7-Bromo-5-oxo-1-pyrrolidin-1-yl-5H-[1,2,4]triazolo[4,3-a]quinazolin-4-ylmethyl)benzonitrile
46  4-(7-Bromo-5-oxo-1-pyrrolidin-1-yl-5H-[1,2,4]triazolo[4,3-a]quinazolin-4-ylmethyl)-benzonitrile
47  4-(7-Bromo-5-oxo-1-pyrrolidin-1-yl-5H-[1,2,4]triazolo[4,3-a]quinazolin-4-ylmethyl)-benzoic acid methyl ester
48  7-Bromo-4-(4-nitro-benzyl)-1-pyrrolidin-1-yl-4H-[1,2,4]triazolo[4,3-a]quinazolin-5-one
49  7-Bromo-4-(4-methoxy-benzyl)-1-pyrrolidin-1-yl-4H-[1,2,4]triazolo[4,3-a]quinazolin-5-one
50  Acetic acid 4-(7-bromo-5-oxo-1-pyrrolidin-1-yl-5H-[1,2,4]triazolo[4,3-a]quinazolin-4-ylmethyl)-phenyl ester
51  7-Bromo-4-(4-hydroxy-benzyl)-1-pyrrolidin-1-yl-4H-[1,2,4]triazolo[4,3-a]quinazolin-5-one.
52  7-Bromo-4-(3,4-dimethoxy-benzyl)-1-pyrrolidin-1-yl-4H-[1,2,4]triazolo[4,3-a]quinazolin-5-one
53  4-Benzo[1,3]dioxol-5-ylmethyl-7-bromo-1-pyrrolidin-1-yl-4H-[1,2,4]triazolo[4,3-a]quinazolin-5-one
54  7-Bromo-4-(3,5-dimethoxy-benzyl)-1-pyrrolidin-1-yl-4H-[1,2,4]triazolo[4,3-a]quinazolin-5-one
55  7-Bromo-1-pyrrolidin-1-yl-4-(3,4,5-trimethoxy-benzyl)-4H-[1,2,4]triazolo[4,3-a]quinazolin-5-one
56  [4-(7-Bromo-5-oxo-1-pyrrolidin-1-yl-5H-[1,2,4]triazolo[4,3-a]quinazolin-4-ylmethyl)-phenyl]-acetic acid
57  1-(pyrrolidin-1-yl)-7-bromo-4-(3-phenylallyl)-4H-[1,2,4]triazolo[4,3-a]quinazolin-5-one 58 7-Bromo-4-(3-phenyl-allyl)-1-pyrrolidin-1-yl-4H-[1,2,4]triazolo[4,3-a]quinazolin-5-one
59 7-Bromo-4-[(E)-3-(4-chloro-phenyl)-allyl]-1-pyrrolidin-1-yl-4H-[1,2,4]triazolo[4,3-a]quinazolin-5-one
60 7-Bromo-4-[3-(4-methoxy-phenyl)allyl]-1-pyrrolidin-1-yl-4H-[1,2,4]triazolo[4,3-a]quinazolin-5-one
61 7-Bromo4-(3-pyridin-3-yl-allyl)-1-pyrrolidin-1-yl4H-[1,2,4]triazolo[4,3-a]quinazolin-5-one
62 7-Bromo-4-((E)-3-pyridin-4-yl-allyl)-1-pyrrolidin-1-yl-4H-[1,2,4]triazolo[4,3-a]quinazolin-5-one
63 7-Bromo-4-(1H-imidazol-4-ylmethyl)-1-pyrrolidin-1-yl-4H-[1,2,4]triazolo[4,3-a]quinazolin-5-one
64 7-Bromo-4-(3,5-dimethyl-isoxazol-4-ylmethyl)-1-pyrrolidin-1-yl-4H-[1,2,4]triazolo[4,3-a]quinazolin-5-one
65 7-Bromo-4-cyclopentylmethyl-1-pyrrolidin-1-yl-4H-[1,2,4]triazolo[4,3-a]quinazolin-5-one
66 7-Bromo-4-butyl-1-pyrrolidin-1-yl-4H-[1,2,4]triazolo[4,3-a]quinazolin-5-one
67 7-Bromo-1-pyrrolidin-1-yl-4-(2,2,2-trifluoro-ethyl)-4H-[1,2,4]triazolo[4,3-a]quinazolin-5-one
68 7-Bromo-4-(2-hydroxy-ethyl)-1-pyrrolidin-1-yl-4H-[1,2,4]triazolo[4,3-a]quinazolin-5-one
69 7-Bromo-4-(2diethylamino-ethyl)-1-pyrrolidin-1-yl-4H-[1,2,4)triazolo[4,3-a]quinazolin-5-one
70 7-Bromo-4-prop-2-ynyl-1-pyrrolidin-1-yl-4H-[1,2,4]triazolo[4,3-a]quinazolin-5-one
71 7-Bromo-4-(2-phenoxy-ethyl)-1-pyrrolidin-1-yl-4H-[1,2,4]triazolo[4,3-a]quinazolin-5-one
72 7-Bromo-4-(2-phenylsulfenyl-ethyl)-1-pyrrolidin-1-yl-4H-[1,2,4]triazolo[4,3-a]quinazolin-5-one
73 (7-Bromo-5-oxo-1-pyrrolidin-1-yl-5H-[1,2,4]triazolo[4,3-a]quinazolin-4-yl)-phenyl-acetic acid methyl ester
74 4-(7-Bromo-5-oxo-1-piperidin-1-yl-5H-[1,2,4]triazolo[4,3-a]quinazolin-4-ylmethyl)-benzonitrile
75 7-Bromo-4-(3,4-dimethoxy-benzyl)-1-piperidin-1-yl-4H-[1,2,4]triazolo[4,3-a]quinazolin-5-one
76 1-(piperidin-1-yl)-7-bromo-4-(3-phenylallyl)-4H-[1,2,4]triazolo[4,3-a]quinazolin-5-one
77 7-Bromo-4(3-pyridin-3-yl-allyl)-1-thiomorpholin-4-yl-4H-[1,2,4]triazolo[4,3-a]quinazolin-5-one
78 Bromo-dimethylamino(4-methyl-benzyl)-4H-[1,2,4]triazolo[4,3-a]quinazolin-5-one
79 4-(7-Bromo-1-dimethylamino-5-oxo-5H-[1,2,4]triazolo[4,3-a]quinazolin-4-ylmethyl)-benzonitrile
80 7-Bromo-1-dimethylamino-4-(4-hydroxy-benzyl)-4H-[1,2,4]triazolo[4,3-a]quinazolin-5-one
81 4-(7-Bromo-1-dimethylamino-5-oxo-5H-[1,2,4]triazolo[4,3-a]quinazolin-4-ylmethyl)-benzoic acid methyl ester
82 [4-(7-Bromo-1-dimethylamino-5-oxo-5H-[1,2,4]triazolo[4,3-a]quinazolin-4-ylmethyl)-phenyl]-acetic acid
83 [4-(7-Bromo-1-dimethylamino-5-oxo-5H-[1,2,4]triazolo[4,3-a]quinazolin-4-ylmethyl)-phenyl]-acetonitrile
84 7-Bromo-1-dimethylamino-4-pyridin-3-ylmethyl-4H-[1,2,4]triazolo[4,3-a]quinazolin-5-one
85 7-Bromo-1-dimethylamino-4-(3-phenyl-allyl)-4H-[1,2,4]triazolo[4,3-a]quinazolin-5-one
86 7-Bromo-1-dimethylamino-4-(3-phenyl-allyl)-4H-[1,2,4]triazolo[4,3-a]quinazolin-5-one
87 7-Bromo-1-dimethylamino-4-(3-pyridin-4-yl-allyl)-4H-[1,2,4]triazolo[4,3-a]quinazolin-5-one
88 7-Bromo-1-dimethylamino-4-prop-2-ynyl-4H-[1,2,4]triazolo[4,3-a]quinazolin-5-one
89 7-Bromo-1-dimethylamino-4(3-phenyl-prop-2-ynyl)-4H-[[1,2,4]triazolo[4,3-a]quinazolin-5-one
90 (7-Bromo-1-dimethylamino-5-oxo-5H-[1,2,4]triazolo[4,3-a]quinazolin-4-yl)-phenyl-acetic acid methyl ester
91 1-Azepan-1-yl-7-methyl-4-pyridin-3-ylmethyl-4H-[1,2,4]triazolo[4,3-a]quinazolin-5-one
92 1-Azepan-1-yl-7-methyl-4-(3-phenyl-allyl)-4H-[1,2,4]triazolo[4,3-a]quinazolin-5-one
93 4-(7-Methyl-5-oxo-1-pyrrolidin-1-yl-5H-[1,2,4]triazolo[4,3-a]quinazolin-4-ylmethyl)-benzonitrile
94 4-(3,4-Dimethoxy-benzyl)-7-methyl-1-pyrrolidin-1-yl-4H-[1,2,4]triazolo[4,3-a]quinazolin-5-one
95 4(7-Methyl-5-oxo-1-pyrrolidin-1-yl-5H-[1,2,4]triazolo[4,3-a]quinazolin-4-ylmethyl)-benzoic acid methyl ester
96 [4-(7-Methyl-5-oxo-1-pyrrolidin-1-yl-5H-[1,2,4]triazolo[4,3-a]quinazolin-4ylmethyl)-phenyl]-acetic acid
97 7-Methyl-4-pyridin-3-ylmethyl-1-pyrrolidin-1-yl-4H-[1,2,4)triazolo[4,3-a]quinazolin-5-one
98 7-Methyl-4-(3-phenyl-allyl)-1-pyrrolidin-1-yl-4H-[1,2,4]triazolo[4,3-a]quinazolin-5-one
99 [4-(7-Methyl-5-oxo-1-thiomorpholin-4-yl-5H-[1,2,4]triazolo[4,3-a]quinazolin-4-ylmethyl)-phenyl]-acetic acid
100 7-Methyl-4-(3-pyridin-3-yl-allyl)-1-thiomorpholin-4-yl-4H-[1,2,4]triazolo[4,3-a]quinazolin-5-one
101 4-(1-Dimethylamino-7-methyl-5-oxo-5H-[1,2,4]triazolo[4,3-a]quinazolin-4-ylmethyl)-benzonitrile
102 [4-(1-Dimethylamino-7-methyl-5-oxo-5H-[1,2,4]triazolo[4,3-a]quinazolin-4-ylmethyl)-phenyl]-acetic acid
103 1-Dimethylamino-7-methyl-4-((E)-3-phenyl-allyl)-4H-[1,2,4]triazolo[4,3-a]quinazolin-5-one
104 1-Dimethylamino-7-methyl-4-(3-pyridin-3-yl-allyl)-4H-[1,2,4]triazolo[4,3-a]quinazolin-5-one
105 1-Dimethylamino-7-methyl-4-(3-pyridin-4yl-allyl)-4H-[1,2,4]triazolo[4,3-a]quinazolin-5-one
106 1-(azepan-1-yl)-8-methyl-4-(3-phenylallyl)-4H-[1,2,4]triazolo[4,3-a]quinazolin-5-one
107 4-(4-Cyano-benzyl)-1-dimethylamino-5-oxo-4,5-dihydro-[1,2,4]triazolo[4,3-a]quinazoline-7-carbonitrile
108 7-Hydroxy-4-((E)-3-phenyl-allyl)-1-pyrrolidin-1-yl-4H-[1,2,4]triazolo[4,3-a]quinazolin-5-one
109 1-(azepan-1-yl)-3-(3-phenylallyl)-3H-[1,2,4]triazolo[4,3-a]-quinazolin-5-one
110 3-Allyl-1-azepan-1-yl-7-chloro-3H-[1,2,4]triazolo[4,3-a]quinazolin-5-one
111 1-(azepan-1-yl)-7-chloro-3-benzyl-3H-[1,2,4]triazolo[4,3-a]-quinazolin-5-one
112 1-Azepan-1-yl-7-chloro-3-(4-methyl-benzyl)-3H-[1,2,4]triazolo[4,3-a]quinazolin-5-one
113 1-(azepan-1-yl)-7-chloro-3-(2-chlorobenzyl)-3H-[1,2,4]triazolo[4,3-a]quinazolin-5-one
114 1-(azepan-1-yl)-7-chloro-3-(3-chlorobenzyl)-3H-[1,2,4]triazolo[4,3-a]quinazolin-5one
115 1-(azepan-1-yl)-7-chloro-3-(4-chlorobenzyl)-3H-[1,2,4]triazolo[4,3-a]quinazolin-5-one
116 1-(azepan-1-yl)-7-chloro-3-(4-bromobenzyl)-3H-[1,2,4]triazolo(4,3-a]quinazolin-5-one
117 1-(azepan-1-yl)-7-chloro-3-(4-fluorobenzyl)-3H-[1,2,4)triazolo[4,3-a]quinazolin-5-one
118 1-(azepan-1-yl)-7-chloro-3-(4-(trifluoromethyl)benzyl)-3H-[1,2,4]triazolo[4,3-a]quinazolin-5-one
119 1-(azepan-1-yl)-7-chloro-3-(4-cyanobenzyl)-3H-[1,2,4]triazolo[4,3-a]quinazolin-5-one
120 1-(azepan-1-yl)-7-chloro-3-(2-methoxybenzyl)-3H-[1,2,4]triazolo[4,3-a]quinazolin-5-one
121 1-(azepan-1-yl)-7-chloro-3-(3-methoxybenzyl)-3H-[1,2,4]triazolo[4,3-a]quinazolin-5-one
122 1-(azepan-1-yl)-7-chloro-3-(4-methoxybenzyl)-3H-[1,2,4]triazolo[4,3-a]quinazolin-5-one
123 1-(azepan-1-yl)-7-chloro-3-(3,4-dichlorobenzyl)-3H-[1,2,4]triazolo[4,3-a]quinazolin-5-one
124 1-(azepan-1-yl)-7-chloro-3-(3,4-dimethoxybenzyl)-3H-[1,2,4]triazolo[4,3-a]quinazolin-5-one 125 1-(azepan-1-yl)-7-chloro-3-(2-pyridylmethyl)-3H-[1,2,4]triazolo[4,3-a]quinazolin-5-one
126 1-(azepan-1-yl)-7-chloro-3-(3-pyridylmethyl)-3H-[1,2,4]triazolo[4,3-a]quinazolin-5-one
127 1-(azepan-1-yl)-7-chloro-3-(2-phenylthyl)-3H-[1,2,4]triazolo[4,3-a]quinazolin-5-one
128 1-(azepan-1-yl)-7-chloro-3-[2-(4-methoxyphenyl)ethyl]-3H-[1,2,4]triazolo[4,3-a]quinazolin-5-one
129 1-(azepan-1-yl)-7-chloro-3-(3-phenylpropyl)-3H-[1,2,4]triazolo[4,3-a]quinazolin-5-one
130 1-Azepan-1-yl-7-chloro-3-(2-oxo-2-phenyl-ethyl)3H-[1,2,4]triazolo[4,3-a]quinazolin-5-one
131 1-(azepan-1-yl)-7-chloro-3-(2-(4-methoxyphenyl)-2-oxoethyl]-3H-[1,2,4]triazolo[4,3-a]quinazolin-5-one
132 1-(azepan-1-yl)-7-chloro-3-[2-(4-chlorophenyl)-2-oxoethyl)-3H-[1,2,4]triazolo[4,3-a]quinazolin-5-one
133 5-[(1-(azepan-1-yl)-7-chloro-5-oxo-5H-[1,2,4]triazolo[4,3-a]-quinazolin-3-yl)acetyl]-2-methoxybenzoic acid methyl ester
133 1-(azepan-1-yl)-7-bromo-3-(4-chlorobenzyl)-3H-[1,2,4]triazolo[4,3-a]quinazolin-5-one
135 1-(azepan-1-yl)-7-bromo-3-(4-fluorobenzyl)-3H-[1,2,4]triazolo[4,3-a]quinazolin-5-one
136 4(1-(azepan-1-yl)-7-bromo-5-oxo-5H-[1,2,4]triazolo[4,3-a]-quinazolin-3-ylmethyl)-benzonitrile
137 1-(azepan-1-yl)-7-bromo-3-(3,4dimethoxybenzyl)-3H-[1,2,4]triazolo[4,3-a]quinazolin-5-one
138 [4-(7-Bromo-5-oxo-1-perhydro-azepin-1-yl-5H-[1,2,4]triazolo[4,3-a]quinazolin-3-ylmethyl)-phenyl]-acetic acid
139 1-(azepan-1-yl)-7-bromo-3-(pyridin-3-ylmethyl)-3H-[1,2,4]triazolo[4,3-a]quinazolin-5-one
140 1-Azepan-1-yl-7-bromo-3-((E)-3-phenyl-allyl)-3H-[1,2,4]triazolo(4,3-a]quinazolin-5-one
141 7-Bromo-3-((E)-3-phenyl-allyl)-1-piperidin-1-yl-3H-[1,2,4]triazolo[4,3-a]quinazolin-5one
142 7-bromo-3-(4-chlorobenzyl)-1-(pyrrolidin-1-yl)-3H-1,2,4]triazolo[4,3-a]quinazolin-5-one
143 7-bromo-3-(4-fluorobenzyl)-1-(pyrrolidin-1-yl)-3H-[1,2,4]triazolo[4,3-a]quinazolin-5-one
144 4-(7-bromo-5-oxo-1-(pyrrolidin-1-yl)-5H-[1,2,4]triazolo[4,3-a]-quinazolin-3-ylmethyl)-benzonitrile
145 4-(7-bromo-5-oxo-1-(pyrrolidin-1-yl)-5H-[1,2,4]triazolo[4,3-a]-quinazolin-3-ylmethyl)benzoic acid methyl ester
146 7-Bromo-3-(4-methoxy-benzyl)-1-pyrrolidin-1-yl-3H-[1,2,4]triazolo[4,3-a]quinazolin-5-one
147 Acetic acid 4-(7-bromo-5-oxo-1-pyrrolidin-1-yl-5H-[1,2,4]triazolo[4,3-a]quinazolin-3-ylmethyl)phenyl ester
148 7-Bromo-1-dimethylamino-3-(4-hydroxy-benzyl)-3H-[1,2,4]triazolo[4,3-a]quinazolin-5-one
149 3-(benzo[1,3]dioxol-5-ylmethyl)-7-bromo-1-(pyrrolidin-1-yl)-3H-[1,2,4]triazolo[4,3-a]quinazolin-5-one
150 7-bromo-3-(3,5-dimethoxy-benzyl)-1-(pyrrolidin-1-yl)-3H-[1,2,4]triazolo-[4,3-a]quinazolin-5-one
151 7-bromo-1-(pyrrolidin-1-yl)-3-(3,4,5-trimethoxybenzyl)-3H-[1,2,4]triazolo[4,3-a]quinazolin-5-one
152 7-Bromo-3-(1H-imidazol-4-ylmethyl)-1-pyrrolidin-1-yl-3H-[1,2,4]triazolo[4,3-a]quinazolin-5-one
153 7-bromo-3-(n-butyl)-1-(pyrrolidin-1-yl)-3H-[1,2,4]triazolo[4,3-a]-quinazolin-5-one
154 (7-Bromo-5oxo-1-pyrrolidin-1-yl-5H-[1,2,4]triazolo[4,3-a]quinazolin-3-yl)-phenyl-acetic acid methyl ester
155 7-Bromo-1-dimethylamino-3-(3-phenyl-allyl)-3H-[1,2,4]triazolo[4,3-a]quinazolin-5-one
156 (7-Bromo-1-dimethylamino-5-oxo-5H-[1,2,4]triazolo[4,3-a]quinazolin-3-yl)-phenyl-acetic acid methyl ester
157 1-(azepan-1-yl)-7-methyl-3-(3-phenylallyl)-3H-[1,2,4]triazolo[4,3-a]quinazolin-5-one
158 7-methyl-3-(3-phenylallyl)-1-(pyrrolidin-1-yl)-3H-[1,2,4]triazolo[4,3-a]quinazolin-5-one
159 1-(azepan-1-yl)-3,8-dimethyl-3H-[1,2,4]triazolo[4,3-a]-quinazolin5one
160 1-Azepan-1-yl-8-methyl-3-((E)-3-phenyl-allyl)-3H-[1,2,4]triazolo[4,3-a]quinazolin-5-one
161 7-hydroxy-3-(3-phenylallyl)-1-(pyrrolidin-1-yl)-3H-[1,2,4]triazolo[4,3-a]quinazolin-5-one
162 1,8-bis(azepan-1-yl)-3-(3-phenylallyl)-3H-[1,2,4]triazolo[4,3-a]quinazolin-5-one
163 1-(azepan-1-yl)-4-benzyl-7-bromo-4H-[1,2,4]triazolo[4,3-a]-quinazolin-5-one
164 4-benzyl-7-bromo-1-(pyrrolidin-1-yl)-4H-[1,2,4]triazolo[4,3-a]-quinazolin-5-one
165 4-Benzyl-7-bromo-1-(butyl-methyl-amino)-4H-[1,2,4]triazolo[4,3-a]quinazolin-5-one
166 4-benzyl-1-pyrrolidin-1-yl)-4H-[1,2,4]triazolo[4,3-a]quinazolin-5-one
167 7-chloro-1-dibutylamino-4-methyl-4H-[1,2,4]triazolo[4,3-a]-quinazolin-5-one
168 7-chloro-4-methyl-1-(piperidin-1-yl)4H-[1,2,4]triazolo[4,3-a]-quinazolin-5-one
169 7-Chloro-4-methyl-1-(4-methyl-piperazin-1-yl)-4H-[1,2,4]triazolo[4,3-a]quinazolin-5-one
170 7-Chloro-4-methyl-1-(1,8,8-trimethyl-3-aza-bicyclo[3.2.1]oct-3-yl)-4H-[1,2,4]triazolo[4,3-a]quinazolin-5-one
171 1-(azepan-1-yl)-7-chloro-4phenyl-4H-[1,2,4]triazolo[4,3-a]-quinazolin-5-one
172 1-(azepan-1-yl)-4-benzyl-7-chloro-4H-[1,2,4]triazolo[4,3-a]-quinazolin-5-one
173 4-benzyl-7chloro-1-(pyrrolidin-1-yl)-4H-[1,2,4]triazolo[4,3-a]-quinazolin-5-one
174 4-benzyl-7-chloro-1-(piperidin-1-yl)-4H-[1,2,4]triazolo[4,3-a]-quinazolin-5-one
175 1-(azepan-1-yl)-8-chloro-4-methyl-4H-[1,2,4]triazolo[4,3-a]-quinazolin-5-one
176 1-(azepan-1-yl)-4-benzyl-8-chloro-4H-[1,2,4]triazolo[4,3-a)-quinazolin-5-one
177 1-(azepan-1-yl)-7-bromo-4-methyl-4H-[1,2,4]triazolo[4,3-a]-quinazolin-5-one
178 4-benzyl-7-bromo-1-(piperidin-1-yl)-4H-[1,2,4]triazolo[4,3-a]-quinazolin-5-one
179 4-Benzyl-7-bromo-1-dimethylamino-4H-[1,2,4]triazolo[4,3-a]quinazolin-5-one
180 4-Benzyl-7-bromo-1-morpholin-4-yl-4H-[1,2,4]triazolo[4,3-a]quinazolin-5-one
181 4-Benzyl-7-bromo-1-thiomorpholin-4-yl-4H-[1,2,4]triazolo[4,3-a]quinazolin-5-one
182 4-Benzyl-7-bromo-1-(4-methyl-piperazin-1-yl)-4H-[1,2,4]triazolo[4,3-a]quinazolin-5-one
183 4-Benzyl-7-bromo-1-(4-phenyl-piperazin-1-yl)-4H-[1,2,4]triazolo[4,3-a]quinazolin-5-one
184 4-Benzyl-1-4-benzyl-piperazin-1-yl)-7-bromo-4H-[1,2,4]triazolo[4,3-a]quinazolin-5-one
185 4-Benzyl-7-bromo-1-(3,6-dihydro-2H-pyridin-1-yl)-4H-[1,2,4]triazolo[4,3-a]quinazolin-5-one
186 4-Benzyl-7-bromo-1-(2,5-dihydro-pyrrol-1-yl)-4H-[1,2,4]triazolo[4,3-a]quinazolin-5-one
187 4-Benzyl-7-bromo-1-(3-hydroxy-pyrrolidin-1-yl)-4H-[1,2,4]triazolo[4,3-a]quinazolin-5-one
188 4-Benzyl-7-bromo-1-methylamino-4H-[1,2,4]triazolo[4,3-a]quinazolin-5-one
189 4-Benzyl-7-iodo-1-pyrrolidin-1-yl-4H-[1,2,4]triazolo[4,3-a]quinazolin-5-one 190 1-Azepan-1-yl-4-benzyl-7-methyl-4H-[1,2,4]triazolo[4,3-a]quinazolin-5-one
191 4-Benzyl-7-methyl-1-pyrrolidin-1-yl-4H-[1,2,4]triazolo[4,3-a]quinazolin-5-one
192 4-Benzyl-1-dimethylamino-7-methyl-4H-[1,2,4]triazolo[4,3-a]quinazolin-5-one p0 193 4-Benzyl-7-methyl-1-thiomorpholin-4-yl-4H-[1,2,4]triazolo[4,3-a]quinazolin-5-one
194 1-Azepan-1-yl-4-benzyl-8-methyl-4H-[1,2,4]triazolo[4,3-a]quinazolin-5-one
195 1-Azepan-1-yl-4-benzyl-7-methoxy-4H-[1,2,4]triazolo[4,3-a]quinazolin-5-one
196 4-Benzyl-7-methoxy-1-pyrrolidin-1-yl-4H-[1,2,4]triazolo[4,3-a]quinazolin-5-one
197 4-Benzyl-5-oxo-1-pyrrolidin-1-yl-4,5-dihydro-[1,2,4]triazolo[4,3-a]quinazoline-7-carbonitrile
198 1-Azepan-1-yl-4-benzyl-7-nitro-4H-[1,2,4]triazolo[4,3-a]quinazolin-5-one
199 1-azepan-1-yl)-4-benzyl-7-chloro-4H-[1,2,4]triazolo[4,3-a]-quinazolin-5-one
200 1-(azepan-1-yl)-4-methyl-4H-[1,2,4]triazolo[4,3-a]quinazolin-5-one
201 1-(azepan-1-yl)-4-benzyl-4H-[1,2,4]triazolo[4,3-a]quinazolin-5-one
202 1-(azepan-1-yl)-6-chloro-4-methyl-4H-[1,2,4]triazolo[4,3-a]-quinazolin-5-one
203 1-(azepan-1-yl)-7-chloro-4-methyl-4H-[1,2,4]triazolo[4,3-a]-quinazolin-5-one
204 1-(azepan-1-yl)-7-chloro-4-ethyl-4H-[1,2,4]triazolo[4,3-a]-quinazolin-5-one
205 7-chloro-4-methyl-1-(pyrrolidin-1-yl)-4H-[1,2,4]triazolo[4,3-a]-quinazolin-5-one
206 7-chloro-4-methyl-1-(morpholin-4-yl)-4H-[1,2,4]triazolo[4,3-a]-quinazolin-5-one
207 1-(azocan-1-yl)-7-chloro-4methyl-4H-[1,2,4]triazolo[4,3-a]-quinazolin-5-one
208 7-chloro-1-(3,4-dihydro-2H-quinolin-1-yl)-4-methyl-4H-[1,2,4]triazolo[4,3-a]quinazolin-5-one
209 7-chloro-1-(3,4-dihydro-1H-isoquinolin-2-yl)-4-methyl-4H-[1,2,4]triazolo[4,3-a]quinazolin-5-one
210 1-(4-benzylpiperidin-1-yl)-7chloro-4-methyl-4H-[1,2,4]triazolo[4,3-a]quinazolin-5-one
211 7-chloro-4-methyl-1-(1,3,3-trimethyl-6-azabicyclo[3,2,1]oct-6yl)-4H-[1,2,4]triazolo[4,3-a]-quinazolin-5-one
212 1-(azepan-1-yl)-7-fluoro-4-methyl-4H-[1,2,4]triazolo[4,3-a]-quinazolin-5-one
213 1-(azepan-1-yl)-7-iodo-4-methyl-4H-[1,2,4]triazolo[4,3-a]quinazolin-5-one
214 1-(azepan-1-yl)-7-methoxy-4-methyl-4H-[1,2,4]triazolo[4,3-a]-2quinazolin-5-one
215 4-Benzyl-7-bromo-1-(ethyl-methyl-amino)-4H-[1,2,4]triazolo[4,3-a]quinazolin-5-one
216 4-Benzyl-1-diethylamino-7-methyl-4H-[1,2,4]triazolo[4,3-a]quinazolin-5-one
217 4-Benzyl-7-bromo-1-pyrrol-1-yl-4H-[1,2,4]triazolo[4,3-a]quinazolin-5-one
218 4-(4-Amino-benzyl)-7-bromo-1-pyrrolidin-1-yl-4H-[1,2,4]triazolo[4,3-a]quinazolin-5-one
219 4Benzyl-7-hydroxy-1-pyrrolidin-1-yl-4H-[1,2,4]triazolo[4,3-a]quinazolin-5-one
220 4-(7-Hydroxy-5-oxo-1-pyrrolidin-1-yl-5H-[1,2,4]triazolo[4,3-a]quinazolin-4-ylmethyl)-benzonitrile
221 N-(4-Benzyl-5-oxo-1-pyrrolidin-1-yl-4,5-dihydro-[1,2,4]triazolo[4,3-a]quinazolin-7-yl)-acetamide
222 N-[5-Oxo-4-(3-phenyl-allyl)-1-pyrrolidin-1-yl-4,5dihydro-[1,2,4]triazolo[4,3-a]quinazolin-7-yl]-acetamide
223 7-Amino-4-((E)-3-phenyl-allyl)-1-pyrrolidin-1-yl-4H-1,2,4]triazolo[4,3-a]quinazolin-5-one
224 7-Amino-1-azepan-1-yl-4-benzyl-4H-[1,2,4]triazolo[4,3-a]quinazolin-5-one
225 7-Amino-4-benzyl-1-pyrrolidin-1-yl-4H-[1,2,4]triazolo[4,3-a]quinazolin-5-one
226 4-(7-Amino-5-oxo-1-pyrrolidin-1-yl-5H-[1,2,4]triazolo[4,3-a]quinazolin-4-ylmethyl)-benzonitrile
227 7-Amino-4-((E)-3-pyridin-3-yl-allyl)-1-pyrrolidin-1-yl-4H-[1,2,4]triazolo[4,3-a]quinazolin-5-one
228 4-(7-Amino-1-dimethylamino-5-oxo-5H-[1,2,4]triazolo[4,3-a]quinazolin-4-ylmethyl)-benzonitrile
229 7-Amino-1-dimethylamino-4-((E)-3-phenyl-allyl)-4H-[1,2,4]triazolo[4,3-a]quinazolin-5-one
230 4-Benzyl-7-methylamino-1-pyrrolidin-1-yl-4H-[1,2,4]triazolo[4,3-a]quinazolin-5-one
231 4-(7-Methylamino-5-oxo-1-pyrrolidin-1-yl-5H-[1,2,4]triazolo[4,3-a]quinazolin-4-ylmethyl)-benzonitrile
232 4-Benzyl-8-methylamino-1-pyrrolidin-1-yl-4H-[1,2,4]triazolo[4,3-a]quinazolin-5-one
233 4-Benzyl-7-ethylamino-1-pyrrolidin-1-yl-4H-[1,2,4]triazolo[4,3-a]quinazolin-5-one
234 4-Benzyl-7-isopropylamino-1-pyrrolidin-1-yl-4H-[1,2,4]triazolo[4,3-a]quinazolin-5-one
235 N-(4-Benzyl-5-oxo-1-pyrrolidin-1-yl-4,5-dihydro-[1,2,4]triazolo[4,3-a]quinazolin-7-yl)-methanesulfonamide
236 4-Benzyl-7-dimethylamino-1-pyrrolidin-1-yl-4H-[1,2,4]triazolo[4,3-a]quinazolin-5-one
237 4-Benzyl-1-dimethylamino-5-oxo-4,5-dihydro-[1,2,4]triazolo[4,3-a]quinazoline-7-carbonitrile
238 4-Benzyl-5-oxo-1-pyrrolidin-1-yl-4,5-dihydro-[1,2,4]triazolo[4,3-a]quinazoline-7-carboxylic acid
239 [4-(7-Bromo-5-oxo-1-pyrrolidin-1-yl-5H-[1,2,4]triazolo[4,3-a]quinazolin4-ylmethyl)-phenyl]-acetic acid methyl ester
240 2-[4-(7-Bromo-5-oxo-1-pyrrolidin-1-yl-5H-[1,2,4]triazolo[4,3-a]quinazolin-4-ylmethyl)-phenyl]-N-methyl-acetamide
241 2-[4-(7-Bromo-1-dimethylamino-5-oxo-5H-[1,2,4]triazolo[4,3-a]quinazolin-4-ylmethyl)-phenyl)-acetamide
242 2-[4-(7-Bromo-5-oxo-1-pyrrolidin-1-yl-5H-[1,2,4]triazolo[4,3-a]quinazolin-4-ylmethyl)phenyl]-N,N-dimethyl-acetamide
243 2-[4-(7-Bromo-5-oxo-1-pyrrolidin-1-yl-5H-[1,2,4]triazolo[4,3-a]quinazolin-4-ylmethyl)-phenyl]-N-hydroxy-acetamide
244 4-(1-Dimethylamino-7-methyl-5-thioxo-5H-[1,2,4]triazolo[4,3-a]quinazolin-4-ylmethyl)-benzonitrile
245 4-(7-Bromo-1-dimethylamino-5-thioxo-5H-[1,2,4]triazolo[4,3-a]quinazolin-4-ylmethyl)-benzonitrile
246 1-Dimethylamino-7-methyl-4-(3-pyridin-3-yl-allyl)-4H-[1,2,4]triazolo[4,3-a]quinazoline-5-thione
247 4-benzyl-7-(N,N-dimethylsulfonylamino)-1-(pyrrolidin-1-yl)-4H-[1,2,4]triazolo[4,3-a]quinazolin-5-one Among the compounds mentioned above, the following compounds are preferred:

1 1-(Azepan-1-yl)-7-chloro-4-(3-phenylallyl)-4H-[1,2,4]triazolo[4,3-a]quinazolin-5-one
3 7-Bromo-1-dimethylamino-4-((E)-3-pyridin-3-yl-allyl)-4H-[1,2,4]triazolo[4,3-a]quinazolin-5-one
11 1-(azepan-1-yl)-7-chloro-4-(4-chlorobenzyl)-4H-[1,2,4]triazolo[4,3-a]quinazolin-5-one
13 1-(azepan-1-yl)-7-chloro-4-(4-fluorobenzyl)-4H-[1,2,4]triazolo[4,3-a]quinazolin-5-one 20 1-(azepan-1-yl)-7chloro-4-(3,4dimethoxybenzyl)-4H-[1,2,4]triazolo[4,3-a]quinazolin-5-one
22 1-(azepan-1-yl)-7chloro-4-(3-pyridylmethyl)-4H-[1,2,4]triazolo[4,3-a]quinazolin-5-one
32 1-(azepan-1-yl)-7-bromo-4-(4-chlorophenylmethyl)-4H-[1,2,4]triazolo[4,3-a]quinazolin-5-one
34 4-(1-Azepan-1-yl-7-bromo-5oxo-5H-[1,2,4]triazolo[4,3-a]quinazolin-4-ylmethyl)-benzonitrile
35 1-Azepan-1-yl-7-bromo-4-(3,4-dimethoxy-benzyl)-4H-[1,2,4]triazolo[4,3-a]quinazolin-5-one
37 1-(azepan-1-yl)-7-bromo-4-(3-phenylallyl)-4H-[1,2,4]triazolo[4,3-a]quinazolin-5-one
40 1-Azepan-1-yl-7-bromo-4-((E)-3-pyridin-3-yl-allyl)-4H-[1,2,4]triazolo[4,3-a]quinazolin-5one
41 1-Azepan-1-yl-7-bromo-4-(3-pyridin-4-yl-allyl)-4H-[1,2,4]triazolo[4,3-a]quinazolin-5-one
42 7-Bromo-4-(4-methyl-benzyl)-1-pyrrolidin-1-yl-4H-[1,2,4]triazolo[4,3-a]quinazolin-5-one
43 7-Bromo-4-(4-chloro-benzyl)-1-pyrrolidin-1-yl-4H-[1,2,4]triazolo[4,3-a]quinazolin-5-one
44 7-Bromo-4-(4-fluoro-benzyl)-1-pyrrolidin-1-yl-4H-[1,2,4]triazolo[4,3-a]quinazolin-5-one
46 4-(7-Bromo-5-oxo-1-pyrrolidin-1-yl-5H-[1,2,4]triazolo[4,3-a]quinazolin-4-ylmethyl)-benzonitrile
47 4-(7-Bromo-5-oxo-1-pyrrolidin-1-yl-5H-[1,2,4]triazolo[4,3-a]quinazolin-4-ylmethyl)-benzoic acid methyl ester
48 7-Bromo-4(4-nitro-benzyl)-1-pyrrolidin-1-yl-4H-[1,2,4]triazolo[4,3-a]quinazolin-5-one
49 7-Bromo-4-(4-methoxy-benzyl)-1-pyrrolidin-1-yl-4H-[1,2,4]triazolo[4,3-a]quinazolin-5-one
50 Acetic acid 4-(7-bromo-5-oxo-1-pyrrolidin-1-yl-5H-[1,2,4]triazolo[4,3-a]quinazolin-4-ylmethyl)phenyl ester
51 7-Bromo-4-(4-hydroxy-benzyl)-1-pyrrolidin-1-yl-4H-[1,2,4]triazolo[4,3-a]quinazolin-5-one
52 7-Bromo-4-(3,4-dimethoxy-benzyl)-1-pyrrolidin-1-yl-4H-[1,2,4]triazolo[4,3-a]quinazolin-5-one
57 1-(pyrrolidin-1-yl)-7-bromo-4-(3-phenylallyl)-4H-[1,2,4]triazolo[4,3-a]quinazolin-5-one
59 7-Bromo-4-[(E3-(4-chloro-phenyl)-allyl]-1-pyrrolidin-1-yl-4H-[1,2,4]triazolo[4,3-a]quinazolin-5-one
60 7-Bromo-4-[3-(4-methoxy-phenyl)-allyl]-1-pyrrolidin-1-yl-4H-[1,2,4]triazolo[4,3-a]quinazolin-5-one
61 7-Bromo-4-(3-pyridin-3-yl-allyl)-1-pyrrolidin-1-yl-4H-[1,2,4]triazolo[4,3-a]quinazolin-5-one
62 7-Bromo-4-((E)-3-pyridin-4-yl-allyl)-1-pyrrolidin-1-yl-4H-[1,2,4]triazolo[4,3-a]quinazolin-5-one
75 7-Bromo-4-(3,4-dimethoxy-benzyl)-1-piperidin-1-yl-4H-[1,2,4]triazolo[4,3-a]quinazolin-5-one
76 1-(piperidin-1-yl)-7-bromo-4-(3-phenylallyl)-4H-[1,2,4]triazolo[4,3-a]quinazolin-5-one
78 7-Bromo-1-dimethylamino-4-(4-methyl-benzyl)-4H-[1,2,4]triazolo[4,3-a]quinazolin-5-one
79 4-(7-Bromo-1-dimethylamino-5-oxo-5H-[1,2,4]triazolo[4,3-a]quinazolin-4-ylmethyl)-benzonitrile
80 7-Bromo-1-dimethylamino-4-(4-hydroxy-benzyl)-4H-[1,2,4]triazolo[4,3-a]quinazolin-5-one
81 4-(7-Bromo-1-dimethylamino-5-oxo-5H-[1,2,4]triazolo[4,3-a]quinazolin-4-ylmethyl)-benzoic acid methyl ester
83 [4-(7-Bromo-1-dimethylamino-5-oxo-5H-[1,2,4]triazolo[4,3-a]quinazolin-4-ylmethyl)-phenyl]-acetonitrile
85 1-Bromo-1-dimethylamino-4-(3-phenyl-allyl)-4H-[1,2,4]triazolo[4,3-a]quinazolin-5-one
89 7-Bromo-1-dimethylamino-4-(3-phenyl-prop-2-ynyl)-4H-[1,2,4]triazolo[4,3-a]quinazolin-5-one
92 1-Azepan-1-yl-7-methyl-4-(3-phenyl-allyl)-4H-[1,2,4]triazolo[4,3-a]quinazolin-5-one
94 4-(3,4-Dimethoxy-benzyl)-7-methyl-1-pyrrolidin-1-yl-4H-[1,2,4]triazolo[4,3-a]quinazolin-5-one
96 [4-(7-Methyl-5-oxo-1-pyrrolidin-1-yl-5H-[1,2,4]triazolo[4,3-a]quinazolin-4-ylmethyl)-phenyl]-acetic acid
98 7-Methyl-4-(3-phenyl-allyl)-1-pyrrolidin-1-yl-4H-[1,2,4]triazolo[4,3-a]quinazolin-5-one
102 [4-(1-Dimethylamino-7-methyl-5-oxo-5H-[1,2,4]triazolo[4,3-a]quinazolin-4-ylmethyl)-phenyl]-acetic acid
103 1-Dimethylamino-7-methyl-4-((E)-3-phenyl-allyl)-4H-[1,2,4]triazolo[4,3-a]quinazolin-5-one
104 1-Dimethylamino-7-methyl-4-(3-pyridin-3-yl-allyl)-4H-[1,2,4]triazolo[4,3-a]quinazolin-5-one
138 [4-(7-Bromo-5-oxo-1-perhydro-azepin-1-yl-5H-[1,2,4]triazolo[4,3-a]quinazolin-3-ylmethyl)-phenyl]-acetic acid
164 4-benzyl-7-bromo-1-(pyrrolidin-1-yl)-4H-[1,2,4]triazolo[4,3-a]-quinazolin-5-one
186 4-Benzyl-7-bromo-1-(2,5-dihydro-pyrrol-1-yl)-4H-[1,2,4]triazolo[4,3-a]quinazolin-5-one
189 4-Benzyl-7-iodo-1-pyrrolidin-1-yl-4H-[1,2,4]triazolo[4,3-a]quinazolin-5-one
190 1-Azepan-1-yl-4-benzyl-7-methyl-4H-[1,2,4]triazolo[4,3-a]quinazolin-5-one
218 4-(4-Amino-benzyl)-7-bromo-1-pyrrolidin-1-yl-4H-[1,2,4]triazolo[4,3-a]quinazolin-5-one
223 7-Amino-4-((E)-3-phenyl-allyl)-1-pyrrolidin-1-yl-4H-[1,2,4]triazolo[4,3-a]quinazolin-5-one
224 7-Amino-1-azepan-1-yl-4-benzyl-4H-[1,2,4]triazolo[4,3-a]quinazolin-5-one
227 7-Amino-4-((E)-3-pyridin-3-yl-allyl)-1-3-pyrrolidin-1-yl-4H-[1,2,4]triazolo[4,3-a]quinazolin-5-one
229 7-Amino-1-dimethylamino-4-((E)-3-phenyl-allyl)-4H-[1,2,4]triazolo[4,3-a]quinazolin-5-one
230 4-Benzyl-7-methylamino-1-pyrrolidin-1-yl-4H-[1,2,4]triazolo[4,3-a]quinazolin-5-one
231 4-(7-Methylamino-5-oxo-1-pyrrolidin-1-yl-5H-[1,2,4]triazolo[4,3-a]quinazolin-4-ylmethyl)-benzonitrile
232 4-Benzyl-8-methylamino-1-pyrrolidin-1-yl-4H-[1,2,4]triazolo[4,3-a]quinazolin-5-one
233 4-Benzyl-7-ethylamino-1-pyrrolidin-1-yl-4H-[1,2,4]triazolo[4,3-a]quinazolin-5-one
234 4-Benzyl-7-isopropylamino-1-pyrrolidin-1-yl-4H-[1,2,4]triazolo[4,3-a]quinazolin-5-one
239 [4-(7-Bromo-5-oxo-1-pyrrolidin-1-yl-5H-[1,2,4]triazolo[4,3-a]quinazolin-4-ylmethyl)phenyl]-acetic acid methyl ester
240 2-[4-(7-Bromo-5-oxo-1-pyrrolidin-1-yl-5H-[1,2,4]triazolo[4,3-a]quinazolin-4-ylmethyl)-phenyl]-N-methyl-acetamide
241 2-[4-(7-Bromo-1-dimethylamino-5-oxo-5H-[1,2,4]triazolo[4,3-a]quinazolin-4-ylmethyl)-phenyl]-acetamide
242 2-[4-(7-Bromo-5-oxo-1-pyrrolidin-1-yl-5H-[1,2,4]triazolo[4,3-a]quinazolin-4-ylmethyl)-phenyl]-N,N-dimethyl-acetamide
243 2-[4-(7-Bromo-5-oxo-1-pyrrolidin-1-yl-5H-[1,2,4]triazolo[4,3-a]quinazolin-4-ylmethyl)-phenyl]-N-hydroxy-acetamide
246 1-Dimethylamino-7-methyl-4-(3-pyridin-3-yl-allyl)-4H-[1,2,4]triazolo[4,3-a]quinazoline-5-thione Among the compounds mentioned above, the following compounds are preferred:

3 7-Bromo-1-dimethylamino-4-((E)-3-pyridin-3-yl-allyl)-4H-[1,2,4]triazolo[4,3-a]quinazolin-5one
20 1-(azepan-1-yl)-7-chloro-4-(3,4-dimethoxybenzyl)-4H-[1,2,4]triazolo[4,3-a]quinazolin-5-one
22 1-(azepan-1-yl)-7-chloro-4-(3-pyridylmethyl)-4H-[1,2,4]triazolo[4,3-a]quinazolin-5-one
34 4-(1-Azepan-1-yl-7-bromo-5-oxo-5H-[1,2,4]triazolo[4,3-a]quinazolin-4-ylmethyl)-benzonitrile 35 1-Azepan-1-yl-7-bromo-4-(3,4-dimethoxy-benzyl)-4H-[1,2,4]triazolo[4,3-a]quinazolin-5-one
37 1-(azepan-1-yl)-7-bromo-4-(3-phenylallyl)-4H-[1,2,4]triazolo[4,3-a]quinazolin-5-one
40 1-Azepan-1-yl-7-bromo-4-((E)-3-pyridin-3-yl-allyl)-4H-[1,2,4]triazolo[4,3-a]quinazolin-5-one
41 1-Azepan-1-yl-7-bromo-4-(3-pyridin-4-yl-allyl)-4H-[1,2,4]triazolo[4,3-a]quinazolin-5-one
42 7-Bromo-4-(4-methyl-benzyl)-1-pyrrolidin-1-yl-4H-[1,2,4]triazolo[4,3-a]quinazolin-5-one
43 7-Bromo-4-(4-chloro-benzyl)-1-pyrrolidin-1-yl-4H-[1,2,4]triazolo[4,3-a]quinazolin-5-one
52 7-Bromo-4-(3,4-dimethoxy-benzyl)-1-pyrrolidin-1-yl-4H-[1,2,4]triazolo[4,3-a]quinazolin-5-one
57 1-(pyrrolidin-1-yl)-7-bromo-4-(3-phenylallyl)-4H-[1,2,4]triazolo[4,3-a]quinazolin-5-one
61 7-Bromo-4-(3-pyridin-3-yl-allyl)-1-pyrrolidin-1-yl-4H-[1,2,4]triazolo[4,3-a]quinazolin-5-one
76 1-(piperidin-1-yl)-7-bromo-4-(3-phenylallyl)-4H-[1,2,4]triazolo[4,3-a]quinazolin-5-one
79 4-(7-Bromo-1-dimethylamino-5-oxo-5H-[1,2,4]triazolo[4,3-a]quinazolin-4-ylmethyl)-benzonitrile
81 4-(Bromo-dimethylamino-oxo-5H-[1,2,4]triazolo[4,3-a]quinazolin-4-ylmethyl)-benzoic acid methyl ester
85 7-Bromo-1-dimethylamino-4-(3-phenyl-allyl)-4H-[1,2,4]triazolo[4,3-a]quinazolin-5-one
89 7-Bromo-1-dimethylamino-4-(3-phenyl-prop-2-ynyl)-4H-[1,2,4]triazolo[4,3-a]quinazolin-5-one
92 1-Azepan-1-yl-7-methyl-4-(3-phenyl-allyl)-4H-[1,2,4]triazolo[4,3-a]quinazolin-5-one
94 4-(3,4-Dimethoxy-benzyl)-7-methyl-1-pyrrolidin-1-yl-4H-[1,2,4]triazolo[4,3-a]quinazolin-5-one
98 7-Methyl-4-(3-phenyl-allyl)-1-pyrrolidin-1-yl-4H-[1,2,4]triazolo[4,3-a]quinazolin-5-one
223 7-Amino-4-((E)-3-phenyl-allyl)-1-pyrrolidin-1-yl-4H-[1,2,4]triazolo[4,3-a]quinazolin-5-one
227 7-Amino-4-((E)-3-pyridin-3-yl-allyl)-1-pyrrolidin-1-yl-4H-[1,2,4]triazolo[4,3-a]quinazolin-5-one
230 4-Benzyl-7-methylamino-1-pyrrolidin-1-yl-4H-[1,2,4]triazolo[4,3-a]quinazolin-5-one
231 4-(7-Methylamino-5-oxo-1-pyrrolidin-1-yl-5H-[1,2,4]triazolo[4,3-a]quinazolin-4-ylmethyl)-benzonitrile
239 [4-(7-Bromo-5-oxo-1-pyrrolidin-1-yl-5H-[1,2,4]triazolo[4,3-a]quinazolin-4-ylmethyl)-phenyl]-acetic acid methyl ester
240 2-[4-(7-Bromo-5-oxo-1-pyrrolidin-1-yl-5H-[1,2,4]triazolo[4,3-a]quinazolin-4-ylmethyl)-phenyl]-N-methyl-acetamide
242 2-[4-(7-Bromo-5-oxo-1-pyrrolidin-1-yl-5H-[1,2,4]triazolo[4,3-a]quinazolin-4-ylmethyl)-phenyl]-N,N-dimethyl-acetamide
246 1-Dimethylamino-7-methyl-4-(3-pyridin-3-yl-allyl)-4H-[1,2,4]triazolo[4,3-a]quinazoline-5-thione The invention relates also to salts acceptable in pharmacy of a formula I or II compounds. We will find a review of pharmacologically acceptable salts in J. Pharm. Sci., 1977, 66, 1–19. However, by a pharmacologically acceptable salt of a formula I or II compound presenting a basic function, we mean the addition salt of a formula I or II compounds from non toxic inorganic or organic acids as for example salts of hydrobromic, hydrochloric, sulfuric, phosphoric, nitric, acetic, succinic, tartric, citric, maleic, hydroxymaleic, benzoic, fumaric, toluene-sulfonic, isethionic acids and others. Various salts of quaternary ammonium of I or II formula are also included in category compounds of this invention. And by pharmacologically acceptable salts of a formula I or II compound presenting an acid function, we mean usual salts of a formula I or II compounds made from non-toxic mineral or organic bases as for example hydroxides of alkaline and alkaline earth metals (sodium, potassium, magnesium and calcium), amines (dibenzylethylenediamine, trimethylamine, piperidine, pyrrolidine, benzylamine and others) or also quaternary ammonium hydroxides like tetramethylammonium hydroxide. As previously mentioned, formula I and II compounds of the current invention are inhibitors of phosphodiesterase enzyme and particularly of phosphodiesterase 4 (PDE4) enzyme.

Consequently, their use is recommended for treatment of diseases or affections relying on therapy by PDE4 inhibition. As an example, compounds of the current invention can be recommended for treatment of septicemia, polyvisceral deficiency, asthma, chronic bronchitis, emphysema, chronic obstructive pneumopathy (or COPD), allergic rhinitis, atopic dermatitis, pulmonary high blood pressure, cardiac or pulmonary insufficiency, congestive cardiac insufficiency, psoriasis, inflammatory diseases of the digestive system such as hemorrhagic rectocolitis and Crohn's disease, diseases linked to elevated TNF-α levels such as acute respiratory distress syndrome in the adult and acute pancreatitis, rhumatoid arthritis, osteoporosis, multiple sclerosis and depression. PDE4 inhibitors of the current invention may also be used for treatment of acute pulmonary attack, neuronal attack caused by ischemia (ischemia-induced neuronal damage), diabetes, chronic lymphoid leukemia, and to attenuate development of tolerance or dependence phenomena to morphine. Compounds of the invention may also contribute to decreasing memory loss of behavior (behavioral memory) such as observed for example in patients suffering from Alzheimer's disease. We may also consider use of the compounds of the current invention in the fields of urology, more particularly in treatment of prostate disease such as benign hypertrophy of the prostate or for prevention of premature child birth, for example by inhibition of contraction triggering before term, preferably by PDE4 inhibitor action on myometrium.

Structure-activity Analysis of Formula I and II Compounds

The inventors, wishing not to be bound in a formal manner to a definitive theory, agree that structural parameters mentioned below may be considered in order to guide the person skilled in the art in the choice of substituents combination which, beyond preferred compounds disclosed in the current application, may allow not only an optimization of the PDB4 inhibitor activity, but also a better optimization of important additional parameters such as solubility, biodisposability and toxicity of considered compounds.

First, the inventors consider that the catalytic site of the enzyme PDE4 is of a sufficiently large size to globally accommodate a fairly wide range of structural changes in substituents of the compounds of the invention which can bind to this site. In this respect, the inventors consider that compounds of the current invention have probably the capacity to interact at least on three distinct points of the catalytic site of the isoenzyme PDE4. One first interaction point may be localized on the aromatic ring including the substituents $X_1$ and $X_2$. A second interaction point is probably localized on substituent R while a third interaction point is probably localized on group $NR_4R_5$. Potential functionality of each binding point is suggested below.

However, it is important to precise here that interaction points mentioned above are not necessarily classified by increasing or decreasing importance order relating to their incidence on inhibitory activity of invention compounds. In fact, it seems possible that each interaction point participates in a different manner in global pharmacological properties of these compounds.

The first interaction point mentioned previously may be localized then on the aromatic ring including substituents $X_1$ and $X_2$. This aromatic ring may participate to the invention compound binding to enzyme PDE4 catalytic site, it seems possible to modulate this binding by substituents $X_1$ and $X_2$ choice.

Experiments performed up-to-date by the inventors tend to demonstrate that substituents $X_1$ and $X_2$ currently preferred are those for which $X_1$ is hydrogen and $X_2$ is chosen among halogen, more particularly Br and Cl, methyl, hydroxy, amino and alkylamino. We establish then that among preferred substituents $X_2$, we simultaneously find some donors (e.g. methyl) and some attractors (e.g. Br, Cl) of electrons. It seems then unlikely that $X_2$ could be chosen solely according to electronic properties of the recommended substituent. The inventors agree that important selection criteria are placed initially on substituent position in the aromatic ring and therefore on the level of some parameters such as substituent steric congestion or presence of donor atom or proton acceptor.

However, it seems established that substituents $X_1$ and $X_2$ position on the aromatic ring could have an influence on final activity of invention compounds. As an example, compounds including a substituent other than hydrogen in position 7 are generally more active that the same compounds including this substituent in position 8. Thus it seems probable than choice and position of substituents $X_1$ and $X_2$ allow to move the aromatic ring inside the cavity of the PDE4 catalytic site and consequently to modulate inhibitory activity of invention compounds. Moreover, it seems that compounds including a substituent in position 7 are more selective of sub-type PDE4 compared to the other isoenzymes PDE5, PDE3 and PDE1 than compounds including a substituent in position 8. These latter have a PDE4 inhibitory activity (although less) but they seem less selective compared to the other isoenzymes. However, it seems clearly also that although $X_1$ and $X_2$ could be chosen among an outstanding number of substituents, we will obtain a better tolerance for this choice if substituent R is well targeted.

The second interaction point of compounds of the current invention with the enzyme PDE4 will be localized on the substituent R. The inventors reckon that it concerns presumably of the most important anchorage point of the molecule to the enzyme. It seems indeed probable that this second interaction is localized in a large cavity inside the PDE4 catalytic site. It is then essential that the substituent R can be anchored to the catalytic site. However, the choice of groups included in the definition of R given above, seems to demonstrate some flexibility on R anchorage to this second binding site. Therefore, it could be possible to obtain a PDE4 inhibitory activity with compounds having rather different substituents R from a structural point of view. As an example, we will prefer the use of a substituent including an aromatic ring, preferably substituted itself, and separated from the principal heterocycle by a chain including between 1 and 4 atoms, particularly some carbon atoms, the said substituent presenting a relatively variable spatial orientation. This observation seems to open the way to the possibility to modulate in a more subtle manner the global properties of invention compounds.

The inventors agree indeed that although substituent R remains most probably a determinant element on PDE4 inhibitory activity of invention compounds, it is probably possible to make it vary and then act on the important extra pharmacological parameters without altering this inhibitory activity in a substantial manner. As an example, some compounds including in substituent R a group $-CH_2CH=CH-C_6H_5$ or a substituted benzyl group, preferably in position 4 (other substituents being identical for the two compounds), have PDE4 inhibitory activity of same magnitude order.

The third interaction site of the compounds of the invention on PDE4 is localized presumably on group $-NR_4R_5$. The inventors agree that it concerns probably a binding site much more specific that the two sites disclosed above although substituent R moving in the enzymatic cavity may however influence on specificity of this third site. Compounds of the invention having the best inhibitory activities are those for which $R_4$ and $R_5$, which represent each a lower alkyl, are bound to form a cycle, preferably including between 5 and 8 carbon atoms, more particularly a cycle with 5 or 7 carbon atoms. The skilled person's scope for manoeuvre on this group's variation seems then more limited.

In summary, experimentation performed by the inventors with compounds of the current invention seem to demonstrate that the size of PDE4 catalytic site is large enough to accommodate several structural changes on the three binding sites disclosed previously. However, the most important handling margin seems anyway to be localized on the substituent R variation.

Galenic Formulation of the Invention Compounds

The compounds of the invention are administrated as an appropriate composition accordingly to the nature and the scale of the disease to treat. The daily posology in humans is usually between 2 mg and 1 g of product that can be absorbed in one or several intakes. The compositions are prepared by usual methods for the skilled man and contain in a general manner 0.5 to 60% by weight of active principle (formula I compounds) and 40 to 99.5% by weight of appropriate pharmaceutical carrier.

The compositions of the current invention are then prepared under forms compatible with the desired administering route. As an example, the following pharmaceutical forms may be considered, although the listing provided below is not limiting:

Forms for Administering by Oral Route

Drinkable solutions, suspensions, powder sachets for drinkable solution, capsules, gastro-resistant capsules, prolonged-release forms, emulsions, HPMR capsules, lyophilisates to melt beneath the tongue.

1) Forms for Administering by Parenteral Route

Intravenous Route

Aqueous solutions, solutions water/co-solvent, solutions using one or several solubilizing agents, colloidal suspensions, emulsions, nano-particle suspensions usable for injection of long-lasting release forms, diffuse forms and liposomes.

Subcutaneous/Intra-muscular Route

In addition, forms usable as intravenous route which are also usable for subcutaneous and intra-muscular routes, other form types such as suspensions, diffused forms, long-lasting release colloids as well as long-lasting release implants can also be used.

2) Forms for Administering by Topic Route

Among the most used topic forms, we distinguish creams, colloids (aqueous phases jellified by polymers), patches, which are dressings to stick directly on skin and which can be used to treat dermatitis without percutaneous penetration of the active substance, sprays, emulsions and solutions.

3) Forms for Administering by Pulmonary Route

In this category we distinguish forms of solutions for aerosols, powders for inhaling apparatus, and other appropriate forms.

4) Forms for Administering by Nasal Route

It concerns mainly here solutions for drops.

5) Forms for Administering by Rectal Route

We will note amongst others suppositories and colloids.

We can also consider the use of forms allowing ophthalmic solution administering or allowing administering of active principle by vaginal route.

Another important category of pharmaceutical form, which can be used in the context of the current invention, relates to forms allowing improvement in solubility of the active principle. As an example, we can consider the use of aqueous solutions of cyclodextrin, and more particularly forms including hydroxypropyl beta cyclodextrin. A detailed review of this type of pharmaceutical form is presented in an article issued in the *Journal of Pharmaceutical Sciences*, 1142–1169, 85(11), 1996, and incorporated herein by.

Different pharmaceutical forms recommended above are disclosed in a detailed manner in the to book ((Pharmacie galénique)) by A. LEHIR (ed. Masson, 1992 ($6^{th}$ edition) incorporated reference.

Intermediaries Compounds

The current invention relates also to general formula III intermediaries compounds:

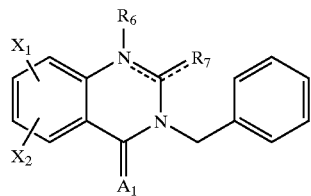

III in which $X_1$, $X_2$, $A_1$, $R_6$ and $R_7$ are such as previously defined.

The invention relates particularly to general formula III intermediaries compounds in which:

$X_1$ and $X_2$ are such as previously defined, and $R_7$ is bound to nitrogen in $R_6$ to form a triazol, substituted in position 1 by a Br, Cl, mercapto or lower thioalkyl group preferably $CH_3$—S—.

Among the groups defined above the following substituents are particularly preferred:

In a general manner for the groups $X_1$, $X_2$, $R_6$ and $R_7$:

halogen: F, Cl, Br, I, preferably Br and Cl, lower alkyl: linear or branched comprising from 1 to 6, preferably from 1 to 3 carbon atoms, lower alkoxy: linear or branched comprising from 1 to 5, preferably 1 to 3 carbon atoms, lower thioalkyl: linear or branched comprising from 1 to 5, preferably 1 to 3 carbon atoms.

In particular manner for the groups $X_1$ and $X_2$:

$X_1$ and $X_2$ are particularly localized in position 6 and 7 of the main quinazolinone cycle.

In particular manner for the groups $R_6$ and $R_7$:

when $R_7$ is bound to the nitrogen in $R_6$ to form a cycle, the formed cycle is preferably a triazole, substituted in position 1 by a group Br, Cl, mercapto or lower thioalkyl, preferably $CH_3$—S—.

A second series of intermediaries includes the following general formula IV compounds:

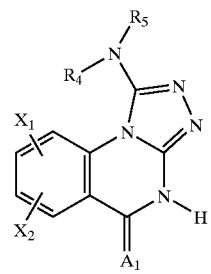

IV in which $X_1$, $X_2$, $A_1$, $R_4$ and $R_5$ are such as previously defined.

For the groups as above, the following substituents are particularly preferred:

In a general manner for the groups $X_1$, $X_2$, $R_4$ and $R_5$:

halogen: F, Cl, Br, I, preferably Br and Cl, lower alkyl: linear or branched comprising from 1 to 6, preferably 1 to 3 carbon atoms, lower alkyl: linear or branched comprising from 1 to 5, preferably 1 to 3 carbon atoms, lower alkyl, $R_4$ and $R_5$ being able to be linked to form a saturated cycle or including one or several double-bonds including one or several heteroatoms chosen among O, S or N and possibly bridged by a lower alkyl, dialkylated gem or substituted by one or several groups chosen among hydroxy, keto, lower alkyl, lower alkoxy, phenyl alkyl or CO—$Q_1$—$Q_2$—$Q_3$, two atoms of the cycle then formed could also be part of another cycle chosen among phenyl or heteroaryl comprising from 4 to 8 atoms with 1 to 4 heteroatoms.

In particular manner for the groups $X_1$ and $X_2$:

$X_1$ and $X_2$ are particularly localized in position 6 and 7 of the main quinazolinone cycle.

In particular manner for the groups $R_4$ and $R_5$:

$R_4$ and $R_5$ are lower alkyl, $R_4$ and $R_5$ being able to be linked to form a saturated cycle or including one or several double-bonds with one or several heteroatoms chosen among O, S or N, substituted by one or several groups chosen among hydroxy, keto, lower alkyl or lower alkoxy. The particularly preferred substituents forming the group $NR_4R_5$ includes pyrrolidine, 3-hydroxy pyrrolidine, thiamorpholine, dimethyl amino, azepanyl and piperidinyl.

A third series of intermediaries includes the following general formula V compounds:

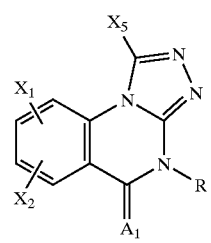

(V)

in which $X_1$, $X_2$, $X_5$, $A_1$ and R are such as previously defined.

For the groups as above, the following substituents are particularly preferred:

In a general manner for the groups $X_1$, $X_2$ and $X_5$:

halogen: F, Cl, Br, I, preferably Br and Cl, lower alkyl: linear or branched comprising from 1 to 6, preferably 1 to 3 carbon atoms, lower alkoxy: linear or branched comprising from 1 to 5, preferably 1 to 3 carbon atoms:

In particular manner for the groups $X_1$ and $X_2$:

$X_1$ and $X_2$ are particularly localized in position 6 and 7 of the main quinazolinone cycle.

In particular manner for the group $X_5$: $X_5$ is F, Br or Cl.

A fourth series of intermediaries includes the following general formula VI compounds:

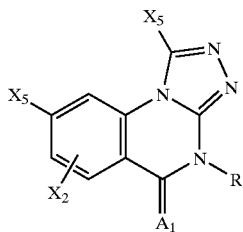

(VI)

in which $X_2$, $X_5$, $A_1$ and R are such as previously defined.

For the groups as above, the following substituents are particularly preferred:

In a general manner for the groups $X_2$ and $X_5$:

halogen: F, Cl, Br, I, preferably Br and Cl, lower alkyl: linear or branched comprising from 1 to 6, preferably 1 to 3 carbon atoms, lower alkoxy: linear or branched comprising from 1 to 5, preferably 1 to 3 carbon atoms.

In particular manner for the group $X_2$:

$X_2$ is particularly localized in position 7 of the main quinazolinone cycle.

In particular mariner for the group $X_5$ : $X_5$ is F, Br or Cl.

A fifth series of intermediaries includes the following general formula VII compounds:

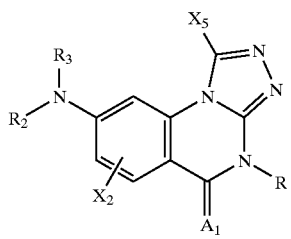

in which $X_2$, $X_5$ $A_1$, $R_2$ $R_3$ are such as previously defined.

For the groups as above, the following substituents are particularly preferred:

In a general manner for the groups $X_2$, $X_5$, $R_2$ and $R_3$:

halogen: F, Cl, Br, I, preferably Br and Cl, lower alkyl: linear or branched comprising from 1 to 6, preferably 1 to 3 carbon atoms, lower alkoxy: linear or branched comprising from 1 to 5, preferably 1 to 3 carbon atoms, hydrogen, lower alkyl, possibly substituted by one or several groups hydroxy, halogen, cyano, lower alkoxy or —CO—$Q_1$—$Q_2$—$Q_3$, $R_2$ and $R_3$ being able to be linked to form a cycle, including one or several heteroatoms chosen among O, S or N and possibly bridged by a lower alkyl, dialkylated gem or substituted by one or several groups chosen among hydroxy, keto, lower alkyl, lower alkoxy or —CO—$Q_1$—$Q_2$—$Q_3$.

In particular manner for the group $X_2$:

$X_2$ is particularly localized in position 7 of the main quinazolinone cycle.

In particular manner for the group $X_5$: $X_5$ is F, Br or Cl.

In particular manner for the groups $R_2$ and $R_3$:

$R_2$ and $R_3$, similar or different, are hydrogen, lower alkyl $R_2$ and $R_3$ being able to be linked to form a cycle, including one or several heteroatoms chosen among O, S or N and possibly substituted by one or several groups chosen among hydroxy, keto, lower alkyl, lower alkoxy or CO—$Q_1$—$Q_2$—$Q_3$. Among the particular preferred embodiments of the substituent $NR_2R_3$, we find the groups azepanyl, pyrrolidine, $NH_2$ and $NHCH_3$.

Synthesis Processes of Formula I and II Compounds

A) The compounds of the current invention can be obtained by bringing several synthesis processes into operation. Some of these synthesis processes are disclosed below.

The compounds of the current invention can be initially obtained in a convergent manner by the method represented in scheme 1.

SCHEME 1

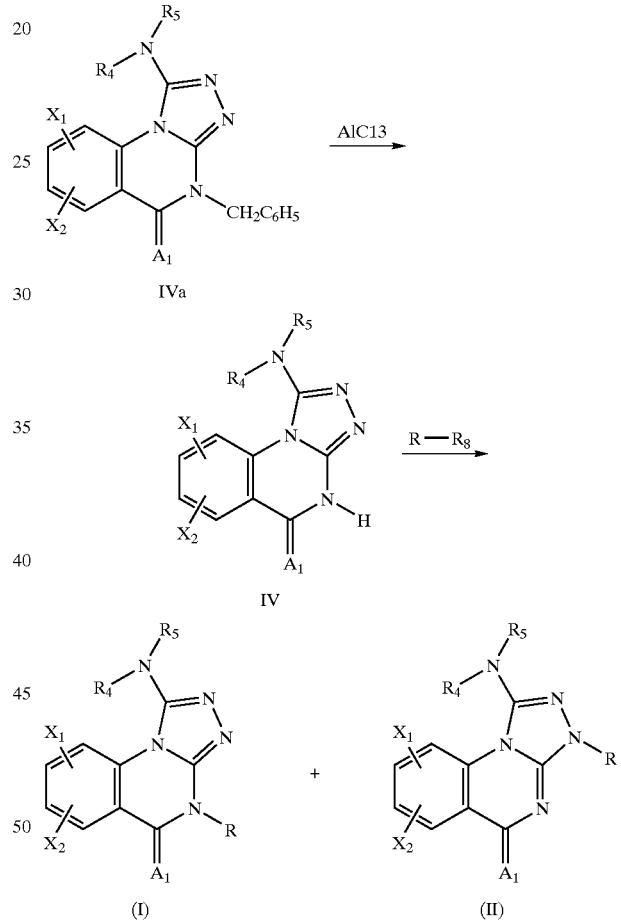

in which $X_1$, $X_2$, $A_1$, R, $R_4$ and $R_5$ are such as previously defined, and $R_8$ represents Cl, Br, $OSO_2CH_3$, $OSO_2CF_3$ or $OSO_2Ar$.

The 4-benzyl 1-amino triazolo[4,3-a]quinazoline-5-one and/ou –5-thione (IVa) is treated by aluminium trichloride in aromatic solvent such as benzene or toluene to make the corresponding compound N-debenzylated (IV). This one is therefore treated in basic conditions by a halide or a sulfonate chosen according to desired substituent R; for example sodium hydride in a solvent such as 1,2-dimethoxyethane (DME) or cesium in dimethylformamide, to lead to 1-amino triazolo[4,3-a]quinazoline-5-ones of formula (I) and (II).

In fact, relying of the basic conditions used, the alkylation is a little regioselective in some cases. Then we obtain a mixture of $N_4$ and $N_3$, regioisomers, (I) and (II) respectively. The two compounds are usually separated by conventional chromatographic methods.

B) Another example of synthesis method used to construct correctly substituted formula (I) triazolo[4,3-a]quinazoline-5-one and/or –5-thione motif is illustrated by scheme 2:

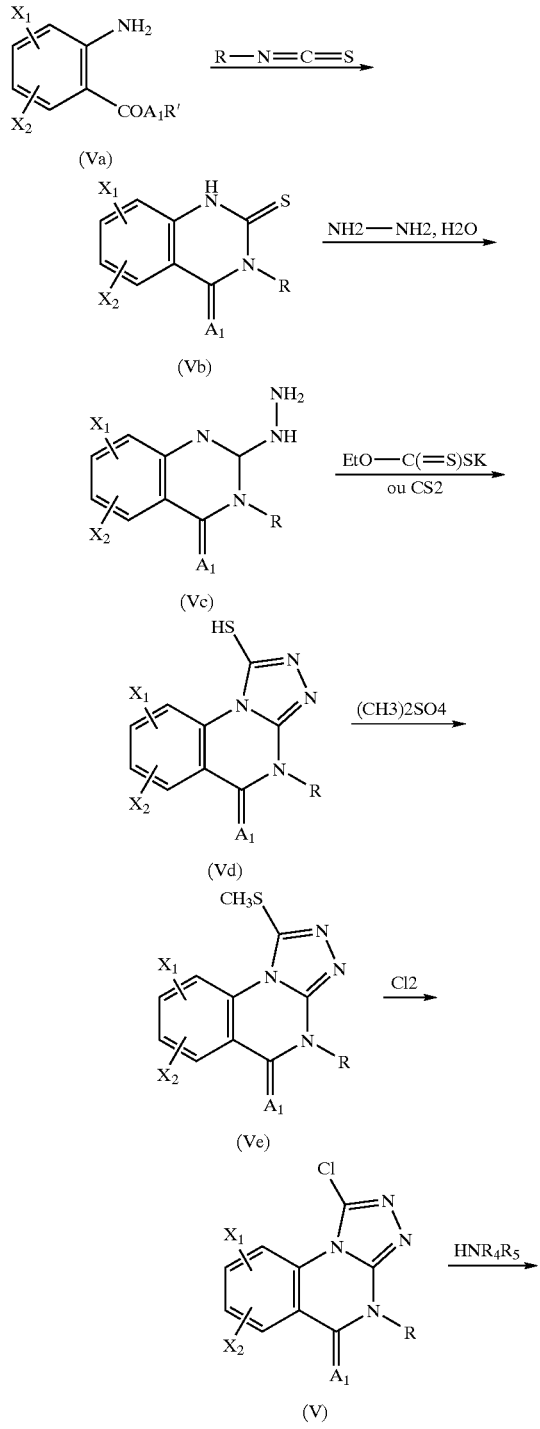

in which $X_1$, $X_2$, $A_1$, R, $R_4$ and $R_5$ are such as previously defined and, R' represents a linear or branched lower alkyl group comprising from 1 to 6, preferably 1 to 3 carbon atoms.

An acid or anthranilic ester which is correctly substituted on the aromatic cycle (Va) is initially transformed into corresponding 2-thio quinazoline-4-one and/or -4-thione (Vb) by cyclization using isothiocyanate of alkyl, aryl or aralkyl, in a solvent such as acetic acid or pyridine.

The thio quinazoline-4-one and/or -4-thione (Vb) is treated by hydrazine hydrate to give 2-hydrazino quinazoline4-one and/or -4-thione (Vc) which is also cyclized into 1-mercapto triazolo[4,3-a]quinazoline-5one and/or -5-thione (Vd) by action of potassium xanthogenate or other reagents such as $CS_2$.

By action of an alkylating agent such as dimethyl sulfate, the thiol (VI) is transformed into derivative 1-methylthio (Ve) which is then converted using chlorine, into 1-chloro triazolo[4,3-a]quinazoline-5-one and/ou -5-thione (V).

This latter is treated by a primary our secondary amine to lead finally to 1-amino triazolo[4,3-a]quinazoline-5-one of formula (I).

C) Another advantageous method in some cases is represented in scheme 3.

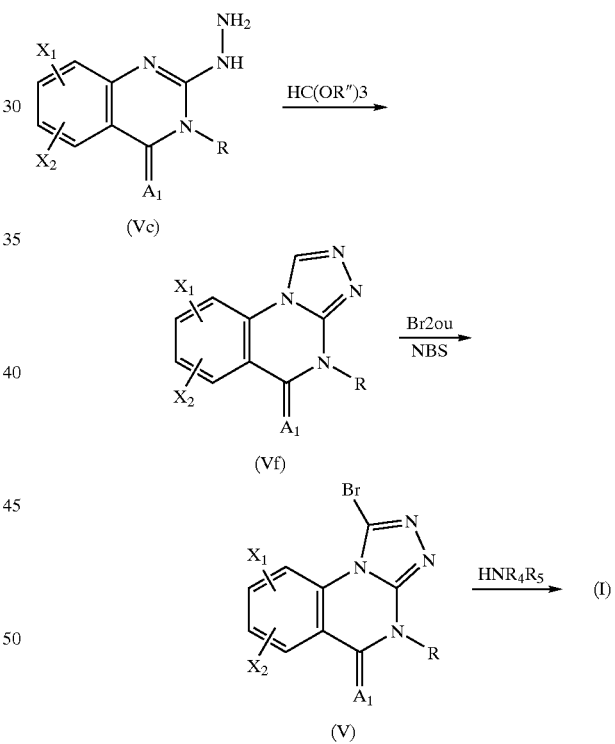

in which $X_1$, $X_2$, $A_1$, R, $R_4$ and $R_5$ are such as previously defined and, R" represents a linear or branched lower alkyl group comprising from 1 to 6, preferably 1 to 3 carbon atoms such as $CH_3$ or $C_2H_5$.

La 2-hydrazino quinazoline-4-one and/or -4-thione (Vc), obtained from an anthranilate in 2 steps (as illustrated in scheme 2), is cyclized using alkyl orthoformiate, in acid medium, into triazolo[4,3-a]quinazoline-5-one and/or -5-thione (Vf).

This is then brominated by bromine or N-bromosuccinimide (NBS) to give 1-bromotriazolo[(4,3-a]quinazoline-5-one and/or -5-thione (V).

This brominated derivative is finally treated by ethanolic solution of primary or secondary amine to lead to formula (I) 1-amino triazolo[4,3-a]quinazoline-5-one and/or -5-thione.

D) When $X_1$ represents H and $X_2$ represent a reactive phenolic function OH, this group must generally be protected during the last steps of compound (I) synthesis. As an example, scheme 4 shows synthesis of such as hydroxyled in position 7 compound. The 4-benzyl-7-hydroxy-4H-[1,2,4]triazolo[4,3-a]quinazolin-5-one and/or -5-thione(Vg), obtained by a method represented in scheme 3, is treated by a compound allowing insertion of oxygen protector group (P) on the function OH. The person skilled in the art will be able to choose without any problem the appropriate protector group. The protector group can be chosen also among silyl trimethyl, methoxymethyl, tolylsulfonyl, methylsulfonyl (mesyl) or also methoxyethylmethoxy (MEM). As an example, the compound (Vg) is treated by tosyl chloride, in a solvent such as methylene chloride, in the presence of a base or an amine such as triethylamine, to give the corresponding O-tosyled phenol (Vf). This is treated by bromine to lead to 4-benzyl-1-bromo-7-(4-tolylsulfonyl)-4H-[1,2,4]triazolo[4,3-a]quinazolin-5-one and/or -5-thione ($V_3$), which reacts with an amine $HNR_4R_5$ by reflux, preferably in the presence of a base like sodium bicarbonate, in a solvent such as dimethylformamide, to give the 1-amino-4-benzyl-7-(4-tolylsulfonyl)-4-H-[1,2,4]triazolo[4,3-a]quinazolin-5-one and/or -5-thione ($IVa_1$).

We can then replace the benzyl group in position 4 by another group R, for example by debenzylating the compound ($IVa_1$) obtained previously using aluminium chloride in a solvent like benzene, then by alkylating the obtained intermediate ($IV_1$) by treatment with a halide or a sulfonate R—$X_5$, in basic conditions, to obtain the 1-amino-7-(4-tolylsulfonyl)-4H-[1,2,4]triazolo[4,3-a]quinazolin-5-one and/or -5-thione (Ia) diversely substituted in position 4. These ones are preferably detosyled into 7-hydroxy derivative (I) for example by heating for several hours in pyrrolidine.

SCHEMA 4

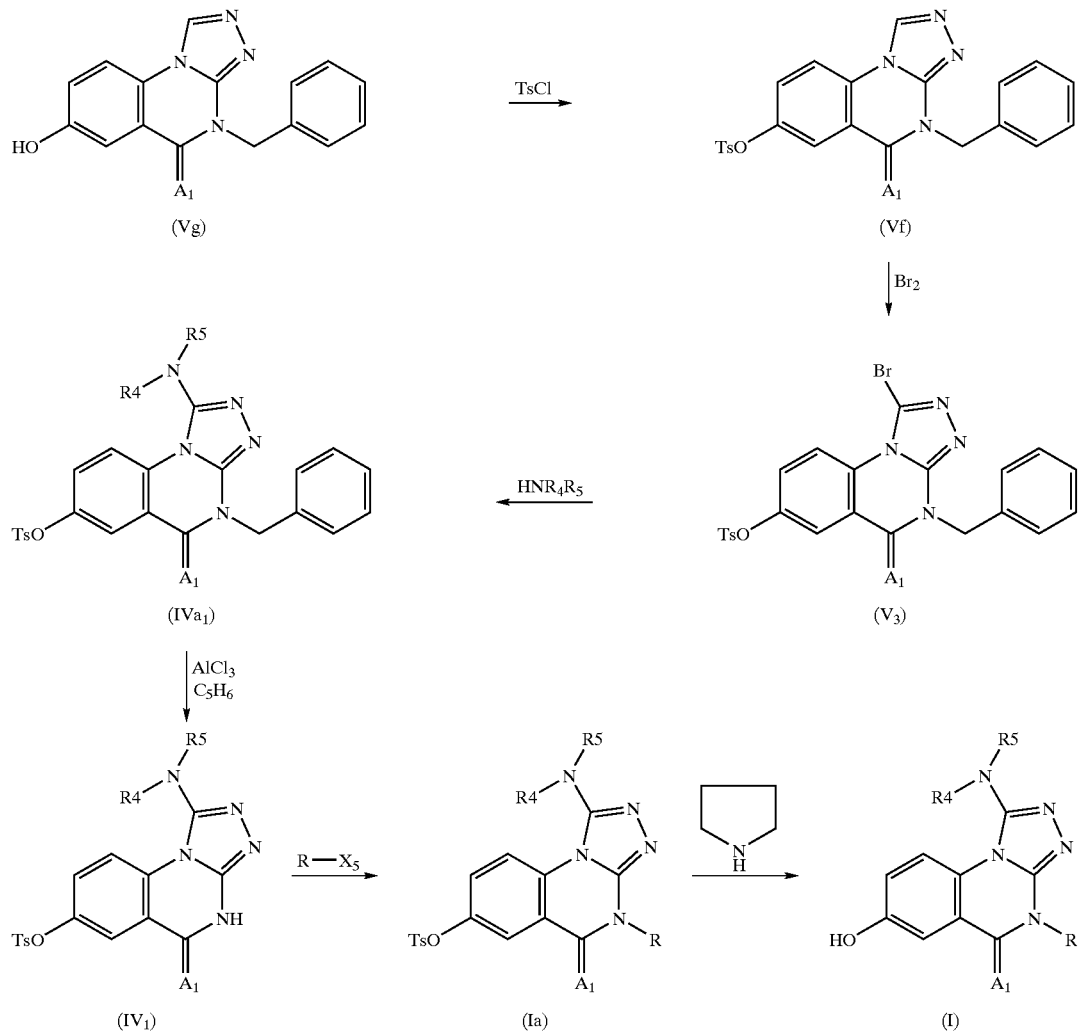

In which $A_1$, $R_4$ and $R_5$ are such as previously defined.

E) When $X_1$ represents H and $X_2$ represents a reactive anilino function NH2, NHR2 or $NR_2R_x$ ($R_2$ such as previously defined and $R_x$ represents $R_2$ or such as previously defined), the amino group $NH_2$ must generally be protected during the last steps of the compound (I) synthesis. As an example, scheme 5 shows synthesis of such as aminated compound in position 7. The 7-acetamido-4-benzyl-4H-[1, 2,4]triazolo[4,3-a]quinazolin-5-one and/or -5-thione (Vf$_1$), obtained by a method represented in scheme 3, is treated by bromine to lead to the 7-acétamido-4-benzyl-1-bromo-4H-[1,2,4]triazolo[4,3-a]quinazolin-5-one and/or -5-thione (V$_4$). This one is used in the reaction with an amine HNR$_4$R$_5$ by reflux, preferably in the presence of a base as sodium bicarbonate, in a solvent such as dimethylformamide, to give the 7-acétamido-1-amino-4-benzyl-4H-[1,2,4]triazolo[4,3-a]quinazolin-5-one and/or -5-thione (IVa$_2$). In the example disclosed above, the protector group (P$_1$) of the function NH is an acetyl group. However the man of art may choose another protector group, for example methylsulfonyl, tolylsulfonyl or phtalimido.

We can also replace the benzyl group in position 4 by another group R, for example by debenzylating the compound (IVa$_2$) obtained previously, using ammonium formiate and palladium on charcoal, in a solvent such as tetrahydrofuran, then by alkylating the obtained intermediate (IV$_2$) by treatment with a halide or a sulfonate R—X$_5$, in basic conditions, to obtain the 7-acetamido-1-amino-4H-[1,2,4]triazolo[4,3-a]quinazolin-5-one and/or -5-thione (I) diversely substituted in position 4. These ones can be N-deacetylated into final compounds (Ib) bearing a function NH2 in position 7, by classic methods like for example by reflux heating in an aqueous solution of hydrochloric acid. The compounds can be treated in at their turn, relying on the case, by a reagent R$_2$—X$_5$ (R$_2$ and X$_5$ having the meaning given previously) to lead to a final N-monosubstituted compound (Ic), which then can be treated by a reagent R$_x$X$_5$ to lead to a final N,N-disubstituted compound (1d). Also it is possible to treat 7-acetamido-1-amino-4H-[1,2,4]triazolo[4,3-a]quinazolin-5-one and/or -5-thione (I) diversely substituted in position 4 initially by a reagent R$_2$X$_5$ to obtain (1b$_2$) which is then N-deacetylated to obtain the compound (Ic).

SCHEMA 5

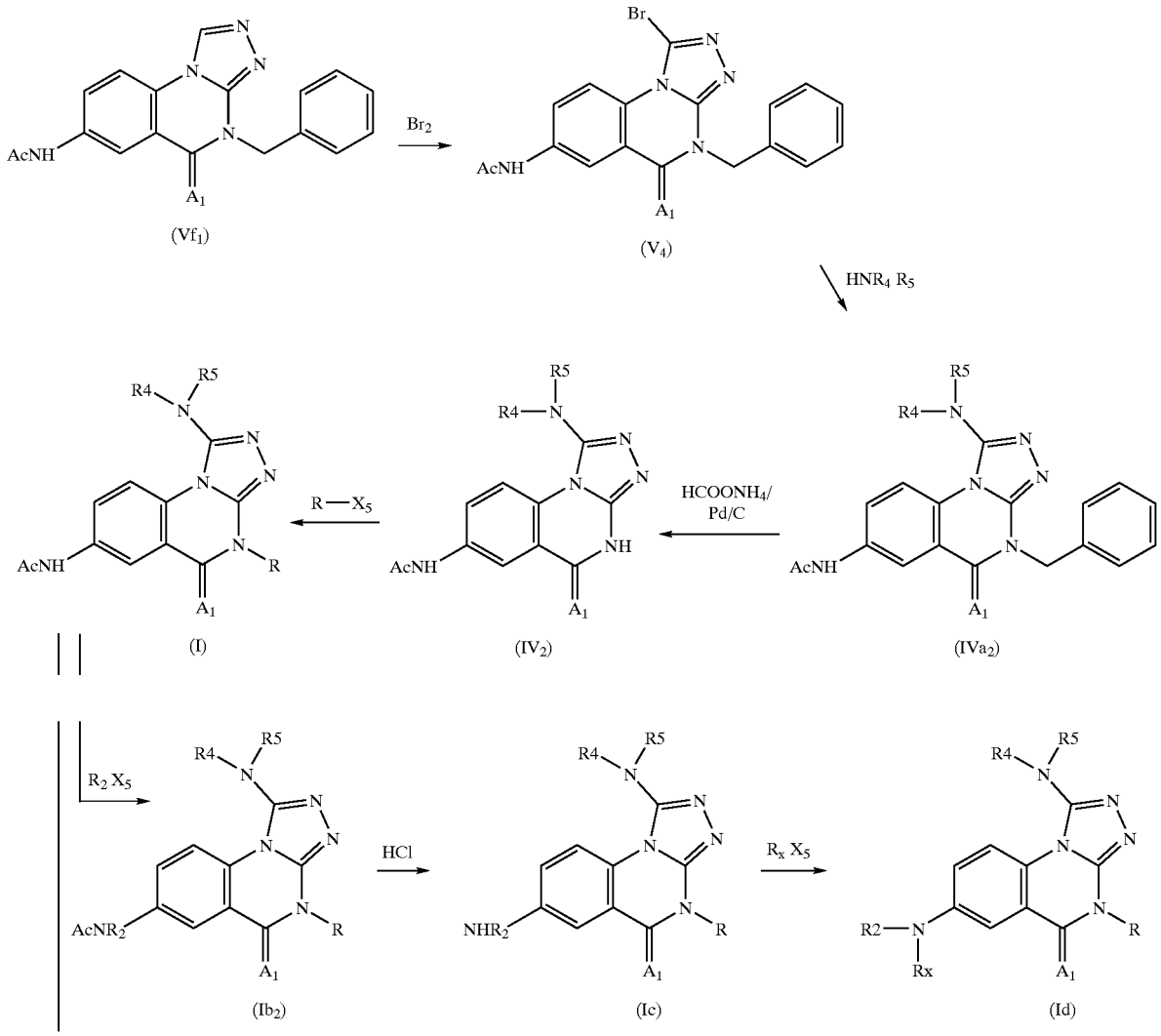

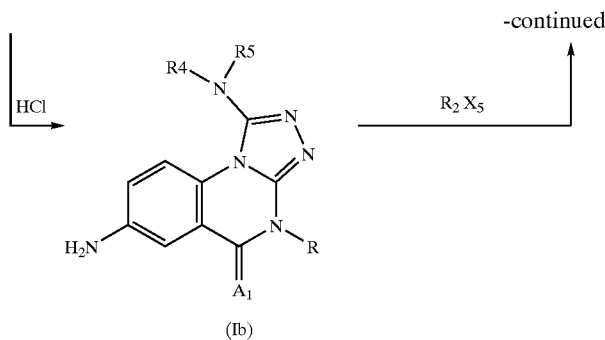

F) When the substituent R in position 4 of compounds (I) represents a group 4-(carboxymethyl)-benzyl, it can be advantageous to transform the carboxylic acid function into ester, amide, nitrile or hydroxamic acid derived. For that, methods represented in scheme 6 can be applied to a general formula acid (Id). This is transformed into chloride of acid (Ie), which is directly condensed either with ammonia to give a primary amide (If), either with a primary or secondary amine to give a secondary (Ih) or tertiary (Ii) amide respectively. (In these structures, $R_{11}$ has the same meaning as $R_2$ and $R_{12}$ have the same meaning as $R_4$, $R_5$ respectively).

The hydroxamic acid (Ij) can be obtained by reaction of chloride of acid (Ie) with hydroxylamine. The primary amide (If) can be dehydrated by classic and current methods, for example using phosphorus pentoxide to lead to corresponding nitrile (Ig).

SCHEMA 6

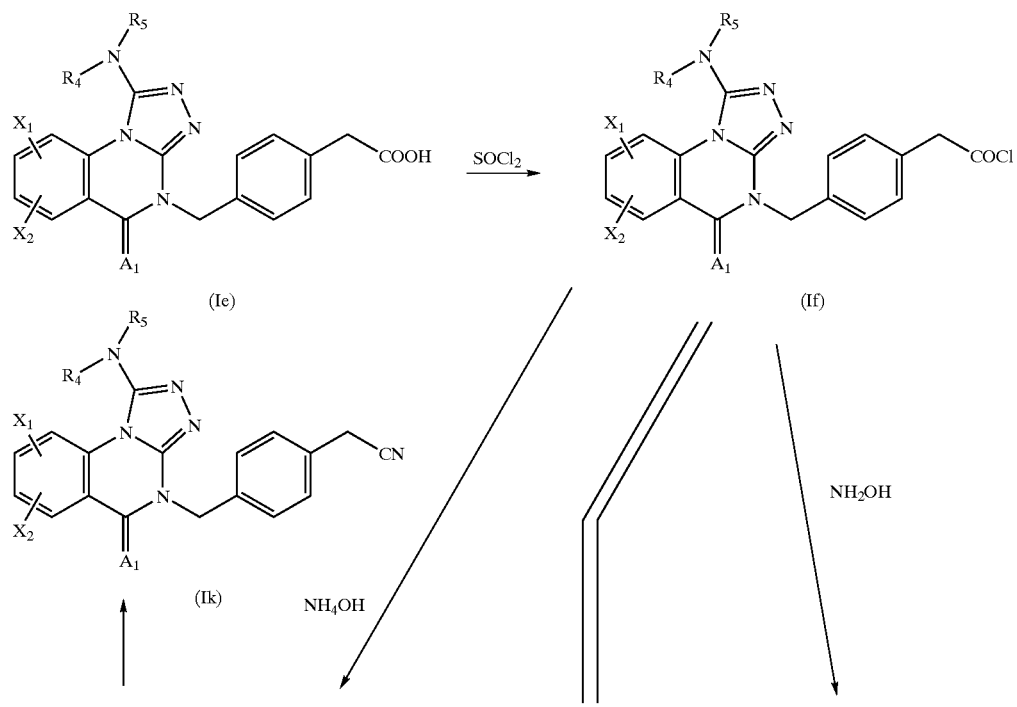

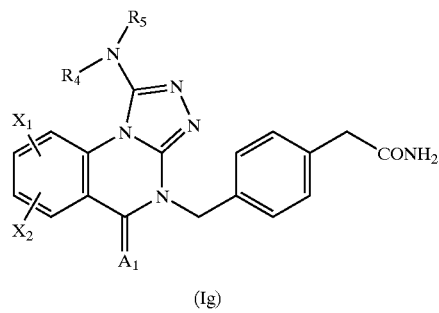

(Ig)

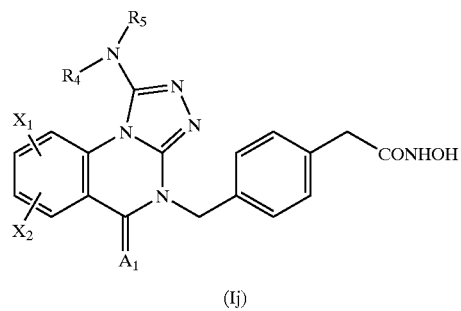

(Ij)

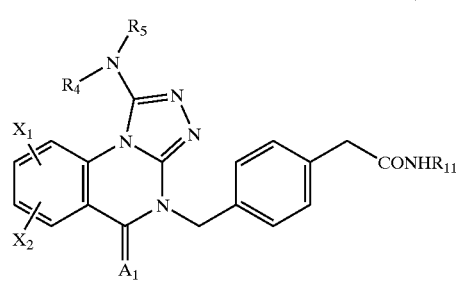

(Ih)

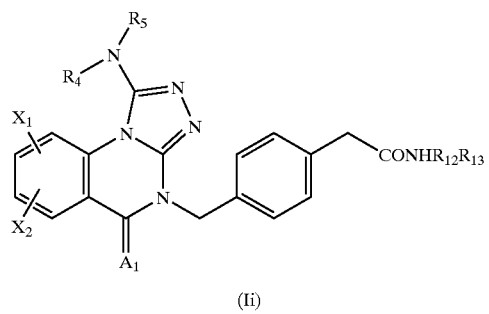

(Ii)

In which $X_1$, $X_2$, $A_1$, $R_4$ and $R_5$ are such as previously defined.

G) The compounds of structure (I) in which $X_1$ or $X_2$ represents an amino $NR_2R_3$ group in position 8 identical to the $NR_4R_5$ group, can also be obtained by heating of corresponding 1-bromo (VI; $X_5$=hal) intermediates in the presence of an excess of $HNR_4R_5$ amine, without solvent or in a solvent such as dimethylformamide as illustrated in scheme 7.

in $X_2$, $X_5$, $A_1$, $R$, $R_4$ and $R_5$ are such as previously defined.

However it is preferable to avoid for this reaction type substituents R including a halogen group able to react in a competitive manner with the reagent $HNR_4R_5$.

H) In the case where two $NR_2R_3$ and $NR_4R_5$ amino groups are different, a slightly modified synthesis path is indicated in scheme 8.

SCHEME 7

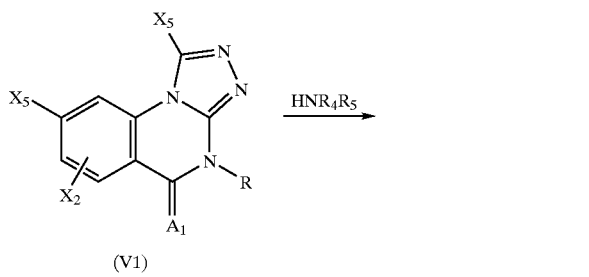

(VI)

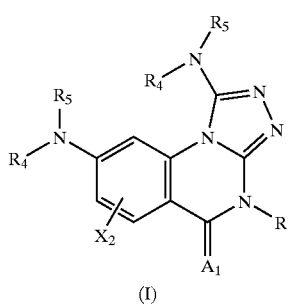

(I)

SCHEME 8

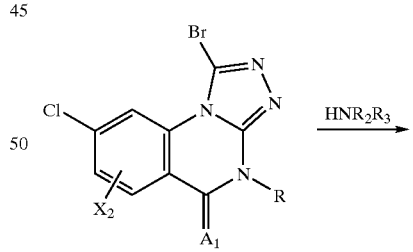

(VI)

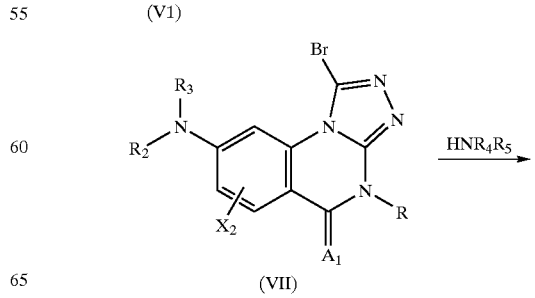

(VII)

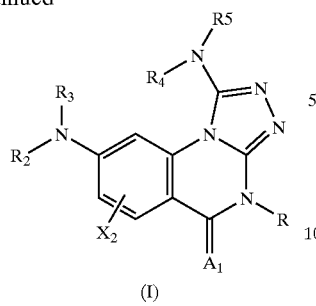

in which $X_2$, $A_1$, R, $R_2$, $R_3$, $R_4$ and $R_5$ are such as previously defined. The substituent amino $NR_2R_3$ is localized in position 8.

1-bromo 8-chlorotriazolo[4,3-a]quinazoline-5-one and/or -5-thione (VIa) correctly substituted in position 4, and prepared as previously by bromination of non-substituted in position 1 derivative, is treated by slight excess of amine $HNR_2R_3$, in a solvent such as dimethylformamide to lead to intermediate (VII).

This intermediate is also heated in an excess of amine $HNR_4R_5$, in a solvent such as dimethylformamide to lead to compound (I).

Surprisingly, the inventors have noticed that reactivity of the halogen atom in position 8 is much more important than reactivity of the other halogen atom of the intermediate. This allows then a first selective reaction on the level of this halogen in position 8 than can be followed by reaction on the level of the second halogen. The example as above illustrates use of chlorine in position 8. However it is possible to use other halogens such as bromine and fluorine, the latter proving to be particularly reactive.

EXAMPLES
A. Type (I) and (II) Compounds

Examples 1 and 2
Method A: 1-Azepanyl-7-chloro-4-(3-phenylallyl)-4H-[1,2,4]triazolo[4,3-a]quinazolin-5-one (ex. 1)

(I): $X_1$=7-Cl; $X_2$=H;

1-Azepanyl-7-chloro-3-(3-phenylallyl)-3H-[1,2,4]triazolo[4,3-a]quinazolin-5-one (ex. 2)

(II): $X_1$=7-Cl; $X_2$=H;

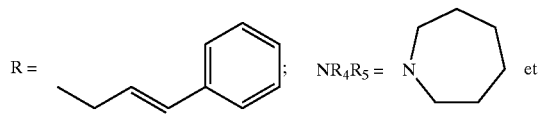

In a reactor protected from humidity, we place 2.5 g (7.87 mmol) of 1-Azepan-yl-7-chloro-4H-[1,2,4]triazolo[4,3-a]quinazolin-5-one, in suspension in 35 ml of 1,2-dimethoxyethane then we shake.

Under inert atmosphere, we then add 240 mg of sodium hydride suspension at 75% (representing 7.90 mmol NaH).

The mixture is heated to 60° C. under shaking for 6 hours. Then we add 1.56 g (7.90 mmol) of cinnamyl bromide by fraction.

The obtained mixture is heated then to 60° C. for 20 hours, under shaking.

After cooling down, the suspension is poured into 200 ml of iced water.

We extract three times with ethyl acetate; the joined organic phases are washed with aqueous solution saturated with sodium chloride, dried on sodium sulfate; then the solvent is evaporated under vacuum.

We obtain 3.5 g of crude mixture of the two regioisomers (theory: 3.4 g).

The 2 isomers are separated by flash chromatography on silica column with elution using methylene chloride 99/methanol 1 mixture.

In order of elution we obtain:

1) 0.58 g of compound from example 1
Yield=17%
F(Tottoli)=125° C.
CCM ($CH_2Cl_2$98/$CH_3OH$ 2)=0.60
RMN[1] H δ (ppm) $CDCl_3$: 1.7–2.0 (m, 8H); 3.3–3.5 (m, 4H); 5.05 (d, 2H); 6.45 (dt, 1H); 6.9 (d, 1H); 7.15–7.3 (m, 3H); 7.35 (d, 2H); 7.75 (d, 1H); 8:35 (s, 1H); 8.4 (d, 1H).

2) 2.1 g of compound from example 2
Yield=61.5%
F(Tottoli)=188° C.
CCM ($CH_2Cl_2$98/$CH_3OH$ 2): Rf=0.35.
RMN [1]H δ (ppm) $CDCl_3$: 1.7–2.0 (m, 8H); 3.4 (m, 4H); 4.9 (d, 2H); 6.35 (d, 1H); 6.75 (d, 1H); 7.2–7.45 (m, 5H); 7.65 (d, 1H); 8.2 (d, 1H); 8.45 (s, 1H)

Example 3

Method B: 7-bromo-1-(N,N-dimethylamino)-4-[3-(3-pyridyl)-allyl]-4H-[1,2,4]triazolo[4,3-a]quinazolin-5-one (ex. 3)

(I): $X_1$=7-Br; $X_2$=H;

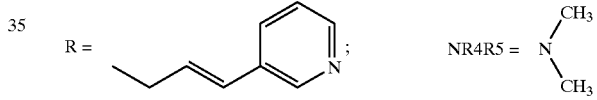

In a reactor equipped with magnetic shaker and refrigeration, we resuspend 7.4 g (0.024 mol) of 7-bromo-1-(N,N-dimethylamino)-4H-[1,2,4]triazolo[4,3-a]quinazolin-5-one in 200 ml de 1,2-dimethoxyethane then we shake. We add 17.0 g (0.052 mol) of cesium carbonate then shake at ambient temperature for 15 minutes. 4.5 g (0.024 mol) of 3-(3-pyridyl)-allyl chloride hydrochloride are then added by fraction, then the mixture is heated to 70° C., under shaking, for 3 hours. The solvent is evaporated under vacuum then the residue is then put in suspension in 300 ml of iced water. After repeated extractions with ethyl acetate, the joined organic phases are washed with aqueous solution saturated with sodium chloride, dried on sodium sulfate then the solvent is evaporated under vacuum.

The residue is chromatographied on silica column by elution using $CH_2Cl_2$98/$CH_3OH$ 2/$NH_4OH$ 0,2 mixture. We recover 6.3 g of isomer (I) pure in CCM. This one is recrystallized in 20 ml of isopropanol to give 5.3 g of example 3 compound:

Yield=52%
RMN[1] H δ (ppm) $CDCl_3$: 2.95 (s, 6H); 5.1 (d, 2H); 6.45 (dt, 1H); 6.8 (d, 1H); 7.15 (m, 1H); 7.65 (d, 1H); 7.9 (d, 1H); 8.25 (d, 1H); 8.4–8.6 (m, 3H).

Examples 4 and 5
Method C: 7-bromo-1-(pyrrolidin-1-yl)-4-[(3-pyridyl)-methyl]-4H-[1,2,4]triazolo[4,3-a]quinazolin-5-one (ex. 4)

(I): $X_1$=7-Br; $X_2$=H;

R = 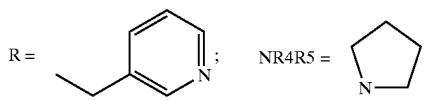 ; NR4R5 =

7-bromo-1-(pyrrolidin-1-yl)-3-[(3-pyridyl)-methyl]-3H-[1,2,4]triazolo[4,3-a]quinazolin-5-one (ex. 5)

(II): X1=7-Br; X2=H;

R = 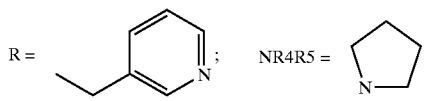 ; NR4R5 =

In a reactor protected from humidity, equipped with magnetic shaking and refrigeration, we add 2.0 g (0.006 mol) of 1-(pyrrolidin-1-yl)-7-bromo-4H-[1,2,4]triazolo[4,3-a]quinazolin-5-one into 125 ml of dimethylsulfoxyde (DMSO) solution then we add 1.0 g (0.018 mol) of finely crushed potash. The mixture is shaken at ambient temperature for 1.5 h, until obtaining of slightly cloudy solution. Then we add once 0.82 g (0.005 mol) of 3-picolyl chloride hydrochloride then keep shaking at ambient temperature for 4 hours.

The obtained mixture is poured into iced water and the resulting suspension is extracted 3 times with ethyl acetate. The joined organic extracts are washed in NaCl saturated solution, dried on $Na_2SO_4$ then concentrated under vacuum. We obtain 2.0 g of crude mixture of the 2 regioisomers which are separated by chromatography on silica column by elution using $CH_2Cl_2$ 98-$CH_3OH$ 2-$NH_4OH$ 0.4 mixture.

In elution order we obtain:

1) 1.2 g of majority product which is recrystallized in methanol to give after drying under vacuum 1, 1 g of example 4 compound.

Yield=57%

F(Tottoli)=206–207° C.

CCM ($CH_2Cl_2$97/$CH_3OH$ 3/NH4OH 0.3): Rf=0.30

RMN[1] H δ (ppm) $CDCl_3$: 1.95–2.1 (m, 4H); 3.35–3.45 (m, 4H); 5.45 (s, 2H); 7.2–7.3 (dd, 1H); 7.85 (d, 1H); 8.0 (d, 1H); 8.2 (d, 1H); 8.45–8.55 (m, 2H); 8.9 (s, 1H).

2) 0.25 g of minority product which is recrystallized in methanol to give after drying under vacuum 0.17 g of example 5 compound.

Yield=12%

F(Tottoli)=261–262° C.

CCM ($CH_2Cl_2$97/$CH_3OH$ 3/NH4OH 0.3): Rf=0.20

RMN[1] H δ (ppm) $CDCl_3$: 1.9–2.05 (m, 4H); 3.2–3.4 (m, 4H); 5.25 (s, 2H); 7.1–7.2 (m, 1H); 7.7 (d, 1H); 7.8 (d, 1H); 7.9 (d, 1H); 8.45–8.60 (m, 2H); 8.65 (s, 1H).

Compounds (I) of examples 6 to 108 and compounds (II) of examples 109 to 162, in which $X_2$=$H_1$ are prepared according to process of example 1:

Compounds (I): Table 1

Compounds (II): Table 2

TABLE 1

| No. Compound | X1 | R | NR4R5 | Yield (%) | MP (° C.) | Method |
|---|---|---|---|---|---|---|
| 6 | H | (E) C6H5CH=CHCH2 | 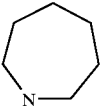 | 11 | 144 | A |
| 7 | 7-Cl | CH2=CHCH2 | 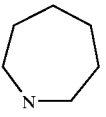 | 9 | — | A |
| 8 | 7-Cl | 4-CH3C6H4CH2 | 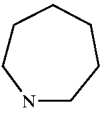 | 16 | 163 | A |
| 9 | 7-Cl | 2-ClC6H4CH2 | 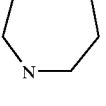 | 6 | 160–162 | A |
| 10 | 7-Cl | 3-ClC6H4CH2 | 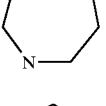 | 35 | 157 | A |
| 11 | 7-Cl | 4-ClC6H4CH2 | 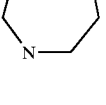 | 20 | 166 | A |

TABLE 1-continued
| No. Compound | X1 | R | NR4R5 | Yield (%) | MP (° C.) | Method |
|---|---|---|---|---|---|---|
| 12 | 7-Cl | 4-BrC6H4CH2 | 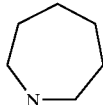 | 25 | 104–110 | A |
| 13 | 7-Cl | 4-FC6H4CH2 | 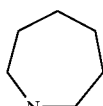 | 48 | 150 | A |
| 14 | 7-Cl | 4-CF3C6H4CH2 | 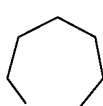 | 22 | 138 | A |
| 15 | 7-Cl | 4-CNC6H4CH2 |  | 49 | 165–168 | A |
| 16 | 7-Cl | 2-(CH3O)C6H4CH2 | 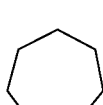 | 6 | 98–100 | A |
| 17 | 7-Cl | 3-(CH3O)C6H4CH2 | 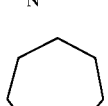 | 22 | 138 | A |
| 18 | 7-Cl | 4-(CH3O)C6H4CH2 | 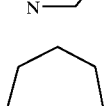 | 26 | 138 | A |
| 19 | 7-Cl | 3,4-Cl2C6H3CH2 | 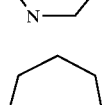 | 19 | — | A |
| 20 | 7-Cl | 3,4-(CH3O)2C6H3CH2 | 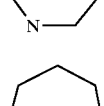 | 41 | 172 | A |
| 21 | 7-Cl | (2-pyridyl)CH2 | 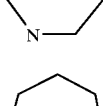 | 16 | 152 | A |
| 22 | 7-Cl | (3-pyridyl)CH2 | 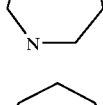 | 29 | 155 | A |
| 23 | 7-Cl | (4-pyridyl)CH2 | 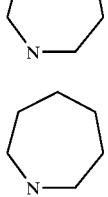 | 64 | 137 | A |

TABLE 1-continued
| No. Compound | X1 | R | NR4R5 | Yield (%) | MP (° C.) | Method |
|---|---|---|---|---|---|---|
| 24 | 7-Cl | C6H5CH2CH2 | 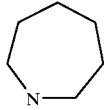 | 5 | 105 | A |
| 25 | 7-Cl | 4-(CH3O)C6H4(CH2)2 |  | 12 | 136 | A |
| 26 | 7-Cl | C6H5(CH2)3 | 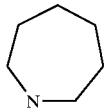 | 17 | — | A |
| 27 | 7-Cl | C6H5C(=O)CH2 | 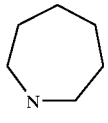 | 26.5 | 105–107 | A |
| 28 | 7-Cl | 4-(CH3O)C6H4C(=O)CH2 |  | 30 | 191 | A |
| 29 | 7-Cl | 4-ClC6H4C(=O)CH2 | 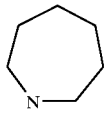 | 36 | 190 | A |
| 30 | 7-Cl | 4-(CH3O)-3-(COOCH3)—C6H3C(=O)CH2 | 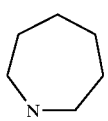 | 18 | 140 | A |
| 31 | 7-Cl | (3-pyridyl)-CH2 | 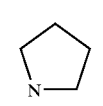 | 39 | 176 | C |
| 32 | 7-Br | 4-ClC6H4CH2 | 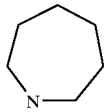 | 8 | 179 | A |
| 33 | 7-Br | 4-FC6H4CH2 | 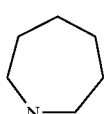 | 21 | 158 | A |
| 34 | 7-Br | 4-CNC6H4CH2 | 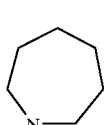 | 21 | 190 | A |
| 35 | 7-Br | 3,4-(CH3O)2C6H3CH2 | 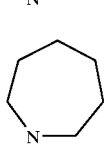 | 23.5 | 185 | A |

TABLE 1-continued
| No. Compound | X1 | R | NR4R5 | Yield (%) | MP (° C.) | Method |
|---|---|---|---|---|---|---|
| 36 | 7-Br | (3-pyridyl)-CH2 | 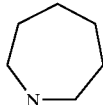 | 4 | 180 | C |
| 37 | 7-Br | (E) C6H5CH=CHCH2 | 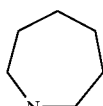 | 64 | 155 | B |
| 38 | 7-Br | (E) 4-Cl—C6H4CH=CHCH2 | 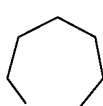 | 25 | 176 | B |
| 39 | 7-Br | (E) 4-(CH3O)C6H4CH=CHCH2 |  | 30 | 129 | B |
| 40 | 7-Br | (E) (3-pyridyl)CH=CHCH2 | 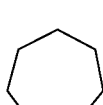 | 12 | 185 | B |
| 41 | 7-Br | (E) (4-pyridyl)CH=CHCH2 | 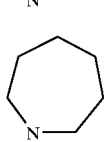 | 39 | 216 | B |
| 42 | 7-Br | 4-CH3C6H4CH2 |  | 53 | 215 | B |
| 43 | 7-Br | 4-ClC6H4CH2 |  | 12 | 105 | A |
| 44 | 7-Br | 4-FC6H4CH2 |  | 42 | 166 | A |
| 45 | 7-Br | 3-CNC6H4CH2 |  | 52 | 206 | B |
| 46 | 7-Br | 4-CNC6H4CH2 |  | 19 | 116 | A |
| 47 | 7-Br | 4-(COOCH3)C6H4CH2 |  | 54 | 205 | A |
| 48 | 7-Br | 4-NO2C6H4CH2 |  | 52 | 200 | B |
| 49 | 7-Br | 4-(CH3O)C6H4CH2 |  | 39 | 169 | B |

TABLE 1-continued
| No. Compound | X1 | R | NR4R5 | Yield (%) | MP (° C.) | Method |
|---|---|---|---|---|---|---|
| 50 | 7-Br | 4-(OCOCH3)C6H4CH2 |  | 21 | 195 | B |
| 51 | 7-Br | 4-OHC6H4CH2 |  | 13 | 288 | B |
| 52 | 7-Br | 3,4-(CH3O)2C6H3CH2 |  | 15 | 151 | A |
| 53 | 7-Br | 3,4-(OCH2O)C6H3CH2 |  | 21 | 194 | A |
| 54 | 7-Br | 3,5-(CH3O)2C6H3CH2 |  | 31 | — | A |
| 55 | 7-Br | 3,4,5-(CH3O)3C6H2CH2 |  | 35 | 141–143 | A |
| 56 | 7-Br | 4-(CH2COOH)C6H4CH2 |  | 17 | 260 | B |
| 57 | 7-Br | (E) C6H5CH=CHCH2 |  | 57 | 152–155 | A |
| 58 | 7-Br | (Z) C6H5CH=CHCH2 |  | 24 | 110 | B |
| 59 | 7-Br | (E) (4-ClC6H4)—CH=CHCH2 |  | 45 | 187 | B |
| 60 | 7-Br | (E) (4-CH3O)C6H4CH=CHCH2 |  | 32 | 171 | B |
| 61 | 7-Br | (E) (3-pyridyl)-CH=CHCH2 |  | 10 | 102 | B |
| 62 | 7-Br | (E) (4-pyridyl)-CH=CHCH2 |  | 38 | 167 | B |
| 63 | 7-Br | 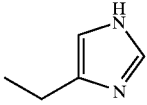 |  | 4 | 290(dec) | B |
| 64 | 7-Br | 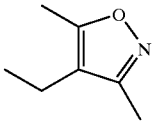 |  | 60 | 221 | B |

TABLE 1-continued

| No. Compound | X1 | R | NR4R5 | Yield (%) | MP (° C.) | Method |
|---|---|---|---|---|---|---|
| 65 | 7-Br | cyclopentylmethyl | pyrrolidinyl | 32 | 155 | B |
| 66 | 7-Br | n-butyl | pyrrolidinyl | 39 | 135 | B |
| 67 | 7-Br | CH2CF3 | pyrrolidinyl | 14 | 202 | B |
| 68 | 7-Br | CH2CH2OH | pyrrolidinyl | 25 | 240 | B |
| 69 | 7-Br | CH2CH2N(C2H5)2 | pyrrolidinyl | 50 | 215 (HCl) | C |
| 70 | 7-Br | CH2C≡CH (propargyl) | pyrrolidinyl | 36 | 204 | B |
| 71 | 7-Br | CH2CH2OC6H5 | pyrrolidinyl | 25 | 171 | B |
| 72 | 7-Br | CH2CH2SC6H5 | pyrrolidinyl | 20 | 122 | B |
| 73 | 7-Br | CH(C6H5)COOCH3 | pyrrolidinyl | 14 | 184 | B |
| 74 | 7-Br | 4-CNC6H4CH2 | piperidinyl | 72 | 200 | B |
| 75 | 7-Br | 3,4-(CH3O)2C6H3CH2 | piperidinyl | 67 | 178 | B |
| 76 | 7-Br | (E) C6H5CH=CHCH2 | piperidinyl | 8 | — | A |
| 77 | 7-Br | (E) (3-pyridyl)CH=CHCH2 | thiomorpholinyl | 48 | 177 | B |
| 78 | 7-Br | 4-CH3C6H4CH2 | N(CH3)2 | 56 | 223 | B |
| 79 | 7-Br | 4-CNC6H4CH2 | N(CH3)2 | 56 | 207 | B |

TABLE 1-continued
| No. Compound | X1 | R | NR4R5 | Yield (%) | MP (° C.) | Method |
|---|---|---|---|---|---|---|
| 80 | 7-Br | 4-OHC6H4CH2 | N(CH3)2 | 15 | 284 | B |
| 81 | 7-Br | 4-(COOCH3)C6H4CH2 | N(CH3)2 | 35 | 197 | B |
| 82 | 7-Br | 4-(CH2COOH)C6H4CH2 | N(CH3)2 | 8 | 246 | B |
| 83 | 7-Br | 4-(CH2CN)C6H4CH2 | N(CH3)2 | <1 | 230 | B |
| 84 | 7-Br | (3-pyridyl)-CH2 | N(CH3)2 | 28 | 142 | B |
| 85 | 7-Br | (E) C6H5CH=CHCH2 | N(CH3)2 | 63 | 171 | B |
| 86 | 7-Br | (Z) C6H5CH=CHCH2 | N(CH3)2 | 28 | 167 | B |
| 87 | 7-Br | (E) (4-pyridyl)-CH=CHCH2 | N(CH3)2 | 48 | 115 | B |
| 88 | 7-Br |  | N(CH3)2 | <1 | 234 | B |
| 89 | 7-Br | C6H5C≡CCH2 | N(CH3)2 | 15 | 159 | B |
| 90 | 7-Br | CH(C6H5)COOCH3 | N(CH3)2 | 18 | 243 | B |
| 91 | 7-CH3 | (3-pyridyl)-CH2 |  | 64 | 175 | C |
| 92 | 7-CH3 | (E) C6H5CH=CHCH2 |  | 16 | 195 | A |
| 93 | 7-CH3 | 4-CNC6H4CH2 |  | 84 | 166 | B |

TABLE 1-continued

| No. Compound | X1 | R | NR4R5 | Yield (%) | MP (° C.) | Method |
|---|---|---|---|---|---|---|
| 94 | 7-CH3 | 3,4-(CH3O)2C6H3CH2 | pyrrolidinyl | 52 | 184 | B |
| 95 | 7-CH3 | 4-(COOCH3)C6H4CH2 | pyrrolidinyl | 44 | 230 | B |
| 96 | 7-CH3 | 4-(CH2COOH)C6H4CH2 | pyrrolidinyl | 21 | 262 | B |
| 97 | 7-CH3 | (3-pyridyl)-CH2 | pyrrolidinyl | 10 | 139 | C |
| 98 | 7-CH3 | (E) C6H5CH=CHCH2 | pyrrolidinyl | 17 | 173 | A |
| 99 | 7-CH3 | 4-(CH2COOH)C6H4CH2 | thiomorpholinyl | 10 | — | B |
| 100 | 7-CH3 | (E) (3-pyridyl)CH=CHCH2 | thiomorpholinyl | 51 | 230 | B |
| 101 | 7-CH3 | 4-CNC6H4CH2 | N(CH3)2 | 73 | 201 | B |
| 102 | 7-CH3 | 4-(CH2COOH)C6H4CH2 | N(CH3)2 | 3 | — | B |
| 103 | 7-CH3 | (E) C6H5CH=CHCH2 | N(CH3)2 | 50 | 171 | B |
| 104 | 7-CH3 | (E) (3-pyridyl)CH=CHCH2 | N(CH3)2 | 53 | 155 | B |
| 105 | 7-CH3 | (E) (4-pyridyl)-CH=CHCH2 | N(CH3)2 | 66 | 119 | B |
| 106 | 8-CH3 | (E) C6H5CH=CHCH2 | hexamethyleneimino | 52 | — | A |
| 107 | 7-CN | 4-CNC6H4CH2 | N(CH3)2 | 43 | 147–149 | B |

TABLE 1-continued

| No. Compound | X1 | R | NR4R5 | Yield (%) | MP (° C.) | Method |
|---|---|---|---|---|---|---|
| 108 | 7-OH | (E) C6H5CH=CHCH2 |  | 3 | 295(dec) | A |

Compound 6
 R.M.N.¹H δ (ppm): 1.7–1.85 (m, 8H); 3.3–3.4 (m, 4H); 4.95 (d, 2H); 6.4–6.5 (dt, 1H); 6.7–6.75 (d, 1H); 7.25 (t, 1H); 7.3 (t, 2H); 7.45 (d, 2H); 7.6 (t, 1H); 7.95 (t, 1H); 8.25 (d, 1H); 8.4 (d, 1H)
 Solvent: DMSO
Compound 7
 R.M.N.¹H δ (ppm): 1.5–1.9 (m, 8H); 3.3 (m, 4H); 4.8 (d, 2H); 5.2 (d, 1H); 5.4 (d, 1H); 5.95 (m, 1H); 7.65 (d, 1H); 8.25 (s, 1H); 8.3 (d, 1H)
 Solvent: CDCl₃
Compound 8
 R.M.N.¹H δ (ppm): 1.7–2.0 (m, 8H); 2.3 (s, 3H); 3.35 (m, 4H); 5.4 (s, 2H); 7.1 (d, 2H); 7.6 (d, 2H); 7.7 (d, 1H); 8.35 (m, 2H)
 Solvent: CDCl₃
Compound 9
 R.M.N.¹H δ (ppm): 1.75–1.95 (m, 8H); 3.4 (m, 4H); 5.6 (s, 2H); 7.05–7.25 (m, 3H); 7.4 (d, 1H); 7.75 (d, 1H); 8.35 (s, 1H); 8.45 (d, 1H)
 Solvent: CDCl₃
Compound 10
 R.M.N.¹H δ (ppm): 1.6–2.0 (m, 8H); 3.35 (m, 4H); 5.4 (s, 2H); 7.2 (m, 2H); 7.55 (s, 1H); 7.65 (s, 1H); 7.7 (d, 1H); 8.35 (m, 2H)
 Solvent: CDCl₃
Compound 11
 R.M.N.¹H δ (ppm): 1.65–1.9 (m, 8H); 3.3 (m, 4H); 5.35 (s, 2H); 7.2 (d, 2H); 7.55 (d, 2H); 7.65 (d, 1H); 8.25 (m, 2H)
 Solvent: CDCl₃
Compound 12
 R.M.N.¹H δ (ppm): 1.7–2 (m, 8H); 3.4 (m, 4H); 5.4 (s, 2H); 7.4 (d, 2H); 7.5 (d, 2H); 7.7 (d, 1H); 8.3 (s, 1H); 8.35 (d, 1H)
 Solvent: CDCl₃
Compound 13
 R.M.N.¹H δ (ppm): 1.75–1.95 (m, 8H); 3.4 (m, 4H); 5.4 (s, 2H); 7.0 (m, 2H); 7.7 (m, 3H); 8.35 (m, 2H)
 Solvent: CDCl₃
Compound 14
 R.M.N.¹H δ (ppm): 1.7–1.95 (m, 8H); 3.4 (m, 4H); 5.5 (s, 2H); 7.55 (d, 2H); 7.7 (d, 1H); 7.8 (d, 2H); 8.3–8.45 (m, 2H)
 Solvent: CDCl₃
Compound 15
 R.M.N.¹H δ (ppm): 1.65–2 (m, 8H); 3.4 (m, 4H); 5.45 (s, 2H); 7.55 (d, 2H); 7.7–7.85 (m, 3H); 8.25–8.45 (m, 2H)
 Solvent: CDCl₃
Compound 16
 R.M.N.¹H δ (ppm): 1.75–1.95 (m, 8H); 3.4 (m, 4H); 3.9 (s, 3H); 5.5 (s, 2H); 6.8 (t, 1H); 6.9 (d, 1H); 7.1 (d, 1H); 7.2 (t, 1H); 8.35 (s, 1H); 8.4 (d, 1H)
 Solvent: CDCl₃
Compound 17
 R.M.N.¹H δ (ppm): 1.75–1.95 (m, 8H); 3.4 (m, 4H); 3.8 (s, 3H); 5.5 (s, 2H); 6.8 (m, 1H); 7.25 (m, 3H); 7.75 (d, 1H); 8.4 (m, 2H)
 Solvent: CDCl₃

Compound 18
 R.M.N.¹H δ (ppm): 1.75–1.95 (m, 8H); 3.4 (m, 4H); 3.75 (s, 3H); 5.4 (s, 2H); 6.85 (d, 2H); 7.7 (m, 3H); 8.35 (m, 2H)
 Solvent: CDCl₃
Compound 19
 R.M.N.¹H δ (ppm): 1.7–2.0 (m, 8H); 3.35 (m, 4H); 5.4 (s, 2H); 7.3 (d, 1H); 7.5 (d, 1H); 7.75 (m, 2H); 8.3 (s, 1H); 8.35 (d, 1H)
 Solvent: CDCl₃
Compound 20
 R.M.N.¹H δ (ppm): 1.75–1.95 (m, 8H); 3.4 (m, 4H); 3.85 (s, 3H); 3.90 (s, 3H); 5.4 (s, 2H); 6.75 (d, 1H); 7.35 (m,2H); 7.7 (d, 1H); 8.35 (m, 2H)
 Solvent: CDCl₃
Compound 21
 R.M.N.¹H δ (ppm): 1.7–1.95 (m, 8H); 3.4 (m, 4H); 5.6 (s, 2H); 7.15 (m, 1H); 7.4 (d, 1H); 7.6 (m, 1H); 7.75 (d, 1H); 8.35 (s, 1H); 8.4 (d, 1H); 8.45 (m, 1H)
 Solvent: CDCl₃
Compound 22
 R.M.N.¹H δ (ppm): 1.6–1.95 (m, 8H); 3.35 (m, 4H); 5.4 (s, 2H); 7.2 (m, 1H); 7.7 (d, 1H); 8.0 (m, 1H); 8.3 (m, 2H); 8.5 (m, 1H); 8.9 (s, 1H)
 Solvent: CDCl₃
Compound 23
 R.M.N.¹H δ (ppm): 1.6–1.9 (m, 8H); 3.3 (m, 4H); 5.35 (s, 2H); 7.4 (d, 2H); 7.65 (d, 1H); 8.25 (s, 1H); 8.3 (d, 1H); 8.45 (d, 2H)
 Solvent: CDCl₃
Compound 24
 R.M.N.¹H δ (ppm): 1.7–2.1 (m, 8H); 3.15 (t, 2H); 3.4 (m, 4H); 4.5 (t, 2H); 7.2–7.45 (m, 5H); 7.7 (d, 1H); 8.35 (s, 1H); 8.35 (s, 1H); 8.4 (d, 1H)
 Solvent: CDCl₃
Compound 25
 R.M.N.¹H δ (ppm): 1.7–1.95 (m, 8H); 3.05 (t, 2H); 3.4 (m, 4H); 3.8 (s, 3H); 4.45 (t, 2H); 6.85 (d, 2H); 7.25 (d, 2H); 7.7 (d, 1H); 8.3 (s, 1H); 8.4 (d, 1H)
 Solvent: CDCl₃
Compound 26
 R.M.N.¹H δ (ppm): 1.7–2.0 (m, 8H); 2.2 (qn, 2H); 2.75 (t, 2H); 3.35 (m, 4H); 4.35 (t, 2H); 7.0–7.2 (m, 5H); 7.7 (d, 1H); 8.3 (s, 1H); 8.35 (d, 1H)
 Solvent: CDCl₃
Compound 27
 R.M.N.1H δ (ppm): 1.65–1.85(m,8H); 3.35(m,4H); 5.7 (s,2H); 7.6(t,2H); 7.75(t,1H); 8.05(d,1H); 8.15(m,3H); 8.4 (d,1H)
 Solvent: DMSO
Compound 28
 R.M.N.¹H δ (ppm): 1.75–1.95 (m, 8H); 3.4 (m, 4H); 3.9 (s, 3H); 5.7 (s, 2H); 7.0 (d, 2H); 7.8 (d, 1H); 8.05 (d, 2H); 8.35 (s, 1H); 8.45 (d, 1H)
 Solvent: CDCl₃
Compound 29
 R.M.N.¹H δ (ppm): 1.75–1.95 (m, 8H); 3.4 (m, 4H); 5.7 (s, 2H); 7.45 (d, 2H); 7.8 (d, 1H); 8 (d, 2H); 8.3 (s, 1H); 8.4 (d, 1H)
 Solvent: CDCl₃

Compound 30
R.M.N.¹H δ (ppm): 1.75–1.95 (m, 8H); 3.4 (m, 4H); 3.9 (s, 3H); 4 (s, 3H); 5.7 (s, 2H); 7.1 (d, 1H); 7.8 (d, 1H); 8.2 (d, 1H); 8.35 (s, 1H); 8.45 (s, 1H); 8.5 (s, 1H)
Solvent: CDCl₃

Compound 31
R.M.N.¹H δ (ppm): 2.0–2.1 (m, 4H); 3.35–3.45 (m, 4H); 5.45 (s, 2H); 7.2–7.3 (dd, 1H); 7.75 (d, 1H); 8.05 (d, 1H); 8.25 (d, 1H); 8.35 (s, 1H); 8.55 (s, 1H); 8.9 (s, 1H)
Solvent: CDCl₃

Compound 32
R.M.N.¹H δ (ppm): 1.7–1.95 (m, 8H); 3.4 (m, 4H); 5.45 (s, 2H); 7.25 (d, 2H); 7.75 (d, 2H); 7.9 (d, 1H); 8.25 (d, 1H); 8.45 (s, 1H)
Solvent: CDCl₃

Compound 33
R.M.N.¹H δ (ppm): 1.7–2.0 (m, 8H); 3.3–3.45 (m, 4H); 5.4 (s, 2H); 6.9–7.0 (m, 2H); 7.65–7.75 (m, 2H); 7.9 (d, 1H); 8.3 (d, 1H); 8.5 (s, 1H)
Solvent: CDCl₃

Compound 34
R.M.N.¹H δ (ppm): 1.8–2 (m, 8H); 3.35–3.5 (m, 4H); 5.5 (s, 2H); 7.6 (dd, 2H); 7.8 (dd,2H); 7.9 (m, 1H); 8.3 (dd, 1H); 8.5 (d, 1H)
Solvent: CHCl₃

Compound 35
R.M.N.¹H δ (ppm): 1.7–2 (m, 8H); 3.3–3.45 (m, 4H); 3.8 (s, 3H); 3.85 (s, 3H); 5.4 (s, 2H); 6.8 (d, 1H); 7.25–7.35 (m, 2H); 7.8 (d, 1H); 8.3 (d, 1H); 8.5 (s, 1H)
Solvent: CDCl₃

Compound 36
R.M.N.¹H δ (ppm): 1.8–1.95 (m, 8H); 3.4 (m, 4H); 5.45 (s, 2H); 7.25 (m, 1H); 7.9 (d, 1H); 8.1 (d, 1H); 8.35 (d, 1H); 8.5 (m, 2H); 8.95 (s, 1H)
Solvent: CDCl₃

Compound 37
R.M.N.¹H δ (ppm): 1.7–1.95 (m, 8H); 3.4 (m, 4H); 5.05 (d, 2H); 6.45 (dt, 1H); 6.9 (d, 1H); 7.15–7.3 (m, 3H); 7.35 (d, 2H); 7.9 (d, 1H); 8.3 (d, 1H); 8.5 (s, 1H)
Solvent: CDCl₃

Compound 38
R.M.N.¹H δ (ppm): 1.7–2 (m, 8H); 3.3–3.5 (m, 4H); 5.05 (d, 2H); 6.35–6.45 (m, 1H); 6.75–6.85 (d, 1H); 7.2–7.35 (m, 4H); 7.85 (m, 1H); 8.3 (m, 1H); 8.5 (s, 1H)
Solvent: CDCl₃

Compound 39
R.M.N.¹H δ (ppm): 1.7–1.95 (m, 8H); 3.3–3.45 (m, 4H); 3.75 (s, 3H); 5.05 (m, 2H); 6.25–6.35 (m, 1H); 6.8 (m, 3H); 7.3 (m, 2H); 7.85 (m, 1H); 8.3 (m, 1H); 8.5 (s, 1H)
Solvent: CDCl₃

Compound 40
R.M.N.¹H δ (ppm): 1.7–2 (m, 8H); 3.3–3.5 (m, 4H); 5.05 (d, 2H); 6.45–6.55 (m, 1H); 6.85 (d, 1H); 7.2 (m, 1H); 7.65 (m, 1H); 7.9 (m, 1H); 8.35 (d, 1H); 8.45 (m, 1H); 8.5 (d, 1H); 8.6 (d, 1H)
Solvent: CDCl₃

Compound 41
R.M.N.¹H δ (ppm): 1.7–2 (m, 8H); 3.3–3.5 (m, 4H); 5.05 (d, 2H); 6.55–6.7 (m, 1H); 6.8 (d, 1H); 7.2 (d, 1H); 7.9 (m, 1H); 8.3 (d, 1H); 8.5 (m, 3H)
Solvent: CDCl₃

Compound 42
R.M.N.¹H δ (ppm): 2–2.1 (m, 4H); 2.3 (s, 3H); 3.3–3.45 (m, 4H); 5.4 (s, 2); 7.1 (d, 2H); 7.6 (d, 2H); 7.8 (d, 1H); 8.1 (d, 1H); 8.5 (s, 1H)
Solvent: CDCl₃

Compound 43
R.M.N.¹H δ (ppm): 1.9–2.05 (m, 4H); 3.25–3.4 (m, 4H); 5.35 (s, 2H); 7.2 (d, 2H); 7.6 (d, 2H); 7.8 (d, 1H); 8.1 (d, 1H); 8.4 (s, 1H)
Solvent: CDCl₃

Compound 44
R.M.N.¹H δ (ppm): 2.0–2.1 (m, 4H); 3.35–3.45 (m, 4H); 5.4 (s, 2H); 6.9–7.0 (m, 2H); 7.6–7.7 (m, 2H); 7.85 (d, 1H); 8.1 (d, 1H); 8.5 (s, 1H)
Solvent: CDCl₃

Compound 45
R.M.N.¹H δ (ppm): 2–2.15 (m, 4H); 3.35–3.5 (m, 4H); 5.45 (s, 2H); 7.45 (t, 1H); 7.55 (d, 1H); 7.85–8.0 (m, 3H); 8.2 (d, 1H); 8.5 (s, 1H)
Solvent: CDCl₃

Compound 46
R.M.N.¹H δ (ppm): 1.95–2.1 (m, 4H); 3.35–3.5 (m, 4H); 5.45 (s, 2H); 7.6 (d, 2H); 7.8 (d, 2H); 7.9 (d, 1H); 8.15 (d, 1H); 8.5 (s, 1H)
Solvent: CDCl₃

Compound 47
R.M.N.¹H δ (ppm): 2–2.1 (m, 4H); 3.35–3.45 (m, 4H); 3.9 (s, 3H); 5.5 (s, 2); 7.7 (d, 2H); 7.9 (d, 1H); 8.0 (d, 2H); 8.15 (d, 1H); 8.5 (s, 1H)
Solvent: CDCl₃

Compound 48
R.M.N.¹H δ (ppm): 2–2.15 (m, 4H); 3.3–3.45 (m, 4H); 5.5 (s, 2H); 7.75–7.9 (m, 3H); 8.1–8.2 (m, 3H); 8.5 (s, 1H)
Solvent: CDCl₃

Compound 49
R.M.N.¹H δ (ppm): 2–2.15 (m, 4H); 3.35–3.5 (m, 4H); 3.75 (s, 3H); 5.4 (s, 2H); 6.8 (d, 2H); 7.65 (d, 2H); 7.8 (d, 1H); 8.15 (d, 1H); 8.5 (s, 1H)
Solvent: CDCl₃

Compound 50
R.M.N.¹H δ (ppm): 2–2.15 (m, 4H); 2.25 (s, 3H); 3.35–3.45 (m, 4H); 5.45 (s, 2H); 7.0 (d, 2H); 7.75 (d, 2H); 7.85 (d, 1H); 8.15 (d, 1H); 8.5 (s, 1H)
Solvent: CDCl₃

Compound 51
R.M.N.¹H δ (ppm): 1.9–2.1 (m, 4H); 3.2–3.45 (m, 4H); 5.2 (s, 2H); 6.7 (d, 2H); 7.35 (d, 2H); 8 (d, 1H); 8.2 (d, 1H); 8.3 (s, 1H); 9.25 (s, 1H)
Solvent: CDCl₃

Compound 52
R.M.N.¹H δ (ppm): 2.0–2.1 (m, 4H); 3.35–3.45 (m, 4H); 3.85 (s, 3H); 3.9 (s, 3H); 5.4 (s, 2H); 6.8 (d, 1H); 7.2–7.35 (m, 2H); 7.8 (d, 1H); 8.15 (d, 1H); 8.5 (s, 1H)
Solvent: CDCl₃

Compound 53
R.M.N.¹H δ (ppm): 2.0–2.1 (m, 4H); 3.3–3.4 (m, 4H); 5.35 (s, 2H); 5.9 (s, 2H); 6.7 (d, 1H); 7.15–7.3 (m, 2H); 7.85 (d, 1H); 8.1 (d, 1H); 8.5 (s, 1H)
Solvent: CDCl₃

Compound 54
R.M.N.¹H δ (ppm): 2–2.1 (m, 4H); 3.35–3.4 (m, 4H); 3.75 (s, 6H); 5.4 (s, 2); 6.35 (s, 1H), 6.8 (s, 2H); 7.85 (d, 1H); 8.2 (d, 1H); 8.5 (s, 1H)
Solvent: CDCl₃

Compound 55
R.M.N.¹H δ (ppm): 2–2.1 (m, 4H); 3.35–3.45 (m, 4H); 3.8 (s, 3H); 3.85 (s, 6H); 5.4 (s, 2H); 7 (s, 2H); 7.85 (d, 1H); 8.2 (d, 1H); 8.5 (s, 1H)
Solvent: CDCl₃

Compound 56
R.M.N.¹H δ (ppm): 1.95–2.1 (m, 4H); 3.25–3.45 (m, 4H); 3.55 (s, 2H); 5.4 (s, 2H); 7.25 (d, 2H); 7.35 (d, 2H); 8.15 (d, 1H); 8.2 (d, 1H); 8.35 (s, 1H); 12.2–12.5 (m, 1H)
Solvent: CDCl₃

Compound 57
R.M.N.¹H δ (ppm): 2.1 (m, 4H); 3.4 (m, 4H); 5.05 (d, 2H); 6.4 (dt, 1H); 6.9 (d, 1H); 7.15–7.3 (m, 3H); 7.35 (d, 2H); 7.9 (d, 1H); 8.15 (d, 1H); 8.5 (s, 1H)
Solvent: CDCl$_3$ Compound 58
R.M.N.¹H δ (ppm): 2.0–2.15 (m, 4H); 3.35–3.5 (m, 4H); 5.2 (d, 2H); 5.7–5.8 (m, 1H); 6.7 (d, 1H); 7.2–7.45 (m, 5H); 7.9 (d, 1H); 8.2 (d, 1H); 8.6 (s, 1H)
Solvent: CDCl$_3$ Compound 59
R.M.N.¹H δ (ppm): 2.05 (m, 4H); 3.4 (m, 4H); 5 (d, 2H); 6.4 (m, 1H); 6.85 (d, 1H); 7.15–7.3 (m, 4H); 7.85 (m, 1H); 8.15 (d, 1H); 8.45 (s, 1H)
Solvent: CDCl$_3$ Compound 60
R.M.N.¹H δ (ppm): 1.95–2.10 (m, 4H); 3.4 (m, 4H); 3.75 (s, 3H); 4.95 (m, 2H); 6.25–6.35 (m, 1H); 6.75–6.9 (m, 3H); 7.2–7.3 (m, 2H); 7.85 (m, 1H); 8.15 (m, 1H); 8.45 (m, 1H)
Solvent: CDCl$_3$ Compound 61
R.M.N.¹H δ (ppm): 1.95–2.15 (m, 4H); 3.3–3.5 (m, 4H); 5.05 (m, 2H); 6.45–6.55 (m, 1H); 6.75–6.9 (d, 1H); 7.2 (m, 1H); 7.6–7.7 (m, 1H); 7.85–7.95 (m, 1H); 8.45 (m, 1H); 8.4 (m, 1H); 8.5 (m, 1H); 8.6 (m, 1H)
Solvent: CDCl$_3$ Compound 62
R.M.N.¹H δ (ppm): 1.9–2.05 (m, 4H); 3.3–3.45 (m, 4H); 5.05 (d, 2H); 6.55–6.7 (m, 1H); 6.8 (d, 1H); 7.25 (m, 2H); 7.9 (m, 1H); 8.2 (m, 1H); 8.45–8.55 (m, 3H)
Solvent: CDCl$_3$ Compound 63
R.M.N.¹H δ (ppm): 1.8–1.9 (m, 2H); 3.25 (m, 2H); 5.1 (s, 2H); 6.9 (s, 1H); 7.4 (s, 1H); 8 (d, 1H); 8.1 (d, 1H); 8.2 (s, 1H); 11.8 (m, 1H)
Solvent: DMSO Compound 64
R.M.N.¹H δ (ppm): 2.05–2.15 (m, 4H); 2.4 (s, 3H); 2.6 (s, 3H); 3.4 (m, 4H); 5.2 (s, 2H); 7.9 (d, 1H); 8.2 (d, 1H); 8.4 (s, 1H)
Solvent: CDCl$_3$ Compound 65
R.M.N.¹H δ (ppm): 1.25–1.75 (m, 8H); 1.9–2.05 (m, 4H); 2.5–2.7 (m, 1H); 3.3–3.4 (m, 4H); 4.2 (d, 2H); 7.8 (d, 1H); 8.1 (d, 1H); 8.45 (s, 1H)
Solvent: CDCl$_3$ Compound 66
R.M.N.¹H δ (ppm): 1 (t, 3H); 1.4–1.55 (m, 2H); 1.8–1.9 (m, 2H); 2.0–2.1 (m, 4H); 3.4–3.5 (m, 4H); 4.3 (t, 2H); 7.9 (d, 1H); 8.2 (d, 1H); 8.5 (s, 1H)
Solvent: CDCl$_3$ Compound 67
R.M.N.¹H δ (ppm): 2–2.15 (m, 4H); 3.35–3.5 (m, 4H); 5.0 (q, 2H); 7.9 (d, 1H); 8.2 (d, 1H); 8.55 (s, 1H)
Solvent: CDCl$_3$ Compound 68
R.M.N.¹H δ (ppm): 2 (m, 4H); 3.15 (m, 1H); 3.3 (m, 4H); 4.05 (m, 2H); 4.5 (m, 2H); 7.08 (m, 1H); 8.15 (m, 1H); 8.4 (s, 1H)
Solvent: CDCl$_3$ Compound 69
R.M.N.¹H δ (ppm): 1.1 (t, 6H); 2.0–2.1 (m, 4H); 2.65 (q, 4H); 2.9 (t, 2H); 3.35–3.45 (m, 4H); 4.4 (t, 2H); 7.9 (d, 1H); 8.2 (d, 1H); 8.5 (s, 1H)
Solvent: CDCl$_3$ Compound 70
R.M.N.¹H δ (ppm): 2–2.15 (m, 4H); 2.3 (s, 1H); 3.35–3.5 (m, 4H); 5.1 (s, 2H); 7.9 (d, 1H); 8.2 (d, 1H); 8.5 (s, 1H)
Solvent: CDCl$_3$ Compound 71
R.M.N.¹H δ (ppm): 2.1 (m, 4H); 3.4 (m, 4H); 4.45 (m, 2H); 4.75 (m, 2H); 6.9 (m, 3H); 7.2–7.3 (m, 2H); 7.9 (m, 1H); 8.2 (m, 1H); 8.5 (s, 1H)
Solvent: CDCl$_3$ Compound 72
R.M.N.¹H δ (ppm): 2.1 (m, 4H); 3.45 (m, 6H); 4.6 (m, 2H); 7.1 (m, 1H); 7.2 (m, 2H); 7.4 (m, 2H); 7.85 (m, 1H); 8.1 (m, 1H); 8.45 (s, 1H)
Solvent: CDCl$_3$ Compound 73
R.M.N.¹H δ (ppm): 1.9–2.05 (m, 4H); 3.3–3.4 (m, 4H); 3.08 (s, 3H); 6.7 (s, 1H); 7.2–7.35 (m, 3H)); 7.7–7.85 (m, 3H); 8.1 (d, 1H); 8.4 (s, 1H)
Solvent: CDCl$_3$ Compound 74
R.M.N.¹H δ (ppm): 1.4–1.6 (m, 1H); 1.7–2 (m, 5H); 3–3.1 (m, 2H); 3.3–3.4 (m, 2H); 5.5 (s, 2H); 7.6 (d, 2H); 7.8 (d, 2H); 7.9 (d, 1H); 8.3 (d, 1H); 8.5 (s, 1H)
Solvent: CDCl$_3$ Compound 75
R.M.N.¹H δ (ppm): 1.4 (m, 1H); 1.7–1.95 (m, 5H); 3–3.1 (m, 2H); 3.3–3.4 (m, 2H); 3.8 (s, 3H); 3.9 (s, 3H); 5.4 (s, 2H); 6.8 (d, 1H); 7.25–7.35 (m, 2H); 7.9 (d, 1H); 8.3 (d, 1H); 8.40 (s, 1H)
Solvent: CDCl$_3$ Compound 76
R.M.N.¹H δ (ppm): 1.35–2.1 (m, 6H); 3.05 (t, 2H); 3.35 (m, 2H); 5.1 (d, 2H); 6.5 (dt, 1H); 6.9 (d, 1H); 7.1–7.5 (m, 5H); 7.9 (d, 1H); 8.3 (d, 1H); 8.55 (s, 1H)
Solvent: CDCl$_3$ Compound 77
R.M.N.¹H δ (ppm): 2.9 (m, 4H); 3.45 (m, 2H); 3.6 (m, 2H); 5.1 (m, 2H); 6.5 (m, 1H); 6.85 (d, 1H); 7.2 (m, 1H); 7.65 (m, 1H); 7.9 (m, 1H); 8.25 (m, 1H); 8.45 (m, 1H); 8.5 (m, 1H); 8.55 (s, 1H)
Solvent: CDCl$_3$ Compound 78
R.M.N.¹H δ (ppm): 2.3 (s, 3H); 2.9 (s, 6H); 5.4 (s, 2H); 7.1 (d, 2H); 7.6 (d, 2H); 7.85 (d, 1H); 8.2 (d, 1H); 8.5 (s, 1H)
Solvent: CDCl$_3$ Compound 79
R.M.N.¹H δ (ppm): 2.95 (s, 6H); 5.45 (s, 2H); 7.55 (d, 2H); 7.75 (d, 2H); 7.9 (d, 1H); 8.2 (d, 1H); 8.5 (s, 1H)
Solvent: CDCl$_3$ Compound 80
R.M.N.¹H δ (ppm): 2.85 (s, 6H); 5.2 (s, 2H); 6.7 (d, 2H); 7.3 (d, 2H); 8 (d, 1H); 8.2–8.3 (m, 2H); 9.3 (s, 1H)
Solvent: CDCl$_3$ Compound 81
R.M.N.¹H δ (ppm): 2.9 (s, 6H); 3.9 (s, 3H); 5.45 (s, 2H); 7.7 (m, 2H); 7.85 (m, 1H); 7.9 (m, 2H); 8.2 (d, 1H); 8.5 (s, 1H)
Solvent: CDCl$_3$ Compound 82
R.M.N.¹H δ (ppm): 2.85 (s, 6H); 3.6 (s, 2H); 5.35 (s, 2H); 7.25 (d, 2H); 7.5 (d, 2H); 8.15 (d, 1H); 8.3 (d, 1H); 8.35 (s, 1H); 12.2–12.45 (m, 1H)
Solvent: DMSO Compound 83
R.M.N.¹H δ (ppm): 2.9 (s, 6H); 3.7 (s, 2H); 5.45 (s, 2H); 7.25 (m, 2H); 7.7 (m, 2H); 7.85 (m, 1H); 8.2 (d, 1H); 8.5 (s, 1H)
Solvent: CDCl$_3$ Compound 84
R.M.N.¹H δ (ppm): 2.9 (s, 6H); 5.5 (s, 2H); 7.25 (m, 1H); 7.85 (m, 1H); 8.05 (m, 1H); 8.25 (d, 1H); 8.5 (m, 2H); 8.9 (s, 1H)
Solvent: CDCl₃

Compound 85
R.M.N.¹H δ (ppm): 2.9 (s, 6H); 5.05 (d, 2H); 6.4–6.55 (dt, 1H); 6.9 (d, 1H); 7.2–7.4 (m, 5H); 7.9 (d, 1H); 8.25 (d, 1H); 8.55 (s, 1H)
Solvent: CDCl₃

Compound 86
R.M.N.¹H δ (ppm): 2.95 (s, 6H); 5.29 (d, 2H); 5.7–5.8 (m, 1H); 6.7 (d, 1H); 7.2–7.45 (m, 5H); 7.9 (d, 1H); 8.25 (d, 1H); 8.5 (s, 1H)
Solvent: CDCl₃

Compound 87
R.M.N.¹H δ (ppm): 2.9 (s, 6H); 5.05 (d, 2H); 6.55–6.7 (m, 1H); 6.85 (d, 1H); 7.2 (m, 2H); 7.85 (m, 1H); 8.25 (d, 1H); 8.5 (m, 3H)
Solvent: CDCl₃

Compound 88
R.M.N.¹H δ (ppm): 2.8 (s, 6H); 3.2 (s, 1H); 4.9 (s, 2H); 8.1 (m, 1H); 8.2 (d, 1H); 8.3 (s, 1H)
Solvent: DMSO Compound 89
R.M.N.¹H δ (ppm): 2.9 (s, 6H); 5.2 (s, 2H); 7.2 (m, 3H); 7.4 (m, 2H); 7.85 (m, 1H); 8.2 (d, 1H); 8.55 (s, 1H)
Solvent: CDCl₃

Compound 90
R.M.N.¹H δ (ppm): 2.95 (s, 6H); 3.85 (s, 3H); 6.8 (s, 1H); 7.3–7.4 (m, 3H); 7.75–7.9 (m, 3H); 8.2 (d, 1H); 8.5 (s, 1H)
Solvent: CDCl₃

Compound 91
R.M.N.¹H δ (ppm): 1.75–1.9 (m, 8H); 2.5 (s, 3H); 3.4–3.5 (m, 4H); 5.5 (s, 2H); 7.2–7.3 (dd, 1H); 7.6–7.65 (d, 1H); 8.05–8.01 (d, 1H); 8.2 (s, 1H); 8.3–8.35 (d, 1H); 8.55 (d, 1H); 8.95 (s, 1H)
Solvent: CDCl₃

Compound 92
R.M.N.¹H δ (ppm): 1.75–2 (m, 8H); 2.5 (s, 3H); 3.4–3.5 (m, 4H); 5.1 (d, 1H); 5.4–5.55 (dt, 1H); 6.9–7 (d, 1H); 7.2–7.3 (m, 4H); 7.4 (d, 2H); 7.6 (d, 1H); 8.2 (s, 1H); 8.3 (d, 1H)
Solvent: CDCl₃

Compound 93
R.M.N.¹H δ (ppm): 2–2.1 (m, 4H); 2.5 (s, 3H); 3.3–3.4 (m, 4H); 5.5 (s, 2H); 7.6 (m, 3H); 7.8 (d, 2H); 8.1–8.2 (m, 2H)
Solvent: CDCl₃

Compound 94
R.M.N.¹H δ (ppm): 2–2.1 (m, 4H); 2.5 (s, 3H); 3.4–3.5 (m, 4H); 3.8 (s, 3H); 3.9 (s, 3H); 5.4 (s, 2H); 6.8 (d, 1H); 7.3–7.4 (m, 2H); 7.5 (d, 1H); 8.1–8.2 (m, 2H);
Solvent: CDCl₃

Compound 95
R.M.N.¹H δ (ppm): 2.1–2.2 (m, 4H); 2.5 (s, 3H); 3.4–3.5 (m, 4H); 3.9 (s, 3H); 5.5 (s, 2H); 7.6 (m, 1H); 7.7 (m, 2H); 7.95–8 (m, 2H); 8.1–8.2 (m, 2H)
Solvent: CDCl₃

Compound 96
R.M.N.¹H δ (ppm): 2 (m, 4H); 2.5 (s, 3H); 3.3–3.4 (m, 4H); 3.6 (s, 2H); 5.3 (s, 2H); 7.3 (m, 2H); 7.45 (m, 2H); 7.8 (m, 2H); 8.1 (s, 1H); 8.2 (d, 2H); 12.4 (m, 1H)
Solvent: DMSO Compound 97
R.M.N.¹H δ (ppm): 1.95 (m, 4H); 2.5 (s, 3H); 3.35 (m, 4H); 5.4 (s, 2H); 7.35 (dd, 1H); 7.55 (d, 1H); 8.05 (s, 1H); 8.15 (d, 1H); 8.5 (d, 1H); 8.7 (s, 1H)
Solvent: DMSO Compound 98
R.M.N.¹H δ (ppm): 2–2.1 (m, 4H); 2.45 (s, 3H); 3.3–3.45 (m, 4H); 5.05 (d, 2H); 6.4–6.5 (dt, 1H); 6.85–6.95 (d, 1H); 7.1–7.45 (m, 5H); 7.6 (d, 1H); 8.1–8.2 (m, 2H)
Solvent: CDCl₃

Compound 99
R.M.N.¹H δ (ppm): 2.4–3.75 (m, 13H); 5.35 (s, 2H); 7.1–7.5 (m, 4H); 7.8 (d, 1H); 8.1 (s, 1H); 8.25 (d, 1H)
Solvent: DMSO Compound 100
R.M.N.¹H δ (ppm): 2.5 (s, 3H); 2.9 (m, 4H); 3.45 (m, 2H); 3.65 (m, 2H); 5.1 (m, 2H); 6.5 (m, 1H); 6.85 (d, 1H); 7.2 (m, 1H); 7.6 (m, 1H); 7.7 (m, 1H); 8.2 (m, 2H); 8.45 (d, 1H); 8.6 (s, 1H)
Solvent: CDCl₃

Compound 101
R.M.N.¹H δ (ppm): 2.5 (s, 3H); 2.95 (s, 6H); 5.5 (s, 2H); 7.6 (m, 3H); 7.8 (m, 2H); 8.15–8.25 (m, 2H)
Solvent: CDCl₃

Compound 102
R.M.N.¹H δ (ppm): 2.2 (s, 3H); 2.6 (s; 6H); 3.25 (s, 2H); 5.1 (s, 2H); 7 (m, 2H); 7.15 (m, 2H); 7.5 (m, 1H); 7.8 (s, 1H); 8 (d, 1H); 12 (m, 1H)
Solvent: DMSO Compound 103
R.M.N.¹H δ (ppm): 2.5 (s, 3H); 3 (s, 6H); 5.1 (d, 2H); 6.4–6.5 (dt, 1H); 6.9 (d, 1H); 7.15–7.4 (m, 6H); 7.6 (d, 1H); 8.2 (m, 1H)
Solvent: CDCl₃

Compound 104
R.M.N.¹δ (ppm): 2.5 (s, 3H); 2.95 (s, 6H); 5.1 (d, 2H); 6.4–6.55 (dt, 1H); 6.8–6.85 (d, 1H); 7.2 (m, 1H); 7.6 (dd, 1H) 7.7 (dd, 1H); 8.2–8.25 (m, 2H); 8.4 (d, 1H); 8.6 (s, 1H)
Solvent : CDCl₃

Compound 105
R.M.N.¹H δ (ppm): 2.5 (s, 3H); 2.95 (s, 6H); 5.1 (d, 2H); 6.6–6.7 (dt, 1H); 6.8 (d, 1H); 7.2 (d, 26H); 7.6 (d, 1H); 8.2–8.25 (dd, 2H) 8.5 (d, 2H)
Solvent: CDCl₃

Compound 106
R.M.N.¹H δ (ppm): 1.7–2 (m, 8H); 2.55 (m, 3H); 3.35–3.6 (m, 4H); 5.1 (d, 2H); 6.45 (dt, 1H); 6.85 (d, 1H); 7.1–7.45 (m, 6H); 8.25 (m, 2H)
Solvent: CDCl₃

Compound 107
R.M.N.¹H δ (ppm): 2.9 (d, 6H); 5.5 (s, 2H ); 7.6 (m, 2H); 7.7 (m, 2H); 8.0 (m, 1H); 8.4 (m, 1H); 8.7 (s, 1H)
Solvent: CDCl₃

Compound 108
R.M.N.¹H δ (ppm): 1.9 (m, 4H); 3.25 (m, 4H); 6.85 (d, 2H); 6.3–6.4 (dt, 1H); 6.6–6.7 (d, 1H); 7.15–7.3 (m, 4H); 7.35–7.4 (d, 2H); 7.5 (s, 1H) 8.05 (d, 1H); 10.1 (m, 1H),
Solvent: DMSO

TABLE 2

| No Compound | X1 | R | NR4R5 | Yield (%) | MP (° C.) | Method |
|---|---|---|---|---|---|---|
| 109 | H | (E) C6H5CH=CHCH2 | azepane | 28 | 176 | A |
| 110 | 7-Cl | CH2=CHCH2 | azepane | 24 | 173 | A |
| 111 | 7-Cl | C6H5CH2 | azepane | 58 | 148 | A |
| 112 | 7-Cl | 4-CH3C6H4CH2 | azepane | 50 | 182 | A |
| 113 | 7-Cl | 2-ClC6H4CH2 | azepane | 77 | 228 | A |
| 114 | 7-Cl | 3-ClC6H4CH2 | azepane | 31 | 166 | A |
| 115 | 7-Cl | 4-ClC6H4CH2 | azepane | 60 | 245 | A |
| 116 | 7-Cl | 4-BrC6H4CH2 | azepane | 38 | 244 | A |
| 117 | 7-Cl | 4-FC6H4CH2 | azepane | 42.5 | 224 | A |
| 118 | 7-Cl | 4-CF3C6H4CH2 | azepane | 39 | 232 | A |
| 119 | 7-Cl | 4-CNC6H4CH2 | azepane | 46 | >260 | A |
| 120 | 7-Cl | 2-(OCH3)C6H4CH2 | azepane | 57 | 184 | A |

TABLE 2-continued
| No Compound | X1 | R | NR4R5 | Yield (%) | MP (° C.) | Method |
|---|---|---|---|---|---|---|
| 121 | 7-Cl | 3-(OCH3)C6H4CH2 | 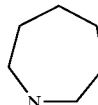 | 46 | 163 | A |
| 122 | 7-Cl | 4-(OCH3)C6H4CH2 | 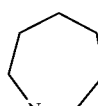 | 32.5 | 164–165 | A |
| 123 | 7-Cl | 3,4-Cl2C6H3CH2 | 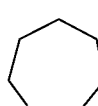 | 60 | 212 | A |
| 124 | 7-Cl | 3,4-(OCH3)2C6H3CH2 | 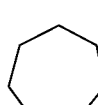 | 39 | 153 | A |
| 125 | 7-Cl | (2-pyridyl)CH2 | 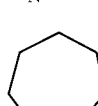 | 9 | 153 | A |
| 126 | 7-Cl | (3-pyridyl)CH2 | 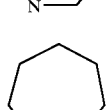 | 8 | 184 | C |
| 127 | 7-Cl | C6H5CH2CH2 | 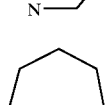 | 7 | 196 | A |
| 128 | 7-Cl | 4(CH3O)C6H4(CH2)2 | 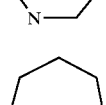 | 61 | 196 | A |
| 129 | 7-Cl | C6H5(CH2)3 | 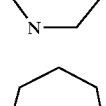 | 36 | 130 | A |
| 130 | 7-Cl | C6H5C(=O)CH2 | 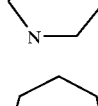 | 38.5 | 230–232 | A |
| 131 | 7-Cl | 4(CH3O)C6H4C(=O)CH2 | 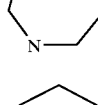 | 42 | 238 | A |
| 132 | 7-Cl | 4-ClC6H4C(=O)CH2 | 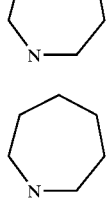 | 59 | 238 | A |

TABLE 2-continued
| No Compound | X1 | R | NR4R5 | Yield (%) | MP (° C.) | Method |
|---|---|---|---|---|---|---|
| 133 | 7-Cl | 4(CH3O)-3-(COOCH3)—C6H3C(=O)CH2 | 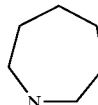 | 30 | 136 | A |
| 134 | 7-Br | 4-ClC6H4CH2 | 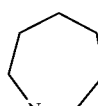 | 57 | 247 | A |
| 135 | 7-Br | 4-FC6H4CH2 | 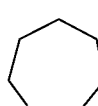 | 54 | 216 | A |
| 136 | 7-Br | 4-CNC6H4CH2 | 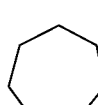 | 53 | 293 | A |
| 137 | 7-Br | 3,4-(CH3O)2C6H3CH2 | 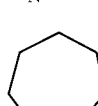 | 61 | 174 | A |
| 138 | 7-Br | 4-(CH2COOH)C6H4CH2 | 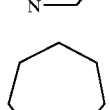 | 1 | 269 | B |
| 139 | 7-Br | (3-pyridyl)CH2 | 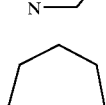 | 4 | 192 | C |
| 140 | 7-Br | (E) C6H5CH=CHCH2 | 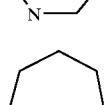 | 70 | 198 | A |
| 141 | 7-Br | (Z) C6H5CH=CHCH2 | 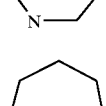 | 57 | 187 | A |
| 142 | 7-Br | 4-ClC6H4CH2 | 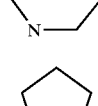 | 18 | 185 | A |
| 143 | 7-Br | 4-FC6H4CH2 | 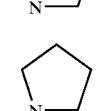 | 16 | 233 | A |
| 144 | 7-Br | 4-CNC6H4CH2 | 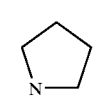 | 52 | 222 | A |
| 145 | 7-Br | 4-(COOCH3)C6H4CH2 | 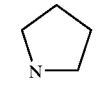 | 31 | 193 | A |

TABLE 2-continued
| No Compound | X1 | R | NR4R5 | Yield (%) | MP (° C.) | Method |
|---|---|---|---|---|---|---|
| 146 | 7-Br | 4-(CH3O)C6H4CH2 |  | 14 | 164 | B |
| 147 | 7-Br | 4-(OCOCH3)C6H4CH2 |  | 24 | 199 | B |
| 148 | 7-Br | 4-OHC6H4CH2 |  | 15 | 283 | B |
| 149 | 7-Br | 3,4-(OCH2O)C6H4CH2 |  | 57 | 234 | A |
| 150 | 7-Br | 3,5-(CH3O)2C6H4CH2 |  | 21 | 168 | A |
| 151 | 7-Br | 3,4,5(CH3O)3C6H2CH2 |  | 21 | 199–201 | A |
| 152 | 7-Br | 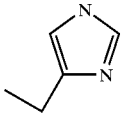 |  | 4 | — | B |
| 153 | 7-Br | n-butyl |  | 13 | 130 | B |
| 154 | 7-Br | CH(C6H5)COOCH3 |  | 55 | 187 | A |
| 155 | 7-Br | (E) C6H5CH=CHCH2 |  | 10 | 206 | B |
| 156 | 7-Br | CH(C6H5)COOCH3 |  | 32 | 83 | B |
| 157 | 7-CH3 | (E) C6H5CH=CHCH2 | 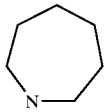 | 43 | 193 | A |
| 158 | 7-CH3 | (E) C6H5CH=CHCH2 |  | 35 | 225 | A |
| 159 | 8-CH3 | CH3 |  | 70 | — | A |

TABLE 2-continued

| No Compound | X1 | R | NR4R5 | Yield (%) | MP (° C.) | Method |
|---|---|---|---|---|---|---|
| 160 | 8-CH3 | (E) C6H5CH=CHCH2 |  | 18 | — | A |
| 161 | 7-OH | (E) C6H5CH=CHCH2 |  | 10 | 255 | A |
| 162 |  | (E) C6H5CH=CHCH2 |  | 28 | — | A |

Compound 109
N.M.R.¹H δ (ppm): 1.7–1.85 (m. 8H); 3.3–3.45 (m. 4H); 5.85 (d. 2H); 6.35–6.45 (dt. 1H); 6.65–6.75 (d. 1H); 7.25 (t. 1H); 7.35 (t. 1H); 7.45 (d. 1H); 7.6 (t. 1H); 7.85 (t,1H); 8.2 (d. 1H); 8.3 (d. 1H)
Solvent: CDCl₃

Compound 110
N.M.R.¹H δ (ppm): 1.65–1.95 (m. 8H); 3.35 (m. 4H); 4.8 (d. 2H); 5.25–5.4 (m. 2H); 5.9–6.1 (m. 1H); 7.55–8.4 (m. 3H)
Solvent: CDCl₃

Compound 111
N.M.R.¹H δ (ppm): 1.7–1.9 (m. 8H); 3.35 (m. 4H); 5.25 (s. 2H); 7.2–7.4 (m. 3H); 7.45 (d. 2H); 7.6 (d. 1H); 8.15 (d. 1H); 8.4 (s. 1H)
Solvent: CDCl₃

Compound 112
N.M.R.¹H δ (ppm): 1.7–1.9 (m. 8H); 2.3 (s. 3H); 3.35 (m. 4H); 5.25 (s. 2H); 7.1–8.45 (m. 7H)
Solvent: CDCl₃

Compound 113
N.M.R.¹H δ (ppm): 1.7–1.95 (m. 8H); 3.4 (m. 4H); 5.45 (s. 2H); 7.15–7.3 (m. 3H); 7.4 (d. 1H); 7.65 (d. 1H); 8.2 (d: 1H); 8.45 (s. 1H)
Solvent: CDCl₃

Compound 114
N.M.R.¹H δ (ppm): 1.7–1.9 (m. 8H); 3.4 (m. 4H); 5.25 (s. 2H); 7.2–7.4 (m. 3H); 7.45 (s. 1H); 7.6 (d. 1H); 8.15 (d. 1H); 8.45 (s. 1H)
Solvent: CDCl₃

Compound 115
N.M.R.¹H δ (ppm): 1.65–1.85 (m. 8H); 3.3 (m. 4H); 5.15 (s. 2H); 7.25 (d. 2H); 7.35 (d. 2H); 7.55 (d. 1H); 8.05 (d. 1H); 8.3 (s. 1H)
Solvent: CDCl₃

Compound 116
N.M.R.¹H δ (ppm): 1.7–1.95 (m. 8H); 3.35 (m. 4H); 5.25 (d. 2H); 7.35 (d. 2H); 7.45 (d. 2H); 7.6 (d. 1H); 8.1 (d. 1H); 8.4 (s. 1H)
Solvent: CDCl₃

Compound 117
N.M.R.¹H δ (ppm): 1.7–1.9 (m. 8H); 3.35 (m. 4H); 5.35 (s. 2H); 7.5–7.7 (m. 5H); 8.15 (d. 1H); 8.4 (s. 1H)
Solvent: CDCl₃

Compound 118
N.M.R.¹H δ (ppm): 1.7–1.9 (m. 8H); 3.4 (m. 4H); 5.35 (s. 2H); 7.5–7.7 (m. 5H); 8.1 (d. 1H); 8.4 (s. 1H)
Solvent: CDCl₃

Compound 119
N.M.R.¹H δ (ppm): 1.7–1.9 (m. 8H); 3.4 (m. 4H); 3.9 (s. 3H); 5.35 (s. 2H); 6.9 (m. 2H); 7.2 (d. 1H); 7.3 (t. 1H); 7.6 (d. 1H); 8.2 (d. 1H); 8.4 (s. 1H)
Solvent: CDCl₃

Compound 120
N.M.R.¹H δ (ppm): 1.7–2.0 (m. 8H); 3.35 (m. 4H); 3.75 (s. 3H); 5.4 (s, 2H); 6.8 (m. 1H); 7.15–7.3 (m. 3H); 7.7 (d. 1H); 8.35 (m. 2H)
Solvent: CDCl₃

Compound 121
N.M.R.¹H δ (ppm): 1.7–1.9 (m. 8H); 3.35 (m. 4H); 3.8 (s. 3H); 5.2 (s. 2H); 6.85 (d. 2H); 7.45 (d. 2H); 7.65 (d. 1H); 8.15 (d. 1H); 8.45 (s. 1H)
Solvent: CDCl₃

Compound 122
N.M.R.¹H δ (ppm): 1.7–1.9 (m. 8H); 3.4 (m. 4H); 5.2 (s. 2H); 7.3 (d. 1H); 7.4 (d. 1H); 7.5 (s. 1H); 7.6 (d. 1H); 8.15 (d. 1H); 8.4 (s. 1H)
Solvent: CDCl₃

Compound 123
N.M.R.¹H δ (ppm): 1.7–1.9 (m. 8H); 3.4 (m. 4H); 3.85 (s. 3H); 3.90 (s. 3H); 5.2 (s. 2H); 6.85 (d. 1H); 7.1 (m. 2H); 7.65 (d. 1H) 8.2 (d. 1H); 8.45 (s. 1H)
Solvent: CDCl₃

Compound 124
N.M.R.¹H δ (ppm): 1.65–195 (m. 8H); 3.4 (m. 4H); 5.45 (s. 2H); 7.2 (m. 1H); 7.3 (d. 1H); 7.65 (m. 2H); 8.2 (d. 1H); 8.4 (s. 1H); 8.55 (d. 1H)
Solvent: CDCl₃

Compound 125
N.M.R.¹H δ (ppm): 1.7–1.95 (m. 8H); 3.4 (m. 4H); 5.3 (s. 2H); 7.25 (m. 1H); 7.6 (d. 1H); 7.85 (d. 1H); 8.15 (d. 1H); 8.45 (s. 1H); 8.6 (d. 1H); 8.75 (s. 1H)
Solvent: CDCl₃

Compound 126
N.M.R.¹H (ppm): 1.55–1.9 (m. 8H); 3.1 (t. 2H); 3.25 (m. 4H); 4.25 (t. 2H); 7.05–7.25 (m.5H); 7.55 (d. 1H); 8.1 (d. 1H); 8.35 (s. 1H)
Solvent: CDCl₃

Compound 127
N.M.R.¹H δ (ppm): 1.75–1.9 (m. 8H); 3.15 (t. 2H); 3.35 (m. 4H); 3.75 (s. 3H); 4.35 (t. 2H); 6.8 (d. 2H); 7.15 (d. 2H); 7.6 (d. 1H); 8.15 (d. 1H); 8.4 (s. 1H)
Solvent: CDCl₃

Compound 128
N.M.R.¹H δ (ppm): 1.7–1.95 (m. 8H); 2.2 (m. 2H); 2.7 (t. 2H); 3.35 (m. 4H); 4.2 (t. 2H); 7–7.3 (m. 5H); 7.65 (d. 1H); 8.1 (d. 1H); 8.45 (s. 1H)
Solvent: DMSO Compound 129
N.M.R.¹H δ (ppm): 1.7–1.9 (m. 8H); 3.4 (m. 4H); 3.9 (s. 3H); 5.6 (s. 2H); 7.0 (d. 2H); 7.7 (d. 1H); 8 (d. 2H); 8.25 (d. 1H); 8.45 (s. 1H)
Solvent: CDCl₃

Compound 130
N.M.R.¹H δ (ppm): 1.6–1.9(m.8H); 3.4(m.4H); 5.8 (s.2H); 7.6(t.2H); 7.75(t.1H); 7.95(d.1H); 8.1(m.3H); 8.3 (d.1H)
Solvent: DMSO Compound 131
N.M.R.¹H δ (ppm): 1.7–1.95 (m. 8H); 3.4 (m. 4H); 5.55 (s. 2H); 7.45 (d. 2H); 7.65 (d. 1H); 7.9 (d. 2H); 8.2 (d. 1H); 8.4 (s. 1H)
Solvent: CDCl₃

Compound 132
N.M.R.¹H δ (ppm): 1.7–1.9 (m. 8H); 3.4 (m. 4H); 3.9 (s. 3H); 4.0 (s. 3H); 5.6 (s. 2H); 7.1 (d. 1H); 7.7 (d. 1H); 8.1 (d. 1H); 8.2 (d. 1H); 8.4 (m. 2H)
Solvent: CDCl₃

Compound 133
N.M.R.¹H δ (ppm): 1.75–1.9 (m. 8H); 3.4 (m. 4H); 3.9 (s. 3H); 4.0 (s. 3H); 5.6 (s. 2H); 7.1 (m. 1H); 7.7 (m. 1H); 8.15–8.45 (m. 4H)
Solvent: CDCl₃

Compound 134
N.M.R.¹H δ (ppm): 1.75–1.9 (m. 8H); 3.35 (m. 4H); 5.25 (s. 2H); 7.25–8.6 (m. 7H);
Solvent: CDCl₃

Compound 135
N.M.R.¹H δ (ppm): 1.65–1.95 (m. 8H); 3.3–3.45 (m. 4H); 5.25 (s. 2H); 6.95–7.1 (m. 2H); 7.4–7.55 (m. 2H); 7.8 (d. 1H); 8.1 (d. 1H); 8.6 (s. 1H)
Solvent: CDCl₃

Compound 136
N.M.R.¹H δ (ppm): 1.75–1.95 (m. 8H); 3.3–3.45 (m. 4H); 5.3 (s. 2H); 7.5–7.7 (m. 4H); 7.8 (m. 1H); 8.1 (dd. 1H); 8.6 (s. 1H)
Solvent: CDCl₃

Compound 137
N.M.R.¹H δ (ppm): 1.7–1.9 (m. 8H); 3.25–3.4 (m. 4H); 3.8 (s. 3H); 3.82 (s. 3H); 5.2 (s. 2H); 6.8 (d. 1H); 7.05–7.1 (m. 2H); 7.75 (d. 1H); 8.05 (d. 1H); 8.6 (s. 1H)
Solvent: CDCl₃

Compound 138
N.M.R.¹H δ (ppm): 1.6–1.85 (m. 8H); 3.2–3.4 (bs. 4H); 3.55 (s. 2H); 5.2 (s. 2H); 7.2 (m. 2H); 7.3 (m. 2H); 8 (m. 1H); 8.2 (m. 1H); 8.25 (s. 1H); 12.3 (bs. 1H)
Solvent: DMSO Compound 139
N.M.R.¹H δ (ppm): 1.75–1.9 (m. 8H); 3.4 (m. 4H); 5.35 (s. 2H); 7.3 (m. 1H); 7.8 (d. 1H); 7.9 (d. 1H); 8.1 (d. 1H); 8.65 (m. 2H); 8.8 (s. 1H)
Solvent: CDCl₃

Compound 140
N.M.R.¹H δ (ppm): 1.8–1.95 (m. 8H); 3.4 (m. 4H); 4.9 (d. 2H); 6.35 (m. 1H); 6.75 (d. 1H); 7.25–7.45 (m. 5H); 7.8–8.65 (m. 3H)
Solvent: CDCl₃

Compound 141
N.M.R.¹H δ (ppm): 1.35–2.05 (m. 6H); 2.95 (t. 2H); 3.4 (d. 2H); 4.9 (d. 2H); 6.35 (dt. 1H); 6.75 (d. 1H); 7.25–7.45 (m. 5H); 7.85 (d. 1H); 8.15 (d. 1H); 8.65 (s. 1H)
Solvent: CDCl₃

Compound 142
N.M.R.¹H δ (ppm): 2–2.1 (m. 4H); 3.3–3.4 (m. 4H); 5.25 (s. 2H); 7.25 (d. 2H); 7.4 (d. 2H); 7.75 (d. 1H); 7.95 (d. 1H); 8.55 (s. 1H)
Solvent: CDCl₃

Compound 143
N.M.R.¹H δ (ppm): 1.95–2.1 (m. 4H); 3.3–3.45 (m. 4H); 5.2 (s. 2H); 6.95–7.1 (m. 2H); 7.35–7.5 (m. 2H); 7.75 (d. 1H); 7.95 (d. 1H); 8.6 (s. 1H)
Solvent: CDCl₃

Compound 144
N.M.R.¹H δ (ppm): 2–2.15 (m. 4H); 3.3–3.45 (m. 4H); 5.3 (s. 2H); 7.55–7.7 (m. 4H); 7.8–7.9 (d. 1H); 8.0 (d. 1H); 8.6 (s. 1H)
Solvent: CDCl₃

Compound 145
N.M.R.¹H δ (ppm): 2–2.1 (m. 4H); 3.3–3.4 (m. 4H); 3.9 (s. 3H); 5.3 (s. 2H); 7.5 (d. 2H); 7.8 (d. 1H); 7.9–8.05 (m. 3H); 8.6 (s. 1H)
Solvent: CDCl₃

Compound 146
N.M.R.¹H δ (ppm): 2–2.1 (m. 4H); 3.3–3.4 (m. 4H); 3.8 (s. 3H); 5.2 (s. 2H); 6.9 (d. 2H); 7.45 (d. 2H); 7.8 (d. 1H); 7.95 (d. 1H); 8.6 (s. 1H)
Solvent: CDCl₃

Compound 147
N.M.R.¹H δ (ppm): 2–2.1 (m. 4H); 2.3 (s. 3H); 3.3–3.4 (m. 4H); 5.25 (s. 2H); 7.05 (d. 2H); 7.5 (d. 2H); 7.8 (d. 1H); 8.0 (d. 1H); 8.6 (s. 1H)
Solvent: CDCl₃

Compound 148
N.M.R.¹H δ (ppm): 2.7 (s. 6H); 5 (s. 2H); 6.6 (d. 2H); 7.1 (d. 2H); 7.9 (d. 1H); 8.0 (d. 1H); 8.1 (s. 1H); 9.35 (s. 1H)
Solvent: CDCl₃

Compound 149
N.M.R.¹H δ (ppm): 2–2.15 (m. 4H); 3.3–3.45 (m. 4H); 5.15 (s. 2H); 5.9 (s. 2H); 6.75 (d. 1H); 6.9–7.0 (m. 2H); 7.8 (d. 1H); 7.9 (d. 1H); 8.6 (s. 1H)
Solvent: CDCl₃

Compound 150
N.M.R.¹H δ (ppm): 2.0–2.1 (m. 4H); 3.3–3.4 (m. 4H); 3.75 (s. 6H); 5.2 (s. 2H); 6.4 (s. 1H); 6.65 (s. 2H); 7.8 (d. 1H); 7.95 (d. 1H); 8.65 (s. 1H)
Solvent: CDCl₃

Compound 151
N.M.R.¹H δ (ppm): 2.0–2.1 (m. 4H); 3.3–3.4 (m. 4H); 3.85 (s. 3H); 3.9 (s. 6H); 5.2 (s. 2H); 6.8 (s. 2H); 7.8 (d. 1H); 7.95 (d. 1H); 8.65 (s. 1H)
Solvent: CDCl₃

Compound 152
N.M.R.¹H δ (ppm): 2 (m. 4H); 3.35 (m. 4H); 5.2 (s. 2H); 7.15 (s. 1H); 7.6 (s. 1H); 8–8.15 (m. 2H); 8.3 (s. 1H); 12 (m. 1H)
Solvent: DMSO Compound153
N.M.R.¹H δ (ppm): 0.95 (t. 3H); 1.35–1.5 (m. 2H); 1.8–1.9 (m. 2H); 2.0–2.1 (m. 4H); 3.4–3.5 (m. 4H); 4.1 (t. 2H); 7.8 (d. 1H); 8.0 (d. 1H); 8.6 (s. 1H)
Solvent: CDCl₃

Compound 154
N.M.R.¹H δ (ppm): 2.45–2.55 (m. 4H); 3.25–3.4 (m. 4H); 3.7 (s. 3H); 6.6 (s. 1H); 7.35–7.50 (m. 3H); 7.55 (d. 2H); 8–8.1 (m. 2H); 8.3 (s. 1H)
Solvent: DMSO Compound 155
N.M.R.¹H δ (ppm): 2.9 (s. 6H); 4.8 (d. 2H); 6.2–6.3 (dt. 1H); 6.7 (d. 1H); 7.1–7.35 (m. 5H); 7.75 (d. 1H); 8.0 (d. 1H); 8.6 (s. 1H)
Solvent: CDCl₃

Compound 156
N.M.R.¹H δ (ppm): 2.9 (s. 6H); 3.8 (s. 3H); 6.6 (s. 1H); 7.35–7.45 (m. 3H); 7.55 (d. 2H); 7.8 (d. 1H); 8 (d. 1H): 8.6 (s. 1H)
Solvent: CDCl₃

Compound 157

N.M.R.¹H δ (ppm): 1.8–1.95 (m. 8H); 2.5 (s. 3H); 3.4–3.5 (m. 4H); 4.9 (d. 2H); 6.3–6.45 (dt. 1H); 6.7–6.8 (d. 1H); 7.2–7.3 (m. 3H); 7.35 (d. 2H); 7.55 (d. 2H); 8.1 (d. 1H); 8.3 (s. 1H)

Solvent: CDCl₃

Compound 158

N.M.R.¹H δ (ppm): 2.1 (m. 4H); 2.5 (s. 3H); 3.4 (m. 4H); 4.9 (d. 2H); 6.3–6.45 (dt. 1H); 6.7–6.8 (d. 1H); 7.2–7.4 (m. 5H); 7.5 (m. 1H); 8 (d. 1H); 8.3 (d. 1H)

Solvent: CDCl₃

Compound 159

N.M.R.¹H δ (ppm): 1.7–1.9 (m. 8H); 2.45 (s. 3H); 3.25–3.35 (m. 4H); 3.65 (s. 3H); 7.2–7.3 (m. 2H); 8 (m. 1H); 8.2–8.3 (m. 1H)

Solvent: CDCl₃

Compound 160

N.M.R.¹H δ (ppm): 1.8–2 (m. 8H); 2.55 (s. 3H); 3.3–3.5 (m. 4H); 4.9 (m. 2H); 6.3–6.4 (m. 1H); 6.7–6.8 (d. 1H); 7.2–7.4 (m. 6H); 8.1 (s. 1H); 8.35 (m. 1H)

Solvent: CDCl₃

Compound 161

N.M.R.¹H δ (ppm): 2 (m. 4H); 3.4 (m. 4H); 4.8 (d. 2H); 6.35–6.4 (dt. 1H); 6.7 (d. 1H); 7.2–7.4 (m. 4H); 7.45 (d. 2H); 7.55 (s. 1H); 8 (d. 1H); 10 (m. 1H)

Solvent: CDCl₃

Compound 162

N.M.R.¹H δ (ppm): 1.5–2.1 (m. 16H); 3.3–3.7 (m. 8H); 4.9 (d. 2H); 6.3–6.4 (dt. 1H); 6.7–6.8 (d. 1H); 6.8–6.9 (d. 1H); 7.2–7.5 (m. 6H); 8.25 (d. 1H)

Solvent: CDCl₃

Example 163

Method A: 1-Azepanyl-4-benzyl-7-bromo-4H-[1,2,4]triazolo[4,3-a]quinazolin-5-one (I): X1=7-Br; X2=H;

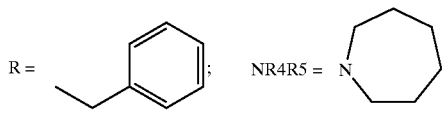

In a 50 ml balloon flask protected from humidity, we resuspend 4.0 g (10.7 mmol) of 4-benzyl-1,7-dibromo-4H-[1,2,4]triazolo[4,3-a]quinazolin-5-one (prepared by method of example 256) 25 ml of hexamethylene imine.

The mixture is then heated by reflux, under shaking, for 16 hours.

After cooling down, the obtained solution is concentrated under vacuum to give 4.8 g of residue which is purified by flash chromatography on silica column, by elution with the mixture CH₂Cl₂ 99.6/CH₃OH 0.4.

The fractions pure in CCM are joined, evaporated until dry and the obtained product (4.0 g) is recrystallized in ethanol.

We obtain 3.2 g of compound from example 163 as crystals.

Yield=66%.

F(Tottoli)=175° C.

CCM (CH₂Cl₂ 99/CH₃OH 1): Rf=0.40

NMR ¹H δ (ppm) CDCl3: 1.7–1.85 (m. 8H); 3.3 (m. 4H); 5.3 (s. 2H); 7.2–7.35 (m. 3H); 7.45 -d. 2H); 8.0 (d. 1H); 8.15 (s. 1H); 8.4 (d. 1H)

Example 164

Method B: 1-(Pyrrolidin-1-yl)-4-benzyl-7-bromo-4H-[1,2,4]triazolo[4,3-a]quinazolin-5-one (I): X1=7-Br; X2 H;

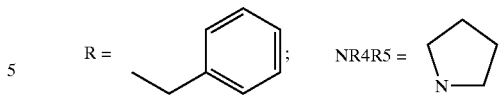

In a reactor protected from humidity, we resuspend 37.0 g (85 mmol) of 4-benzyl-1,7-dibromo-4H-[1,2,4]triazolo[4,3-a]quinazolin-5-one in 750 ml of dimethylformamide (DMF) and add 14.3 g (340 mmol) of sodium bicarbonate then 12.1 g (340 mmol) of pyrrolidine. The mixture is then heated by reflux, under shaking, for 6 hours.

After cooling down, the solvent is evaporated under vacuum, the obtained residue is resuspended in a mixture water/ethyl acetate and the insoluble fraction is triturated then filtered and dried: we obtain then from a first round 18.3 g of compound from example 164, this compound being pure by CCM.

The aqueous and organic phases are separated, the ethyl acetate phase is washed in water and dried on Na₂SO₄. After solvent concentration under vacuum, we obtain from a second round 14.2 g of compound from example 164, also pure by CCM.

Yield (as crude product)=90%; the product will be used like this in the next step.

A 0.35 g sample is recrystallized in methanol to give 0.32 g of pure compound as crystal.

F(Tottoli)=173° C.

CCM (CH2Cl2 99/CH3OH 1)=0.35

N.M.R.¹H δ (ppm): 2.1 (m. 4H); 3.4 (m. 4H); 5.45 (s. 2H); 7.3 (m. 3H); 7.65 (d. 2H); 7.85 (d. 1H); 8.15 (d. 1H); 8.45 (s. 1H)

Solvent: CDCl₃

Example 165

Method C: 1-[N-(n-butyl), N-methylamino]-4-benzyl-7-bromo-4H-[1,2,4]triazolo[4,3-a]quinazolin-5-one (I): X1=7-Br; X2=H

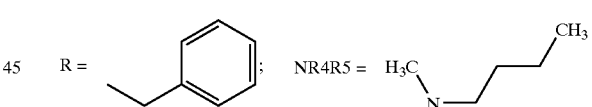

In a pressure reactor, we resuspend 2.5 g (5.75 mmol) of 4-benzyl-1,7-dibromo-4H-[1,2,4]triazolo[4,3-a]quinazolin-5-one in 30 ml of ethanol. We add 5.0 g of n-butyl-methylamine (57.5 mmol), we hermetically seal the reactor then we heat in an oil bath at 160° C. for 8 hours. After cooling down and leaving aside for 2 days, the residual oil (2.8 g) is chromatographied on silica column by elution with the mixture CH₂Cl₂ 99.5-CH₃OH 0.5. We obtain 1.8 g of compound from example 165.

Yield=70%.

CCM (CH₂Cl₂ 98.5/CH₃OH 1.5): Rf=0.45

N.M.R.¹H δ (ppm): 0.9 (t. 3H); 1.25–1.4 (m. 2H); 1.55–1.7 (m. 2H); 2.85 (s. 3H); 2.9–3.5 (m. 2H); 5.5 (s. 2H); 7.2–7.35 (m. 3H); 7.7 (d. 2H); 7.9 (d. 1H); 8.25 (s. 1H)

Solvent: CDCl₃

The compounds (I) from examples 166 to 198 (table 3) are prepared according to one of the methods A, B or C described in examples 163 to 165.

TABLE 3
| No Compound | X1 | R | NR4R5 | Yld (%) | MP (° C.) | Method |
|---|---|---|---|---|---|---|
| 166 | H | C6H5CH2 |  | 70 | 167 | B |
| 167 | 7-Cl | CH3 | 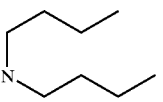 | 17 | 112 | A |
| 168 | 7-Cl | CH3 |  | 35 | 192 | A |
| 169 | 7-Cl | CH3 | 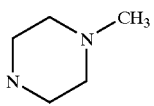 | 50 | 180–182 | A |
| 170 | 7-Cl | CH3 |  | 60 | 185 | A |
| 171 | 7-Cl | C6H5 | 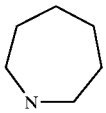 | 5 | 179 | A |
| 172 | 7-Cl | C6H5CH2 |  | 88 | 162 | A |
| 173 | 7-Cl | C6H5CH2 |  | 78 | 163 | B |
| 174 | 7-Cl | C6H5CH2 | 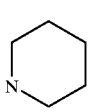 | 68 | 178 | B |
| 175 | 8-Cl | CH3 | 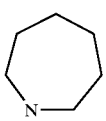 | 11 | 179 | A |
| 176 | 8-Cl | C6H5CH2 | 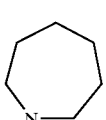 | 1 | – | B |
| 177 | 7-Br | CH3 | 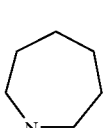 | 72 | 174 | A |
| 178 | 7-Br | C6H5CH2 | 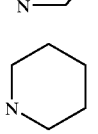 | 67 | 183–185 | A |

TABLE 3-continued
| No Compound | X1 | R | NR4R5 | Yld (%) | MP (° C.) | Method |
|---|---|---|---|---|---|---|
| 179 | 7-Br | C6H5CH2 | 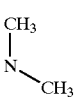 N(CH3)2 | 53 | 171 | B |
| 180 | 7-Br | C6H5CH2 |  morpholine | 50 | 189 | B |
| 181 | 7-Br | C6H5CH2 |  thiomorpholine | 49 | 235 | B |
| 182 | 7-Br | C6H5CH2 | 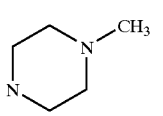 N-methylpiperazine | 60 | 230 | B |
| 183 | 7-Br | C6H5CH2 | 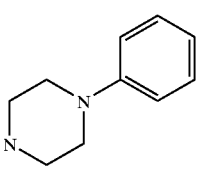 N-phenylpiperazine | 51 | 238 | B |
| 184 | 7-Br | C6H5CH2 | 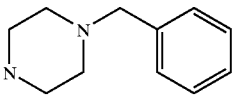 N-benzylpiperazine | 50 | 226 | B |
| 185 | 7-Br | C6H5CH2 |  tetrahydropyridine | 82 | 172 | B |
| 186 | 7-Br | C6H5CH2 | 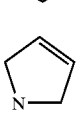 pyrroline | 85 | 210 | B |
| 187 | 7-Br | C6H5CH2 | 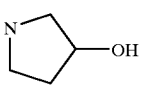 3-hydroxypyrrolidine | 79 | 176 | B |
| 188 | 7-Br | C6H5CH2 | NHCH3 | 52 | 238 | C |
| 189 | 7-I | C6H5CH2 |  pyrrolidine | 100 | 184 | B |
| 190 | 7-CH3 | C6H5CH2 | 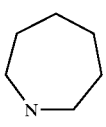 azepane | 90 | 183 | B |
| 191 | 7-CH3 | C6H5CH2 |  pyrrolidine | 60 | 189 | B |
| 192 | 7-CH3 | C6H5CH2 |  N(CH3)2 | 75 | 186 | B |

TABLE 3-continued

| No Compound | X1 | R | NR4R5 | Yld (%) | MP (° C.) | Method |
|---|---|---|---|---|---|---|
| 193 | 7-CH3 | C6H5CH2 | thiomorpholine | 78 | 265 | B |
| 194 | 8-CH3 | C6H5CH2 | azepane | 50 | 202 | A |
| 195 | 7-OCH3 | C6H5CH2 | azepane | 42 | 153 | B |
| 196 | 7-OCH3 | C6H5CH2 | pyrrolidine | 65 | 154 | B |
| 197 | 7-CN | C6H5CH2 | pyrrolidine | 77 | 219 | B |
| 198 | 7-NO2 | C6H5CH2 | azepane | 32 | 206 | A |

Compound 166
N.M.R.$^1$H δ (ppm): 2 (m. 4H); 3.3 (m. 4H); 5.35 (s. 2H); 7.2–7.3 (m. 3H); 7.4 (d. 2H); 7.6 (t. 1H); 7.9 (t. 1H); 8.2 (m. 2H)
Solvent: DMSO Compound 167
N.M.R.$^1$H δ (ppm): 0.8 (m. 6H); 1.15–1.25 (m. 4H); 1.35–1.55 (m. 4H); 3 (m. 2H); 3.2 (m 2H); 3.7 (s. 3H); 7.65 (m. 1H); 8.3 (m. 1H); 8.45 (m. 1H)
Solvent: CDCl$_3$ Compound 168
N.M.R.1H δ (ppm): 1.3–1.9 (m. 6H); 2.9 (t. 2H); 3.3 (m. 2H); 3.5 (s. 3H); 8.0 (d. 1H); 8.1 (d. 1H); 8.3 (d. 1H)
Solvent: CDCl3

Compound 170
N.M.R.1H δ (ppm): 0.7 (s. 3H); 0.8 (s. 3H); 1.0 (s. 3H); 1.5–1.9 (m. 5H); 2.55 (d. 1H); 2.85 (d. 1H); 3.15 (m. 4H); 3.4 (m. 4H); 7.9 (d. 1H); 8.0 (s. 1H); 8.4 (m. 1H)
Solvent: DMSO Compound 171
N.M.R.$^1$H δ (ppm): 1.7–1.8 (m. 8H); 3.3 (m. 4H(+H$_2$O); 7.45–7.6 (m. 5H); 8.05 (m. 1H); 8.15 (s. 1H); 8.45 (d. 1H)
Solvent: DMSO Compound 172
N.M.R.$^1$H δ (ppm): 1.7–1.85 (m. 8H); 3.3 (s. 4H); 5.3 (s. 2H); 7.25–7.5 (m. 5H); 8.0 (m. 1H); 8.15 (d. 1H); 8.4 (d. 1H)
Solvent: DMSO Compound 173
N.M.R.$^1$H δ (ppm): 2.05 (m. 6H); 3.4 (m. 42); 5.45 (s. 2H); 7.2–7.35 (m. 3H); 7.65–7.75 (m. 3H); 8.2 (dd. 1H); 8.35 (s. 1H)
Solvent: CDCl$_3$ Compound 174
N.M.R.$^1$H δ (ppm): 1.4–1.6 (m. 1H); 1.7–2 (m. 4H); 3–3.15 (m. 2H); 3.3–3.45 (m. 2H); 5.45 (s. 2H); 7.25–7.35 (m. 3H); 7.7–7.8 (m. 3H); 8.3–8.4 (m. 2H)
Solvent: CDCl$_3$ Compound 175
N.M.R.$^1$H δ (ppm): 1.85–1.95 (m. 4H); 3.4 (m. 4H+H$_2$O); 3.65 (s. 3H); 7.7 (d. 1H); 8.3 (d. 1H); 8.55 (s. 1H)
Solvent: DMSO Compound 176
N.M.R.$^1$H δ (ppm): 1.8–2 (m. 8H); 3.3–3.5 (m. 4H); 5.4 (s. 2H); 7.2–7.35 (m. 3H); 7.4–7.45 (m. 2H); 7.65–7.7 (m. 2H); 8.25–8.3 (m. 2H); 8.6 (s. 1H)
Solvent: CDCl$_3$ Compound 177
N.M.R.$^1$H δ (ppm): 1.7–1.85 (m. 8H); 3.4 (m. 4H); 3.7 (s. 3H); 7.75 (m. 1H); 8.25 (m. 1H); 8.4 (m. 1H)
Solvent: CDCl$_3$ Compound 178
N.M.R.$^1$H δ (ppm): 1.35–1.95 (m. 6H); 3.05 (t. 2H); 3.35 (d. 2H); 5.45 (s. 2H); 7.3 (m. 3H); 7.75 (d. 2H); 7.95 (d. 1H); 8.3 (d. 1H); 8.5 (s. 1H)
Solvent: CDCl$_3$ Compound 179
N.M.R.$^1$H δ (ppm): 2.9 (s. 6H); 5.5 (s. 2H); 7.25–7.35 (m. 3H); 7.7 (d. 2H); 7.85 (d. 1H); 8.2 (d. 1H); 8.5 (s. 1H)
Solvent: CDCl$_3$ Compound 180
N.M.R.$^1$H δ (ppm): 3.2–3.4 (m. 4H); 3.75–3.9 (m. 2H); 3.9–4.1 (m. 2H); 5.5 (s. 2H); 7.2–7.35 (m. 3H); 7.7 (d. 2H); 7.9 (d. 1H); 8.25 (d. 1H); 8.5 (s. 1H)
Solvent: CDCl$_3$ Compound 181
N.M.R.$^1$H δ (ppm): 2.8–3.0 (m. 4H); 3.35–3.5 (m. 2H); 3.5–3.7 (m. 2H); 5.45 (s. 2H); 7.2–7.35 (m. 3H); 7.7 (d. 2H); 7.9 (d. 1H); 8.2 (d. 1H); 8.5 (s. 1H)
Solvent: CDCl$_3$ Compound 182N.M.R.¹H δ (ppm): 2.3–2.45 (m. 5H); 2.9–3.0 (m. 2H); 3.25–3.35 (m. 4H); 5.5 (s. 2H); 7.2–7.35 (m. 3H); 7.7 (d. 2H); 7.9 (d. 1H); 8.25 (d. 1H); 8.5 (s. 1H)

Solvent: CDCl₃

Compound 183

N.M.R.¹H δ (ppm): 3.0–3.2 (m. 2H); 3.35–3.5 (m. 4H); 3.6–3.75 (m. 2H); 5.5 (s. 2H); 6.9–7.05 (m. 3H); 7.2–7.35 (m. 5H); 7.7 (d. 2H); 7.85 (d. 1H); 8.3 (d. 1H); 8.55 (s. 1H);

Solvent: CDCl₃

Compound 184

N.M.R.¹H δ (ppm): 2.4 (m. 2H); 3 (m. 2H); 3.3 (m. 4H); 5.5 (s. 2H); 7.3 (m. 8H); 7.7 (m. 2H); 7.9 (d. 1H); 8.2 (d. 1H); 8.5 (s. 1H)

Solvent: CDCl₃

Compound 185

N.M.R.¹H δ (ppm): 2.2–2.65 (m. 2H); 3.2–3.9 (m. 4H); 5.45 (s. 2H); 5.8–5.9 (m. 1H); 5.9–6.0 (m. 1H); 7.2–7.35 (m. 3H); 7.7 (d. 2H); 7.9 (d. 1H); 8.25 (d. 1H); 8.5 (s. 1H)

Solvent: CDCl₃

Compound 186

N.M.R.¹H δ (ppm): 4.3 (s. 4H); 5.5 (s. 2H); 5.95 (s. 2H); 7.25–7.4 (m. 3H); 7.7 (d. 2H); 7.9 (d. 1H); 8.25 (d. 1H); 8.5 (s. 1H)

Solvent: CDCl₃

Compound 187

N.M.R.¹H δ (ppm): 2–2.1 (m. 1H); 2.3–2.4 (m. 1H); 3.2–3.6 (m. 5H); 4.6–4.7 (m. 1H); 5.45 (s. 2H); 7.2–7.3 (m. 3H); 7.65 (d. 1H); 7.85 (d. 1H); 8.3 (d. 2H); 8.5 (s. 1H)

Solvent: CDCl₃

Compound 188

N.M.R¹H δ (ppm): 3.05 (s. 3H); 3.9–4.0 (m. 1H); 5.35 (s. 2H); 7.15–7.25 (m. 3H); 7.6 (d. 2H); 7.7 (d. 1H); 7.95 (d. 1H); 8.4 (s. 1H)

Solvent: CDCl₃

Compound 189

N.M.R.¹H δ (ppm): 2 (m. 4H); 3.4 (m. 4H); 5.3 (s. 2H); 7.3 (m. 3H); 7.4 (m. 2H); 8.0 (m. 1H); 8.2 (m. 1H); 8.5 (m. 1H)

Solvent: DMSO

Compound 190

N.M.R.¹H δ (ppm): 1.75–1.95 (m. 8H); 2.45 (s. 3H); 3.35–3.45 (m. 4H); 5.45 (s. 2H); 7.2–7.35 (m. 3H); 7.45 (dd. 1H); 7.7 (dd. 2H); 8.15 (s. 1H); 8.3 (d. 1H)

Solvent: CDCl₃

Compound 191

N.M.R.¹H δ (ppm): 2 (m. 4H); 2.5 (s. 3H); 3.3 (m. 4H); 5.3 (s. 2H); 7.2–7.55 (m. 5H); 7.7 (d. 1H); 8 (s. 1H); 8.15 (d. 1H)

Solvent: CDCl₃

Compound 192

N.M.R.¹H δ (ppm): 2.45 (s. 3H); 2.9 (s. 6H); 5.45 (s. 2H); 7.2–7.3 (m. 3H); 7.45 (d. 1H); 7.7 (d. 2H); 8.2 (d. 2H)

Solvent: CDCl₃

Compound 193

N.M.R.¹H δ (ppm): 2.5 (s. 3H); 2.8–3.05 (m. 4H); 3.35–3.75 (m. 4H); 5.5 (s. 2H); 7.15–7.4 (m. 3H); 7.6 (d. 1H); 7.7 (d. 2H); 8.1–8.25 (m. 2H)

Solvent: CDCl₃

Compound 194

N.M.R.¹H δ (ppm): 1.8–1.95 (m. 8H); 2.55 (s. 3H); 3.4 (m. 4H); 5.4 (s. 2H); 7.25–7.35 (m. 4H); 7.7 (m. 2H); 8.25 (m. 2H)

Solvent: CDCl₃

Compound 195

N.M.R.¹H δ (ppm): 1.8–1.95 (m. 8H); 3.35–3.40 (m. 4H); 3.9 (s. 3H); 5.4 (s. 2H); 7.25–7.35 (m. 4H); 7.7 (dd. 2H); 7.8 (d. 1H); 8.35 (d. 1H)

Solvent: CDCl₃

Compound 196

N.M.R.¹H δ (ppm): 2 (m. 4H); 3.35 (m. 4H); 3.9 (s. 3H); 5.35 (s. 2H); 7.25–7.35 (m. 3H); 7.45 (d. 2H); 7.55 (d. 1H); 7.7 (s. 1H); 8.2 (d. 1H)

Solvent: DMSO

Compound 197

N.M.R.¹H δ (ppm): 2.4 (m. 4H); 3.2 (m. 4H); 5.2 (s. 2H); 7.1–7.25 (m. 3H); 7.35 (m. 2H); 8.25 (m. 2H); 8.5 (s. 1H)

Solvent: CDCl₃

Compound 198

N.M.R.¹H δ (ppm): 1.7–1.85 (m. 8H); 3.3 (s. 4H+H₂O); 5.35 (s. 2H); 7.3 (m. 3H); 7.5 (m. 2H); 8.55 (d. 1H); 8.75 (d. 1H); 8.9 (s. 1H)

Solvent: DMSO

Example 199

1-Azepanyl-4-benzyl-7-chloro-4H-[1,2,4]triazolo[4,3-a]quinazolin-5-one (I); X1=7-Cl; X2=H R = 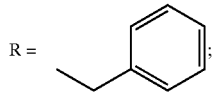 ; NR4R5 = 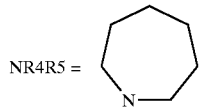

In a 50 ml balloon flask, equipped with a shaker and refrigeration, we resuspend 0.44 g (1,27 mmol) of 4-benzyl-1,7-dichloro-4H-[1,2,4]triazolo[4,3-a]quinazolin-5-one (example 254) in 2.5 ml of hexamethylene imine. Under shaking, the mixture is heated by reflux for 16 hours. The obtained brown solution is then left aside to ambient temperature until complete cooling down; then we pour in a mixture of water and methylene chloride, shake and separate the 2 phases by decantation. The organic phase is washed twice in water, dried on Na₂SO₄ then evaporated under vacuum to give 0.59 g of brown solid residue.

This is chromatographied on silica column by elution with the mixture CH₂Cl₂ 99.5/CH₃OH 0.5.

We obtain after joining and evaporation of pure by CCM fractions, 0.46 g of compound from example 199. This is recrystallized in ethanol to give 0.4 g of colorless crystal.

Yield=77%

F(Tottoli)=162° C.

CCM (CH₂Cl₂ 98.5/CH₃OH 1.5): Rf=0.35

N.M.R.¹H δ (ppm): 1.7–1.85 (m. 8H); 3.3 (s. 4H); 5.3 (s. 2H); 7.25–7.5 (m. 5H); 8.0 (m. 1H); 8.15 (d. 1H); 8.4 (d. 1H)

Solvent: DMSO

The compounds (I) from examples 200 to 214 (table 4) are prepared according to the process from example 199.

TABLE 4
| No Compound | X1 | R | NR4R5 | Yld (%) | MP (° C.) | Method |
|---|---|---|---|---|---|---|
| 200 | H | CH3 | 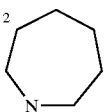 | 40 | 199–203 | A |
| 201 | H | C6H5CH2 | 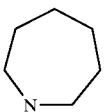 | 66 | 157 | A |
| 202 | 6-Cl | CH3 | 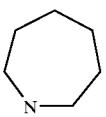 | 8.5 | >275 | A |
| 203 | 7-Cl | CH3 | 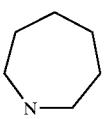 | 77 | 145 | A |
| 204 | 7-Cl | CH3CH2 | 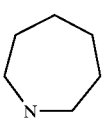 | 11 | 98–100 | A |
| 205 | 7-Cl | CH3 |  | 50 | 203–205 | A |
| 206 | 7-Cl | CH3 | 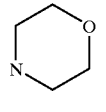 | 25 | 232 | A |
| 207 | 7-Cl | CH3 | 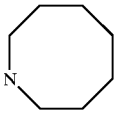 | 25 | 123–125 | A |
| 208 | 7-Cl | CH3 | 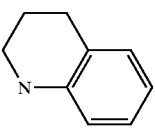 | 15 | 204 | A |
| 209 | 7-Cl | CH3 | 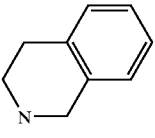 | 30 | 272 | A |
| 210 | 7-Cl | CH3 | 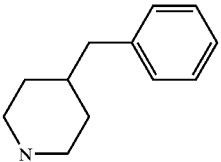 | 25 | 180 | A |

TABLE 4-continued

| No Compound | X1 | R | NR4R5 | Yld (%) | MP (° C.) | Method |
|---|---|---|---|---|---|---|
| 211 | 7-Cl | CH3 | (bicyclic amine structure) | 25 | 165 | A |
| 212 | 7-F | CH3 | (azepane) | 13 | 136 | A |
| 213 | 7-I | CH3 | (azepane) | 47 | 206 | A |
| 214 | 7-OCH3 | CH3 | (azepane) | 34 | 203 | A |

Compound 200
N.M.R.1H δ (ppm): 1.75–1.9 (m. 8H); 3.4 (m. 4H); 3.6 (s. 3H); 7.6 (t. 1H); 8 (t. 1H); 8.25 (d. 1H); 8.4 (d. 1H)
Solvent: DMSO Compound 201
N.M.R.1H δ (ppm): 1.7–1.85 (m. 8H); 3.3 (m. 4H); 5.3 (s. 2H); 7.2–7.35 (m. 3H); 7.45 (d. 2H); 7.6 (t. 1H); 7.95 (t. 1H); 8.2 (d. 1H); 8.4 (d. 1H)
Solvent: DMSO Compound 202
N.M.R.1H δ (ppm): 1.5–1.8 (m. 8H); 3.4 (m. 4H); 3.5 (s.3H); 7.05 (d. 1H); 7.5 (t. 1H); 8.4 (d. 1H)
Solvent: DMSO Compound 203
N.M.R.1H δ (ppm): 1.7–1.85 (m. 8H); 3.3 (m. 4H); 3.5 (s. 3H); 7.95 (d. 1H); 8.1 (s. 1H); 8.35 (d. 1H)
Solvent: DMSO Compound 204
N.M.R.1H δ (ppm): 1.3 (t. 3H); 1.7–1.9 (m. 8H); 3.3 (m. 4H); 4.15 (q. 2H); 7.95 (d. 1H); 8.1 (s. 1H); 8.35 (d. 1H)
Solvent: DMSO Compound 205
N.M.R.1H δ (ppm): 2.0 (m. 4H); 3.35 (m. 4H); 3.75 (s. 3H); 7.65 (d. 1H); 8.15 (d. 1H); 8.3 (s. 1H)
Solvent: CDCl3

Compound 206
N.M.R.1H δ (ppm): 3.1–3.35 (m. 4H); 3.65 (s. 3H); 3.85 (m. 2H); 4.0 (m. 2H); 7.75 (d. 1H); 8.35 (m. 2H)
Solvent: CDCl3

Compound 207
N.M.R.1H δ (ppm): 1.8 (m. 10H); 3.4 (m. 4H); 3.75 (s. 3H); 7.75 (d. 1H); 8.35 (s. 1H); 8.4(d. 1H)
Solvent: CDCl3

Compound 208
N.M.R.1H δ (ppm): 2.1 (m. 2H); 2.8–3.1 (m. 2H); 3.65 (m.1H); 3.75 (s.3H); 3.9 (m.1H); 6.15 (d.1H); 6.75 (t. 1H); 6.85 (t.1H); 7.1 (d. 1H); 7.5 (d. 1H); 7.85 (d.1H); 8.3 (s. 1H)
Solvent: CDCl3

Compound 209
N.M.R.1H δ (ppm): 2.9 (m. 1H); 3.2 (m. 1H); 3.4 (m. 1H); 3.6 (m. 1H); 3.7 (s. 3H); 4.3 (d. 1H); 4.45 (d. 1H); 7.05 (d. 1H); 7.2 (m. 3H); 7.6 (d. 1H); 8.2 (d. 1H); 8.3 (s. 1H)
Solvent: CDCl3

Compound 210
N.M.R.1H δ (ppm): 1.4 (m. 2H); 1.7 (m. 3H); 2.6 (d. 2H); 2.9–3.15 (m. 2H); 3.3–3.5 (m. 2H); 3.65 (s. 3H); 7.0–7.35 (m. 5H); 7.7 (d. 1H); 8.3 (m. 2H)
Solvent: CDCl3

Compound 211
N.M.R.1H δ (ppm): 1 (s. 3H); 1.1 (s. 3H); 1.25–1.4 (m. 5H); 1.45 (d. 1H); 1.6 (m. 2H); 1.9 (d.1H); 2.05 (m. 1H); 3.35 (d.1H); 3.45 (d. 1H); 3.7 (s. 3H); 4 (m. 1H); 7.65 (d. 1H); 8.3 (s. 1H); 8.6 (d. 1H)
Solvent: CDCl3

Compound 212
N.M.R.1H δ (ppm): 1.7–1.8 (m. 8H); 3.3 (m. 4H (+H2O)); 3.5 (s. 3H); 7.8 (m. 1H); 7.9 (m. 1H); 8.4 (m.1H)
Solvent: DMSO Compound 213
N.M.R.1H δ (ppm): 1.7–1.9 (m. 8H); 3.3 (m. 4H); 3.7 (s. 3H); 8.0 (d. 1H); 8.1 (d. 1H); 8.65 (s. 1H)
Solvent: CDCl3

Compound 214
N.M.R1H δ (ppm): 1.7–1.85 (m. 8H); 3.3 (s. 4H); 3.5 (s. 3H); 3.9 (s. 3H); 7.5 (d. 1H); 7.6 (s. 1H); 8.3 (d. 1H)
Solvent: CDCl3

Example 215

4-benzyl-7-bromo-1-(N-ethyl, N-methylamino)-4H-[1,2,4]triazolo[4,3-a]quinazolin-5-one 0.3 g (0.8 mmol) of 4-benzyl-7-bromo-1-(N-methylamino)-4H-[1,2,4]triazolo-[4,3-a]quinazolin-5-one (compound from example 188) is dissolved in 5 ml of DMF. We add 0.135 g (0.85 mmol) of methyl iodide and 0.13 g (0.93 mmol) of potassium carbonate. The obtained mixture is shaken at ambient temperature for a night then heated at 100° C. for 6 hours. After cooling down, the solvent is evaporated under vacuum, the residue is resuspended in water and ethyl acetate. The organic phase is separated by decantation, washed with a saturated solution of sodium chloride, dried on $Na_2SO_4$ and evaporated under vacuum. We obtain 0.3 g of crude product which is purified by chromatography on silica column by elution with the mixture $CH_2Cl_2$ 99/$CH_3OH$ 1. The fractions containing the desired product are joined, concentrated under vacuum then the residue is recrystallized in methanol to give 0.05 g of pure compound from example 215.

Yield=22%

F(Tottoli)=148° C.

CCM ($CH_2Cl_2$ 98.5/$CH_3OH$ 1.5): Rf=0.45

N.M.R.1H δ (ppm): 1.25 (t. 3H); 2.9 (s. 3H); 3.2–3.4 (m. 2H); 5.45 (s. 2H); 7.2–7.35 (m. 3H); 7.7 (d. 2H); 7.9 (d. 1H); 8.3 (d. 1H); 8.5 (s. 1H)

Solvent: CDCl3

Example 216

4-benzyl-1-(N,N-diethyl)-7-methyl-4H-[1,2,4]triazolo[4,3-a]quinazolin-5-one 2.3 g (5.87 mmol) of 4-benzyl-7-methyl-1-(thiamorpholin-4-yl)-4H-[1,2,4]triazolo[4,3-a]quinazolin-5-one (compound from example 193) are resuspended in 250 ml of ethanol. We add a catalytic amount of Raney's nickel and we heat by reflux, under shaking, for 24 hours. The catalyzer is eliminated by filtration on Celite and the alcoholic solution is concentrated under vacuum: we obtain 1.6 g of crude product which is purified by chromatography on silica column by elution using $CH_2Cl_2$ and methanol gradient from 99.5/0.5 to give 0.9 g of pure by CCM product. A sample is recrystallized in ethanol to determinate physical parameters.

Yield=42%

F(Tottoli)=154° C.

CCM ($CH_2Cl_2$ 99/$CH_3OH$ 1): Rf=0.35

N.M.R.1H δ (ppm): 1–1.3 (m. 6H); 2.4 (s. 3H); 2.9–3.45 (m. 4H); 5.4 (s. 2H); 7.1–7.3 (m. 3H); 7.45 (d. 1H); 7.6 (d. 2H); 8.15 (s. 1H); 8.3 (d. 1H)

Solvent: CDCl3

Example 217

4-benzyl-7-bromo-1-(pyrrol-1-yl)-4H-[1,2,4]triazolo[4,3-a]quinazolin-5-one

In a 25 ml balloon flask, we resuspend 0.7 g (1.8 mmol) of 1-amino-4-benzyl-7-bromo-4H-[1,2,4]triazolo[4,3-a]quinazolin-5-one (intermediate 10 compound of example 271) in 5 ml of acetic acid. We add 0.25 g (1.9 mmol) of 2.5-dimethoxytetrahydrofuran then heat the mixture by reflux for 1 hour. After cooling down and evaporation of acetic acid under vacuum, we obtain 0.8 g of highly colored solid which is purified by chromatography on silica column by elution with the mixture $CH_2Cl_2$/$CH_3OH$ (99,4/0,6 then 99/1). The solid obtained from pure fractions is recrystallized in ethanol to give 0.45 g of compound from example 217.

Yield=55%

F(Tottoli)=214° C.

CCM ($CH_2Cl_2$ 99/$CH_3OH$ 1): Rf=0.5

N.M.R.1H δ (ppm): 5.55 (s. 2H); 5.8 (d. 1H); 6.5 (s. 2H); 6.9 (s. 2H); 7.25–7.4 (m. 3H); 7.7 (d. 1H); 7.75 (d. 2H); 8.55 (s. 1H)

Solvent: CDCl3

Example 218

4-(4-aminobenzyl)-7-bromo-1-(pyrrolidin-1-yl)-4H-[1,2,4]triazolo[4,3-a]quinazolin-5-one In a 50 ml balloon flask, we resuspend 0.45 g (0.96 mmol) of 7-bromo-4-(4nitrobenzyl)-1-(pyrrol-1-yl)-4H-[1,2,4]triazolo[4,3-a]quinazolin-5-one (compound from example 48) in 10 ml ethanol. We add 1.08 g (24 mmol) of dehydrate stannous chloride then heat at 70° C., under shaking, for 30 minutes. After cooling down, the mixture is poured into iced water. We extract several times by ethyl acetate with a little of $CHCl_3$, the organic phase is washed in a solution sodium chloride saturated, dried on $Na_2SO_4$ then concentrated under vacuum. The obtained solid residue (0.35 g) is washed in methanol (50 ml) to give 0.25 g of pure by CCM product.

Yield=83%

F(Tottoli)=263° C.

CCM ($CH_2Cl_2$ 98/$CH_3OH$ 2): Rf=0.25

N.M.R.1H δ (ppm): 1.9–2.05 (m. 4H); 3.3–3.4 (m. 4H); 5 (s. 2H); 5.1 (s. 2H); 6.5 (d. 2H); 7.2 (d. 2H); 8.1 (d. 1H); 8.2 (d. 1H); 8.3 (s. 1H)

Solvent: DMSO

Example 219

4-(benzyl)-7-hydroxy-1-(pyrrolidin-1-yl)-4H-[1,2,4]triazolo[4,3-a]quinazolin-5-one Example 219-1/ 4-benzyl-7-(4-tolylsulfonyloxy-4H-[1,2,4]triazolo[4,3-a]quinazolin-5-one In a reactor equipped with a shaker and refrigeration, we resuspend 1.46 g (5 mmol) of 4-benzyl-7-hydroxy-4H-[1,2,4]triazolo[4,3-a]quinazolin-5-one (intermediate obtained by method from example 255) in 15 ml of dry methylene chloride. We add 0.95 g (5 mmol) of tosyl chloride and then add, under shaking within 5 minutes, 1 ml (7.5 mmol) of triethylamine, the reaction being slightly exothermic. After additional shaking at ambient temperature for 2 hours, the obtained organic solution is washed in water and dried on $Na_2SO_4$ to give, after solvent evaporation, a colored amorphous residue which is purified by chromatography on silica column by elution with ethyl acetate. We obtain 1.9 g of pure product by CCM. This one will be used like this in the next step.

Yield=85%

2/ Example 219-2/ 4-benzyl-1-bromo-7-(4-tolylsulfonyloxy-4H-[1,2,4]triazolo[4,3-a]quinazolin-5-one 0.4 g of this compound is obtained from 0.45 g of 4-benzyl-7-(4-tolylsulfonyloxy-4H-[1,2,4]triazolo[4,3-a]quinazolin-5-one (example 219-1) by bromination method described in example 256.

Yield=76%

3/ Example 219-3/ 4-benzyl-1-(pyrrolidin-1-yl)-7-(4-tolylsulfonyloxy)-4H-[1,2,4]triazolo[4,3-a]quinazolin-5-one and 4-benzyl-7-hydroxy-1-(pyrrolidin-1-yl)-4H-[1,2,4]triazolo[4,3-a]quinazolin-5-one 0.83 g of the brominated derived obtained in example 219-2 is treated by pyrrolidine in conditions of example 164.

After treatment, we obtain 1.0 g of crude mixture of 2 majoritary compounds which are separated by chromatography on silica column after elution with the mixture $CH_2Cl_2$ 98/$CH_3OH$ 2. The fractions containing the first pure product are joined and concentrated to give 0.375 g of 4-benzyl-1-(pyrrolidin-1-yl)-7-(4-tolylsulfonyloxy-4H-[1,2,4]triazolo[4,3-a]quinazolin-5-one.

Yield=45%

The fractions containing the second pure product are joined and evaporated under vacuum to give 0.12 g of 4-benzyl-7-hydroxy-1-(pyrrolidin-1-yl)-4H-[1,2,4]triazolo[4,3-a]quinazolin-5-one.

Yield=15%

F(Tottoli)=287° C.

N.M.R.1H δ (ppm): 1.95 (m. 4H); 3.3 (m. 4H); 7.3 (s. 2H); 7.2–7.6 (m. 7H); 8.1 (d. 1H): 10.2 (s. 1H)

Solvent: DMSO

Example 220

4-(4-cyanobenzyl)-7-hydroxy-1-(pyrrolidin-1-yl)-4H-1,2,4]triazolo[4,3-a]quinazolin-5-one 1/ Example 220-1/ 1-(pyrrolidin-1yl)-7-(4-tolylsulfonyloxy)-4H-[1,2,4]triazolo[4,3-a]quinazolin-5-one 1.3 g of this compound is obtained from 2.4 g of 4-benzyl-1-(pyrrolidin-1yl)-7-(4-tolylsulfonyloxy-4H-[1,2,4]triazolo[4,3-a]quinazolin-5-one (example 219-3) by debenzylation method described in example 263.

Yield=68%

2/ Example 220-2/ 4-(4-cyanobenzyl)-1-(pyrrolidin-1-yl)-7-(4-tolylsulfonyloxy-4H-[1,2,4]triazolo[4,3-a]quinazolin-5-one 0.48 g of this compound is obtained from of 0.66 g of 1-(pyrrolidin-1yl)-7-(4-tolylsulfonyloxy-4H-[1,2,4]triazolo[4,3-a]quinazolin-5-one (example 220-1) by N-alkylation method described in example 3.

Yield=52%

3/ Example 220-3/ 4-(4-cyanobenzyl)-7-hydroxy-1-(pyrrolidin-1-yl)-4H-[1,2,4]triazolo[4,3-a]quinazolin-5-one 0.3 g (0.55 mmol) of 4-(4-cyanobenzyl)-1-(pyrrolidin-1-yl)-7-(4-tolylsulfonyloxy-4H-[1,2,4]triazolo[4,3-a]quinazolin-5-one (described in example 220-2) is dissolved in 1 ml of dry DMF. We add 0.27 ml of pyrrolidine (2.75 mmol) then heat at 140° C., under shaking, for 6 hours. The solvent is evaporated under vacuum and the residue is resuspended by a mixture of ethyl acetate/aqueous N hydrochloric acid solution. The insoluble residue is separated by filtration, washed in water until neutral pH and dried under vacuum; we obtain 0.13 g of crude product, which is crystallized in 5 ml of ethanol, filtered and dried to give 0.085 g of pure product.

Yield=40%

F(Tottoli)=305° C.

N.M.R.1H δ (ppm): 2 (m. 4H); 3.3 (m. 4H); 5.35 (s. 2H); 7.35 (d. 1H); 7.6–7.7 (m. 3H); 7.8 (d. 2H); 8.1 (d. 1H); 10.2 (s. 1H)

Solvent: DMSO

Example 221

7-acetamido-4-benzyl-1-(pyrrolidin-1-yl)-4H-[1,2,4]triazolo[4,3-a]quinazolin-5-one 1/ Example 221-1/ 7-acetamido-4-benzyl-1-bromo-4H-[1,2,4]triazolo[4,3-a]quinazolin-5-one 0.45 g of this compound is obtained from 0.5 g of 7-acetamido-4-benzyl-4H-[1,2,4]triazolo [4,3-a]quinazolin-5-one by bromination method which is described in example 256.

Yield=72%

2/ Example 221-2/ 7-acetamido-4-benzyl-1-(pyrrolidin-1-yl)-4H-[1,2,4]triazolo[4,3-a]quinazolin-5-one 8.7 g (21 mmol) of brominated derived which is obtained in example 221-1 are treated by 3.7 ml (42 mmol) of pyrrolidine and 3.54 g (42 mmol) of sodium bicarbonate in 80 ml of DMF in conditions of example 164. After treatment, we obtain 8.0 g of crude product which is purified by chromatography on silica column by elution with the mixture $CH_2Cl_2$ 98/$CH_3OH$ 2. The fractions containing the pure product are joined and concentrated, then the residue is crystallized in ethanol to give 6.6 g of 7-acetamido-4-benzyl-1-(pyrrolidin-1-yl)-4H-[1,2,4]triazolo[4,3-a]quinazolin-5-one.

Yield=78%

F(Tottoli)=265° C.

N.M.R.1H δ (ppm): 2–2.1 (m. 4H); 2.25 (s. 3 H); 3.4 (m. 4H); 5.45 (s. 2H); 7.2–7.3 (m. 3H); 7.6 (d. 2H); 8.1 (s. 1H); 8.2 (m. 2H); 8.4 (d. 1H)

Solvent: CDCl3

Example 222

7-acetamido-4-[(E)-3-phenylallyl]-1-(pyrrolidin-1-yl)-4H-[1,2,4]triazolo[4,3-a]quinazolin-5-one From 1.2 g (3.0 mmol) of 7-acetamido-4-benzyl-1-(pyrrolidin-1yl)-4H-[1,2,4]triazolo[4,3-a]quinazolin-5-one (described in example 221) debenzylated in 7-acetamido-1-(pyrrolidin-1yl)-4H-[1,2,4]triazolo[4,3-a]quinazolin-5-one by Palladium/C method described in example 257, then directly treated with 0.59 g of cinnamyl bromide in the presence of 0.98 g cesium carbonate, in 15 ml of DMF, according to a method described in example 3. We obtain, after purification by chromatography on silica column and recrystallization in ethanol, 0.4 g of pure compound from example 222.

Yield=31%.

F(Tottoli)=248° C.

CCM ($CH_2Cl_2$ 95/$CH_3OH$ 5): Rf=0.30

NMR $^1H$ δ (ppm) CDCl3: 2.0–2.1 (m.4H); 2.25 (s. 3H); 3.45 (m. 4H); 5 (d. 2H); 6.35–6.4(dt. 1H); 6.8 (d. 1H); 7.15–7.35 (m. 5H); 8.1 (s. 1H); 8.2–8.3 (m. 2H); 8.4 (m. 1H)

Example 223

7-amino-4-[(E)-3-phenylallyl]-1-(pyrrolidin-1-yl)-4H-[1,2,4]triazolo[4,3-a]quinazolin-5-one In a 20 ml balloon flask, we resuspend 0.2 g (0.46 mmol) of 7-acetamido-4-[(E)-3-phenylallyl]-1-(pyrrolidin-1-yl)-4H-[1,2,4]triazolo[4,3-a]quinazolin-5-one (describe example 222) in 5 ml of 6N hydrochloric acid solution and heat by reflux, under shaking, for 15 minutes. After cooling down, the obtained solution is alkalinized by soda solution, extracted 3 times by methylene chloride. The joined organic phases are washed with a NaCl-saturated solution, dried on $Na_2SO_4$ then evaporated under vacuum. The crude product (0.12 g) is recrystallized in ethanol to give 0.08 g of the pure compound from example 223.

Yield =44%

F(Tottoli)=199° C.

NMR $^1H$ δ (ppm) CDCl3: 2.1 (m. 4H); 3.4 (m. 4H); 4.0 (m. 2H); 5.1 (d. 2H); 6.5–6.6 (dt. 1H); 6.85 (d. 1H); 7.0–7.3 (m. 3H); 7.6 (m. 1H); 7.7 (m. 1H); 8.1 (m. 1H); 8.45 (s. 1H); 8.6 (s. 1H).

The general formula (I) compounds of examples 224 to 233 in table5 are prepared by method from example 223.

TABLE 5

| No Compound | X1 | R | NR4R5 | Yld (%) | MP (° C.) |
|---|---|---|---|---|---|
| 224 | 7-NH2 | C6H5CH2 | azepane (7-membered N ring) | 40 | 240(dec) |
| 225 | 7-NH2 | C6H5CH2 | pyrrolidine | 60 | 230 |
| 226 | 7-NH2 | 4-CNC6H4CH2 | pyrrolidine | 67 | 152 |
| 227 | 7-NH2 | (E) (3-pyridyl)-CH=CHCH2 | pyrrolidine | 70 | 201 |
| 228 | 7-NH2 | 4-CNC6H4CH2 | N(CH3)2 | 68 | 163 |
| 229 | 7-NH2 | (E) C6H5CH=CHCH2 | N(CH3)2 | 67 | 198 |
| 230 | 7-CH3NH | C6H5CH2 | pyrrolidine | 58 | 171 |
| 231 | 7-CH3NH | 4-CNC6H4CH2 | pyrrolidine | 91 | 270 |
| 232 | 8-CH3NH | C6H5CH2 | pyrrolidine | 76 | — |
| 233 | 7-C2H5NH | C6H5CH2 | pyrrolidine | 67 | 225 |

Compound 224
N.M.R.1H δ (ppm): 1.8–1.9 (m. 8H); 3.4–3.45 (m. 4H); 4 (s. 2H); 5.4 (s. 2); 7 (m. 1H); 7.25–7.35 (m. 3H); 7.55 (s. 1H); 7.65–7.80 (m. 2H); 8.15–8.2 (m. 1H)
Solvent: CDCl3

Compound 225
N.M.R.1H δ (ppm): 2.1 (m. 4H); 3.4 (m. 4H); 4 (s. 2H); 5.45 (s. 2H); 7 (d. 1H); 7.2–7.35 (m. 3H); 7.6 (s. 1H); 7.7–7.8 (d. 2H)); 8–8.1 (d. 1H)
Solvent: CDCl3

Compound 226
N.M.R.1H δ (ppm): 2–2.1 (m. 4H); 3.35–3.45 (m. 4H); 4.05 (s. 2H); 8.5 (s. 2H); 7.05 (m. 1H); 7.4–7.5 (m. 3H); 7.8 (s. 1H); 8.05 (d. 1H)
Solvent: CDCl3

Compound 227
N.M.R.1H δ (ppm): 2.1 (m. 4H); 3.4 (m. 4H); 4 (m. 2H); 5.1 (d. 2H); 6.4–6.5 (dt. 1H); 6.9 (d. 1H); 7.05 (m. 1H); 7.2–7.3 (m. 2H); 7.35 (d. 2H); 7.6 (s. 1H); 8.1 (d. 1H)
Solvent: CDCl3

Compound 228
N.M.R.1H δ (ppm): 2.8 (s. 6H); 5.4 (s. 2H); 5.7 (m. 2H); 7.10–7.15 (m. 1H); 7.4 (s. 1H); 7.6 (d. 2H); 7.8 (d. 2H); 8.05 (d. 1H)
Solvent: DMSO Compound 229
N.M.R.1H δ (ppm): 2.9 (s. 6H); 4.95 (d. 2H); 5.75 (m. 2H); 6.45–6.5 (dt. 1H); 6.7–6.8 (d. 1H); 7.2 (m. 1H); 7.25–7.4 (m. 6H); 8.1 (d. 1H)
Solvent: DMSO Compound 230
N.M.R.1H δ (ppm): 2.1 (m. 4H); 2.95 (s. 3H); 3.4 (m. 4H); 4.1 (m. 1H); 5.4 (s. 2H); 6.95 (d. 1H); 7.3 (m. 3H); 7.45 (s. 1H); 7.75 (dd. 2H); 8.1 (d. 1H)
Solvent: CDCl3

Compound 231
N.M.R.1H δ (ppm): 2.1 (m. 4H); 2.9 (s. 3H); 3.4 (m. 4H); 5.5 (s. 2H); 7 (m. 1H); 7.45 (s. 1H); 7.6 (m. 2H); 7.8 (m. 2H); 8.1 (d. 1H)
Solvent: CDCl3

Compound 232

N.M.R.1H δ (ppm): 1.9–2 (m. 4H); 2.85 (d. 3H); 3.3 (m. 4H); 5.3 (s. 2H); 6.7 (d. 1H); 7.2 (q. 1H); 7.25–7.45 (m. 6H); 7.9 (d. 1H)

Solvent: DMSO

Compound 233

N.M.R.1H δ (ppm): 1.3 (t. 3H); 2.1 (m. 4H); 3.25 (m. 2H); 3.4 (m. 4H); 3.9 (m. 1H); 5.45 (s. 2H); 7 (m. 1H); 7.2–7.3 (m. 3H); 7.45 (s. 1H); 7.7 (m. 2H); 8.1 (d. 1H)

Solvent: CDCl3

Example 234

4-benzyl-7-(N-isopropylamino)-1-(pyrrolidin-1-yl)-4H-[1,2,4]triazolo[4,3-a]quinazolin-5-one In a 20 ml balloon flask, we resuspend 0.31 g (0.86 mmol) of 7-amino-4-benzyl-1-pyrrolidin-1-yl)-4H-[1,2,4]triazolo[4,3-a]quinazolin-5-one (described in example 225) in 10 ml methylene chloride. We add 0.14 ml (1.9 mmol) of acetone, 0.115 ml (1.9 mmol) of pure acetic acid then 0.546 g (2.6 mmol) of sodium detriacetoxyborohydrid. The mixture is shaken for 48 hours at ambient temperature, under nitrogen atmosphere. The solvent is evaporated under vacuum and the residue is resuspended in ethyl acetate. The organic phase is washed in a sodium bicarbonate solution, then in NaCl-saturated solution. After drying on $Na_2SO_4$ and solvent elimination under vacuum, we obtain 0.3 g of crude product which is purified by chromatography on silica column, after elution with mixture $CH_2Cl_2$ 98/$CH_3OH$ 2 to give 0.2 g of pure by CCM compound from example 234.

Yield=58%

F(Tottoli)=208° C. [EtOH]

N.M.R.1H δ (ppm): 1.2 (m. 6H); 2.05 (m. 4H); 3.4 (m. 4H); 3.7–3.85 (m. 2H); 5.5 (s. 2H); 6.9 (m. 1H); 7.2–7.3 (m. 3H); 7.4 (s. 1H); 7.7 (m. 2H); 8.1 (m. 1H)

Solvent: CDCl3

Example 235

4-benzyl-7-methylsulfonylamino-1-(pyrrolidin-1-yl)-4H-[1,2,4]triazolo[4,3-a]quinazolin-5-one and example 247: 4-benzyl-7-(N,N-dimethylsulfonylamino)-1-(pyrrolidin-1-yl)-4H-[1,2,4]triazolo[4,3-a]quinazolin-5-one In a 20 ml balloon flask, we resuspend 0.55 g (1.5 mmol) of 7-amino-4-benzyl-1-(pyrrolidin-1-yl)-4H-[1,2,4]triazolo[4,3-a]quinazolin-5-one (described in example 225) in 10 ml methylene chloride. We add 0.42 ml (3.0 mmol) of triethylamine then 0.24 ml (3.0 mmol) of methanesulfonyl chloride. The obtained solution is shaken for 24 hours at ambient temperature. After cooling down, the obtained solution is washed in water, dried on $Na_2SO_4$ then evaporated under vacuum. The crude mixture of the 2 obtained compounds (0.85 g) is chromatographied on silica column by elution with the mixture $CH_2Cl_2$ 99/$CH_3OH$ 1/$NH_4OH$ 0.1. The fractions containing the first product by elution order are joined and evaporated under vacuum to give 0.65 g of 4-benzyl-7-(N,N-dimethylsulfonylamino)-1-(pyrrolidin-1-yl)-4H-[1,2,4]triazolo[4,3-a]quinazolin-5-one.

F(Tottoli)=221° C.

N.M.R.1H δ (ppm) DMSO: 2.2–2.3 (m. 4H); 2.9 (s. 3H); 3.15 (m. 4H); 5.15 (s. 2H); 7.1–7.2 (m. 3H); 7.25 (m. 2H); 7.5–7.6 (d. 1H); 7.85 (s. 1H); 8.05–8.1 (d. 1H); 10.05 (s. 1H)

The fractions containing the second product by elution order are treated in a similar manner to give 0.15 g of 4-benzyl-7-methylsulfonylamino-1-(pyrrolidin-1-yl)-4H-[1,2,4]triazolo[4,3-a]quinazolin-5-one.

Yield=23%

F(Tottoli)=283° C. [EtOH]

N.M.R.$^1$H δ (ppm) DMSO: 2 (m. 4H); 3.45 (m. 4H); 3.5 (s. 3H); 5.45 (s. 2H); 7.3 (m. 3H);7.7 (m. 3H); 6.35 (m. 2H)

Example 236

7-(N,N-dimethylamino)-4-benzyl-1-(pyrrolidin-1-yl)-4H-[1,2,4]triazolo[4,3-a]quinazolin-5-one In a balloon flask, we resuspend 0.75 g (2.05 mmol) of 7-amino-4-benzyl-1-(pyrrolidin-1-yl)-4H-[1,2,4]triazolo[4,3-a]quinazolin-5-one (described in example 225) in 0.8 ml of formic acid and 0.8 ml of formol. Under shaking, the mixture is heated at 100° C. for 1 hour. After cooling down, the obtained solution is poured into iced water, the suspension is extracted several times with ethyl acetate; the joined organic phases are washed in a aqueous NaCl-saturated solution, dried on $Na_2SO_4$ then concentrated under vacuum.

The obtained crude product (0.8 g) is purified by chromatography on silica column by elution with methylene mixture chloride 98/methanol 2. We obtain 0.23 g of pure by CCM product from example 236.

Yield=29%

F(Tottoli)=194° C. [EtOH]

CCM ($CH_2Cl_2$ 97/$CH_3OH$ 3): Rf=0.65

N.M.R.1H δ (ppm): 2.1 (m. 4H); 3.05 (s. 6H); 3.45 (m. 4H); 5.45 (s. 2H); 7.1 (m. 1H); 7.3 (m. 3H); 7.6 (d. 1H); 7.75 (m. 2H); 8.1 (d. 1H)

Solvent: CDCl3

Example 237

4-benzyl-7-cyano-1-(N,N-dimethylamino)-4H-[1,2,4]triazolo[4,3-a]quinazolin-5-one In a 500 ml balloon flask, equipped with a shaker, refrigeration and nitrogen feeding, we add 10.8 g (27.1 mmol) of 4-benzyl-7-bromo-1-(pyrrolidin-1-yl)-4H-[1,2,4]triazolo[4,3-a]quinazolin-5-one (example 164) in 100ml of N-methylpyrrolidinone (NMP). We add 4.4 g (49 mmol) of cuprous cyanide then heat the mixture, under shaking and under nitrogen for 12 hours. The solvent is eliminated by evaporation under vacuum; the residue is stirred in mixture of methylene chloride and 2N ammonia solution, the insoluble residue is eliminated by filtration, then the phases are separated by decantation. The organic phase is washed in a NaCl-saturated solution, dried on $Na_2SO_4$ and evaporated to give 24.0 g of crude product. This is purified by chromatography on silica column by elution using mixture of ethyl acetate 65/cyclohexane 35. The fractions pure in CCM are joined and evaporated under vacuum: we obtain 8.4 g of compound from example 237.

Yield=90%.

F(Tottoli)=212–214° C.

N.M.R.1H δ (ppm): 2.9 (s. 6H); 5.3 (s. 2H); 7.3 (m. 3H); 7.5 (m. 2H); 8.4 (m. 1H); 8.5 (m. 1H); 8.6 (m. 1H)

Solvent: DMSO

Example 238

4-benzyl-7-carboxy-1-(pyrrolidin-1-yl)-4H-[1,2,4]triazolo[4,3-a]quinazolin-5-one In a 250 ml balloon flask, we add 5.0 g (13.5 mmol) of 4-benzyl-7-cyano-1-(pyrrolidin-1-yl)-4H-[1,2,4]triazolo[4,3-a]quinazolin-5-one in 100 ml of 16 N hydrochloric acid solution then heat by reflux for 3 hours, under shaking.

After cooling down, the precipitate is filtered, washed several times in water, dried and purified by chromatography on silica column, by elution with the mixture $CH_2Cl_2$ 97/$CH_3OH$ 3, to give 2.3 g of pure by CCM compound from example 238.

Yield=44%

F(Tottoli)=335–337° C.

N.M.R.1H δ (ppm): 1.9 (s. 4H); 3.4 (s. 4H); 5.3 (s. 2H); 7.3 (m. 3H); 7.4 (m. 2H); 8.2 (m. 1H); 8.4 (m. 1H); 8.7 (s. 1H)

Solvent: DMSO

Example 239

7-bromo-4-[(4-methoxycarbonylmethyl)benzyl]-1-(pyrrolidin-1-yl)-4H-[1,2,4]triazolo[4,3-a]quinazolin-5-one 0.8 g (1.65 mmol) of 7-bromo-4-[(4-carboxymethyl)benzyl]-1-(pyrrolidin-1-yl)-4H-[1,2,4]triazolo[4,3-a]quinazolin-5-one (example 56) and 0.25 g of potassium carbonate are resuspended in 10 ml of DMF. We add 0.26 g (1.82 mmol) of methyl iodide then heat at 80° C., under shaking, for 2 hours. The solvent is evaporated under vacuum, the residue is resuspended in water, this latter being extracted 3 times by ethyl acetate; the joined organic phases are washed in sodium chloride saturated solution, dried on $Na_2SO_4$ then the solvent is evaporated under vacuum to give 0.7 g of crude product.

This is purified by chromatography on silica column by elution with mixture $CH_2Cl_2$ 99/$CH_3OH$ 1. We obtain 0.5 g of pure by CCM product.

Yield=61%

F(Tottoli)=161–162° C. [C2H5OH]

N.M.R.1H δ (ppm): 2–2.1 (m. 4H); 3.35–3.45 (m. 4H); 3.6 (s. 2H); 3.7 (s. 3H); 5.45 (s. 2H); 7.2 (d. 2H); 7.65 (d. 2H); 7.85 (d. 1H); 8.15 (d. 1H); 8.5 (s. 1H)

Solvent: CDCl3

Example 240

7-bromo-4-[(4-(N-methylcarbamoyl)methyl)benzyl]-1-(pyrrolidin-1-yl)-4H-[1,2,4]triazolo[4,3-a]quinazolin-5-one 240-1/ 7-bromo-4-[(4-chloroformylmethyl)benzyl]-1-(pyrrolidin-1-yl)-4H-[1,2,4]triazolo[4,3-a]quinazolin-5-one 0.85g (1.76 mmol) of 7-bromo-4-[(4-carboxymethyl)benzyl]-1-pyrrolidin-1-yl)-4H-(1,2,4]triazolo[4,3-a]quinazolin-5-one (example XX) is added in 85 ml of dry chloroform. Under nitrogen feeding, we shake then add 0.42 g (3.52 mmol) of thionyl chloride maintaining temperature below 5° C. After 90 minutes, the reaction is almost complete and chloride acid tends to precipitate as crystal. This solution will be used like in the next step.

240-2/ 7-bromo-4-[(4-(N-methylcarbamoyl)methyl)benzyl]-1-(pyrrolidin-1-yl)-4H-[1,2,4]triazolo[4,3-a]quinazolin-5-one To the solution cooled down at 0° C. of 0.6 g (8.8 mmol) of methylamine chlorhydrate and 1.06 g of triethylamine in 85 ml of acetone, we add slowly the obtained solution from example 240-1, maintaining temperature below 5° C. Shaking is then maintained at 0° C. for 15 minutes then the obtained solution is concentrated under vacuum. We dissolve the residue in methylene chloride, wash the organic phase twice in water, dry on $Na_2SO_4$, evaporate the solvent under vacuum and recover then 1.0 g of crude product. This is chromatographied on silica column by elution using mixture $CH_2Cl_2$ 96/$CH_3OH$ 4 to give 0.4 g which is recrystallized in ethanol. We obtain 0.27 g of pure compound after drying.

Yield=31%

F(Tottoli)=240° C.

CCM ($CH_2Cl_2$ 92/$CH_3OH$ 8): Rf=0.5

N.M.R.1H δ (ppm): 1.95–2.1 (m. 4H); 2.7 (d. 3H); 3.35–3.45 (m. 4H); 3.5 (s. 2H); 5.3–5.5 (m. 3H); 7.15 (d. 2H); 7.65 (d. 2H); 7.9 (d. 1H); 8.2 (d. 1H); 8.5 (s. 1H)

Solvent: CDCl3

The compounds (I) from examples 241 to 243 (table6) are prepared according to process in example 240.

TABLE 6

| No Compound | R | NR4R5 | Yld (%) | MP (° C.) |
|---|---|---|---|---|
| 241 | 4-(NH2COCH2)C6H4CH2 | pyrrolidin-1-yl | 38 | 268 |
| 242 | 4-(Me2NCOCH2)C6H4CH2 | pyrrolidin-1-yl | 74 | 202 |
| 243 | 4-(HONHCOCH2)C6H4CH2 | pyrrolidin-1-yl | 47 | 229 |

Compound 241

N.M.R.1H δ (ppm): 2.7 (s. 6H); 3.2 (s. 2H); 5.1 (s. 2H); 6.7 (s. 1H); 7.05 (d. 2H); 7.2 (m. 3H); 7.95 (m. 1H); 8.05 (d. 1H); 8.15 (s. 1H)

Solvent: DMSO

Compound 242

N.M.R.1H δ (ppm): 2–2.15 (m. 4H); 2.9 (s. 3H); 2.95 (s. 3H); 3.35–3.45 (m. 4H); 3.7 (s. 2H); 5.45 (s. 2H); 7.15 (d. 2H); 7.65 (d. 2H); 7.85 (d. 1H); 8.15 (d. 1H); 8.5 (s. 1H)

Solvent: CDCl3

Compound 243

N.M.R.1H δ (ppm): 1.95–2.1 (m. 4H); 3.3 (s. 2H); 3.3–3.4 (m. 4H); 5.3 (s. 2); 7.25 (d. 2H); 7.45 (d. 2H); 8.15 (d. 1H); 8.25 (d. 1H); 8.35 (s. 1H); 8.8 (s. 1H); 10.7 (s. 1H)

Solvent: DMSO

Example 244

7-methyl-4-(4-cyanobenzyl-1-(N,N-dimethylamino)-4H-[1,2,4]triazolo[4,3-a]quinazolin-5-thione 244-1/ 7-methyl-1-(N,N-dimethylamino)-4H-[1,2,4]triazolo[4,3-a]quinazolin-5-thione In a three-necked balloon flask equipped with shaker, refrigeration and nitrogen feeding, we add 1.0 g (4.1 mmol) of 7-methyl-1-(N,N-dimethylamino)-4H-[1,2,4]triazolo[4, 3-a]quinazolin-5-one in 70 ml of toluene and add at once 3.3 g (8.2 mmol) of Lawesson's reagent.

Under shaking, the mixture is heated by reflux for 24 hours. After cooling down, we add 30 ml of 5% hydrochloric acid solution, then we pour in 250 ml of methanol under shaking. We add 250 ml of cyclohexane and we eliminate the insoluble residue by filtration. The methanolic acid phase is separated by decantation, concentrated under vacuum and the residue is resuspended in ice and is triturated several times. The insoluble residue recovered as a resin is dissolved in 10 ml of isopropanol; from the obtained solution, shaken for 30 minutes, the yellow crystals which have precipitated are filtered, washed in isopropanol then in ether and dried under vacuum. We obtain 0.98 g of product that will be used like this in the next step.

Yield=80%

244-2/ 4-(4-cyanobenzyl)-1-(N,N-dimethylamino)-7-methyl-4H-[1,2,4]triazolo[4,3-a]quinazolin-5-thione From 0.5 g (1.93 mmol) of 7-methyl-1-(N,N-dimethylamino)-4H-[1,2,4]triazolo[4,3-a]quinazolin-5-thione (example 244-2), by using method B described in example 3, we obtain, after recrystallization in ethanol, 0.29 g of compound from example 244.

Yield=40%

F(Tottoli)=236° C.

N.M.R.1H δ (ppm): 2.9(s.6H); 3.7(s.2H); 5.45(s.2H); 7.25(m.2H); 7.7(m.2H); 7.85(m.1H); 8.2(d.1H); 8.5(s.1H)

Solvent: CDCl$_3$

The compounds (I) of examples 245 to 246 (table7) are prepared according to process in example 244.

TABLE 7

| No. Compound | X1 | R | NR4R5 | Yld (%) | MP (° C.) |
|---|---|---|---|---|---|
| 245 | 7-Br | 4-CNC6H4CH2 | 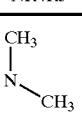 | 13 | 276 |
| 246 | 7-CH3 | (E)(pyridin-3-yl)-CH=CHCH2 |  | 26 | 133 |

Compound 245

N.M.R.1H δ (ppm): 2.9 (s. 6H); 4.7 (s. 2H); 7.65 (d. 2H); 7.75 (d. 2H); 8.1 (m. 2H); 8.4 (d. 1H)

Solvent: DMSO

Compound 246

N.M.R.1H δ (ppm): 2.5 (s. 3H); 3.0 (s. 6H); 4.25 (d. 2H); 6.45 (dt. 1H); 6.75 (d. 1H); 7.2 (m. 1H); 7.6 (d. 1H); 7.7 (d. 1H); 7.9 (s. 1H); 8.4 (m. 2H); 8.6 (bs. 1H)

Solvent: CDCl3

B. Intermediate Compounds

Particularly preferred intermediate compounds of the current invention may be prepared according to the following examples. However, the person skilled in the art may modify easily operative procedures described below depending on the desired intermediate.

Example 250

Intermediate 1

1,2,3,4-tetrahydro-3-benzyl-6-bromo-4-oxo-2-thia-quinazoline from 5-bromo anthranilic acid.

In a reactor equipped with shaker, refrigeration and bromide funnel, 150 g (694 mmol) of 5-bromo-2-amino-benzoic acid are resuspended in 1.5 l of acetic acid.

Under shaking, the mixture is heated by reflux, then 92 ml (103 g; 694 mmol) of benzyl isothiocyanate are added slowly and regularly using the bromide funnel.

After addition, shaking and heating by reflux are maintained for 6 hours, solubilization is realized gradually during this period.

After cooling down to ambient temperature, the solid that has precipitated is filtered and washed in acetic acid.

The product obtained is dried under vacuum at 60° C. to give 125.2 g of expected pure by CCM compound (elution solvent: CH$_2$Cl$_2$ 99.2/CH$_3$OH 0.8; Rf=0.9)

Yield=52%

NMR $^1$H and $^{13}$C spectra are compatible with the expected structure.

Example 251

Intermediate 2

3,4-Dihydro-3-benzyl-6-bromo-2-hydrazino-quinazolin-4-one.

In a reactor equipped with shaker, refrigeration, 125.2 g (360 mmol) of 1,2,3,4-tetrahydro-3-benzyl-6-bromo-4-oxo-2-thia-quinazoline (Intermediate 1) are added in 3.5 l of ethanol.

Under shaking, we add 167.6 g (3.348 mmol) of hydrazine hydrate.

The obtained suspension is heated by reflux for 18 hours, during which solubilization is gradually realized.

After cooling down to ambient temperature, about half of solvent is evaporated under vacuum and the obtained residual solution is left aside in a ice bath for 1 hour.

After filtration of the precipitate, cold ethanol wash then drying under vacuum at 60° C., we obtain 89.7 g of expected pure by CCM compound, (elution solvent: CH$_2$Cl$_2$ 99/CH$_3$OH 1; Rf=0.1)

Yield=72%

NMR $^1$H and $^{13}$C spectra are compatible with the expected structure.

Example 252

Intermediate 3

4-benzyl-7-chloro-1-mercapto-4H-[1,2,4]triazolo[4,3-a]quinazoline -5-one

In a reactor equipped with shaker and refrigeration, we resuspend 47.7 g (158 mmol) of 3,4-dihydro-3-benzyl-6-chloro-2-hydrazino-quinazolin-4-one (prepared in a similar manner as intermediate 2) in 600 ml of pyridine.

We add then 25.3 g (158 mmol) of potassium xanthogenate by fraction, the obtained solution is heated by reflux for 7 hours, under shaking, during which the solid is gradually precipitated.

After one night's rest at ambient temperature, the precipitate is separated by filtration then redissolved in 1.5 l of water.

The obtained solution is neutralized by acid acetic, then the formed precipitate is filtered, washed in water until neutral pH and dried.

We obtain 54.0 g of crude product which will be used like this in the next step.

Yield≈100%

Example 253

Intermediate 4

4-benzyl-7-chloro-1-methylthio-4H-[1,2,4]triazolo[4,3-a]quinazolin-5-one.

In a reactor equipped with a shaker and bromide funnel, we resuspend 6.72 g of soda in 1200 ml of water then add 57.0 g (166 mmol) of 4-benzyl-7-chloro-1-mercapto-triazolo[4,3-a]quinazolin-5-one (Intermediate 3).

Under shaking, we add 15.74 ml (166 mmol) of dimethyl sulfate at ambient temperature, over a 30 minutes period. Shaking is maintained for 7 hours.

After leaving aside at ambient temperature for a night, the precipitate is filtered, washed in water then dried under vacuum.

We obtain 51.2 g of crude solid which is used like this in the next step.

Yield=100%

Example 254

Intermediate 5: 4-benzyl-1,7-dichloro-4H-[1,2,4]triazolo[4,3-a]quinazolin-5-one

In a reactor equipped with shaker, plunging tube and refrigeration, we add 51.0 g (143 mmol) of 4-benzyl-7-chloro-1-methylthio-triazolo[4,3-a]quinazolin-5-one (Intermediate 4) in a mixture of 1.5 l of chloroform and 0.9 l of water.

Under shaking, we cool down to 0° C., then allow a chlorine stream to flow, maintaining temperature below 10° C. for 2 hours.

We then stop chlorine feeding, leave the mixture to return to ambient temperature then maintain shaking for 2 hours.

The 2 phases are separated by decantation, the chloroformic phase is dried on $Na_2SO_4$ and concentrated under vacuum.

We obtain 50.9 g of crude solid residue. This is resuspended in 400 ml of ethanol and the heterogeneous mixture is shaken for 30 minutes. The insoluble residue is filtered, washed in ethanol and dried at 50° C. under vacuum to give 46.5 g of pure expected by CCM compound (elution solvent $CH_2Cl_2$ 99/$CH_3OH$ 1; Rf=0.50)

Yield=94%

Proton and $^{13}C$ NMR spectra are compatible with the expected structure.

Example 255

Intermediate 6: 4-benzyl-7-bromo-4H-[1,2,4]triazolo[4,3-a]quinazolin-5-one

In a 6 liter reactor, equipped with shaker, we add 89.7 g (260 mmol) of 3,4-dihydro-3-benzyl-6-bromo-2-hydrazino-quinazolin-4-one (Intermediate 2) in 2.9 l of dry chloroform.

We shake, cool the suspension down to 0° C. using an ice bath, then add 216 ml (192.5 g; 1.299 mmol) of triethyl orthoformiate, leading to a slight temperature increase (up to 6° C.). Maintaining the temperature below 5° C., we add 8.2 ml of concentrated sulfuric acid in a single go. We shake then for 15 min at temperature below 5° C., then remove the ice bath, shaking is maintained for 4 additional hours during which a solid gradually precipitates.

We add 1.5 l of water and 0.7 l of chloroform, shake until complete distribution between the 2 phases then neutralize the aqueous phase to pH 7 by sodium bicarbonate.

The organic phase is decanted, washed with NaCl-saturated solution, dried on $Na_2SO_4$ and evaporated under vacuum to give 91.3 g of expected pure by CCM compound, (elution solvent: $CH_2Cl2$ 97/$CH_3OH$ 3/$NH4OH$ 0.3; Rf=0.5).

Yield=99%

PF(Tottoli)=237° C.

NMR $^1H$ and $^{13}C$ spectra are compatible with the expected structure.

Example 256

Intermediate 7: 4-benzyl-1,7-dibromo-4H-[1,2,4]triazolo[4,3-a]quinazolin-5-one

In a 3 liter reactor equipped with shaker, refrigeration and bromide funnel, we add 35 g (98.5 mmol) of 4-benzyl-7-bromo-4H-[1,2,4]triazolo[4,3-a]quinazoline-5-one (Intermediate 6) in 630 ml of chloroform and 11 ml of pyridine.

Under shaking, 16.4 ml (320 mmol) of bromine are then added at ambient temperature over a 30 minute period.

After addition, shaking is maintained at ambient temperature for 1 hour; the reaction medium is then distributed between 1 l of water and 1.5 l of chloroform and the heterogeneous mixture shaken for 15 min.

The insoluble residue is dried, washed in water to a neutral pH then triturated in ethanol.

After drying under vacuum at 50° C., we obtain a first fraction of 8.2 g of pure by CCM expected compound (elution solvent: $CH_2Cl_2$ 99/$CH_3OH$ 1; Rf=0.6).

After separation of the chloroformic phase, washing in sodium bicarbonate solution then in water, drying on $Na_2SO_4$, evaporation of solvent under vacuum then triturating of residue in ethanol, filtration and drying of solid at 50° C., we obtain 33.1 g of a second fraction of expected compound, equivalent by CCM to the precedent fraction.

Yield total (of the 2 fractions)=96%

NMR $^1H$ spectrum is compatible with the expected structure.

Example 257

Intermediate 8: 1-Azepanyl-4H-[1,2,4]triazolo[4,3-a]quinazolin-5-one

In a 150 ml balloon flask equipped with shaker and refrigeration , we dissolve 1.0 g (2.68 mmol) of 1-Azepanyl-4-benzyl-4H-[1,2,4]triazolo[4,3-a]quinazolin-5-one in 60 ml of tetrahydrofuran.

We add 2.0 g of ammonium formiate then 1.5 g of 10% activated palladium on charcoal. The mixture is shaken and heated by solvent reflux for 5 hours.

After cooling down, the suspension is filtered, and then the solvent is evaporated under vacuum to give 0.55 g of residual solid.

This is chromatographied on silica column by elution using mixture $CH_2Cl_2$ 97/$CH_3OH$ 3; the fractions pure in CCM are gathered together and concentrated under vacuum to give 0.42 g of residual solid.

Yield=55%

F(Tottoli)=222–224° C.

CCM ($CH_2Cl_2$ 95/$CH_3OH$ 5): Rf=0.4

N.M.R.$^1H$ δ (ppm): 1.65–1.85 (m. 8H); 3.25 (m. 4H); 7.5 (t.1H); 7.9 (t. 1H); 8.15 (d. 1H); 8.3 (d.1H); 12.6 (m. 1H)

Solvent: DMSO

The compounds (I; R=H) of examples 258 to 262 (table8) are prepared according to the process in example 257.

TABLE 8

| No Compound | X1 | NR4R5 | Yld (%) | MP (° C.) |
|---|---|---|---|---|
| 258 | 7-Br | (azepane ring) | 96 | >290 |
| 259 | 8-CH3 | (azepane ring) | 64 | — |
| 260 | 8- | (bis-azepane) | 75 | — |

TABLE 8-continued

| No Compound | X1 | NR4R5 | Yld (%) | MP (° C.) |
|---|---|---|---|---|
| 261 | 7-Br | piperidinyl | 89 | >300 |
| 262 | 7-Br | pyrrolidinyl | 90.5 | >300 |

Example 263

Intermediate 9: 1-Azepanyl-7-chloro-4H-[1,2,4]triazolo[4,3-a]quinazolin-5-one 10.0 g of 1-Azepanyl-4-benzyl-7-chloro-4H-[1,2,4]triazolo[4,3-a]quinazolin-5-one (24.5mmol) then 19.6 g (147 mmol) of dry aluminium chloride are resuspended in 200 ml of anhydrous benzene.

The suspension is shaken and heated at 50° C. in the absence of humidity.

After 90 minutes, we allow to cool down, add some ice to the reaction mixture then shake the mixture vigorously for 30 minutes.

The obtained precipitate is dried, washed in water to a neutral pH and dried at 50° C. to give 7.5 g of pure by CCM solid.

Yield=96%

F(Tottoli): >300° C.

CCM ($CH_2Cl_2$ 95/$CH_3OH$ 5): Rf=0.35

N.M.R. $^1H$ δ (ppm): 1.65–1.9 (m. 8H); 3.3 (m. 4H); 7.95 (d. 1H); 8.05 (s. 1H); 8.3 (d. 1H); 12.8 (m.1H)

TABLE 9

| N° Compound | X1 | NR4R5 | MP (° C.) |
|---|---|---|---|
| 264 | H | pyrrolidinyl | 283 |
| 265 | 7-CH3 | azepanyl | 298 |
| 266 | 7-CH3 | pyrrolidinyl | >300 |
| 267 | 7-CH3 | N(CH3)2 | — |
| 268 | 7-OH | piperidinyl | 295 |
| 269 | 7-CN | pyrrolidinyl | >300 |
| 270 | 7-CN | N(CH3)2 | — |

Example 271

Intermediate 10: 1-amino-4-benzyl-7-bromo-4H-[1,2,4]triazolo[4,3-a]quinazolin-5-one In a 500 ml reactor equipped with shaker, refrigeration equipped with a potash keeper, thermometer and nitrogen feeding, we resuspend 5.0 g (14.5 mmol) of 3,4-dihydro-3-benzyl-6-bromo-2-hydrazino-quinazolin-4-one (prepared according example XX) in 150 ml of dry methanol. We add 1.62 g (15.3 mmol) of cyanogene bromide and shake the heterogeneous mixture for 1 hour at ambient temperature, then by reflux for 5 hours After cooling down, we add drop by drop, under vigorous shaking, aqueous solution of saturated sodium bicarbonate to pH 8. The insoluble solid is filtered, washed several times in water and dried under vacuum to give 4.9 g of crude product.

The latter is triturated in 100 ml of methanol, the insoluble fraction is separated by filtration, washed in methanol and dried under vacuum. We obtain 4.6 g of pure by CCM product. NMR $^1H$ and $^{13}C$ spectra are compatible with the expected structure.

Yield=86.5%

F(Tottoli)=287° C.

CCM ($CH_2Cl_2$ 95/$CH_3OH$ 5): Rf=0.5

Evaluation of in vitro Activity of the Preferred Compounds of the Invention

Inhibition of the Phosphodiesterase

The capacity of the formula (I) compounds of the invention to inhibit the cyclic nucleotide phosphodiesterases is evaluated by their $Cl_{50}$ measurement (necessary concentration to inhibit 50% of enzymatic activity).

The type 4 phosphodiesterases are obtained from a cytosolic preparation extracted from the human origin cellular line U937 according to a method adapted from T. J. Torphy and al., 1992, J.Pharm.Exp. Ther. 263: 1195–1205

The other classes of phosphodiesterases are obtained after partial purification FPLC on Mono Q column. (anion exchange column) according to a method adapted from Lavan B. E., Lakey T., Houslay M. D. Biochemical Pharmacology, 1989, 38(22), 4123–4136., and from Silver P. J and al., 1988, Eur.J. Pharmacol. 150: 85–94, either, from human origin cellular lines for PDE 1 (monocytar line TPH1) and PDE5 (line MCF7 issued from an adenocarcinoma), or from dog aorta for PDE 3, or for the human PDE3A, from gene cloning in insect cells SF21 in baculovirus, according to a method adapted from Luckow, V. A. and al., 1991 in Recombinant DNA Technology&Applications.,eds. Prokop, Bajpai,R. K.&Ho, C. S., pp97–152. The enzymatic activity measurement of the different PDE classes, and in particular the PDE 4, is performed according to a method adapted from W. J. Thompson and al. 1979, Advances in Cyclic Nucleotide Research, Vol. 10: 69–92, ed. G. Brooker and al. Raven Press, NY.

For the $Cl_{50}$ determination, the enzymatic activity is measured in the presence of inhibitor within concentration margins of 0.1 to 100 μM.

The following table illustrates the PDE4 inhibitory activity from enzymatic preparation obtained from the line U937.

| N° Compound | IC$_{50}$ ($\mu$M) |
|---|---|
| 1 | 0.054 |
| 3 | 0.079 |
| 11 | 0.080 |
| 13 | 0.060 |
| 20 | 0.04 |
| 22 | 0.41 |
| 32 | 0.053 |
| 34 | 0.056 |
| 35 | 0.020 |
| 37 | 0.015 |
| 40 | 0.014 |
| 41 | 0.018 |
| 42 | 0.024 |
| 43 | 0.030 |
| 44 | 0.090 |
| 46 | 0.090 |
| 47 | 0.050 |
| 48 | 0.025 |
| 49 | 0.080 |
| 50 | 0.035 |
| 51 | 0.027 |
| 52 | 0.030 |
| 57 | 0.014 |
| 59 | 0.090 |
| 60 | 0.050 |
| 61 | 0.011 |
| 62 | 0.053 |
| 75 | 0.078 |
| 76 | 0.070 |
| 78 | 0.038 |
| 79 | 0.14 |
| 80 | 0.073 |
| 81 | 0.016 |
| 83 | 0.012 |
| 85 | 0.041 |
| 89 | 0.027 |
| 92 | 0.030 |
| 94 | 0.029 |
| 96 | 0.058 |
| 98 | 0.029 |
| 102 | 0.060 |
| 103 | 0.039 |
| 104 | 0.077 |
| 164 | 0.090 |
| 156 | 0.090 |
| 189 | 0.078 |
| 190 | 0.19 |
| 218 | 0.048 |
| 223 | 0.012 |
| 224 | 0.075 |
| 227 | 0.028 |
| 229 | 0.080 |
| 230 | 0.002 |
| 231 | 0.00027 |
| 233 | 0.18 |
| 234 | 2.69 |
| 239 | 0.005 |
| 240 | 0.013 |
| 242 | 0.011 |
| 243 | 0.028 |
| 246 | 0.041 |

The examination of the results from the above table shows that the preferred products of the invention tested in the trial inhibit the enzyme PDE4 in vitro in an efficient manner.

Inhibition of TNFα Production by Human Leukocytes Stimulated by Lipopolysaccharid This test aims to evaluate capacity of the compounds of the invention to inhibit TNFα (tumor necrosis-α) production by human leukocytes in the presence of high human serum concentration (75%). Indeed, it appears that a number of compounds having a capacity any longer to inhibit phosphodiesterase 4 in enzymatic or cellular tests do not present anymore this capacity when the test is performed in human blood. The test described here is based on the use of human leukocytes cultivated in 75% of human serum. It had been previously documented that these conditions simulate the observed situation when TNFα dosage is performed in human blood.

The compounds to test are dissolved into 20 mM (sometimes 6 mM) of DMSO. 100 $\mu$l of DMSO are distributed into 7 wells of a a 96 well microtiter plate (wells B to H). 150 $\mu$l of the compound solution are distributed into line A wells. 50 $\mu$l are then sequentially transferred 7 times. 20 $\mu$l of this serial dilutions of compounds are sequentially transferred twice in wells containing 180 $\mu$l of RPMI 1640 (Gibco). 50 $\mu$l of these dilutions are then transferred in wells where cells will be added.

Each test includes a series of eight wells without LPS (100% of inhibition), eight wells with LPS (0% of inhibition) and a series of Rolipram dilutions in order to enable comparison of the tests between each other and then to evaluate their variability.

A leukocyte vial is unfrozen in bain-marie (37° C.), its content is transferred into a 15 ml tube containing 10 ml of RPMI added with 5% of human serum (RPMI-5% HS). The cells are sedimented (800 g, 6 minutes, 4° C.), resuspended in 10 ml of the same medium and counted by dilution in Trypan blue solution. After centrifugating (800 g, 6 minutes, 4° C.), the cells are resuspended to 2×10$^6$/ml in human serum.

To 50 $\mu$l aliquots of different dilutions of compounds, 100 $\mu$l of cells are added. The plates are then incubated 30 minutes at 37° C., then 50 $\mu$l of solution 4 $\mu$g/ml of LPS prepared in human serum are added. The plates are incubated for the night at 37° C.

After incubation for 15–18 hours, 90 $\mu$l of growth supernatant are taken and transferred into rounded-bottom microtiter wells. The TNFα presence is then evaluated by ELISA (Pharmingen) by using 50 $\mu$l of supernatant. The protocol described by the manufacturer is strictly applied.

Results obtained for some of the preferred compounds of the current invention are illustrated in the following table.

| Compound | Inhibition (human leukocytes) IC$_{50}$ $\mu$M |
|---|---|
| 3 | 3.4 |
| 104 | 8.1 |
| 94 | 6.3 |
| 101 | 8.6 |
| 85 | 6.8 |
| 98 | — |
| 79 | 5.2 |
| 91 | — |
| 93 | 4.3 |
| 103 | 10.7 |
| 46 | — |
| 35 | |

Evaluation of in vivo Activity f Compounds of the Invention In vivo TNFα Model in Wistar Rat The TFNα is a cytokin playing a central role in inflammation mechanisms. Its production may be induced by injection of lipopolysaccharid (LPS). It has been shown that the intracellular AMPc increase, produced in particular by PDE4 inhibitors, decreases the TNFα production in in vitro and in vivo models. Therefore it matters here to quantify in vivo anti-inflammatory potential of the compounds of the invention, administrated by oral route (p.o.) by measuring inhibition of TNFα production in plasma in rat, the latter having received a intraperitoneal injection (i.p.) of lipolysaccharid (LPS). The treatment by the compounds of the invention or the carrier is administrated by oral route in male Wistar rats, 30 min. before LPS injection. The rats are sacrificed 90 min. after LPS stimulation, the blood is harvested on EDTA and TNFα concentration is measured in each plasma sample. The results obtained from some of the compounds of the current invention are presented in the table below.

| Compound | % Inhibition to 10 mg/kg |
|---|---|
| 3 | −98% |
| 104 | −94% |
| 94 | −87% |
| 101 | −80% |
| 85 | −77% |
| 98 | −75% |
| 79 | −72% |
| 91 | −70% |
| 93 | −67% |
| 163 | −64% |
| 46 | −58% |
| 35 | −51% |

REFERENCES

Chen, Y. L., the Vraux, V., Giroud, J. P. and Chauvelot-Moachon L. (1994). Anti-tumor necrosis factor properties of non-peptide drugs in acute-phase responses. Eur. J. Pharmacol., 271 (2–3), 319–27.

Prabhakar, U., Lipshutz, D., O'Leary Barthus, J., Slivjak, J., Smith III E. F., Lee, J. C. and Esser K. M. (1994). Characterization of cAMP-dependent inhibition of LPS-induced TNFα production by rolipram, a specific phosphodiesterase IV (PDE IV) inhibitor. Int. J. Immunopharmacol., 16 (10), 805–816.

Model of Eosinophily in Rat

The studies undertaken from this experimental model aim to evaluate inhibitory effect of the compounds of the invention on the rush of inflammatory cells and in particular of eosinophils in the opening of trachea-bronchial shaft in rat. The eosinophils play a major role in asthma physiopathology in human by releasing on the level of pulmonary parenchyma some pro-inflammatory mediators like leukotriens, proteins and specific enzymes (ECP, EPO, MBP) and cytokins. The massive recruitment of this cellular type air passages in asthmatic patient leads to a progressive degradation of pulmonary tissue explaining bronchial hyperactivity, chronic disease and exacerbation in the absence of treatment. This model uses Brown Norway rats, whose particularity is to produce, like atopic patients, immunoglobulin E (IgE) rates in response to a sensibilization by antigen. The protocol used involves two sensibilizations to ovalbumin at fourteen days interval then a challenge seven days later with ovalbumin aerosol. Forty-eight hours after the antigenic challenge, the animals undergo a bronchoalveolar wash under anesthesia in order to harvest inflammatory cells infiltrate in lung. These cells are then counted and differentiated according to morphological criteria. The products of the invention are administrated by oral route, 1 hour before the antigenic challenge. Most of the preferred compounds of the current invention tested in this model have also demonstrated an excellent activity.

REFERENCES

Corrigan and al. (1992) Immunology today 13: 501–507
Elwood and al. (1995) Inflamm Res 44: 83–86

Model of Neutrophily in Mouse

The studies undertaken from this experimental protocol aim to evaluate modulating effect of the compounds of the invention on the rush of pro-inflammatory cells (precocious phase) in the opening of trachea-bronchial shaft in mouse. This cellular rush is consecutive to stimulation simulating a bacterial infection (bacterial lipopolysaccharid or LPS). This precocious inflammatory step results from events combination among which the main ones are synthesis and release of stimulating (TNFαi) and chimiotactic (IL-8ii) factors, increase of vascular permeability at trachea-bronchial micro-circulation level and neutrophilic polynuclear infiltration which is concomitant to plasmatic protein exudation in pulmonary tissues.

This pathological process is retrieved in chronic obstructive broncho-pneumopathy disease (COPD) in which neutrophils, with macrophage, play a key role in launching of neutrophil recruitment amplification, but also in destructuration of pulmonary tissues (decline of pulmonary functions), hypersecretion of trachea-bronchial mucus (clogging of aerial tracts), tissular inflammation (release of inflammatory mediators and free radicals) and basal tonus increase of pulmonary muscular smooth fibers (chronic respiratory distress). Some of the compounds of the examples have demonstrated an activity in this model.

REFERENCES i SUTER P. M., SUTER S., GIRARDIN E., ROUX-LOMBARD P., GRAU G. E. and DAYER J.-M. 1992. High bronchoalveolar levels of tumor necrosis factor and its inhibitors, interleukin-1, interferon and elastase, in patients with adult respiratory distress syndrome after trauma, shock or sepsis. Am. Rev. Respir. Dis. 145: 1016–1022.

ii MARTIN T. R. and GOODMAN R. B. 1999. The role of chemokines in the pathology of the acute respiratory distress syndrome. Chapter 6 in Chemokines in disease: Biology and clinical research edited by: C. A. Hebert, Humana Press Inc., Totowa, N.J.

iii REPINE J. E. and BEEHLER C. J. 1991. Neutrophils and the adult respiratory distress syndrome: two interlocking perspectives. Am. Rev. Respir. Dis. 144: 251–252.

REFERENCES

Barad, M. and al., PNAS, 1998, Vol. 95(25), p. 15020–15025

Belayev, L. and al., Brain Res., 1998 Mar. 23, Vol. 787(2), p. 277–285

Block, F. and al., Neuroreport, 1997 Dec. 1, Vol. 8(17), p. 3829–3832

Egawa, T. and al., Jon J. Pharmacol., 1997 November, Vol. 75(3), p. 275–281

Gonccalves of Moraes, V.-L. and al., Br. J. Pharmacol., 1998 February, Vol. 123(4), p. 631–636

Hasko, G. and al., Eur. J. Immunol., 1998 February, Vol. 28(2), p. 468–472

Herzer, W.-A. and al., J. Cardiovasc. Pharmacol., 1998, Vol. 32(5), p. 769–776

Itoh, A. and al., Methods and Findings in Exp. and Clin. Pharm., 1998, Vol. 20(7), p. 619–625

Kim, O. H., Lerner A., Blood, 1998 Oct. 1, Vol. 92(7), p. 2484–2494

Lelkas, Z. and al., Pharmacol. Biochem. Behav., 1998 August, Vol. 60(4), p. 835–839

Liang, L. and al., Diabetes, 1998 April, Vol. 47(4), p. 570–575

Merz, K.-H. and al., J. Med. Chem., 1998 Nov. 19, Vol. 41(24), p.4733–4743

Miotta, J.-M. and al., Am. J. Respir. Cell. Mol. Biol., 1998 March, Vol. 18(3), p. 411–420

What is claimed is:

1. A compound of Formula I or Formula II:

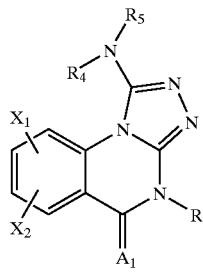
I

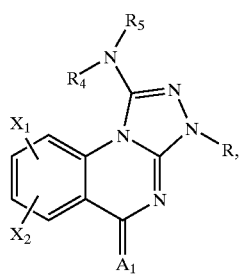
II wherein:
$A_1$ is O or S;
$X_1$ and $X_2$ are independently
hydrogen, hydroxy, halogen, amino, nitro, mercapto, cyano or carboxyl;
$(C_1-C_6)$alkyl, $(C_1-C_6)$alkoxy or $—S(O)_mR_8$, said alkyl and alkoxy being optionally substituted on carbon with one to three halogen;
$—CO—Q_1—Q_2—Q_3$;
$—NH—R_1$; or
$—NR_2R_3$;
R is
$(C_1-C_6)$alkyl, $(C_2-C_6)$alkenyl, $(C_2-C_6)$alkynyl, aryl $(C_2-C_6)$alkynyl, or 2-, 3- or 4-pyridyl$(C_1-C_6)$alkyl optionally substituted with $(C_1-C_6)$alkyl, $(C_1-C_6)$ alkoxy, hydroxy. halogen or amino; or

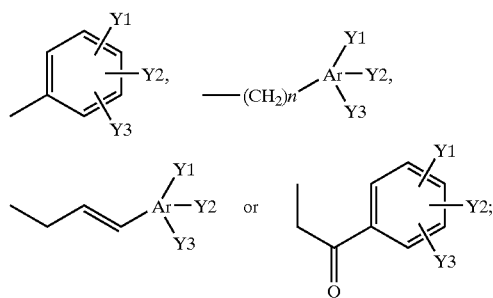

$R_4$ and $R_5$ are taken separately, are identical, and are $(C_1-C_6)$alkyl; or
$R_4$ and $R_5$ are taken separately, are different, and are aryl$(C_1-C_6)$alkyl, $(C_3-C_7)$cycloalkyl or $(C_3-C_7)$cycloalkyl$(C_1-C_6)$alkyl; or
$R_4$ and $R_5$ are taken together with the nitrogen atom to which they are attached to form a 4-, 5-, 6- or 7-membered saturated or partially unsaturated ring, said ring optionally containing one to three hetero atoms selected from O, S and N, said ring being optionally substituted with $(C_1-C_6)$alkyl, hydroxy or $(C_1-C_6)$alkoxy, said ring being optionally bridged with a $(C_1-C_6)$alkyl which may be gem-di$(C_1-C_6)$alkylated or substituted with one to three hydroxy, oxo, $(C_1-C_6)$ alkyl, $(C_1-C_6)$alkoxy, phenyl$(C_1-C_6)$alkyl or $CO—Q_1—Q_2—Q_3$, said ring being optionally fused via two adjacent atoms shared with another ring selected from phenyl and heteroaryl, said heteroaryl ring containing four to eight carbon atoms which may be optionally replaced with one to three hetero atoms selected from O, S and N;

m is 0, 1 or 2;
$R_6$ is $(C_1-C_6)$alkyl, said alkyl being optionally substituted with one to three halogen;
$—Q_1—$ is a bond, $—O—$,

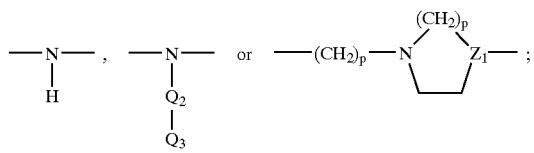

$—Q_2—$ is:
a) $—(CH_2)_q—$;
b) $—(CH_2CH_2—O)_r$;
$—Q_3$ is: $—H$, $—OH$, $(C_1-C_6)$alkoxy, $—O—CO—X_3$, $—NHX_3$, or

$R_1$ is $(C_1-C_6)$alkyl optionally substituted with one to three halogen, hydroxy, cyano, $(C_1-C_6)$alkoxy or $—CO—Q_1—Q_2—Q_3$;
$R_2$ and $R_3$ are taken separately and are independently $(C_1-C_6)$alkyl optionally substituted with one to three hydroxy, halogen, cyano, $(C_1-C_6)$alkoxy or $—CO—Q_1—Q_2—Q_3$; or
$R_2$ and $R_3$ are taken together with the nitrogen atom to which they are attached to form a 4-, 5-, 6- or 7-membered ring, said ring containing one to three O, S or N, said ring being optionally bridged with a $(C_1-C_6)$alkyl which may be gem-dialkylated or substituted with one to three hydroxy, oxo, $(C_1-C_6)$alkyl, $(C_1-C_6)$alkoxy or $—CO—Q_1—Q_2—Q_3$;
n is 1, 2, 3, 4 or 5;
Ar is a 5- or 6-membered aromatic ring containing 0 to 3 hetero atoms selected from O, S and N;
Y1, Y2 and Y3 are independently
hydrogen, hydroxy, mercapto, amino, nitro, halogen, $—NHR_1$, $—NR_2R_3$,
$—(CH_2)_sCN$ or $—(CH_2)_sCO—Q_1—Q_2—Q_3$;
$—(C_1-C_6)$alkyl, $(C_1-C_6)$alkoxy or $—S(O)_mR_8$;
s is 0, 1, 2, 3, 4, 5 or 6;
p is 0, 1, 2 or 3;
$Z_1$ is CH, N, O or S;
q is 0, 1, 2, 3, or 4;

r is 2, 3, or 4; and $X_3$ and $X_4$ are taken separately and are independently $(C_1-C_6)$alkyl; or $X_3$ and $X_4$ are taken together with the nitrogen atom to which they are attached to form a 4-, 5-, 6- or 7-membered ring, said ring containing one to three additional hetero atoms selected from O, S and N;

a racemic or isomeric form thereof or a pharmaceutically acceptable salt of said compound, racemic or isomeric form.

2. A compound of claim 1 wherein $A_1$ is O; $X_1$ is H; $X_2$ is halogen, amino, $(C_1-C_6)$alkyl, hydroxy or —$NHR_1$; and R is —$(C_1-C_6)$alkyl, $(C_2-C_6)$alkenyl, aryl$(C_2-C_6)$alkynyl or 2-, 3- or 4-pyridyl$(C_1-C_6)$alkyl group optionally substituted on said pyridyl ring with $(C_1-C_6)$alkyl, halogen or hydroxy; or R is

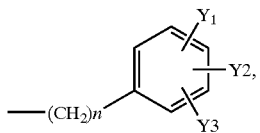

wherein n is 1, 2 or 3;

Y1, Y2 and Y3 are each independently H or $(C_1-C_6)$ alkoxy; or

Y1 and Y2 are each H; and Y3 is $(C_1-C_6)$alkoxy, amino, —NHR, —$NR_2R_3$, nitro, hydroxy, —$(CH_2)_sCO$—$Q_1$—$Q_2$—$Q_3$, —$(CH_2)_s$—CN, or $(C_1-C_6)$alkyl optionally substituted with one to three halogen; or Y1 is H and Y2 and Y3 are each independently hydroxy, halogen or $(C_1-C_6)$alkoxy; or R is

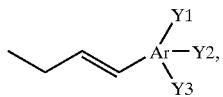

wherein

Y1, Y2 and Y3 are each H; or

Y1 and Y2 are each H and Y3 is $(C_1-C_6)$alkoxy or halogen.

3. A compound of claim 2 wherein $X_1$ is H; $X_2$ is halogen, amino, $(C_1-C_6)$alkyl, hydroxy or —$NHR_1$;

R is

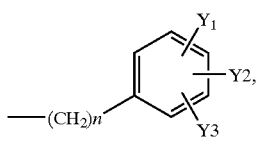

wherein n is 1, 2 or 3;

Y1, Y2 and Y3 are each H or $(C_1-C_6)$alkoxy; or

Y1 and Y2 are each H; and Y3 is $(C_1-C_6)$alkoxy;

amino;

—NHR;

—$NR_2R_3$;

nitro;

hydroxy;

$(C_1-C_6)$alkyl optionally substituted with one to three halogen;

—$(CH_2)_sCO$—$Q_1$—$Q_2$—$Q_3$ in which s is 0 or 1; $Q_1$ is O, —NH— or a bond; $Q_2$ is —$(CH_2)_q$—, wherein q is 0, 1, 2, 3 or 4; and $Q_3$ is H, OH or —$NX_3X_4$; or —$(CH_2)_s$—CN wherein s is 0 or 1; or Y1 is H; and Y2 and Y3 are each independently hydroxy, halogen or $(C_1-C_6)$alkoxy; or R is

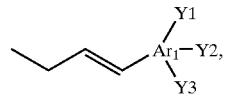

wherein $Ar_1$ is a 6-membered aromatic ring optionally containing N in the 2-, 3- or 4-position;

Y1, Y2 and Y3 are each H; or, when $Ar_1$ does not contain N, then Y1 and Y2 are each H and Y3 is $(C_1-C_6)$alkoxy or halogen.

4. A compound of claim 3 wherein said $(C_1-C_6)$alkyl is 2,2,2-trifluoroethyl, 3,3,3-trifluoropropyl, 1-trifluoromethylethyl, 4,4,4-trifluoro-n-butyl, 2-trifluoromethylpropyl, 1-trifluoromethylpropyl, 1-methyl-1-trifluoromethylethyl, 3,3,3-trifluoro-1-methylpropyl, 2,2,2-trifluoroethoxy, 3,3,3-trifluoropropoxy, 1-trifluoromethylethoxy, 4,4,4-trifluoro-n-butoxy, 2-trifluoromethylpropoxy, 1-trifluoromethylpropoxy, 1-methyl-1-trifluoromethylethoxy, 3,3,3-trifluoro-1-methylpropoxy, 2,2,2-trifluoroethylthio, 3,3,3-trifluoropropylthio, 1-trifluoromethylethylthio, 4,4,4-trifluoro-n-butylthio, 2-trifluoromethylpropylthio, 1-trifluoromethylpropylthio, 1-methyl-1-trifluoromethylethylthio, or 3,3,3-trifluoro-1-methylpropylthio.

5. A compound of claim 1 wherein $X_1$ and $X_2$ are independently H, hydroxy, halogen, amino, nitro, mercapto, cyano, carboxyl, $(C_1-C_6)$alkyl, $(C_1-C_6)$alkoxy or —S(O)$_mR_8$;

R is

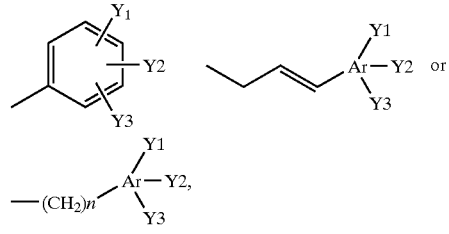

wherein

Y1, Y2 and Y3 are independently H, hydroxy, mercapto, amino, —$NHR_1$, —$NR_2R_3$, nitro, halogen, —$(CH_2)_sCO$—$Q_1$—$Q_2$—$Q_3$, $(CH_2)_6$—CN, $(C_1-C_6)$alkyl, $(C_1-C_6)$alkoxy, or —$S(O)_mR_8$;

$R_4$ and $R_5$ are taken together with the nitrogen atom to which they are attached to form a 4-, 5-, 6- or 7-membered saturated or partially saturated ring containing one to three O, S or N, said ring being optionally bridged with $(C_1-C_6)$alkyl which may be gem-dialkylated or substituted with one to three hydroxy, oxo, $(C_1-C_6)$alkyl, $(C_1-C_6)$alkoxy, phenyl$(C_1-C_8)$alkyl or CO—$Q_1$—$Q_2$—$Q_3$.

6. A compound of claim 5 which is
1-dimethylamino-7-methyl-4-(3-pyrid-3-ylallyl)-4H-[1,2,4]triazolo[4,3-a]quinazolin-5-one;
4-(3,4-dimethoxybenzyl)-7-methyl-1-pyrrolidin-1-yl-4H-[1,2,4]triazolo[4,3-a]quinazolin-5-one;
4-(1-dimethylamino-7-methyl-5oxo-5H-[1,2,4]triazolo[4,3-a]quinazolin-4-ylmethyl)benzonitrile;
7-bromo-1-dimethylamino-4-(3-phenylallyl)-4H-[1,2,4]triazolo[4,3-a]quinazolin-5-one;
7-methyl-(3-phenylallyl)-1-pyrrolidin-1-yl-4H-[1,2,4]triazolo[4,3-a]quinazolin-5-one;
4-(7-bromo-1-dimethylamino-5-oxo-5H-[1,2,4]triazolo[4,3-a]quinazolin-4-ylmethyl)benzonitrile;
1-azepan-1-yl-7-methyl-4-pyrid-3-ylmethyl-4H-[1,2,4]triazolo[4,3-a]quinazolin-5-one;
4-(7-methyl-5-oxo-1-pyrrolidin-1-yl-5H-[1,2,4]triazolo[4,3-a]quinazolin-4-ylmethyl)benzonitrile;
1-dimethylamino-methyl-((E)-3-phenylallyl)-4H-[1,2,4]triazolo[4,3-a]quinazolin-5-one;
4-(7-bromo-5-oxo-1-pyrrolidin-1-yl-5H-[1,2,4]triazolo[4,3-a]quinazolin-4-ylmethyl)benzonitrile; or
1-azepan-1-yl-7-bromo-4-(3,4-dimethoxybenzyl)-4H-[1,2,4]triazolo[4,3-a]quinazolin-5-one.

7. A compound of claim 1 which is
1-(azepan-1-yl)-7-chloro-4-(3-phenylallyl)-4H-[1,2,4]triazolo[4,3-a]quinazolin-5-one;
1-(azepan-1-yl)-7-chloro-3-(3-phenylallyl)-3H-[1,2,4]triazolo[4,3-a]quinazolin-5-one;
7-bromo-1-dimethylamino-4-((E)-3-pyrid-3-ylallyl)-4H-[1,2,4]triazolo[4,3-a]quinazolin-5-one;
7-bromo-4-pyrid-3-ylmethyl-1-pyrrolidin-1-yl-4H-[1,2,4]triazolo[4,3-a]quinazolin-5-one;
7-bromo-3-pyrid-3-ylmethyl-1-pyrrolidin-1-yl-3H-[1,2,4]triazolo[4,3-a]quinazolin-5one;
1-azepan-1-yl-4-(3-phenylallyl)-4H-[1,2,4]triazolo[4,3-a]quinazolin-5-one;
1-(azepan-1-yl)-7-chloro-4-allyl-4H-[1,2,4]triazolo[4,3-a]quinazolin-5-one;
1-(azepan-1-yl)-7-chloro-4-(4-methylbenzyl)-4H-[1,2,4]triazolo[4,3-a]quinazolin-5-one;
1-(azepan-1-yl)-7-chloro-4-(2-chlorobenzyl)-4H-[1,2,4]triazolo[4,3-a]quinazolin-5-one;
1-(azepan-1-yl)-7-chloro-4-(3-chlorobenzyl)-4H-[1,2,4]triazolo[4,3-a]quinazolin-5-one;
1-(azepan-1-yl)-7-chloro-4-(4-chlorobenzyl)-4H-[1,2,4]triazolo[4,3-a]quinazolin-5-one;
1-(azepan-1-yl)-7-chloro-4-(4-bromobenzyl)-4H-[1,2,4]triazolo[4,3-a]quinazolin-5-one;
1-(azepan-1-yl)-7-chloro-4-(4-fluorobenzyl)-4H-[1,2,4]triazolo[4,3-a]quinazolin-5-one;
1-(azepan-1-yl)-7-chloro-4-(4-(trifluoromethyl)benzyl)-4H-[1,2,4]triazolo[4,3-a]quinazolin-5-one;
1-azepan-1-yl-7-chloro-4-(4-cyanobenzyl)-4H-[1,2,4]triazolo[4,3,-a]quinazolin-5-one;
1-(azepan-1-yl)-7-chloro-4-(2-methoxybenzyl)-4H-[1 2,4]triazolo[4,3-a]quinazolin-5-one;
1-(azepan-1-yl)-7-chloro-4-(3-methoxybenzyl)-4H-[1,2,4]triazolo[4,3-a]quinazolin-5-one;
1-(azepan-1-yl)-7-chloro-4-(4-methoxybenzyl)-4H-[1,2,4]triazolo[4,3-a]quinazolin-5-one;
1-(azepan-1-yl)-7-chloro-4-(3,4-dichlorobenzyl)-4H-[1,2,4]triazolo[4,3-a]quinazolin-5-one;
1-(azepan-1-yl)-7-chloro-4-(3,4-dimethoxybenzyl)-4H-[1,2,4]triazolo[4,3-a]quinazolin-5-one;
1-(azepan-1-yl)-7-chloro-4(2-pyridylmethyl)-4H-[1,2,4]triazolo[4,3-a]quinazolin-5-one;
1-(azepan-1-yl)-7-chloro-4-(3-pyridylmethyl)-4H-[1,2,4]triazolo[4,3-a]quinazolin-5-one;
1-(azepan-1-yl)-7-chloro-4-(4-pyridylmethyl)-4H-[1,2,4]triazolo[4,3-a]quinazolin-5-one
1(azepan-1-yl)-7-chloro-4-(2-phenylethyl)-4H-[1,2,4]triazolo[4,3-a]quinazolin-5-one
1-(azepan-1-yl)-7-chloro-4-[2-(4-methoxyphenyl)ethyl]-4H-[1,2,4]triazolo[4,3-a]quinazolin-5-one;
1-(azepan-1-yl)-7-chloro-4-(3-phenylpropyl)-4H-[1,2,4]triazolo[4,3-a]quinazolin-5-one;
1-azepan-1-yl-7-chloro-4-(2-oxo-2-phenylethyl)-4H-[1,2,4]triazolo[4,3-a]quinazolin-5-one;
1-(azepan-1-yl)-7-chloro-4[2-(4-methoxyphenyl)-2-oxoethyl]-4H-[1,2,4]triazolo[4,3-a]quinazolin-5one;
1-(azepan-1-yl)-7-chloro-4-[2-(4-chlorophenyl)-2-oxoethyl]4H-1,2,4]triazolo[4,3-a]quinazolin-5-one;
5-[(1-(azepan-1-yl)-7-chloro-5-oxo-5H-[1,2,4]triazolo[4,3-a]quinazolin-4-yl)acetyl]-2-methoxybenzoic acid methyl ester;
7-chloro-4-pyrid-3-ylmethyl-1-pyrrolidin-1-yl-4H-[1,2,4]triazolo[4,3-a]quinazolin-5-one;
1-(azepan-1-yl)-7-bromo-4-(4-chlorophenylmethyl)-4H-1,2,4]triazolo[4,3-a]quinazolin-5-one;
1-azepan-1-yl-7-bromo-4-(4-fluorobenzyl-4H-[1,2,4]triazolo[4,3-a]quinazolin-5-one;
4-(1-azepan-1-yl-7-bromo-5-oxo-5H-[1,2,4]triazolo[4,3-a]quinazolin-4-ylmethyl)benzonitrile;
1-azepan-1-yl-7-bromo-4-(3,4-dimethoxybenzyl)-4H-[1,2,4]triazolo[4,3-a]quinazolin-5-one;
1-(azepan-1-yl)-7-bromo-4-(3-pyridinylmethyl)-4H-[1,2,4]triazolo[4,3a]quinazolin-5-one;
1-(azepan-1-yl)-7-bromo-4-(3-phenylallyl)-4H-[1,2,4]triazolo[4,3-a]quinazolin-5-one;
1-azepan-1-yl-7-bromo-4-[3-(4-chlorophenyl)-allyl]-4H-[1,2,4]triazolo[4,3-a]quinazolin-5-one;
1-azepan-1-yl-7-bromo-4-[3-(4-methoxyphenyl)-allyl]-4H-[1,2,4]triazolo[4,3-a]quinazolin-5-one;
1-azepan-1-yl-7-bromo-4-((E)-3-pyrid-3-ylallyl)-4H-[1,2,4]triazolo[4,3-a]quinazolin-5-one;
1-azepan-1-yl-7-bromo-4-(3-pyrid-4-ylallyl)-4H-[1,2,4]triazolo[4,3-a]quinazolin-5-one;
7-bromo-4-(4-methylbenzyl)-1-pyrrolidin-1-yl-4H-[1,2,4]triazolo[4,3-a]quinazolin-5one;
7-bromo-4-(4-chlorobenzyl)-1-pyrrolidin-1-yl-4H-[1,2,4]triazolo[4,3-a]quinazolin-5-one;
7-bromo-4-(4-fluorobenzyl)-1-pyrrolidin-1-yl-4H-[1,2,4]triazolo[4,3-a]quinazolin-5-one;
3-(7-bromo-5-oxo-1-pyrrolidin-1-yl-5H-[1,2,4]triazolo[4,3-a]quinazolin-4-ylmethyl)benzonitrile;
4-(7-bromo-5-oxo-1-pyrrolidin-1-yl-5H-[1,2,4]triazolo[4,3-a]quinazolin-4-ylmethyl)benzonitrile;
4-(7-bromo-5-oxo-1-pyrrolidin-1-yl-5H-[1,2,4]triazolo[4,3-a]quinazolin-4-ylmethyl)benzoic acid methyl ester;
7-bromo-4-(4-nitrobenzyl)-1-pyrrolidin-1-yl-4H-[1,2,4]triazolo[4,3-a]quinazolin-5-one;
7-bromo-4-(4-methoxybenzyl)-1-pyrrolidin-1-yl-4H-[1,2,4]triazolo[4,3-a]quinazolin-5-one;
acetic acid 4-(7-bromo-5-oxo-1-pyrrolidin-1-yl-5H-[1,2,4]triazolo[4,3-a]quinazolin-4-ylmethyl)phenyl ester;
7-bromo-4-(4-hydroxybenzyl)-1-pyrrolidin-1-yl-4H-[1,2,4]triazolo[4,3-a]quinazolin-5one;
7-bromo-4-(3,4-dimethoxybenzyl)-1-pyrrolidin-1-yl-4H-[1,2,4]triazolo[4,3-a]quinazolin-5-one;
4-benzo[1,3]dioxol-5-ylmethyl-7-bromo-1-pyrrolidin-1-yl-4H-[1,2,4]triazolo[4,3-a]quinazolin-5-one;

7-bromo-4-(3,5-dimethoxybenzyl)-1-pyrrolidin-1-yl-4H-[1,2,4]triazolo[4,3-a]quinazolin-5-one;
7-bromo-1-pyrrolidin-1-yl-4-(3,4,5-trimethoxybenzyl)-4H-[1,2,4]triazolo[4,3-a]quinazolin-5-one;
[4-(7-bromo-5-oxo-1-pyrrolidin-1-yl-5H-[1,2,4]triazolo[4,3-a]quinazolin-4-ylmethyl)phenyl]acetic acid;
1-(pyrrolidin-1-yl)-7-bromo-4-(3-phenylallyl)-4H-[1,2,4]triazolo[4,3-a]quinazolin-5-one;
7-bromo-4-(3-phenylallylyl)-1-pyrrolidin-1-yl-4H-[1,2,4]triazolo[4,3-a]quinazolin-5-one;
7-bromo-4-[(E)-3-(4-chlorophenyl)-allyl]-1-pyrrolidin-1-yl-4H-[1,2,4]triazolo[4,3-a]quinazolin-5-one;
7-bromo-4-[3-(4-methoxyphenyl)-ally]-1-pyrrolidin-1-yl-4H-[1,2,4]triazolo[4,3-a]quinazolin-5-one;
7-bromo-4-(3-pyrid-3-ylallyl)-1-pyrrolidin-1-yl-4H-[1,2,4]triazolo[4,3-a]quinazolin-5-one;
7-bromo-4-((E)-3-pyrid-4-ylallyl)-1-pyrrolidin-1-yl-4H-[1,2,4]triazolo[4,3-a]quinazolin-5-one;
7-bromo-4-(1H-imidazol-4ylmethyl)-1-pyrrolidin-1-yl-4H-[1,2,4]triazolo[4,3-a]quinazolin-5-one;
7-bromo-4-(3,5-dimethyl-isoxazol-4ylmethyl)-1-pyrrolidin-1-yl-4H-[1,2,4]triazolo[4,3-a]quinazolin-5-one;
7-bromo-4-cyclopentylmethyl-1-pyrrolidin-1-yl-4H-[1,2,4]triazolo[4,3-a]quinazolin-5-one;
7-bromo-4-butyl-1-pyrrolidin-1-yl-4H-[1,2,4]triazolo[4,3-a]quinazolin-5-one;
7-bromo-1-pyrrolidin-1-yl-4-(2,2,2-trifluoroethyl)-4H-[1,2,4]triazolo[4,3-a]quinazolin-5-one;
7-bromo-4-(2-hydroxyethyl)-1-pyrrolidin-1-yl-4H-[1,2,4]triazolo[4,3-a]quinazolin-5-one;
7-bromo-4-(2-diethylaminoethyl)-1-pyrrolidin-1-yl-4H-[1,2,4]triazolo[4,3-a]quinazolin-5-one;
7-bromo-4-prop-2-ynyl-1-pyrrolidin-1-yl-4H-[1,2,4]triazolo[4,3-a]quinazolin-5-one;
7bromo-4-(2-phenoxyethyl)-1-pyrrolidin-1-yl-4H-[1,2,4]triazolo[4,3-a]quinazolin-5-one;
7-bromo-4-(2-phenylsulphenylethyl)-1-pyrrolidin-1-yl-4H-[1,2,4]triazolo[4,3-a]quinazolin-5-one;
(7-bromo-5-oxo-1-pyrrolidin-1-yl-5H-[1,2,4]triazolo[4,3-a]quinazolin-4-yl)phenylacetic acid methyl ester;
4-(7-bromo-5-oxo-1-piperid-1-yl-5H-[1,2,4]triazolo[4,3-a]quinazolin-4-ylmethyl)benzonitrile;
7-bromo-4-(3,4-dimethoxybenzyl)-1-piperid-1-yl-4H-[1,2,4]triazolo[4,3-a]quinazolin-5-one;
1-(piperid-1-yl)-7-bromo-4-(3-phenylallyl)-4H-[1,2,4]triazolo[4,3-a]quinazolin-5-one;
7-bromo-4-(3-pyrid-3-ylallyl)-1-thiomorpholin-4-yl-4H-[1,2,4]triazolo[4,3-a]quinazolin-5-one;
7-bromo-1-dimethylamino-4-(4-methylbenzyl)-4H-[1,2,4]triazolo[4,3-a]quinazolin-5-one;
4-(7-bromo-1-dimethylamino-5-oxo-5H-[1,2,4]triazolo[4,3-a]quinazolin-4-ylmethyl)benzonitrile;
7-bromo-1-dimethylamino-4-(4-hydroxybenzyl)-4H-[1,2,4]triazolo[4,3-a]quinazolin-5-one;
4-(7-bromo-1-dimethylamino-5-oxo-5H-[1,2,4]triazolo[4,3-a]quinazolin-4-ylmethyl)benzoic acid methyl ester;
[4-(7-bromo-1-dimethylamino-5-oxo-5H-[1,2,4]triazolo[4,3-a]quinazolin-4-ylmethyl)phenyl]acetic acid;
[4-(7-bromo-1-dimethylamino-5-oxo-5H-[1,2,4]triazolo[4,3-a]quinazolin-4-ylmethyl)phenyl]acetonitrile;
7-bromo-1-dimethylamino-4-(pyrid-3-ylmethyl)-4H-[1,2,4]triazolo[4,3-a]quinazolin-5-one;
7-bromo-1-dimethylamino-4-(3-phenylallyl)-4H-[1,2,4]triazolo[4,3-a]quinazolin-5-one;
7-bromo-1-dimethylamino-4-(3-phenylallyl)-4H-[1,2,4]triazolo[4,3-a]quinazolin-5-one;
7-bromo-1-dimethylamino-4-(3-pyrid-4-ylallyl)-4H-[1,2,4]triazolo[4,3-a]quinazolin-5-one;
7-bromo-1-dimethylamino-4-prop-2-ynyl-4H-[1,2,4]triazolo[4,3-a]quinazolin-5-one;
7-bromo--dimethylamino-4-(3-phenyl-prop-2-ynyl)-4H-[1,2,4]triazolo[4,3-a]quinazolin-5-one;
4-(7-bromo-1-dimethylamino-5-oxo-5H-[1,2,4]triazolo[4,3-a]quinazolin-4yl)phenylacetic acid methyl ester;
1-azepan-1-yl-7-methyl-4-pyrid-3-ylmethyl-4H-[1,2,4]triazolo[4,3-a]quinazolin-5-one;
1-azepan-1-yl-7-methyl-4-(3-phenylallyl)-4H-[1,2,4]triazolo[4,3-a]quinazolin-5-one;
4-(7-methyl-5-oxo-1-pyrrolidin-1-yl-5H-[1,2,4]triazolo[4,3-a]quinazolin-4-ylmethyl)benzonitrile;
4-(3,4-dimethoxybenzyl)-7-methyl-1-pyrrolidin-1-yl-4H-[1,2,4]triazolo[4,3-a]quinazolin-5-one;
4-(7-methyl-5-oxo-1-pyrrolidin-1-yl-5H-[1,2,4]triazolo[4,3-a]quinazolin-4-ylmethyl)benzoic acid methyl ester;
[4-(7-methyl-5-oxo-1-pyrrolidin-1-yl-5H-[1,2,4]triazolo[4,3-a]quinazolin-4-ylmethyl)phenyl]acetic acid;
7-methyl-4-pyrid-3-ylmethyl-1-pyrrolidin-1-yl-4H-[1,2,4]triazolo[4,3-a]quinazolin-5-one;
7-methyl-4-(3-phenylallyl)-1-pyrrolidin-1-yl-4H-[1,2,4]triazolo[4,3-a]quinazolin-5-one;
[4-(7-methyl-5-oxo-1-thiomorpholin-4-yl-5H-[1,2,4]triazolo[4,3-a]quinazolin-4-ylmethyl)phenyl]acetic acid;
7-methyl-4-(3-pyrid-3-ylallyl)-1-thiomorpholin-4-yl-4H-[1,2,4]triazolo[4,3-a]quinazolin-5-one;
4-(1-dimethylamino-7-methyl-5-oxo-5H-[1,2,4]triazolo[4,3-a]quinazolin-4-ylmethyl)benzonitrile;
[4-(dimethylamino-methyl-oxo-5H-[1,2,4]triazolo[4,3-a]quinazolin-4-ylmethyl)phenyl]acetic acid;
1-dimethylamino-7-methyl-4-((E)-3-phenylallyl)-4H-[1,2,4]triazolo[4,3-a]quinazolin-5-one;
1-dimethylamino-7-methyl-4-(3-pyrid-3-ylallyl)-4H-[1,2,4]triazolo[4,3-a]quinazolin-5-one;
1-dimethylamino-7-methyl-4-(3-pyrid-4-ylallyl)-4H-[1,2,4]triazolo[4,3-a]quinazolin-5-one;
1-(azepan-1-yl)-8-methyl-4-(3-phenylallyl)-4H-[1,2,4]triazolo[4,3-a]quinazolin-5-one;
(4-cyanobenzyl)-dimethylamino-oxo-4,5-dihydro-[1,2,4]triazolo[4,3-a]quinazoline-7-carbonitrile;
7-hydroxy-4-((E)-3-phenylallyl)-1-pyrrolidin-1-yl-4H-[1,2,4]triazolo[4,3-a]quinazolin-5-one;
1-(azepan-1-yl)-3-(3-phenylallyl)-3H-[1,2,4]triazolo[4,3-a]quinazolin-5-one;
3-alkyl-1-azepan-1-yl-7-chloro-3H-[1,2,4]triazolo[4,3-a]quinazolin-5-one;
1-(azepan-1-yl)-7-chloro-3-benzyl-3H-[1,2,4]triazolo[4,3-a]quinazolin-5-one;
1-azepan-1-yl-7-chloro-3-(4-methylbenzyl)-3H-[1,2,4]triazolo[4,3-a]quinazolin-5-one;
1-(azepan-1-yl)-7-chloro-3-(2-chlorobenzyl)-3H-[1,2,4]triazolo[4,3-a]quinazolin-5-one;
1-(azepan-1-yl)-7-chloro-3-(3-chlorobenzyl)-3H-[1,2,4]triazolo[4,3-a]quinazolin-5-one;
1-(azepan-1-yl)-7-chloro-3-(4-chlorobenzyl)-3H-[1,2,4]triazolo[4,3-a]quinazolin-5-one;
1-(azepan-1-yl)-7-chloro-3-(4-bromobenzyl)-3H-[1,2,4]triazolo[4,3-a]quinazolin-5-one;
1-(azepan-1-yl)-7-chloro-3-(4-fluorobenzyl)-3H-[1,2,4]triazolo[4,3-a]quinazolin-5-one;
1-(azepan-1-yl)-7-chloro-3-(4-(trifluoromethyl)benzyl)-3H-[1,2,4]triazolo[4,3-a]quinazolin-5-one;
1-(azepan-1-yl)-7-chloro-3-(4-cyanobenzyl)-3H-[1,2,4]triazolo[4,3-a]quinazolin-5-one;
1-(azepan-1-yl)-7-chloro-3-(2-methoxybenzyl)-3H-[1,2,4]triazolo[4,3-a]quinazolin-5-one;
1-(azepan-1-yl)-7-chloro-3-(3-methoxybenzyl)-3H-[1,2,4]triazolo[4,3-a]quinazolin-5-one;

1-(azepan-1-yl)-7-chloro-3-(4-methoxybenzyl)-3H[1,2,4]triazolo[4,3-a]quinazolin-5-one;
1-(azepan-1-yl)-7-chloro-3-(3,4-dichlorobenzyl)-3H-[1,2,4]triazolo[4,3-a]quinazolin-5-one;
1-(azepan-1-yl)-7-chloro-3-(3,4-dimethoxybenzyl)-3H-[1,2,4]triazolo[4,3-a]quinazolin-5-one;
1-(azepan-1-yl)-7-chloro-3-(2-pyridylmethyl)-3H-[1,2,4]triazolo[4,3-a]quinazolin-5-one;
1-(azepan-1-yl)-7-chloro-3-(3-pyridylmethyl)-3H-[1,2,4]triazolo[4,3-a]quinazolin-5-one;
1-(azepan-1-yl)-7-chloro-3-(2-phenylethyl-3H-[1,2,4]triazolo[4,3-a]quinazolin-5-one;
1-(azepan-1-yl)-7-chloro-3[2-(4-methoxyphenyl)ethyl]-3H-[1,2,4]triazolo[4,3-a]quinazolin-5-one;
1-(azepan-1-yl)-7-chloro-3-(3-phenylpropyl)-3H-[1,2,4]triazolo[4,3-a]quinazolin-5-one;
1-azepan-1-yl-7-chloro-3-(2-oxo-2-phenylethyl-3H-[1,2,4]triazolo[4,3-a]quinazolin-5-one;
1-(azepan-1-yl)-7-chloro-3-[2-(4-methoxyphenyl)-2-oxoethyl]-3H-[1,2,4]triazolo[4,3-a]quinazolin-5-one;
1-(azepan-1-yl)-7-chloro-3-[2-(4-chlorophenyl)-2-oxoethyl]-3H-[1,2,4]triazol[4,3-a]quinazolin-5-one;
5-[(1-(azepan-1-yl)-7-chloro-5-oxo-5H-[1,2,4]triazolo[4,3-a]quinazolin-3-yl)acetyl]-methoxybenzoic acid methyl ester;
1-azepan-1-yl)-7-bromo-3-(4-chlorobenzyl)-3H-[1,2,4]triazolo[4,3-a]quinazolin-5-one;
1-(azepan-1-yl)-7-bromo-3-(4-fluorobenzyl)-3H-[1,2,4]triazolo[4,3-a]quinazolin-5-one;
4-(1-(azepan-1-yl)-7-bromo-5-oxo-5H-[1,2,4]triazolo[4,3-a]quinazolin-3-ylmethyl)benzonitrile;
1-(azepan-1-yl)-7-bromo-3-(3,4-dimethoxybenzyl)-3H-[1,2,4]triazolo[4,3-a]quinazolin-5one;
[4-(7-bromo-5-oxo-1-perhydro-azepin-1-yl-5H-[1,2,4]triazolo[4,3-a]quinazolin-3-ylmethyl)phenyl]acetic acid;
1-(azepan-1-yl)-7-bromo-3-(pyrid-3-ylmethyl)-3H-[1,2,4]triazolo[4,3-a]quinazolin-5-one;
1-azepan-1-yl-7-bromo-3-((E)-3-phenylallyl)-3H-[1,2,4]triazolo[4,3-a]quinazolin-5-one;
7-bromo-3-((E)-3-phenylallyl)-1-piperid-1-yl-3H-[1,2,4]triazolo[4,3-a]quinazolin-5-one;
7-bromo-3-(4-chlorobenzyl)-1-(pyrrolidin-1-yl)-3H-[1,2,4]triazolo[4,3-a]quinazolin-5one;
7-bromo-3-(4-fluorobenzyl)-1-(pyrrolidin-1-yl)-3H-[1,2,4]triazolo[4,3-a]quinazolin-5-one;
4-(7-bromo-5-oxo-1-(pyrrolidin-1-yl)-5H-[1,2,4]triazolo[4,3-a]quinazolin-3-ylmethyl)benzonitrile;
4-(7-bromo-5-oxo-1-(pyrrolidin-1-yl)-5H-[1,2,4]triazolo[4,3-a]quinazolin-3-ylmethyl)benzoic acid methyl ester;
7-bromo-3-(4-methoxybenzyl-1-pyrrolidin-1-yl-3H-[1,2,4]triazolo[4,3-a]quinazolin-5-one;
acetic acid 4-(7-bromo-5-oxo-1-pyrrolidin-1-yl-5H-[1,2,4]triazolo[4,3-a]quinazolin-3-ylmethyl)phenyl ester;
7-bromo-1-dimethylamino-3-(4-hydroxybenzyl)-3H-[1,2,4]triazolo[4,3-a]quinazolin-5-one;
3-(benzo[1,3]dioxol-5-ylmethyl)-7-bromo-1-(pyrrolidin-1-yl)-3H-[1,2,4]triazolo[4,3-a]quinazolin-5-one;
7-bromo-3-(3,5-dimethoxybenzyl)-1-(pyrrolidin-1-yl)-3H-[1,2,4]triazolo-[4,3-a]quinazolin-5-one;
7-bromo-1-(pyrrolidin-1-yl)-3-(3,4,5-trimethoxybenzyl)-3H-[1,2,4]triazolo[4,3-a]quinazolin-5-one;
7-bromo-3-(1H-imidazol-4ylmethyl)-1-pyrrolidin-1-yl-3H-[1,2,4]triazolo[4,3-a]quinazolin-5-one;
7-bromo-3-(n-butyl 1-(pyrrolidin-1-yl)-3H-[1,2,4]triazolo[4,3-a]quinazolin-5-one;
(7-bromo-5-oxo-1-pyrrolidin-1-yl-5H-[1,2,4]triazolo[4,3-a]quinazolin-3-yl)phenylacetic acid methyl ester;
7-bromo-1-dimethylamino-3-(3-phenylallyl)-3H-[1,2,4]triazolo[4,3-a]quinazolin-5-one;
4-(7-bromo-1-dimethylamino-5-oxo-5H-[1,2,4]triazolo[4,3-a]quinazolin-3-yl)phenylacetic acid methyl ester;
1-(azepan-1-yl)-7-methyl-3-(3-phenylallyl)-3H-[1,2,4]triazolo[4,3-a]quinazolin-5-one;
7-methyl-3-(3-phenylallyl)-1-(pyrrolidin-1-yl)-3H-[1,2,4]triazolo[4,3-a]quinazolin-5-one;
1-(azepan-1-yl)-3,8-dimethyl-3H-[1,2,4]triazolo[4,3-a]quinazolin-5one;
1-azepan-1-yl-8-methyl-3-((E)-3-phenylallyl)-3H-[1,2,4]triazolo[4,3-a]quinazolin-5-one;
7-hydroxy-3-(3-phenylallyl)-1-(pyrrolidin-1-yl)-3H-[1,2,4]triazolo[4,3-a]quinazolin-5-one;
1,8-bis(azepan-1-yl)-3-(3-phenylallyl)-3H-[1,2,4]triazolo[4,3-a]quinazolin-5-one;
1-(azepan-1-yl)-4-benzyl-7-bromo-4H-[1,2,4]triazolo[4,3-a]quinazolin-5-one;
4-benzyl-7bromo-1-(pyrrolidin-1-yl)-4H-[1,2,4]triazolo[4,3-a]quinazolin-5-one;
4-benzyl-7-bromo-1-(butyl-methyl-amino)-4H-[1,2,4]triazolo[4,3-a]quinazolin-5-one;
4-benzyl-1-(pyrrolidin-1-yl)-4H-[1,2,4]triazolo[4,3-a]quinazolin-5-one;
7-chloro-1-dibutylamino-4-methyl-4H-[1,2,4]triazolo[4,3-a]quinazolin-5-one;
7-chloro-4-methyl-1-(piperid-1-yl)-4H-[1,2,4]triazolo[4,3-a]quinazolin-5-one;
7-chloro-4-methyl-1-(4-methyl-piperazin-1-yl)-4H-[1,2,4]triazolo[4,3-a]quinazolin-5-one;
7-chloro-4-methyl-1-(1,8,8-trimethyl-3-azabicyclo[3.2.1]oct-3-yl)-4H-[1,2,4]triazolo[4,3-a]quinazolin-5-one;
1-(azepan-1-yl)-7-chloro-4-phenyl-4H-[1,2,4]triazolo[4,3a]quinazolin-5-one;
1-(azepan-1-yl)-4-benzyl-7-chloro-4H-[1,2,4]triazolo[4,3-a]quinazolin-5-one;
4-benzyl-7-chloro-1-(pyrrolidin-1-yl)-4H-[1,2,4]triazolo[4,3-a]quinazolin-5-one;
4-benzyl-7-chloro-1-(piperid-1-yl)-4H-[1,2,4]triazolo[4,3-a]quinazolin-5-one;
1-(azepan-1-yl)-8-chloro-4-methyl-4H-[1,2,4]triazolo[4,3-a]quinazolin-5-one;
1-(azepan-1-yl)-4-benzyl-8-chloro-4H-[1,2,4]triazolo[4,3-a]quinazolin-5-one;
1-(azepan-1-yl)-7-bromo-4-methyl-4H-[1,2,4]triazolo[4,3-a]quinazolin-5-one;
4-benzyl-7-bromo-1-(piperid-1-yl)-4H-[1,2,4]triazolo[4,3-a]quinazolin-5-one;
4-benzyl-7-bromo-1-dimethylamino-4H-[1,2,4]triazolo[4,3-a]quinazolin-5-one;
4-benzyl-7-bromo-1-morpholin-4yl-4H-[1,2,4]triazolo[4,3-a]quinazolin-5-one;
4-benzyl-7-bromo-1-thiomorpholin-4-yl-4H-[1,2,4]triazolo[4,3-a]quinazolin-5-one;
4-benzyl-7-bromo-1-(4-methylpiperazin-1-yl)-4H-[1,2,4]triazolo[4,3-a]quinazolin-5-one;
4-benzyl-7-bromo-1-(4-phenylpiperazin-1-yl)-4H-[1,2,4]triazolo[4,3-a]quinazolin-5-one;
4-benzyl-1-(4-benzylpiperazin-1-yl)-7-bromo-4H-[1,2,4]triazolo[4,3-a]quinazolin-5one;
4-benzyl-7-bromo-1-(3,6dihydro-2H-pyrid-1-yl)-4H-[1,2,4]triazolo[4,3-a]quinazolin-5-one;
4-benzyl-7-bromo-1-(2,5-dihydropyrrol-1-yl)-4H-[1,2,4]triazolo[4,3-a]quinazolin-5-one;
4-benzyl-7-bromo-1-(3-hydroxypyrrolidin-1-yl)-4H-[1,2,4]triazolo[4,3-a]quinazolin-5-one;
4-benzyl-7-bromo-1-methylamino-4H-[1,2,4triazolo[4,3-a]quinazolin-5-one;

4-benzyl-7-iodo-1-pyrrolidin-1-yl-4H-[1,2,4]triazolo[4,3-a]quinazolin-5-one;

1-azepan-1-yl-4-benzyl-7-methyl-4H-[1,2,4]triazolo[4,3-a]quinazolin-5-one;

4-benzyl-7-methyl-1-pyrrolidin-1-yl-4H-[1,2,4]triazolo[4,3-a]quinazolin-5-one;

4-benzyl-1-dimethylamino-7-methyl-4H-[1,2,4]triazolo[4,3-a]quinazolin-5-one;

4-benzyl-7-methyl-1-thiomorpholinyl-4H-[1,2,4]triazolo[4,3-a]quinazolin-5-one;

1-azepan-1-yl-4benzyl-8-methyl-4H-[1,2,4]triazolo[4,3-a]quinazolin-5-one;

1-azepan-1-yl-4-benzyl-7-methoxy-4H-[1,2,4]triazolo[4,3a]quinazolin-5-one;

4-benzyl-7-methoxy-1-pyrrolidin-1-yl-4H-[1,2,4]triazolo[4,3-a]quinazolin-5-one;

4-benzyl-5-oxo-1-pyrrolidin-1-yl-4,5-dihydro-[1,2,4]triazolo[4,3-a]quinazoline-7-carbonitrile;

1-azepan-1-yl-4-benzyl-7-nitro-4H-[1,2,4]triazolo[4,3-a]quinazolin-5-one;

1-(azepan-1-yl)-4-benzyl-7-chloro-4H-[1,2,4]triazolo[4,3-a]quinazolin-5-one;

1-(azepan-1-yl)-4-methyl-4H-[1,2,4]triazolo[4,3-a]quinazolin-5-one;

1-(azepan-1-yl)-4-benzyl-4H-[1,2,4]triazolo[4,3-a]quinazolin-5-one;

1-(azepan-1-yl)-6-chloro-4-methyl-4H-[1,2,4]triazolo[4,3-a]quinazolin-5-one;

1-(azepan-1-yl)-7-chloro-4-methyl-4H-[1,2,4]triazolo[4,3-a]quinazolin-5-one;

1-(azepan-1-yl)-7-chloro-4-ethyl-4H-[1,2,4]triazolo[4,3-a]quinazolin-5-one;

7-chloro-4-methyl-1-(pyrrolidin-1-yl)-4H-[1,2,4]triazolo[4,3-a]quinazolin-5-one;

7-chloro-4-methyl-1-morpholin-4-yl)-4H-[1,2,4]triazolo[4,3-a]quinazolin-5-one;

1-(azocan-1-yl)-7-chloro-4-methyl-4H-[1,2,4]triazolo[4,3-a]quinazolin-5-one;

7-chloro-1-(3,4-dihydro-2H-quinolin-1-yl)-4-methyl-4H-[1,2,4]triazolo[4,3-a]quinazolin-5-one;

7-chloro-1-(3,4-dihydro-1H-isoquinolin-2-yl)-4methyl-4H-[1,2,4]triazolo[4,3-a]quinazolin-5-one;

1-(4-benzylpiperid-1-yl)-7-chloro-4-methyl-4H-[1,2,4]triazolo[4,3-a]quinazolin-5-one;

7chloro-4-methyl-1-(1,3,3-trimethyl-6-azabicyclo[3,2,1]oct-6-yl)-4H-[1,2,4]triazolo[4,3-a]quinazolin-5-one;

1-(azepan-1-yl)-7-fluoro-4-methyl-4H-[1,2,4]triazolo[4,3-a]quinazolin-5-one;

1-(azepan-1-yl)-7-iodo-4-methyl-4H-[1,2,4]triazolo[4,3-a]quinazolin-5-one;

1-(azepan-1-yl)-7-methoxymethyl-4H-[1,2,4]triazolo[4,3-a]quinazolin-5-one;

4-benzyl-7-bromo-1-(ethylmethylamino)-4H-[1,2,4]triazolo[4,3-a]quinazolin-5-one;

4-benzyl-1-diethylamino-7-methyl-4H-[1,2,4]triazolo[4,3-a]quinazolin-5-one;

4-benzyl-7-bromo-1-pyrrol-1-yl-4H-[1,2,4]triazolo[4,3-a]quinazolin-5-one;

4-(4-aminobenzyl)-7-bromo-1-pyrrolidin-1-yl-4H-[1,2,4]triazolo[4,3-a]quinazolin-5-one;

4-benzyl-7-hydroxy-1-pyrrolidin-1-yl-4H-[1,2,4]triazolo[4,3-a]quinazolin-5-one;

4-(7-hydroxy-5-oxo-1-pyrrolidin-1-yl-5H-[1,2,4]triazolo[4,3-a]quinazolin-4-ylmethyl)benzonitrile;

N-(4-benzyl-5-oxo-1-pyrrolidin-1-yl-4,5-dihydro-[1,2,4]triazolo[4,3-a]quinazolin-7-yl)acetamide;

N-[5-oxo-4-(3-phenylallyl)-1-pyrrolidin-1-yl-4,5-dihydro-[1,2,4]triazolo[4,3a]quinazolin-7-yl]acetamide;

7-amino-4-((E)3-phenylallyl)-1-pyrrolidin-1-yl-4H-[1,2,4]triazolo[4,3-a]quinazolin-5-one;

7-amino-1-azepan-1-yl-4-benzyl-4H-[1,2,4]triazolo[4,3-a]quinazolin-5-one;

7-amino-4-benzyl-1-pyrrolidin-1-yl-4H-[1,2,4]triazolo[4,3-a]quinazolin-5-one;

4-(7-amino-5-oxo-1-pyrrolidin-1-yl-5H-[1,2,4]triazolo[4,3-a]quinazolin-4-ylmethyl)benzonitrile;

7-amino-4-((E)-3-pyrid-3-ylallyl)-1-pyrrolidin-1-yl-4H-[1,2,4]triazolo[4,3-a]quinazolin-5-one;

4-(amino-dimethylamino-oxo-5H-[1,2,4]triazolo[4,3-a]quinazolin-4-ylmethyl)benzonitrile;

7-amino-1-dimethylamino-4-((E)-3-phenylallyl)-4H-[1,2,4]triazolo[4,3-a]quinazolin-5-one;

4-benzyl-7-methylamino-1-pyrrolidin-1-yl-4H-[1,2,4]triazolo[4,3-a]quinazolin-5-one;

4-(7-methylamino-5-oxo-1-pyrrolidin-1-yl-5H-[1,2,4]triazolo[4,3-a]quinazolin-4-ylmethyl)benzonitrile;

4-benzyl-8-methylamino-1-pyrrolidin-1-yl-4H-[1,2,4]triazolo[4,3-a]quinazolin-5-one;

4-benzyl-7-ethylamino-1-pyrrolidin-1-yl-4H-[1,2,4]triazolo[4,3-a]quinazolin-5-one;

4-benzyl-7-isopropylamino-1-pyrrolidin-1-yl-4H-[1,2,4]triazolo[4,3-a]quinazolin-5-one;

N-(4-benzyl-5-oxo-1-pyrrolidin-1-yl-4,5-dihydro[1,2,4]triazolo[4,3-a]quinazolin-7-yl)methanesulphonamide;

4-benzyl-7-dimethylamino-1-pyrrolidin-1-yl-4H-[1,2,4]triazolo[4,3-a]quinazolin-5-one;

4-benzyl-1-dimethylamino-5-oxo-4,5-dihydro[1,2,4]triazolo[4,3-a]quinazoline-7-carbonitrile;

4-benzyl-5-oxo-1-pyrrolidin-1-yl-4,5-dihydro[1,2,4]triazolo[4,3-a]quinazoline-7-carboxylic acid;

[4-(7-bromo-5-oxo-1-pyrrolidin-1-yl-5H-[1,2,4]triazolo[4,3-a]quinazolin-4-ylmethyl)phenyl]acetic acid methyl ester;

2-[4-(7-bromo-5-oxo-1-pyrrolidin-1-yl-5H-[1,2,4]triazolo[4,3-a]quinazolin-4-ylmethyl)phenyl]-N-methylacetamide;

2-[4-(7-bromo-1-dimethylamino-5-oxo-5H-[1,2,4]triazolo[4,3-a]quinazolin-4-ylmethyl)phenyl]acetamide;

2-[4-(7-bromo-5-oxo-1-pyrrolidin-1-yl-5H-[1,2,4]triazolo[4,3-a]quinazolin-4-ylmethyl)phenyl]-N,N-dimethylacetamide;

2-[4-(7-bromo-5-oxo-1-pyrrolidin-1-yl-5H-[1,2,4]triazolo[4,3-a]quinazolin-4-ylmethyl)phenyl]-N-hydroxyacetamide;

4-(1-dimethylamino-7-methyl-5-thioxo-5H-[1,2,4]triazolo[4,3a]quinazolin-4-ylmethyl)benzonitrile;

4-(7-bromo-1-dimethylamino-5-thioxo-5H-[1,2,4]triazolo[4,3-a]quinazolin-4-ylmethyl)benzonitrile;

1-dimethylamino-7-methyl-4-(3-pyrid-3-ylallyl)-4H-[1,2,4]triazolo[4,3-a]quinazoline-5-thione; or 4-benzyl-7-(N,N-dimethylsulphonylamino)-1-(pyrrolidin-1-yl)-4H-[1,2,4]triazolo[4,3-a]quinazolin-5-one.

8. A compound of claim 1 which is 1-(azepan-1-yl)-7-chloro-4-(3-phenylallyl)-4H-[1,2,4]triazolo[4,3-a]quinazolin-5-one;

7-bromo-1-dimethylamino-4-((E)-3-pyrid-3-ylallyl)-4H-[1,2,4]triazolo[4,3-a]quinazolin-5-one;

1-(azepan-1-yl)-7-chloro-4-(4-chlorobenzyl)-4H-[1,2,4]triazolo[4,3-a]quinazolin-5-one;

1-(azepan-1-yl )-7-chloro-4-(4-fluorobenzyl)-4H-[1,2,4]triazolo[4,3-a]quinazolin-5-one;

1-(azepan-1-yl)-7-chloro-4-(3,4-dimethoxybenzyl)-4H-[1,2,4]triazolo[4,3-a]quinazolin-5-one;

1-(azepan-1-yl)-7-chloro-4-(3-pyridylmethyl)-4H-[1,2,4]triazolo[4,3-a]quinazolin-5-one;

1-(azepan-1-yl)-7-bromo-4-(4-chlorophenylmethyl)-4H-[1,2,4]triazolo[4,3-a]quinazolin-5one;
4-(1-azepan-1-yl-7-bromo-5-oxo-5H-[1,2,4]triazolo[4,3-a]quinazolin-4-ylmethyl)benzonitrile;
1-azepan-1-yl-7-bromo-4-(3,4-dimethoxybenzyl)-4H-[1,2,4]triazolo[4,3-a]quinazolin-5-one;
1-(azepan-1-yl)-7-bromo-4-(3-phenylallyl)-4H-[1,2,4]triazolo[4,3-a]quinazolin-5-one;
1-azepan-1-yl-7-bromo-4-((E)-3-pyrid-3-ylallyl)-4H-[1,2,4]triazolo[4,3-a]quinazolin-5-one;
1-azepan-1-yl-7-bromo-4-(3-pyrid-4-ylallyl)-4H-[1,2,4]triazolo[4,3-a]quinazolin-5-one;
7-bromo-4-(4-methylbenzyl)-1-pyrrolidin-1-yl-4H-[1,2,4]triazolo[4,3-a]quinazolin-5-one;
7-bromo-4-(4-chlorobenzyl)-1-pyrrolidin-1-yl-4H-[1,2,4]triazolo[4,3-a]quinazolin-5-one;
7-bromo-4-(4-fluorobenzyl)-1-pyrrolidin-1-yl-4H-[1,2,4]triazolo[4,3-a]quinazolin-5-one;
4-(7-bromo-5-oxo-1-pyrrolidin-1-yl-5H-[1,2,4]triazolo[4,3-a]quinazolin-4-ylmethyl)benzonitrile;
4-(7-bromo-5-oxo-1-pyrrolidin-1-yl-5H-[1,2,4]triazolo[4,3-a]quinazolin-4-yl-benzoic acid methyl ester;
7-bromo-4-(4-nitrobenzyl)-1-pyrrolidin-1-yl-4H-[1,2,4]triazolo[4,3-a]quinazolin-5-one;
7-bromo-4-(4-methoxybenzyl)-1-pyrrolidin-1-yl-4H-[1,2,4]triazolo[4,3-a]quinazolin-5-one;
acetic acid 4-(7-bromo-5-oxo-1-pyrrolidin-1-yl-5H-[1,2,4]triazolo[4,3-a]quinazolin-4-ylmethyl)phenyl ester;
7-bromo-4-(4-hydroxybenzyl)-1-pyrrolidin-1-yl-4H-[1,2,4]triazolo[4,3-a]quinazolin-5-one;
7-bromo-4-(3,4-dimethoxybenzyl)1-pyrrolidin-1-yl-4H-[1,2,4]triazolo[4,3-a]quinazolin-5-one;
1-(pyrrolidin-1-yl)-7-bromo-4-(3-phenylallyl)-4H-[1,2,4]triazolo[4,3-a]quinazolin-5-one;
7-bromo-4-[(E)-3-(4-chlorophenyl)allyl]-1-pyrrolidin-1-yl-4H-1,2,4]triazolo[4,3-a]quinazolin-5-one;
7-bromo-4-[3-(4-methoxyphenyl)allyl]-1-pyrrolidin-1-yl-4H-[1,2,4]triazolo[4,3-a]quinazolin-5-one;
7-bromo-4-(3-pyrid-3-ylallyl)-1-pyrrolidin-1-yl-4H-[1,2,4]triazolo[4,3-a]quinazolin-5-one;
7-bromo-4-((E)-3-pyrid-4-ylallyl)-1-pyrrolidin-1-yl-4H-[1,2,4]triazolo[4,3-a]quinazolin-5-one;
7-bromo-4-(3,4-dimethoxybenzyl)-1-piperid-1-yl-4H-[1,2,4]triazolo[4,3-a]quinazolin-5-one;
1-(piperid-1-yl)-7-bromo-4-(3-phenylallyl)-4H-[1,2,4]triazolo[4,3-a]quinazolin-5-one;
7-bromo-1-dimethylamino-4-(4-methylbenzyl)-4H-[1,2,4]triazolo[4,3-a]quinazolin-5-one;
4-(7-bromo-1-dimethylamino-5-oxo-5H-[1,2,4]triazolo[4,3-a]quinazolin-4-ylmethyl)benzonitrile;
7-bromo-1-dimethylamino-4-(4-hydroxybenzyl)-4H-[1,2,4]triazolo[4,3-a]quinazolin-5-one;
4-(bromo-dimethylamino-oxo-5H-[1,2,4]triazolo[4,3-a]quinazolin-4-ylmethyl)benzoic acid methyl ester;
[4-(7-bromo-1-dimethylamino-5-oxo-5H-[1,2,4]triazolo[4,3-a]quinazolin-4-ylmethyl)phenyl]acetonitrile;
7-bromo-1-dimethylamino-4-(3-phenylallyl)-4H-[1,2,4]triazolo[4,3-a]quinazolin-5-one;
7-bromo-1-dimethylamino-4-(3-phenyl-prop-2-ynyl)-4H-[1,2,4]triazolo[4,3-a]quinazolin-5-one;
1-azepan-1-yl-7-methyl-4-(3-phenylallyl)-4H-[1,2,4]triazolo[4,3-a]quinazolin-5-one;
4-(3,4-dimethoxybenzyl)-7-methyl-1-pyrrolidin-1-yl-4H-[1,2,4]triazolo[4,3-a]quinazolin-5-one;
[4-(7-methyl-5-oxo-1-pyrrolidin-1-yl-5H-[1,2,4]triazolo[4,3-a]quinazolin-4-ylmethyl)phenyl]acetic acid;
7-methyl-4-(3-phenylallyl)-1-pyrrolidin-1-yl-4H-[1,2,4]triazolo[4,3-a]quinazolin-5-one;
[4-(dimethylamino-methyl-oxo-5H-[1,2,4]triazolo[4,3-a]quinazolin-4-ylmethyl)phenyl]acetic acid;
1-dimethylamino-7-methyl-4-((E)-3-phenylallyl)-4H-[1,2,4]triazolo[4,3-a]quinazolin-5-one;
1-dimethylamino-7-methyl-4-(3-pyrid-3-ylallyl)-4H-[1,2,4]triazolo[4,3-a]quinazolin-5-one;
[4-(7-bromo-5-oxo-1-perhydroazepin-1-yl-5H-[1,2,4]triazolo[4,3-a]quinazolin-3-ylmethyl)phenyl]acetic acid;
4-benzyl-7-bromo-1-(pyrrolidin-1-yl)-4H-[1,2,4]triazolo[4,3-a]quinazolin-5-one;
4-benzyl-7-bromo-1-(2,5-dihydropyrrol-1-yl)-4H-[1,2,4]triazolo[4,3-a]quinazolin-5-one;
4-benzyl-7-iodo-1-pyrrolidin-1-yl-4H-[1,2,4]triazolo[4,3-a]quinazolin-5-one;
1-azepan-1-yl-4-benzyl-7-methyl-4H-[1,2,4]triazolo[4,3-a]quinazolin-5-one;
4-(4-aminobenzyl)-7-bromo-1-pyrrolidin-1-yl-4H-[1,2,4]triazolo[4,3-a]quinazolin-5-one;
7-amino-4-((E)-3-phenylallyl)-1-pyrrolidin-1-yl-4H-[1,2,4]triazolo[4,3-a]quinazolin-5-one;
7-amino-1-azepan-1-yl-4-benzyl-4H-[1,2,4]triazolo[4,3-a]quinazolin-5-one;
7-amino-4-((E)-3-pyrid-3-ylallyl)-1-pyrrolidin-1-yl-4H-[1,2,4]triazolo[4,3-a]quinazolin-5-one;
7-amino-1-dimethylamino-4-((E)-3-phenylallyl)-4H-[1,2,4]triazolo[4,3-a]quinazolin-5-one;
4-benzyl-7-methylamino-1-pyrrolidin-1-yl-4H-[1,2,4]triazolo[4,3-a]quinazolin-5-one;
4-(7-methylamino-5-oxo-1-pyrrolidin-1-yl-5H-[1,2,4]triazolo[4,3-a]quinazolin-4-ylmethyl)benzonitrile;
4-benzyl-8-methylamino-1-pyrrolidin-1-yl-4H-[1,2,4]triazolo[4,3-a]quinazolin-5-one;
4-benzyl-7-ethylamino-1-pyrrolidin-1-yl-4H-[1,2,4]triazolo[4,3-a]quinazolin-5-one;
4-benzyl-7-isopropylamino-1-pyrrolidin-1-yl-4H-[1,2,4]triazolo[4,3-a]quinazolin-5-one
[4-(7-bromo-5-oxo-1-pyrrolidin-1-yl-5H-[1,2,4]triazolo[4,3-a]quinazolin-4-ylmethyl)phenyl]acetic acid methyl ester;
2-[4-(7-bromo-5-oxo-1-pyrrolidin-1-yl-5H-[1,2,4]triazolo[4,3-a]quinazolin-4-ylmethyl)phenyl]-N-methylacetamide;
2-[4-(7-bromo-1-dimethylamino-5-oxo-5H-[1,2,4]triazolo[4,3-a]quinazolin-4-ylmethyl)phenyl]acetamide;
2-[4-(7-bromo-5-oxo-1-pyrrolidin-1-yl-5H-[1,2,4]triazolo[4,3-a]quinazolin-4-ylmethyl)phenyl]-N,N-dimethylacetamide;
2-[4-(7-bromo-5-oxo-1-pyrrolidin-1-yl-5H-[1,2,4]triazolo[4,3-a]quinazolin-4-ylmethyl)phenyl]-N-hydroxyacetamide; or
1-dimethylamino-7-methyl-4-(3-pyrid-3-ylallyl)-4H-[1,2,4]triazolo[4,3-a]quinazoline-5-thione.

9. A compound of claim 1 which is bromo-dimethylamino-((E)-3-pyrid-3-ylallyl)-4H-[1,2,4]triazolo[4,3-a]quinazolin-5-one;
1-(azepan-1-yl)-7-chloro-4-(3,4-dimethoxybenzyl)-4H-[1,2,4]triazolo[4,3-a]quinazolin-5-one;
1-(azepan-1-yl)-7-chloro-4-(3-pyridylmethyl)-4H-[1,2,4]triazolo[4,3-a]quinazolin-5-one;
4-(1-azepan-1-yl-7-bromo-5-oxo-5H-[1,2,4]triazolo[4,3-a]quinazolin-4-ylmethyl)benzonitrile;
1-azepan-1-yl-7-bromo-4-(3,4-dimethoxybenzyl)-4H-[1,2,4]triazolo[4,3-a]quinazolin-5-one;

1-(azepan-1-yl)-7-bromo-4-(3-phenylallyl)-4H-[1,2,4]triazolo[4,3-a]quinazolin-5-one;
1-azepan-1-yl-7-bromo-4-((E)-3-pyrid-3-ylallyl)-4H-[1,2,4]triazolo[4,3-a]quinazolin-5-one;
1-azepan-1-yl-7-bromo-4-(3-pyrid-4-ylally)-4H-[1,2,4]triazolo[4,3-a]quinazolin-5-one;
7-bromo-4-(4-methylbenzyl)-1-pyrrolidin-1-yl-4H-[1,2,4]triazolo[4,3-a]quinazolin-5-one;
7-bromo-4-(4-chlorobenzyl)-1-pyrrolidin-1-yl-4H-[1,2,4]triazolo[4,3-a]quinazolin-5-one;
7-bromo-4-(3,4-dimethoxybenzyl)-1-pyrrolidin-1-yl-4H-[1,2,4]triazolo[4,3-a]quinazolin-5-one;
1-(pyrrolidin-1-yl)-7-bromo-4-(3-phenylallyl)-4H-[1,2,4]triazolo[4,3-a]quinazolin-5-one;
7-bromo-4-(3-pyrid-3-ylallyl)-1-pyrrolidin-1-yl-4H-[1,2,4]triazolo[4,3-a]quinazolin-5-one;
1-(piperid-1-yl)-7-bromo-4-(3-phenylallyl)-4H-[1,2,4]triazolo[4,3-a]quinazolin-5-one;
4-(7-bromo-1-dimethylamino-5-oxo-5H-[1,2,4]triazolo[4,3-a]quinazolin-4-ylmethyl)benzonitrile;
4-(bromo-dimethylamino-oxo-5H-[1,2,4]triazolo[4,3-a]quinazolin-4-ylmethyl)benzoic acid methyl ester;
7-bromo-1-dimethylamino-4-(3-phenylallyl)-4H-[1,2,4]triazolo[4,3-a]quinazolin-5-one;
7-bromo-1-dimethylamino-4-(3-phenylprop-2-ynyl)-4H-[1,2,4]triazolo[4,3-a]quinazolin-5-one;
1-azepan-1-yl-7-methyl-4-(3-phenylallyl)-4H-[1,2,4]triazolo[4,3-a]quinazolin-5-one;
4-(3,4-dimethoxybenzyl)-7-methyl-1-pyrrolidin-1-yl-4H-[1,2,4]triazolo[4,3-a]quinazolin-5-one;
7-methyl-4-(3-phenylallyl)-1-pyrrolidin-1-yl-4H-[1,2,4]triazolo[4,3-a]quinazolin-5-one;
7-amino-4-((E)-3-phenylallyl)-1-pyrrolidin-1-yl-4H-[1,2,4]triazolo[4,3-a]quinazolin-5-one;
7-amino-4-((E)-3-pyrid-3-ylallyl)-1-pyrrolidin-1-yl-4H-[1,2,4]triazolo[4,3-a]quinazolin-5-one;
4-benzyl-7-methylamino-1-pyrrolidin-1-yl-4H-[1,2,4]triazolo[4,3-a]quinazolin-5-one;
4-(7-methylamino-5-oxo-1-pyrrolidin-1-yl-5H-[1,2,4]triazolo[4,3-a]quinazolin-4-ylmethyl)benzonitrile;
[4-(7-bromo-5-oxo-1-pyrrolidin-1-yl-5H-[1,2,4]triazolo[4,3-a]quinazolin-4-ylmethyl)phenyl]acetic acid methyl ester;
2-[4-(7-bromo-5-oxo-1-pyrrolidin-1-yl-5H-[1,2,4]triazolo[4,3-a]quinazolin-4-ylmethyl)phenyl]-N-methylacetamide;
2-[4-(7-bromo-5-oxo-1-pyrrolidin-1-yl-5H-[1,2,4]triazolo[4,3-a]quinazolin-4-ylmethyl)phenyl]-N,N-dimethylacetamide; or
1-dimethylamino-7-methyl-4-(3-pyrid-3-ylallyl)-4H-[1,2,4]triazolo[4,3-a]quinazoline-5-thione.

10. A compound of Formula III,

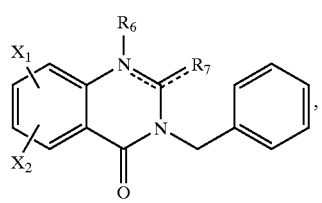

III wherein
$X_1$ and $X_2$ are independently hydrogen, hydroxy, halogen, amino, nitro, mercapto, cyano or carboxyl;
$(C_1-C_6)$alkyl, $(C_1-C_6)$alkoxy or $—S(O)_mR_8$, said alkyl and alkoxy being optionally substituted on carbon with one to three halogen;

—CO—$Q_1$—$Q_2$—$Q_3$;

—NH—$R_1$; or

—$NR_2R_3$;

the dashed lines represent optional double bonds;

$R_6$ and $R_7$ are taken together with the atoms to which they are attached to form a 5- or 6-membered ring, said ring optionally containing one or two additional N or one or two O or S, said ring being optionally substituted with one, two or three $(C_1-C_6)$thioalkyl, mercapto or halogen;

m is 0, 1 or 2;

$R_8$ is $(C_1-C_6)$alkyl, said alkyl being optionally substituted with one to three halogen;

—$Q_1$— is a bond, —O—,

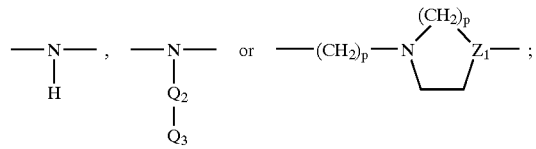

—$Q_2$— is:
a) —$(CH_2)_q$—;
b) —$(CH_2—CH_2—O)_r$;

—$Q_3$ is: —H, —OH, $(C_1-C_6)$alkoxy, —O—CO—$X_3$, —NH$X_3$, or —N$X_3X_4$;

p is 0, 1, 2 or 3;

$Z_1$ is CH, N, O or S;

q is 0, 1, 2, 3, or 4;

r is 2, 3, or 4;

$X_3$ and $X_4$ are taken separately and are independently $(C_1-C_6)$alkyl; or $X_3$ and $X_4$ are taken together with the nitrogen atom to which they are attached to form a 4-, 5-, 6- or 7-membered ring, said ring containing one to three additional hetero atoms selected from O, S and N;

$R_1$ is $(C_1-C_6)$alkyl optionally substituted with one to three halogen, hydroxy, cyano, $(C_1-C_6)$alkoxy or —CO—$Q_1$—$Q_2$—$Q_3$; and $R_2$ and $R_3$ are taken separately and are independently $(C_1-C_6)$alkyl optionally substituted with one to three hydroxy, halogen, cyano, $(C_1-C_6)$alkoxy or —CO—$Q_1$—$Q_2$—$Q_3$; or $R_2$ and $R_3$ are taken together with the nitrogen atom to which they are attached to form a 4-, 5-, 6- or 7-membered ring, said ring containing one to three O, S or N, said ring being optionally bridged with a $(C_1-C_6)$alkyl which may be gem-dialkylated or substituted with one to three hydroxy, oxo, $(C_1-C_6)$alkyl, $(C_1-C_6)$alkoxy or —CO—$Q_1$—$Q_2$—$Q_3$.

11. A compound of Formula IV,

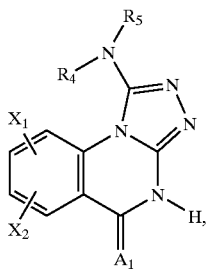

IV wherein

A$_1$ is O or S;

X$_1$ and X$_2$ are independently hydrogen, hydroxy, halogen, amino, nitro, mercapto, cyano or carboxyl;

(C$_1$–C$_6$)alkyl, (C$_1$–C$_6$)alkoxy or —S(O)$_m$R$_8$, said alkyl and alkoxy being optionally substituted on carbon with one to three halogen;

—CO—Q$_1$—Q$_2$—Q$_3$;

—NH—R$_1$; or

—NR$_2$R$_3$;

R$_4$ and R$_5$ are taken separately, are identical, and are (C$_1$–C$_6$)alkyl; or R$_4$ and R$_5$ are taken separately, are different, and are aryl(C$_1$–C$_6$)alkyl, (C$_3$–C$_7$)cycloalkyl or (C$_3$–C$_7$)cycloalkyl(C$_1$–C$_6$)alkyl; or R$_4$ and R$_5$ are taken together with the nitrogen atom to which they are attached to form a 4-, 5-, 6- or 7-membered saturated or partially unsaturated ring, said ring optionally containing one to three hetero atoms selected from O, S and N, said ring being optionally substituted with (C$_1$–C$_6$)alkyl, hydroxy or (C$_1$–C$_6$)alkoxy, said ring being optionally bridged with a (C$_1$–C$_6$)alkyl which may be gem-di(C$_1$–C$_6$)alkylated or substituted with one to three hydroxy, oxo, (C$_1$–C$_6$) alkyl, (C$_1$–C$_6$)alkoxy, phenyl(C$_1$–C$_6$)alkyl or CO—Q$_1$—Q$_2$—Q$_3$, said ring being optionally fused via two adjacent atoms shared with another ring selected from phenyl and heteroaryl, said heteroaryl ring containing four to eight carbon atoms which may be optionally replaced with one to three hetero atoms selected from O, S and N;

m is 0, 1 or 2;

R$_8$ is (C$_1$–C$_6$)alkyl, said alkyl being optionally substituted with one to three halogen;

—Q$_1$— is a bond, —O—,

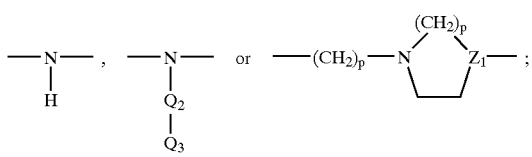

—Q$_2$— is:

a) —(CH$_2$)$_q$—;

b) —(CH$_2$—CH$_2$—O)$_r$;

—Q$_3$ is: —H, —OH, (C$_1$–C$_6$)alkoxy, —O—CO—X$_3$, —NHX$_3$, or

R$_1$ is (C$_1$–C$_6$)alkyl optionally substituted with one to three halogen, hydroxy, cyano, (C$_1$–C$_6$)alkoxy or —CO—Q$_1$—Q$_2$—Q$_3$;

R$_2$ and R$_3$ are taken separately and are independently (C$_1$–C$_6$)alkyl optionally substituted with one to three hydroxy, halogen, cyano, (C$_1$–C$_6$)alkoxy or —CO—Q$_1$—Q$_2$—Q$_3$; or R$_2$ and R$_3$ are taken together with the nitrogen atom to which they are attached to form a 4-, 5-, 6- or 7-membered ring, said ring containing one to three O, S or N, said ring being optionally bridged with a (C$_1$–C$_6$)alkyl which may be gem-dialkylated or substituted with one to three hydroxy, oxo, (C$_1$–C$_6$)alkyl, (C$_1$–C$_6$)alkoxy or

—CO—Q$_1$—Q$_2$—Q$_3$;

p is 0, 1, 2 or 3;

Z$_1$ is CH, N, O or S;

q is 0, 1, 2, 3, or 4;

r is 2, 3, or 4; and

X$_3$ and X$_4$ are taken separately and are independently (C$_1$–C$_6$)alkyl; or X$_3$ and X$_4$ are taken together with the nitrogen atom to which they are attached to form a 4-, 5-, 6- or 7-membered ring, said ring containing one to three additional hetero atoms selected from O, S and N.

12. A compound of Formula V,

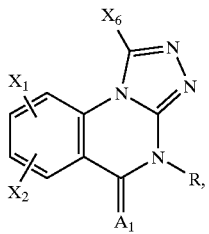

(V)

wherein

A$_1$ is O or S;

X$_1$ and X$_2$ are independently hydrogen, hydroxy, halogen, amino, nitro, mercapto, cyano or carboxyl;

(C$_1$–C$_6$)alkyl, (C$_1$–C$_6$)alkoxy or —S(O)$_m$R$_8$, said alkyl and alkoxy being optionally substituted on carbon with one to three halogen;

—CO—Q$_1$—Q$_2$—Q$_3$;

—NH—R$_1$; or

—NR$_2$R$_3$;

R is (C$_1$–C$_6$)alkyl, (C$_2$–C$_6$)alkenyl, (C$_2$–C$_6$)alkynyl, aryl (C$_2$–C$_6$)alkynyl, or 2-, 3- or 4-pyridyl(C$_1$–C$_6$)alkyl optionally substituted with (C$_1$–C$_6$)alkyl, (C$_1$–C$_6$) alkoxy, hydroxy, halogen or amino; or

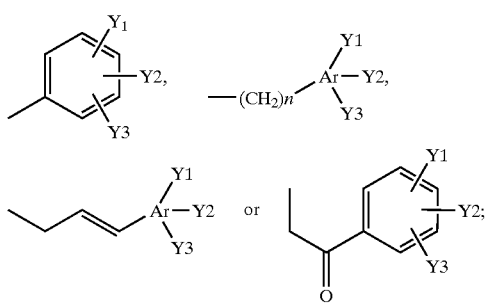

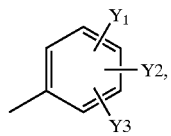

m is 0, 1 or 2;

$R_8$ is $(C_1-C_6)$alkyl, said alkyl being optionally substituted with one to three halogen; —$Q_1$— is a bond, —O—,

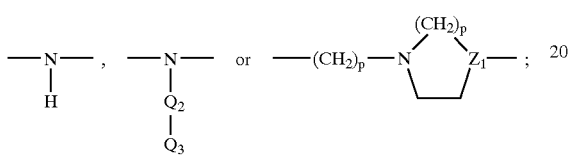

—$Q_2$— is:
a) —$(CH_2)_q$—;
b) —$(CH_2-CH_2-O)_r$—;

—$Q_3$ is: —H, —OH, $(C_1-C_6)$alkoxy, —O—CO—$X_3$, —$NHX_3$, or

$R_1$ is $(C_1-C_6)$alkyl optionally substituted with one to three halogen, hydroxy, cyano, $(C_1-C_6)$alkoxy or —CO—$Q_1$—$Q_2$—$Q_3$;

$R_2$ and $R_3$ are taken separately and are independently $(C_1-C_6)$alkyl optionally substituted with one to three hydroxy, halogen, cyano, $(C_1-C_6)$alkoxy or —CO—$Q_1$—$Q_2$—$Q_3$; or $R_2$ and $R_3$ are taken together with the nitrogen atom to which they are attached to form a 4-, 5-, 6- or 7-membered ring, said ring containing one to three O, S or N, said ring being optionally bridged with a $(C_1-C_6)$alkyl which may be gem-dialkylated or substituted with one to three hydroxy, oxo, $(C_1-C_6)$alkyl, $(C_1-C_6)$alkoxy or —CO—$Q_1$—$Q_2$—$Q_3$;

n is 1, 2, 3, 4 or 5;

Ar is a 5- or 6-membered aromatic ring containing 0 to 3 hetero atoms selected from O, S and N;

Y1, Y2 and Y3 are independently
hydrogen, hydroxy, mercapto, amino, nitro, halogen, —$NHR_1$, —$NR_2R_3$,
$(CH_2)_sCN$ or —$(CH_2)_sCO$—$Q_1$—$Q_2$—$Q_3$;
$(C_1-C_6)$alkyl, $(C_1-C_6)$alkoxy or —$S(O)_mR_8$;

s is 0, 1, 2, 3, 4, 5 or 6;

p is 0, 1, 2 or 3;

$Z_1$ is CH, N, O or S;

q is 0, 1, 2, 3, or 4;

r is 2, 3, or 4; and $X_3$ and $X_4$ are taken separately and are independently $(C_1-C_6)$alkyl; or $X_3$ and $X_4$ are taken together with the nitrogen atom to which they are attached to form a 4-, 5-, 6- or 7-membered ring, said ring containing one to three additional hetero atoms selected from O, S and N;

$X_5$ is halogen, —$OCOX_7$, —$OSO_2X_7$ or —$SO_2X_7$; and $X_7$ is $(C_1-C_6)$alkyl or aryl;

provided that when $X_1$ and $X_2$ are each H, $A_1$ is O, R is

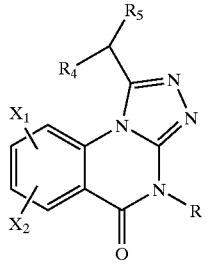

Y1 and Y2 are each H, and Y3 is halo, then $X_5$ is not —$SO_2X_7$.

13. A process for preparing a compound of Formula I or Formula II,

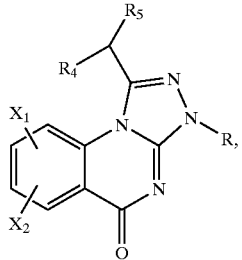

wherein $X_1$ and $X_2$ are independently
hydrogen, hydroxy, halogen, amino, nitro, mercapto, cyano or carboxyl;
$(C_1-C_6)$alkyl, $(C_1-C_6)$alkoxy or —$S(O)_mR_8$, said alkyl and alkoxy being optionally substituted on carbon with one to three halogen;
—CO—Q—$Q_1$—$Q_2$—$Q_3$;
—NH—$R_1$; or
—$NR_2R_3$;

R is
$(C_1-C_6)$alkyl, $(C_2-C_6)$alkenyl, $(C_2-C_6)$alkynyl, aryl $(C_2-C_6)$alkynyl, or 2-, 3- or 4-pyridyl$(C_1-C_6)$alkyl optionally substituted with $(C_1-C_6)$alkyl, $(C_1-C_6)$alkoxy, hydroxy, halogen or amino; or

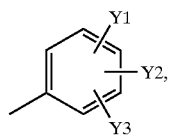 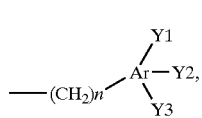

-continued

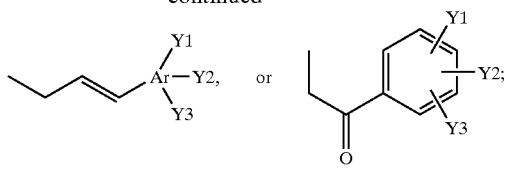

$R_4$ and $R_5$ are taken separately, are identical, and are $(C_1-C_6)$alkyl; or $R_4$ and $R_5$ are taken separately, are different, and are aryl$(C_1-C_6)$alkyl, $(C_3-C_7)$cycloalkyl or $(C_3-C_7)$cycloalkyl$(C_1-C_6)$alkyl; or $R_4$ and $R_5$ are taken together with the nitrogen atom to which they are attached to form a 4-, 5-, 6- or 7-membered saturated or partially unsaturated ring, said ring optionally containing one to three hetero atoms selected from O, S and N, said ring being optionally substituted with $(C_1-C_6)$alkyl, hydroxy or $(C_1-C_6)$alkoxy, said ring being optionally bridged with a $(C_1-C_6)$alkyl which may be gem-di$(C_1-C_6)$alkylated or substituted with one to three hydroxy, oxo, $(C_1-C_6)$alkyl, $(C_1-C_6)$alkoxy, phenyl$(C_1-C_6)$alkyl or CO—$Q_1$—$Q_2$—$Q_3$, said ring being optionally fused via two adjacent atoms shared with another ring selected from phenyl and heteroaryl, said heteroaryl ring containing four to eight carbon atoms which may be optionally replaced with one to three hetero atoms selected from O, S and N;

m is 0, 1 or 2;

$R_8$ is $(C_1-C_6)$alkyl, said alkyl being optionally substituted with one to three halogen;

—$Q_1$— is a bond, —O—,

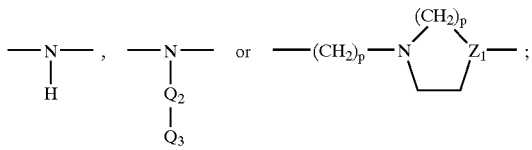

—$Q_2$— is:
a) —$(CH_2)_q$—;
b) —$(CH_2-CH_2-O)_r$;

—$Q_3$ is: —H, —OH, $(C_1-C_6)$alkoxy, -O—CO—$X_3$, —NHX$_3$, or

$R_1$ is $(C_1-C_6)$alkyl optionally substituted with one to three halogen, hydroxy, cyano, $(C_1-C_6)$alkoxy or —CO—$Q_1$—$Q_2$—$Q_3$;

$R_2$ and $R_3$ are taken separately and are independently $(C_1-C_6)$alkyl optionally substituted with one to three hydroxy, halogen, cyano, $(C_1-C_6)$alkoxy or —CO—$Q_1$—$Q_2$—$Q_3$; or $R_2$ and $R_3$ are taken together with the nitrogen atom to which they are attached to form a 4-, 5-, 6- or 7-membered ring, said ring containing one to three O, S or N, said ring being optionally bridged with a $(C_1-C_6)$alkyl which may be gem-dialkylated or substituted with one to three hydroxy, oxo, $(C_1-C_6)$alkyl, $(C_1-C_6)$alkoxy or —CO—$Q_1$—$Q_2$—$Q_3$;

n is 1, 2, 3, 4 or 5;

Ar is a 5- or 6-membered aromatic ring containing 0 to 3 hetero atoms selected from O, S and N;

Y1, Y2 and Y3 are independently
hydrogen, hydroxy, mercapto, amino, nitro, halogen,
—NHR,, —NR$_2$R$_3$,
—$(CH_2)_s$CN or —$(CH_2)_s$CO—$Q_1$—$Q_2$—$Q_3$;
—$(C_1-C_6)$alkyl, $(C_1-C_6)$alkoxy or —S(O)$_m$R$_8$;

s is 0, 1, 2, 3, 4, 5 or 6;

p is 0, 1, 2 or 3;

$Z_1$ is CH, N, O or S;

q is 0, 1, 2, 3, or 4;

r is 2, 3, or 4; and $X_3$ and $X_4$ are taken separately and are independently $(C_1-C_6)$alkyl; or $X_3$ and $X_4$ are taken together with the nitrogen atom to which they are attached to form a 4-, 5-, 6- or 7-membered ring, said ring containing one to three additional hetero atoms selected from O, S and N;

comprising reacting a compound of Formula IV,

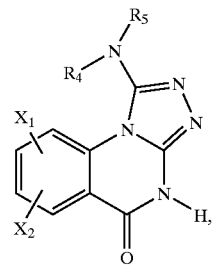

IV wherein $X_1$, $X_2$, $R_4$ and $R_5$ are as defined hereinabove, with a compound of the formula

R—X' wherein X' is halogen, —OCOX$_7$ or —OSO$_2$X$_7$ and X$_7$ is $(C_1-C_6)$alkyl or aryl group; to afford a compound of Formula I and its corresponding isomer of Formula II; and, optionally, separating said compound of Formula I and Formula II from each other.

14. A process for a compound of Formula I,

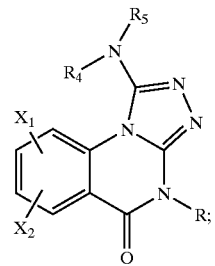

I wherein $X_1$ and $X_2$ are independently
hydrogen, hydroxy, halogen, amino, nitro, mercapto, cyano or carboxyl;

$(C_1-C_6)$alkyl, $(C_1-C_6)$alkoxy or —S(O)$_m$R$_8$, said alkyl and alkoxy being optionally substituted on carbon with one to three halogen;

—CO—$Q_1$—$Q_2$—$Q_3$;
—NH—$R_1$; or
—$NR_2R_3$;

R is
(C$_1$–C$_6$)alkyl, (C$_2$–C$_6$)alkenyl, (C$_2$–C$_6$)alkynyl, aryl(C$_2$–C$_6$)alkynyl, or 2-, 3 or 4-pyridyl(C$_1$–C$_6$)alkyl optionally substituted with (C$_1$–C$_6$)alkyl, (C$_1$–C$_6$)alkoxy, hydroxy, halogen or amino; or

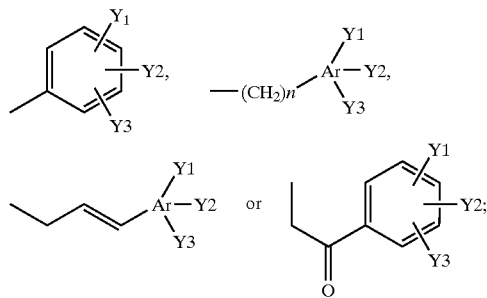

$R_4$ and $R_5$ are taken separately, are identical, and are (C$_1$–C$_6$)alkyl; or $R_4$ and $R_5$ are taken separately, are different, and are aryl(C$_1$–C$_6$)alkyl, (C$_3$–C$_7$)cycloalkyl or (C$_3$–C$_7$)cycloalkyl(C$_1$–C$_6$)alkyl; or $R_4$ and $R_5$ are taken together with the nitrogen atom to which they are attached to form a 4-, 5-, 6- or 7-membered saturated or partially unsaturated ring, said ring optionally containing one to three hetero atoms selected from O, S and N, said ring being optionally substituted with (C$_1$–C$_6$)alkyl, hydroxy or (C$_1$–C$_6$)alkoxy, said ring being optionally bridged with a (C$_1$–C$_6$)alkyl which may be gem-di(C$_1$–C$_6$)alkylated or substituted with one to three hydroxy, oxo, (C$_1$–C$_6$) alkyl, (C$_1$–C$_6$)alkoxy, phenyl(C$_1$–C$_6$)alkyl or CO—$Q_1$—$Q_2$—$Q_3$, said ring being optionally fused via two adjacent atoms shared with another ring selected from phenyl and heteroaryl, said heteroaryl ring containing four to eight carbon atoms which may be optionally replaced with one to three hetero atoms selected from O, S and N;

m is 0, 1 or 2;

$R_8$ is (C$_1$–C$_6$)alkyl, said alkyl being optionally substituted with one to three halogen;

—$Q_1$— is a bond, —O—,

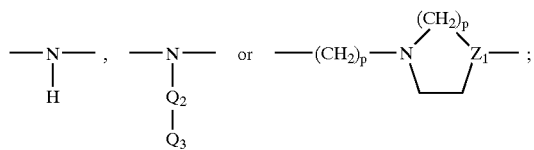

—$Q_2$— is:
a) —(CH$_2$)$_q$—;
b) —(CH$_2$—CH$_2$—O)$_r$—;

—$Q_3$ is: —H, —OH, (C$_1$–C$_6$)alkoxy, —O—CO—$X_3$, —NHX$_3$, or

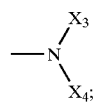

$R_1$ is (C$_1$–C$_6$)alkyl optionally substituted with one to three halogen, hydroxy, cyano, (C$_1$–C$_6$)alkoxy or —CO—$Q_1$—$Q_2$—$Q_3$;

$R_2$ and $R_3$ are taken separately and are independently (C$_1$–C$_6$)alkyl optionally substituted with one to three hydroxy, halogen, cyano, (C$_1$–C$_6$)alkoxy or —CO—$Q_1$—$Q_2$—$Q_3$; or $R_2$ and $R_3$ are taken together with the nitrogen atom to which they are attached to form a 4-, 5-, 6- or 7-membered ring, said ring containing one to three O, S or N, said ring being optionally bridged with a (C$_1$–C$_6$)alkyl which may be gem-dialkylated or substituted with one to three hydroxy, oxo, (C$_1$–C$_6$)alkyl, (C$_1$–C$_6$)alkoxy or —CO—$Q_1$—$Q_2$—$Q_3$;

n is 1, 2, 3, 4 or 5;

Ar is a 5- or 6-membered aromatic ring containing 0 to 3 hetero atoms selected from O, S and N;

Y1, Y2 and Y3 are independently
hydrogen, hydroxy, mercapto, amino, nitro, halogen,
—NHR$_1$, —NR$_2$R$_3$,
—(CH$_2$)$_s$CN or —(CH$_2$)$_s$CO—$Q_1$—$Q_2$—$Q_3$;
—(C$_1$–C$_6$)alkyl, (C$_1$–C$_6$)alkoxy or —S(O)$_m$R$_8$;

s is 0, 1, 2, 3, 4, 5 or 6;
p is 0, 1, 2 or 3;
$Z_1$ is CH, N, O or S;
q is 0, 1, 2, 3, or 4;
r is 2, 3, or 4; and $X_3$ and $X_4$ are taken separately and are independently (C$_1$–C$_6$)alkyl; or $X_3$ and $X_4$ are taken together with the nitrogen atom to which they are attached to form a 4-, 5-, 6- or 7-membered ring, said ring containing one to three additional hetero atoms selected from O, S and N;

comprising reacting a compound of Formula V,

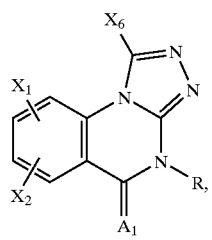

(V)

wherein
wherein $X_1$, $X_2$ and R are as defined hereinabove and $X_5$ is halogen, —OCOX$_7$, —OSO$_2$X$_7$ or —SO$_2$X$_7$; and $X_7$ is (C$_1$–C$_8$)alkyl or aryl, with a compound of the formula

HNR$_4$R$_5$ wherein
$R_4$ and $R_5$ are taken separately, are identical, and are (C$_1$–C$_6$)alkyl; or $R_4$ and $R_5$ are taken separately, are different, and are aryl(C$_1$–C$_6$)alkyl, (C$_3$–C$_7$)cycloalkyl or (C$_3$–C$_7$)cycloalkyl(C$_1$–C$_6$)alkyl; or $R_4$ and $R_5$ are taken together with the nitrogen atom to which they are attached to form a 4-, 5-, 6- or 7-membered saturated or partially unsaturated ring, said ring optionally containing one to three hetero atoms selected from O, S and N, said ring being optionally substituted with $(C_1-C_6)$alkyl, hydroxy or $(C_1-C_6)$alkoxy, said ring being optionally bridged with a $(C_1-C_6)$alkyl which may be gem-di$(C_1-C_6)$alkylated or substituted with one to three hydroxy, oxo, $(C_1-C_6)$ alkyl, $(C_1-C_6)$alkoxy, phenyl$(C_1-C_6)$alkyl or CO—$Q_1$—$Q_2$—$Q_3$, said ring being optionally fused via two adjacent atoms shared with another ring selected from phenyl and heteroaryl, said heteroaryl ring containing four to eight carbon atoms which may be optionally replaced with one to three hetero atoms selected from O, S and N;

to obtain said compound of Formula I.

15. A process of claim 14 wherein when $X_1$ is —$NR_2R_3$ and —$NR_2R_3$ and —$NR_4R_5$ are identical, said compound of Formula I is prepared by reacting a compound of general formula VI

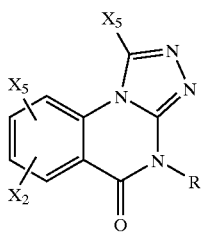

VI with a compound of the formula

$HNR_2R_3$ to give a compound of Formula I having the structure of Formula Ia:

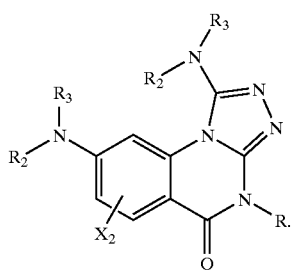

Ia

16. A process of claim 14 wherein when $X_1$ is —$NR_2R_3$ and —$NR_2R_3$ and —$NR_4R_5$ are different, said compound of Formula I is obtained by reacting a compound of Formula VII:

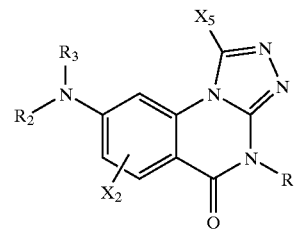

VII with a compound of the formula:

$HNR_4R_5$ to afford a compound of Formula I having the structure of Formula Ib:

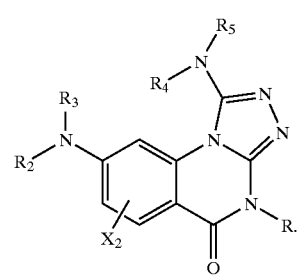

Ib

17. A pharmaceutical composition comprising a compound of claim 1 and a pharmaceutically acceptable excipient.

18. A method of treating a condition or complaint mediated by inhibition of a phosphodiesterase IV receptor selected from the group consisting of asthma, chronic bronchitis or acute pulmonary attack and acute respiratory distress syndrome in a mammal comprising administering to said mammal a compound of claim 1, a pharmaceutically acceptable salt of said compound or a pharmaceutical composition said compound or said salt and a pharmaceutically acceptable excipient.

19. A method of claim 18 wherein said condition is asthma.

20. A method of claim 18 wherein said condition is chronic bronchitis or acute pulmonary attack.

21. A method of claim 18 wherein said condition is acute respiratory distress syndrome.

22. A method for attenuating the development of tolerance or morphine-dependency phenomena in a mammal comprising administering to said mammal a compound of claim 1, a pharmaceutically acceptable salt of said compound or a pharmaceutical composition said compound or said salt and a pharmaceutically acceptable excipient.

23. A compound of claim 2 wherein R is

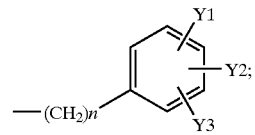

n is 1, 2 or 3; and Y1, Y2 and Y3 are each independently H or methoxy.

24. A compound of claim 2 wherein R is

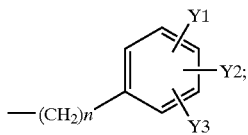

n is 1, 2 or 3; Y1 and Y2 are each H; and Y3, substituted at the 4-position, is $(C_1–C_6)$alkoxy, amino, nitro, hydroxy, —$(CH_2)_sCO$—$Q_1$—$Q_2$—$Q_3$, —$(CH_2)_s$—CN, or $(C_1–C_6)$ alkyl optionally substituted with one to three halo.

25. A compound of claim 3 wherein R is

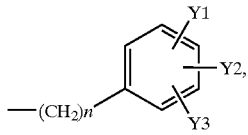

wherein n is 1, 2 or 3; and Y1, Y2 and Y3 are each H or methoxy.

26. A compound of claim 25 wherein Y1, Y2 and Y3, substituted at the 3-, 4- and 5-position, respectively, are each methoxy.

27. A compound of claim 3 wherein R is

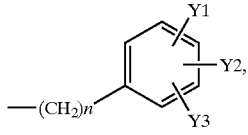

wherein n is 1, 2 or 3; Y1 and Y2 are each H; and
Y3, substituted at the 4-position, is $(C_1–C_6)$alkoxy;

amino;

nitro;

hydroxy;

$(C_1–C_6)$alkyl optionally substituted with one to three halo;

—$(CH_2)_sCO$—$Q_1$—$Q_2$—$Q_3$ in which s is 0 or 1; $Q_1$ is O, —NH— or a bond; $Q_2$ is —$(CH_2)_q$—, wherein q is 0, 1, 2, 3 or 4; and $Q_3$ is H, OH or —$NX_3X_4$; or —$(CH_2)_s$—CN wherein s is 0 or 1.

28. A compound of claim 3 wherein

R is

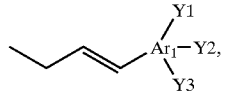

wherein said N is substituted at the 3-position.

29. A compound of claim 12 wherein said halogen is F, Br or Cl.

30. A compound of claim 14 wherein said halogen is F, Br or Cl.

* * * * *